United States Patent
Sharma et al.

(10) Patent No.: US 11,384,126 B2
(45) Date of Patent: Jul. 12, 2022

(54) COMPOSITIONS AND METHODS FOR INHIBITING DHHC-TYPE PALMITOYLTRANSFERASES FOR CANCER TREATMENT

(71) Applicant: DANA-FARBER CANCER INSTITUTE, INC., Boston, MA (US)

(72) Inventors: Chandan Sharma, Brookline, MA (US); Martin E. Hemler, Newton, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 0 days.

(21) Appl. No.: 16/766,942

(22) PCT Filed: Nov. 30, 2018

(86) PCT No.: PCT/US2018/063341
§ 371 (c)(1),
(2) Date: May 26, 2020

(87) PCT Pub. No.: WO2019/108951
PCT Pub. Date: Jun. 6, 2019

(65) Prior Publication Data
US 2021/0032298 A1    Feb. 4, 2021

Related U.S. Application Data

(60) Provisional application No. 62/653,160, filed on Apr. 5, 2018, provisional application No. 62/593,571, filed on Dec. 1, 2017.

(51) Int. Cl.
*A61K 31/00* (2006.01)
*A61P 35/00* (2006.01)
*C07K 14/47* (2006.01)
*A61K 38/00* (2006.01)
*A61K 45/06* (2006.01)

(52) U.S. Cl.
CPC .......... *C07K 14/4703* (2013.01); *A61K 31/00* (2013.01); *A61P 35/00* (2018.01); *A61K 38/00* (2013.01); *A61K 45/06* (2013.01)

(58) Field of Classification Search
CPC .............................. A61K 31/00; A61P 35/00
See application file for complete search history.

(56) References Cited

U.S. PATENT DOCUMENTS

| 2002/0197654 A1* | 12/2002 | Carton | A61P 1/04 435/7.21 |
| 2006/0210568 A1* | 9/2006 | Serrero | A61K 31/426 424/155.1 |
| 2013/0210890 A1* | 8/2013 | Ren | A61P 35/00 514/44 A |
| 2016/0304607 A1* | 10/2016 | Sadineni | A61K 47/18 |

FOREIGN PATENT DOCUMENTS

| WO | 2002/074924 A2 | 9/2002 |
| WO | 2016/089873 A1 | 6/2016 |
| WO | 2016/090276 A1 | 6/2016 |

OTHER PUBLICATIONS

Runkle et al., 2016, Inhibition of DHHC20 mediated EGFR palmiytoylation creates a dependence on EGFR signaling, Mol Cell, 62(3): 385-396.*
Jennings et al., 2009, 2-Bromopalmitate and 2-(2-hydroxy-5-nitro-benzylidene)-benzo[b]thiophen-3-one inhibit DHHC-mediated palmitoylation in vitro, Journal of Lipid Research, 50: 233-242.*
Burr et al., "CMTM6 maintains the expression of PD-L1 and regulates anti-tumour immunity," Nature, 2017, 549(7670):101-105.
Chamoto et al., "Mitochondrial activation chemicals synergize with surface receptor PD-1 blockade for T cell-dependent antitumor activity," Proc Natl Acad Sci USA, 114(5):761-770, 2017.
Jennings et al., "2-Bromopalmitate and 2-(2-hydroxy-5-nitro-benzylidene)-benzo[b] thiophen-3-one inhibit DHHC-mediated palmitoylation in vitro," J Lipid Res, 50(2):233-242, 2009.
Sharma et al., "Protein Acyltransferase DHHC3 Regulates Breast Tumor Growth, Oxidative Stress, and Senescence," Cancer Research, 77(24):6880-6890, 2017.
Tian et al., "Systematic siRNA Screen Unmasks NSCLC Growth Dependence by Palmitoyltransferase DHHC5," Mol Cancer Res, 2015, 13(4):784-794.
Tkachev et al., "Programmed death-1 controls T cell survival by regulating oxidative metabolism," J Immunol, 2015, 194(12):5789-5800.

* cited by examiner

*Primary Examiner* — Amber D Steele
(74) *Attorney, Agent, or Firm* — Burns & Levinson, LLP; Daniel W. Clarke

(57) ABSTRACT

The present invention relates to compositions and methods for inhibiting DHHC3 palmitoyltransferase for treating cancer. Described herein, are methods of inhibiting expression or activity of programmed death-ligand 1 (PD-L1) in a cell of a subject, e.g., a human subject, in need thereof are carried out by administering to the subject an effective amount of a palmitoyltransferase inhibitor, thereby inhibiting the expression or activity of PD-L1 in the subject. The palmitoyltransferase comprises an Asp-His-His-Cys motif (DHHC)-type protein. Exemplary DHHC-type proteins include DHHC3, DHHC5, DHHC7, and DHHC17.

25 Claims, 72 Drawing Sheets
Specification includes a Sequence Listing.

COMPOSITIONS AND METHODS FOR INHIBITING DHHC-TYPE PALMITOYLTRANSFERASES FOR CANCER TREATMENT

RELATED APPLICATIONS

This application is a national stage application, filed under 35 U.S.C. § 371, of International Application No. PCT/US18/063341, filed Nov. 30, 2018, which claims the benefit of priority under 35 U.S.C. § 119(e) to U.S. Provisional Application No. 62/593,571, filed Dec. 1, 2017 and to U.S. Provisional Application No. 62/653,160, filed Apr. 5, 2018, each of which is incorporated herein by reference in its entirety.

GOVERNMENT LICENSE RIGHTS

This invention was made with government support under grant number CA042368 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 15, 2021 is named 52095-559N01US_ST25.txt and is 29,910 bytes in size

BACKGROUND OF THE INVENTION

An estimated 1,685,210 new cases of cancer are diagnosed in the United States annually, and 595,690 people will die each year from the disease. In the last decade, it has become increasingly clear that mobilization of the patient's immune system greatly aids in the treatment of many cancer types, including breast cancer. Unfortunately, tumor cells make "immune checkpoint blockade" molecules, such as programmed death-ligand 1 (PD-L1), which serve as signals to "turn off" killer T cells, which would otherwise kill the tumor cells. Direct inhibition of the "immune checkpoint inhibitor," PD-L1, has limitations in the treatment of breast cancer and other cancers. Thus, prior to the invention described herein, there was a pressing need to develop additional and combinatorial cancer treatments to improve tumor clearance in resistant or untreatable tumors.

SUMMARY OF THE INVENTION

The present invention is based upon the surprising discovery that inhibition of a palmitoyltransferase, DHHC3 (a protein with an Asp-His-His-Cys (SEQ ID NO: 7) motif; also known as Golgi-specific DHHC zinc finger protein (GODZ)), results in decreased expression of programmed death-ligand 1 (PD-L1; also known as cluster of differentiation 247 (CD247)), thereby enabling killer T cells to better attack cancer cells, e.g., breast cancer cells or prostate cancer cells. Specifically, as described herein, DHHC3 inhibition in breast and prostate tumor cells reduces growth and metastasis of tumors. More specifically, the protein acyltransferase, DHHC3, regulates breast tumor growth, oxidative stress, and senescence. Prior to the invention described herein, there was no link between DHHC3 (or any of the other 23 mammalian DHHC enzymes) to oxidative stress, cell senescence, or regulation of innate and adaptive immunity.

Methods of inhibiting expression or activity of programmed death-ligand 1 (PD-L1) in a cell of a subject, e.g., a human subject, in need thereof are carried out by administering to the subject an effective amount of a palmitoyltransferase inhibitor, thereby inhibiting the expression or activity of PD-L1 in the subject. For example, the palmitoyltransferase comprises an Asp-His-His-Cys (SEQ ID NO: 7) motif (DHHC)-type protein. Exemplary DHHC-type proteins include DHHC3, DHHC5, DHHC7, and DHHC17. For example, the DHHC-type protein comprises DHHC3.

The palmitoyltransferase inhibitor decreases DHHC3-dependent palmitoylation of chemokine-like factor (CKLF)-like MARVEL transmembrane domain containing family member 6 (CMTM6). For example, the palmitoyltransferase inhibitor decreases DHHC3-dependent palmitoylation of CMTM6 at an amino acid selected from the group consisting of C90, C76, C65, C52, and C55.

In some cases, the subject has been diagnosed with cancer or is at risk of developing cancer. For example, the cancer is breast carcinoma, thyroid carcinoma, skin cutaneous melanoma, uterine corpus endometrial carcinoma, sarcoma, bladder urothelial carcinoma, papillary thyroid carcinoma, colon cancer, or prostate cancer. Exemplary breast cancers include ductal carcinoma in situ, invasive ductal carcinoma, triple negative breast cancer, inflammatory breast cancer, metastatic breast cancer, medullary carcinoma, tubular carcinoma, mucinous carcinoma, human epidermal growth factor receptor 2 (HER2)+ breast cancer, and estrogen receptor (ER)+ breast cancer.

Preferably, the palmitoyltransferase inhibitor, e.g., the DHHC3 inhibitor, inhibits tumor growth and/or tumor metastasis, e.g., lung metastasis, of a tumor in the subject. For example, tumor growth or metastasis is inhibited by 5%, 10%, 15%, 20%, 25%, 30%, 40%, 45%, 50%, 55%, 60%, 65%, 70%, 75%, 80%, 85%, 90%, 95%, or 100%.

Suitable modes of administration of the palmitoyltransferase inhibitor include oral administration, intramuscular administration, subcutaneous administration, and intravenous administration.

For example, the palmitoyltransferase inhibitor comprises a small molecule inhibitor, ribonucleic acid interference (RNAi), an antibody, an antibody fragment, an antibody drug conjugate, an aptamer, a chimeric antigen receptor (CAR), or any combination thereof.

In one aspect, the palmitoyltransferase inhibitor, e.g., the DHHC protein inhibitor, comprises 1-Benzyl-4-(5-chloro-2-nitro-benzyl)-piperazine; II-Methyl-4-(4-nitro-benzyl)-1,2,3,3a,4,5,6,7-octahydro-[1,4]diazepino[3,2,1-jk]carbanzole; {2-[2-(4-Chloro-phenyl)-1,3a,8-triaza-cyclopenta[a]inden-1-yl]ethyl}-diethyl-amine; 2-(2-Hydroxy-5-nitro-benzylidene)-benzo[b]thiophen-3-one; or 2 Bromopalmitate.

In one aspect, inhibiting the DHHC-type palmitoyltransferase, e.g., DHHC3, increases clearance of senescent tumor cells by the innate immune system of the subject. Additionally, inhibiting the DHHC-type palmitoyltransferase, e.g., DHHC3, increases the adaptive immunity of the subject.

For example, the PD-L1 activity comprises reducing the infiltration or activity of tumor-specific cytotoxic lymphocytes (CTLs). Accordingly, administration of the palmitoyltransferase inhibitor, e.g., DHHC3 inhibitor, results in increased infiltration or activity of tumor-specific CTLs as compared to infiltration of activity of tumor-specific CTLs in the absence of the palmitoyltransferase inhibitor. For example, administration of the palmitoyltransferase inhibitor results in a 5%, 10%, 15%, 20%, 25%, 30%, 40%, 45%, 50%, 55%, 60%, 65%, 70%, 75%, 80%, 85%, 90%, 95%, or 100% increase in infiltration or activity of tumor-specific cytotoxic lymphocytes (CTLs).

Additionally, infiltration or activity of natural killer (NK) cells and/or M1-like macrophages is increased as compared to infiltration or activity of NK cells and/or M1-like macrophages in the absence of the palmitoyltransferase inhibitor, thereby resulting in increased tumor clearance. For example, administration of the palmitoyltransferase inhibitor results in a 5%, 10%, 15%, 20%, 25%, 30%, 40%, 45%, 50%, 55%, 60%, 65%, 70%, 75%, 80%, 85%, 90%, 95%, or 100% increase in infiltration or activity of NK cells and/or M1-like macrophages.

In some cases, the methods further comprise administering a PD-L1 inhibitor prior to, simultaneously with, or after administration of the palmitoyltransferase inhibitor, e.g., DHHC3 inhibitor, wherein the PD-L1 inhibitor comprises atezolizumab, avelumab, or durvalumab.

Alternatively, or in addition, the methods further comprise administering a chemotherapeutic agent prior to, simultaneously with, or after administration of the palmitoyltransferase inhibitor, wherein the chemotherapeutic agent is selected from the group consisting of camptothecin, 5-fluorouracil, cyclophosphamide, methotrexate, doxorubicin, paclitaxel, docetaxel, and epirubicin.

Preferably, the palmitoyltransferase inhibitor, e.g., DHHC3 inhibitor, increases oxidative stress and/or tumor cellular senescence as compared to oxidative stress and/or tumor cellular senescence in the absence of the palmitoyltransferase inhibitor.

Also provided are methods of inhibiting intrinsic or acquired resistance to chemotherapy or increasing the potency of chemotherapy in a cell of a subject in need thereof comprising administering to the subject an effective amount of a palmitoyltransferase inhibitor, wherein the palmitoyltransferase comprises DHHC3, thereby inhibiting intrinsic or acquired resistance to chemotherapy or increasing the potency of chemotherapy in a cell of a subject.

In some cases, the methods further comprise administering an oxidative stress-dependent anti-cancer agent selected from the group consisting of camptothecin and 5-Fluorouracil.

In another case, the methods further comprise administering a chemotherapeutic agent that increases oxidative stress. Because inhibition of DCCH3 reduces protection from oxidative stress, DHHC3 inhibition increases sensitivity to chemotherapeutic agents. For example, the chemotherapeutic agent is selected from the group consisting of cyclophosphamide, methotrexate, doxorubicin, paclitaxel, docetaxel, and epirubicin. Suitable chemotherapeutic agents useful in the methods described herein include actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, Vemurafenib, vinblastine, vincristine, vindesine, and vinorelbine.

Methods of inhibiting a tumor or enhancing anti-tumor immunity in a subject are carried out by administering to the subject an inhibitor of a DHHC-type palmitoyltransferase, e.g., DHHC3. In some cases, the methods further comprise administering a PD-L1 inhibitor, wherein the PD-L1 inhibitor comprises atezolizumab, avelumab, or durvalumab. Alternatively, or in addition, the methods further comprise administering a chemotherapeutic agent selected from the group consisting of camptothecin, 5-fluorouracil, cyclophosphamide, methotrexate, doxorubicin, paclitaxel, docetaxel, and epirubicin.

Also provided is a method of determining the prognosis of a subject that has been diagnosed with breast cancer or prostate cancer comprising obtaining a test sample from a subject with breast cancer or prostate cancer; determining an expression level of palmitoyltransferase, DHHC3, in the test sample; comparing the expression level of palmitoyltransferase, DHHC3, in the test sample with the expression level of palmitoyltransferase, DHHC3, in a reference sample; and determining that survival of the subject is shortened if the expression level of the palmitoyltransferase, DHHC3, in the test sample is higher as compared to the level of palmitoyltransferase, DHHC3, in the reference sample.

In one aspect, the methods further comprise determining that the breast cancer or prostate cancer is likely to metastasize if the expression level of the palmitoyltransferase, DHHC3, in the test sample is higher as compared to the level of palmitoyltransferase, DHHC3, in the reference sample.

Also provided are methods of increasing the immunogenicity of a tumor cell or increasing the effectiveness of an effector T cell in a subject comprising administering to the subject an effective amount of a palmitoyltransferase inhibitor, e.g., a DHHC3 inhibitor, thereby increasing the immunogenicity of a tumor cell or increasing the effectiveness of an effector T cell in a subject. For example, the effector T cell comprises a cluster of differentiation 4 (CD4+) T cell or a CD8+ T cell.

In some cases, the inhibitor of a DHHC-type palmitoyltransferase, e.g., DHHC3, decreases DHHC3-dependent palmitoylation of endoplasmic reticulum-Golgi intermediate compartment protein 3 (ERGIC3). In one aspect, the expression or activity of thioredoxin-interacting protein (TXNIP) is increased.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

The phrase "aberrant expression" is used to refer to an expression level that deviates from (i.e., an increased or decreased expression level) the normal reference expression level of the gene.

By "agent" is meant any small compound, antibody, nucleic acid molecule, or polypeptide, or fragments thereof.

By "alteration" is meant a change (increase or decrease) in the expression levels or activity of a gene or polypeptide as detected by standard art-known methods such as those described herein. As used herein, an alteration includes at least a 1% change in expression levels, e.g., at least a 2%, 3%, 4%, 5%, 6%, 7%, 8%, 9%/c, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence, or amount of the agent (e.g., a nucleic acid molecule, for example deoxyribonucleic acid (DNA) or ribonucleic acid (RNA)) to be detected.

By "detectable label" is meant a composition that when linked (e.g., joined—directly or indirectly) to a molecule of interest renders the latter detectable, via, for example, spectroscopic, photochemical, biochemical, immunochemical, or chemical means. Direct labeling can occur through bonds or interactions that link the label to the molecule, and indirect labeling can occur through the use of a linker or bridging moiety which is either directly or indirectly labeled. Bridging moieties may amplify a detectable signal. For example, useful labels may include radioactive isotopes, magnetic beads, metallic beads, colloidal particles, fluorescent labeling compounds, electron-dense reagents, enzymes (for example, as commonly used in an enzyme-linked immunosorbent assay (ELISA)), biotin, digoxigenin, or haptens. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthaldehyde and fluorescamine. The molecule can also be detectably labeled using fluorescence emitting metals such as 152 Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

A "detection step" may use any of a variety of known methods to detect the presence of nucleic acid (e.g., methylated DNA) or polypeptide. The types of detection methods in which probes can be used include Western blots, Southern blots, dot or slot blots, and Northern blots.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound (s) used to practice the present invention for therapeutic treatment of a disease varies depending upon the manner of administration, the age, body weight, and general health of the subject. Ultimately, the attending physician or veterinarian decides the appropriate amount and dosage regimen. Such amount is referred to as an "effective" amount.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic complementary deoxyribonucleic acid (cDNA), a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by high performance liquid chromatography (HPLC) analysis.

By "marker" is meant any protein or polynucleotide having an alteration in expression level or activity that is associated with a disease or disorder.

By "modulate" is meant alter (increase or decrease). Such alterations are detected by standard art-known methods such as those described herein.

The term, "normal amount" refers to a normal amount of a complex in an individual known not to be diagnosed with disease. The amount of the molecule can be measured in a test sample and compared to the "normal control level," utilizing techniques such as reference limits, discrimination limits, or risk defining thresholds to define cutoff points and abnormal values. The "normal control level" means the level of one or more proteins (or nucleic acids) or combined protein indices (or combined nucleic acid indices) typically found in a subject known not to be suffering from disease. Such normal control levels and cutoff points may vary based on whether a molecule is used alone or in a formula combining other proteins into an index.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but typically exhibit substantial identity, e.g., at least 80%, at least 85%, at least 90%, at least 95%, or at least 99% identity. Polynucleotides having "substantial identity" to an endogenous sequence are typically capable of hybridizing with at least one strand of a double-stranded nucleic acid molecule.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

The term "sample" as used herein refers to a biological sample obtained for the purpose of evaluation in vitro. With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, at least 70%, at least 80%, at least 85%, at least 90%, at least 95%, or at least 99% identical at the amino acid level or nucleic acid to the sequence used for comparison.

The term "subject" as used herein includes all members of the animal kingdom prone to suffering from the indicated disorder. In some aspects, the subject is a mammal, and in some aspects, the subject is a human. The methods are also applicable to companion animals such as dogs and cats as well as livestock such as cows, horses, sheep, goats, pigs, and other domesticated and wild animals.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It is appreciated that, although not precluded, treating a disorder or condition does not require that the disorder, condition or symptoms associated therewith be completely eliminated.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in the methods described herein. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and National Center for Biotechnology Information (NCBI) submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a Kaplan-Meier overall survival plot comparing breast invasive carcinoma patients with elevated or not elevated ZDHHC3 gene expression. Elevated expression is defined as mRNA expression Z score≥2.0 (data from cBioPortal analysis of TCGA data (Cerami et al., 2012 Cancer Discov, 2:401-4; Gao et al., 2013 Sci Signal, 6:11)). FIG. 1B is a series of photomicrographs, wherein immunohistochemistry (IHC) expression analysis for DHHC3 was performed on paraffin-embedded normal, malignant and metastatic human breast tumor tissue sections (Scale bar 100 μM). FIG. 1C is a bar chart showing quantitation of the DHHC3 expression, i.e., % DHCC3 staining, wherein human tissue microarray samples included 42 "others" (normal breast tissue, cancer adjacent to normal breast, inflamed tissue, hyperplastic and benign tissue), 104 "malignant" and 31 "metastatic". The percent of each group expressing high (score=2+, 3+; black bars) or low (score=0, 1+; white bars) DHHC3 is indicated. FIG. 1D is a line graph and a bar chart, wherein MDA-MB-231 cells±ZDHHC3 ablation were injected orthotopically into female nude mice (5 mice per group with 2 tumors/mouse), and tumor volumes (left panel) and weights (at 35 days, right panel) were determined. FIG. 1E is a series of photomicrographs and a bar chart showing an assessment of metastatic foci in lung sections via hematoxylin and eosin (H&E) staining in severe combined immunodeficiency (SCID) beige mice injected with MDA-MB-231 cells±ZDHHC3. Specifically, MDA-MB-231 cells±ZDHHC3 ablation were injected into tail veins of SCID beige mice (3 mice per group). After 30 days, metastatic foci (arrows) in lungs were assessed by H&E staining (bar, 200 μm) and colony diameters were quantitated (N=77 control, 86 D3 knockdown colonies).

FIG. 2A is a flow cytometry plot and a bar chart, wherein MDA-MB-231 cells±stable ZDHHC3 ablation were loaded with CellROX dye and oxidative stress was assessed using flow cytometry. The lower panel is a bar chart that shows mean percent of cells with staining elevated above cut-off line (±S.D.; N=3). FIG. 2B is a series of photographs of immunoblots, wherein MDA-MB-231 cells±ZDHHC3 ablation with small interfering ribonucleic acid (siRNA) or short hairpin ribonucleic acid (shRNA) were lysed, focal adhesion kinase (FAK) and epidermal growth factor receptor (EGFR) proteins were immunoprecipitated, and resulting samples were blotted with tyrosine phosphorylation antibody, 4G10. Also, cell lysates were directly blotted with anti-phosphotyrosine-signal transducer and activator of transcription 3 (STAT3) and anti-phosphoserine extracellular signal-regulated kinases (ERK) antibodies. Control panels show total FAK, EGFR, STAT3 and ERK proteins. Numbers at the bottom of western blots indicate levels of p-FAK and p-STAT3 normalized against total FAK and STAT3 levels, respectively. Bottom panels show DHHC3 levels±siRNA and shRNA ablation. The images shown are representative of each experiment performed multiple times. FIG. 2C is a series of photographs of immunoblots showing the effects of oxidative stress inhibitors (NAC, α-LA and atorvastatin) on FAK phosphorylation (p-FAK) and monocyte chemoattractant protein-1 (MCP-1) secretion in/from control and ZDHHC3 ablated MDA-MB-231 cells.

FIG. 3A is a flow cytometry graph, wherein MDA-MB-231 cells±stable ZDHHC3 ablation, were loaded with senescence indicator dye C12FDG, which was measured using flow cytometry. Mean percent elevated staining (±S.D.; N=3) is shown. FIG. 3B is a bar chart, wherein MDA-MB-231 cells, f stable ZDHHC3 ablation, were cultured for 30 hrs, and cell supernatants were analyzed. Results for 7 chemokines are shown (mean±S.D., N=2 replicates). 24 other chemokines were not detected and/or not different. FIG. 3C is a photograph of an immunoblot, wherein enhanced secretion of MCP-A chemokine from ZDHHC3-ablated MDA-MB-231 cells is validated by western blotting (representative of multiple experiments), with vascular endothelial growth factor (VEGF) secretion used as a control. FIG. 3D is a photograph of an immunoblot, wherein enhanced MCP-1 secretion was also assessed in supernatants from cells obtained from xenograft tumors. C/1L and C/4R cell samples are cultured from control xenograft tumors; D3/1R, D3/3R and D3/5R samples are from ZDHHC3-ablated tumor-derived cells. Numbers at the bottom represent MCP-1 levels normalized against VEGF levels.

FIG. 4A is a series of photomicrographs and a bar graph, wherein immunohistochemistry for iNOS (marker for anti-tumor "M1-like" macrophages) is shown on representative paraffin sections of control and ZDHHC3-ablated orthotopic tumors (at 35 days, as in FIG. 1D, FIG. 9A). The bar graph shows percent iNOS positive area from multiple sections (3 tumors per group, quantitated using Image J software; mean±S.D). FIG. 4B is a bar graph, wherein expression of pan-macrophage marker CD68 was assessed, using reverse transcription polymerase chain reaction (RT-PCR), from 2 tumor sections each from control and DHHC3 ablated xenografts. FIG. 4C and FIG. 4D is a series of bar graphs, wherein quantitative polymerase chain reaction (q-PCR) was used to assess expression of Arginase 1 (marker for pro-tumor "M2-like" macrophages) and granzyme F (secreted by NK cells). q-PCR results are shown as mean+S.D. N=6 in each group. FIG. 4E is a bar graph, wherein RT-PCR was used to assess expression of NK cell marker NKTR in control and ZDHHC3 ablated xenograft tumors. Shown is mean±S.D; N=2 tumors per group).

FIG. 5A is a series of flow cytometry graphs and a bar graph showing oxidative stress via CellRox dye. FIG. 5B is a series of photographs of an immunoblot showing tyrosine phosphorylation of STAT3 and FAK proteins. FIG. 5C is a bar graph showing senescence via C12FDG assay. FIG. 5D is a photograph of an immunoblot showing secreted MCP-1 chemokine. Values at the bottom of western blots are normalized levels of p-STAT3, p-FAK and MCP-1 proteins. Data shown are representative of multiple experiments, and bar graphs in FIG. 5A and FIG. 5C show mean+SD; N=3.

FIG. 6A is a photograph of an immunoblot showing MCP-1 secretion. FIG. 6B is a photograph of an immunoblot showing FAK protein tyrosine phosphorylation (p-FAK). FIG. 6C is a photograph of an immunoblot showing TXNIP expression. Blots shown are representative of multiple experiments, and values at the bottom represent normalized protein levels. FIG. 6D is a series of line graphs, wherein, ectopic xenograft growth in female nude mice (4 mice in each group with 2 tumors/mouse) was carried out simultaneously for control and ZDHHC3 ablated cells (upper graph) and reconstituted ($D3^R$, $D3^{R+/S}$) cells (lower graph).

FIG. 7A is a photograph of an immunoblot after MDA-MB-231 cells were transfected with control (C), DHHC3 (D3), and ERGIC3 (E3) siRNAs (60 hr), expression of TXNIP, ERGIC3 and DHHC3 proteins were assessed by western blotting. FIG. 7B is a photograph of an immunoblot after reduction and alkylation steps (see Methods), protein lysates from control (C) and DHHC3 (D3) siRNA ablated MDA-MB-231 cells were treated with hydroxylamine (HA) to cleave thioester bonds from palmitoylated proteins. Newly exposed SH moieties (which should be less abundant in putative substrates for DHHC3) were biotinylated. After immunoprecipitation using neutrAvidin agarose beads, and transfer to nylon membrane, blotting with ERGIC3 antibody was carried out. Numbers indicate relative amounts in "D3" vs "C" lanes. FIG. 7C is a photomicrograph showing distribution of ERGIC3 in control and DHHC3 ablated cells was analyzed in permeabilized MDA-MB-231 cells by immunohistochemical staining using anti-ERGIC3 antibody (green). Nuclei are stained with DAPI (blue). Results similar to those in panels FIG. 7A, FIG. 7B, and FIG. 7C were obtained in multiple independent experiments.

FIG. 8A is a bar chart showing immunohistochemical analysis of DHHC3 in human breast tumor tissue sections from indicated subtypes of malignant cancer. FIG. 8B is a bar chart showing immunohistochemical analysis of DHHC3 in human breast tumor tissue sections from indicated subtypes of metastatic cancer. White bars represent low staining (score=0, +1) and black bars represent high staining (score=+2, +3). Values for N are indicated at the top of each bar. FIG. 8C is a series of photographs of representative tumors from the orthotopic injection experiment (35 days; data used in FIG. 1D). FIG. 8D is a line graph and a bar chart showing results from an s.c. (ectopic) injection experiment (5 mice in each group with 2 tumors/mouse). Tumor volumes (left panel) and weights (at 35 days, right panel) were determined. FIG. 8E is a line graph showing xenograft tumor growth of MDA-MB-231 cells ablated using control shRNA or DHHC3 shRNA #18 (7 tumors/group). (This shRNA is distinct from that used in FIG. 1D, FIG. 8D). FIG. 8F is a photograph and a bar chart showing mean numbers of lung colonies, visualized using India ink (bar, 5 mm), were determined (±S.D.; N=3 lungs).

FIG. 9A is a photograph showing western blot analysis of DHHC3 protein in MDA-MB-231 cells after stable ablation by "#10" D3 shRNA (used in FIG. 1D, FIG. 8C). FIG. 9B is a series of photographs showing immunohistochemical staining of DHHC3 in paraffin embedded tumor xenograft sections (upper panels) and H&E staining of the same samples (lower panels). FIG. 9C is a series of photographs showing immunohistochemical staining of CD31 in paraffin embedded sections from control and ZDHHC3 ablated xenograft tumors. FIG. 9D is a histogram, wherein proliferation of MDA-MB-231 cells±ZDHHC3 shRNA ablation was assessed using a cell counter (Countess 11, Invitrogen, Carlsbad, Calif.) and is presented as mean±S.D. for N=3. FIG. 9E is a series of photographs and a bar chart showing soft agar 3D growth, measured as described (TV Kolesnikova, Neoplasia, 2009, vol 11, p77), and assessed after 14 days, is shown in representative panels (top) and quantitated (bottom), as mean±S.D. for N=2, based on three replicates in each group. FIG. 9F is a series of photographs and a bar chart, wherein MDA-MB-231 cells, ±ZDHHC3 siRNA ablation, were added to the top of Matrigel-coated transwell chambers. After 24 h, cells invaded in response to complete medium (in lower chamber), were counted on the underside of membranes (representative panels; top) and quantitated (mean±S.D.; N=3; scale bar=100 μm).

FIG. 10A is a bar graph showing the effects of ZDHHC3 ablation on oxidative stress in MCF-7 cells assessed using CellRox assay. Values plotted are mean±S.D.; N=3. FIG. 10B is a bar graph showing that partial reversal of oxidative stress, in ZDHHC3 ablated MDA-MB-231 cells, upon treatment with oxidative stress inhibitor N-acetyl cysteine. FIG. 10C is a series of photographs of immunoblots showing the effects of ZDHHC3 ablation on STAT3 tyrosine phosphorylation in MCF-7 and ZR-75 breast cancer cells. FIG. 10D is a series of photographs of immunoblots showing that FAK dephosphorylation in control and ZDHHC3 ablated MDA-MB-231 cells, upon cell suspension for indicated times. FAK protein was immunoprecipitated and then blotted with anti-tyrosine antibody 4G10. Numbers represent percent tyrosine phosphorylation relative to total FAK at each time point. FIG. 10E is a scatter plot showing increased senescence (assessed using C12FDG) due to ZDHHC3 ablation in MCF-7 breast cancer cells. Values plotted are mean+S.D.; N=3.

FIG. 11A is a photograph of an immunoblot showing that expression of iNOS consistent with THP1 cell differentiation into M1-like macrophages. FIG. 11B is a bar graph showing that migration in vitro of model M1 macrophages towards conditioned media from control and ZDHHC3 ablated MDA-MB-231 cells. The values plotted are mean t S.D.; N=2, based on two replicates in each group. FIG. 11C is a photograph showing immunoblotting of MCP-1 and IL-8 chemokines in conditioned media from control and ZDHHC3 ablated MDA-MB-231 cells. FIG. 11D is a series of photographs of immunoblots showing changes in TXNIP protein levels (upper panels) resulting from ZDHHC3 ablation (lower panels) in five different human breast cancer cell lines, representing different subtypes. These blots are representative of multiple experiments. FIG. 11E is a series of photographs of immunoblots showing TXNIP protein (upper panel) in xenograft tumor lysates, ±ZDHHC3 ablation (confirmed in lower panel).

FIG. 12A is a schematic diagram of reconstitution vector for unmutated and mutated DHHC3 (at "DHHC" site). U6=promoter upstream of DHHC3 shRNA; hPGK=promoter upstream of DHHC3 cDNA; 2A=linker peptide; GFP=Green Fluorescent Protein tag at C-terminus of DHHC3. FIG. 12B is a flow cytometry graph showing levels of DHHC3-GFP present in MDA-MB-231 cells as assessed by flow cytometry. FIG. 12C is a schematic showing ablation of intratumor DHHC3 (Step 1) leads to diminished palmitoylation of ERGIC3 and other substrates (Step 2). Disruption of ERGIC3 causes upregulation of oxidative stress inducer TXNIP (Step 3). Diminished palmitoylation of other substrates (including several antioxidant proteins), together with TXNIP upregulation, leads to oxidative stress (Step 4), which then triggers senescence (Step 5), and a SASP (senescence associated secretory protein) response leads to tumor clearance by innate immune cells (Step 6), resulting in reduced tumor growth (Step 7).

FIG. 13A is a schematic showing that DHHC3 ablation leads to loss of CMTM6 palmitoylation, diminished PD-L1 expression, and amplified anti-tumor T cell adaptive immunity. FIG. 13B is a schematic showing that DHHC3 ablation also leads to diminished palmitoylation of ERGIC3 and likely other substrates, resulting in elevated oxidative stress and ER stress, which triggers premature senescence and tumor clearance by innate immune cells (Sharma et al., 2017 Cancer Research, 77(24): 6880-6890; Panieri et al., 2013 Free Radic Biol Med, 57:176-87; Perez-Mancera et al., 2014 Nat Rev Cancer, 14:547-58).

FIG. 14A is a photograph of an immunoblot, wherein after reduction and alkylation steps (see, Sharma et al., 2017 Cancer Research, 77(24): 6880-6890), protein lysates from control (C) and DHHC3 (D3) siRNA ablated MDA-MB-231 cells were treated with hydroxylamine (HA) to cleave thioester bonds from palmitoylated proteins. Newly exposed SH moieties (which should be less abundant in putative substrates for DHHC3) were biotinylated. Proteins in total cell lysate (lanes 1, 2), or from immunoprecipitation using neutrAvidin agarose beads (lanes 3, 4), were transferred to nylon membrane and blotted with CMTM6 antibody. FIG. 14B is a photograph of an immunoblot, wherein lysates from MDA-MB-231 cells (±DHHC3 ablation) were blotted for PD-L1 or HSP-70 (loading control) proteins. FIG. 14C is a photograph of an immunoblot, wherein MDA-MB-231 cells were ablated (D3) or reconstituted with wild type (D3R) or palmitoylation-defective mutant (D3R+C/S) DHHC3 as described in (Sharma et al., 2017 Cancer Research, 77(24): 6880-6890), and then lysed and blotted for PD-L1.

FIG. 17B, left) and ER+MCF7 cells (FIG. 17A, right; FIG. 17B, right) using shRNA or siRNA as indicated. Cells were incubated with either Cell-ROX® Deep Red (FIG. 17A; to detect ROS) or C12FDG (FIG. 17B; to detect β-gal) and cell staining (% above control) was determined by flow cytometry. Different shRNA and siRNA targeting sequences yielded similar results (P values; Students t test).

FIG. 18A is a photomicrograph, wherein immunohistochemistry for DHHC3 was done on paraffin embedded normal, malignant and metastatic human breast tumor tissue sections (Scale bar 100 μM). FIG. 18B is a bar chart, wherein human tissue microarray samples included 42 "others" (normal breast tissue, cancer adjacent to normal breast, inflamed tissue, hyperplastic and benign tissue), 104 "malignant" and 31 "metastatic". The percent of each group expressing high (score=2+, 3+; black bars) or low (score=0, 1+; white bars) DHHC3 is indicated. FIG. 18C is a Kaplan-Meier overall survival plot comparing breast invasive carcinoma patients with elevated or not elevated ZDHHC3 gene expression. Elevated expression equals mRNA expression Z score≥2.0 (data from cBioPortal analysis of TCGA data (Gao et al., 2013 Sci Signal, 6:11; Cerami et al., 2012 Cancer Discov, 2:4014).

FIG. 23A is an immunoblot showing that CMTM6 C90 is needed for DHHC3-mediated palmitoylation. FIG. 23B is a photomicrograph depicting peroxiredoxin-4 (PRDX4) subcellular distribution where MDA-MB-231 cells±DHHC3 ablation were cultured on slides. FIG. 23C is a photomicrograph depicting NPC1 subcellular distribution where MDA-MB-231 cells±DHHC3 ablation were cultured on slides.

DETAILED DESCRIPTION OF THE INVENTION

Figure 1A:
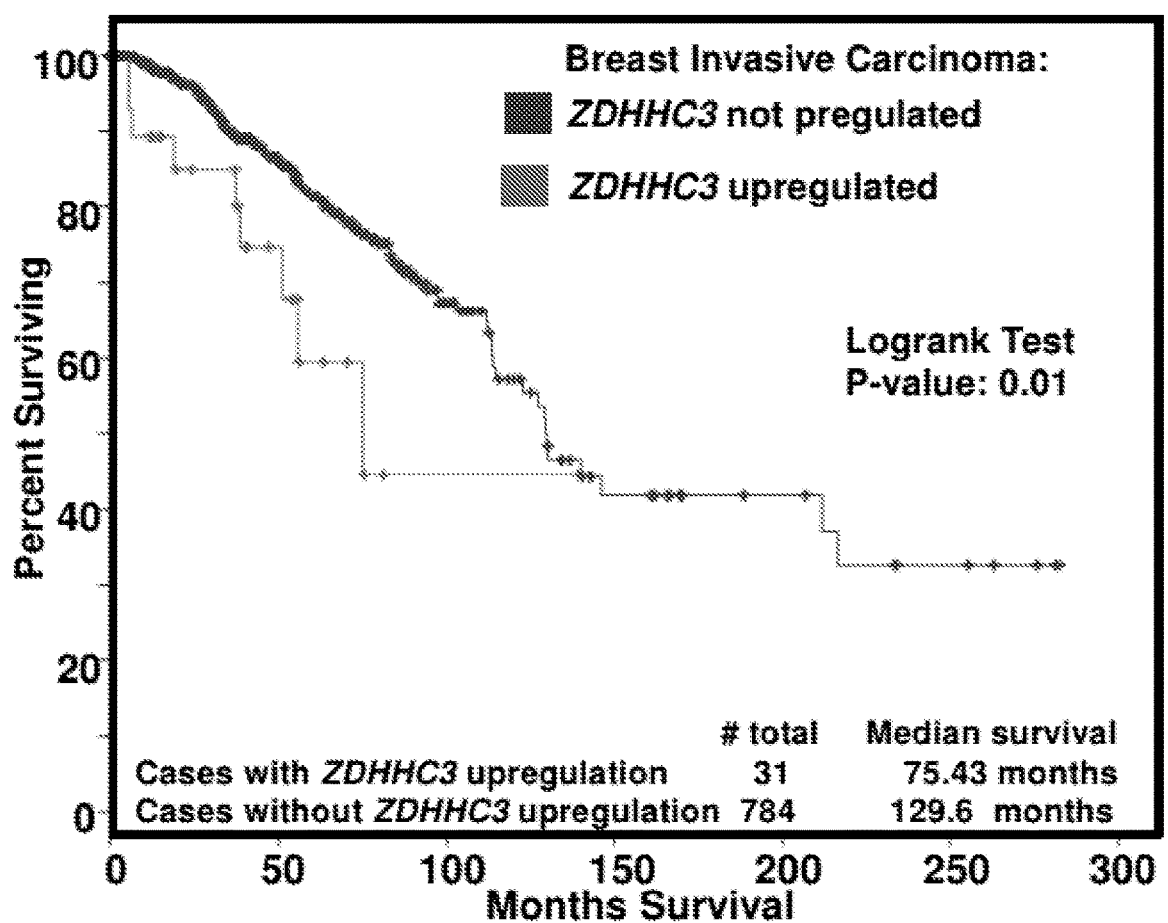
FIG. 1A-FIG. 1E is a series of line graphs, bar charts, and photomicrographs showing DHHC3 expression, patient survival, and breast carcinoma growth.

The present invention is based upon the surprising discovery that inhibition of a palmitoyltransferase, DHHC3 (a protein with an Asp-His-His-Cys (SEQ ID NO: 7) motif), results in decreased expression of programmed death-ligand 1 (PD-L1), thereby enabling killer T cells to better attack cancer cells, e.g., breast cancer cells.

As described in detail below, the appearance of PD-L1 on tumor cells is dependent upon the expression of a cell surface protein, chemokine-like factor Superfamily Member 6 (CMTM6; also known as chemokine-like factor (CKLF)-like MARVEL transmembrane domain containing family member 6). However, prior to the invention described herein, little was known regarding the properties of CMTM6, including the factors that regulate its expression and function. As described herein, an enzyme, called DHHC3, is required to add a single molecule of lipid/fatty acid to modify the structure of CMTM6. When DHHC3 is removed from breast cancer cells, CMTM6 is no longer modified with the fatty acid, and consequently can no longer support the appearance of PD-L1 on breast cancer cells. Thus, as described in detail below, removal of DHHC3, which disrupts CMTM6, and causes loss of PD-L1, unleashes an enhanced anti-tumor response by killer T cells. Also, removal of DHHC3 not only activates adaptive immunity by diminishing PD-L1, but it also activates clearance of tumor cells by the innate immune system.

As described herein, DHHC3 inhibition in breast and prostate tumor cells reduces growth and metastasis of tumors. Specifically, described herein is the inhibition of DHHC3 for cancer treatment through enhancing tumor cell clearance. The results presented herein provide an indirect way to regulate PD-L1 through ablation of an enzyme, DHHC3, which reduces CMTM6 palmitoylation, and makes it unable to support expression of PD-L1. Also described herein is the utilization of DHHC3 expression as an indicator of patient survival in breast cancer. As described herein, elevated DHHC3 expression is a biomarker for poor patient outcome in several cancers.

As described in detail below, DHHC-type protein acyltransferases regulate the localization, stability and/or activity of their substrates. Experiments described herein show that the protein palmitoyltransferase, DHHC3, is upregulated in malignant and metastatic human breast cancer. As described in the Examples below, elevated expression of DHHC3 correlated with diminished patient survival in breast cancer and six other human cancer types. Moreover, ZDHHC3 ablation in human MDA-MB-231 mammary tumor cell xenografts reduced the sizes of both the primary tumor and metastatic lung colonies. Gene array data and fluorescence dye assays documented increased oxidative stress and senescence in ZDHHC3-ablated cells. As described in the Examples below, ZDHHC3-ablated tumors also showed enhanced recruitment of innate immune cells (anti-tumor macrophages, natural killer cells) associated with clearance of senescent tumors. These anti-tumor effects were reversed upon reconstitution with wildtype, but not enzyme-active site-deficient DHHC3. Finally, as described herein, concomitant ablation of the upregulated oxidative stress protein TXNIP substantially negated the effects of ZDHHC3 depletion on oxidative stress and senescence. Diminished DHHC3-dependent palmitoylation of ERGIC3 protein likely played a key role in TXNIP upregulation. In conclusion, the results presented herein demonstrate that DHHC3-mediated protein palmitoylation supports breast tumor growth by modulating cellular oxidative stress and senescence.

Post-translational palmitoylation affects protein localization, stability, molecular interactions and functions (Mitchell et al., 2006 J Lipid Res, 47:1118-27; Linder M E and Deschenes, R J. 2007 Nat Rev Mol Cell Biol, 8:74-84). Protein palmitoylation is typically mediated by protein acyl transferases (PATs), containing conserved DHHC (Asp-His-His-Cys (SEQ ID NO: 7)) motifs needed for enzymatic activity (Mitchell et al., 2006 J Lipid Res, 47:1118-27; Politis et al., 2005 J Biol Chem, 280:10156-63). Among 23 mammalian DHHC enzymes, only DHHC17 (HIP-14) and DHHC5 were so far suggested to affect tumor xenograft growth (Ducker et al., 2004 Oncogene, 23:9230-7; Tian et al., 2015 Mol Cancer Res, 13:784-94), but mechanistic details were lacking prior to the invention described herein. Golgi-resident enzyme DHHC3 (GODZ), is upregulated in breast, prostate and colon carcinomas (Lukk et al., 2010 Nat Biotechnol, 28:322-4), but prior to the invention described herein, a possible role in cancer had not been previously addressed.

Moderate oxidative stress levels can promote early cancer stages, but excess levels limit tumor growth (Trachootham et al., 2009 Nat Rev Drug Discov, 8:579-91, Gorrini et al., 2013 Nat Rev Drug Discov, 12:931-47). One major consequence of tumor cell oxidative stress is senescence (Hwang et al., 2013 Free Radic Biol Med, 61:95-110; Mahmood et al., 2013 Antioxid Redox Signal, 19:1266-303), leading to clearance by the innate immune system (Perez-Mancera et al., 2014 Nat Rev Cancer, 14:547-58; Ben-Porath I and Weinberg R A, 2005 Int J Biochem Cell Biol, 37:961-76). The results presented herein show DHHC3 upregulation in human breast cancer, elevated ZDHHC3 expression correlating with reduced survival in multiple human cancers, and DHHC3 actively supporting breast tumor xenograft growth. Furthermore, as described in the Examples below, ZDHHC3-ablation upregulates tumor cell oxidative stress, senescence, and infiltration by innate immune cells, leading to diminished in vivo tumor growth.

Palmitoylation and DHHC

Protein acyltransferases (PATs) catalyze the addition of palmitate. Protein palmitoylation refers to the process of posttranslational attachment of long-chain fatty acids, e.g., palmitate, to residues, e.g., cysteine residues, in proteins, e.g., via a thioester linkage. The effects of protein palmitoylation are diverse and include effects on protein localization, trafficking, and stability. Because the bond between palmitic acid and protein is often a thioester bond, palmitoylation is potentially reversible. A family of integral membrane enzymes that typically reside on the cytoplasmic/luminal face of cell membranes mediate palmitate addition to substrate proteins that can span cell membranes or reside within the cytoplasm. Included in this family of proteins are those that share a conserved DHHC (Asp-His-His-Cys (SEQ ID NO: 7)) cysteine-rich domain.

DHHC (a protein with a conserved Asp-His-His-Cys (SEQ ID NO: 7) motif in its sequence; also known as zinc finger DHHC domain-containing protein (ZDHHC) or Golgi-specific DHHC zinc finger protein (GODZ)) is a palmitoyltransferase. The DHHC domain is a protein domain that acts as an enzyme, which adds a palmitoyl chemical group to proteins to anchor them to cell membranes or to modify their distribution and/or functions within membranes. In mammals, 23 members of the DHHC family have been identified (see, e.g., Sharma C and Hemler M 2017, Oncoscience, 1-2, incorporated herein by reference). Protein acyltransferase activity is dependent upon the DHHC domain and mutation of the cysteine of the DHHC motif abolishes catalytic activity of the enzyme. Human proteins containing this DHHC domain include ZDHHC1, ZDHHC2, ZDHHC3, ZDHHC4, ZDHHC5, ZDHHC6, ZDHHC7, ZDHHC8, ZDHHC9, ZDHHC11, ZDHHC11B, ZDHHC12, ZDHHC13, ZDHHC14, ZDHHC15, ZDHHC16, ZDHHC17, ZDHHC18, ZDHHC19, ZDHHC20, ZDHHC21, ZDHHC22, ZDHHC23, and ZDHHC24.

Recently, five chemical classes of small molecules that inhibit cellular processes associated with palmitoylation were identified (Ducker et al., 2006 Mol Cancer Ther, 5: 1647-1659, incorporated herein by reference). These inhibitors include 1-Benzyl-4-(5-chloro-2-nitro-benzyl)-piperazine; 11-Methyl-4-(4-nitro-benzyl)-1,2,3,3a,4,5,6,7-octahydro-[1,4]diazepino[3,2,1-jk]carbanzole; {2-[2-(4-Chlorophenyl)-1,3a,8-triaza-cyclopenta[a]inden-1-yl]ethyl}-diethyl-amine; 2-(2-Hydroxy-5-nitro-benzylidene)-benzo[b]thiophen-3-one; and 2 Bromopalmitate. Of the 5 classes studied, 2-(2-hydroxy-5-nitro-benzylidene)-benzo[b]thiophen-3-one, and 2-bromopalmitate (2BP) inhibited the palmitoyltransferase activity of all DHHC proteins tested (Jennings et al., 2008 Journal of Lipid Research, 50: 233-242, incorporated herein by reference).

An exemplary human DHHC3 amino acid sequence is set forth below (SEQ ID NO: 1; GenBank Accession No: NP_001336309, Version NP_001336309.1, incorporated herein by reference):

```
  1  mmlipthhfr nierkpeylq pekcvpppyp gpvgtmwfir dgcgiacaiv twflvlyaef
 61  vvlfvmlips rdyvysiing ivfnllafla lashcramlt dpgavpkgna tkefieslql
121  kpgqvvykcp kccsikpdra hhcsvckrci rkmdhhcpwv nncvgennqk yfvlftmyia
181  lislhalimv gfhflhcfee dwtkcssfsp pttvillill cfegllflif tsvmfgtqvh
241  sictdetgie qlkkeerrwa kktkwmnmka vfghpfslgw aspfatpdqg kadpyqyvv
```

An exemplary human DHHC3 nucleic acid sequence is set forth below (SEQ ID NO: 2; GenBank Accession No: NM_001349380, Version NM_001349380.1, incorporated herein by reference):

```
  1  agcgcgtcat caacctgcgc ggcggccgct cctgcagccg cggccgccgc cactgccggg
 61  agagctcgat gggcttctcc tgcgcgccgc ccggtgtctg gccgagtcca gagagccgcg
121  gcgcctcgtt ccgaggagcc atcgccgaag cccgaggccg ggtcccgggt tggggactgc
181  aggggaaggc agcggcggcg gcggcgggag ccccaccggg gtctgggact ggggaactgc
241  ctccggcttc acgggcacc taaaaggaag acagcttgca gggttggact ttgccttcca
301  gggaaactga aagaggtgaa gccggaagga tttcctccct aatgaaggca cagatgccag
361  tatggacaga atagcttatg atgcttatcc ccacccacca cttccgaaac attgagcgga
421  aaccagaata cctccagcca gagaagtgtg tcccaccccc ctaccctggt cctgtgggaa
481  ccatgtggtt tatccgtgac ggctgtggca tcgcctgtgc catcgttacc tggtttctgg
541  tcctctatgc ggagttcgtg gtcctctttg tcatgctgat tccatctcga gactacgtgt
601  atagcatcat caacggaatt gtgttcaacc tgctggcctt cttggccctg gcctcccact
661  gccgggccat gctgacggac cccgggcag tgcccaaagg aaatgccact aaagaattca
721  tcgagagttt acagttgaag cctgggcagg tggtgtacaa gtgccccaaa tgctgcagca
781  tcaagcccga ccgagcccac cactgcagtg tttgtaagcg gtgcattcgg aagatggacc
```

-continued

```
 841  accactgtcc ctgggtcaac aactgtgtag gcgagaacaa ccagaagtac ttcgtcctgt
 901  ttacaatgta catagctctc atttccttgc acgccctcat catggtggga ttccacttcc
 961  tgcattgctt tgaagaagat tggacaaagt gcagctcctt ctctccaccc accacagtga
1021  ttctcccttat cctgctgtgc tttgagggcc tgctcttcct cattttcaca tcagtgatgt
1081  ttgggaccca ggtgcactcc atctgcacag atgagacggg aatagaacaa ttgaaaaagg
1141  aagagagaag atgggctaaa aaaacaaaat ggatgaacat gaaagccgtt tttggccacc
1201  ccttctctct aggctgggcc agccccttttg ccacgccaga ccaagggaag gcagacccgt
1261  accagtatgt ggtctgaagg accccgaccg gcatgccac tcagacacaa gtccacacca
1321  cagcactacc gtcccatccg ttctcatgaa tgtttaaatc gaaaaagcaa aacaactact
1381  cttaaaactt tttttatgtc tcaagtaaaa tggctgagca ttgcagaaa aaaaaaagt
1441  ccccacattt tatttttttaa aaaccatcct ttcgatttct tttggtgacc gaagctgctc
1501  tcttttcctt ttaaaatcac ttctctggcc tctggtttct ctctgctgtc tgtctggcat
1561  gactaatgta gagggcgctg tctcgcgctg tgcccattct actaactgag tgagacatga
1621  cgctgtgcgt ggatggaata gtctggacac ctggtggggg atgcatggga aagccaggag
1681  ggccctgacc tcccactgcc caggaggcag tggcgggctc ccgatgggaa cataaaacct
1741  caccgaagat ggatgcttac cccttgaggc ctgagaaggg caggatcaga agggaccttg
1801  gcacagcgac ctcatccccc aagtggacac ggtttgcctg ctaactcgca aagcaattgc
1861  ctgccttgta ctttatgggc ttggggtgtg tagaatgatt ttgcggggga gtggggagaa
1921  agatgaaaga ggtcttattt gtattctgaa tcagcaatta tattccctgt gattatttgg
1981  aagagtgtgt aggaaagacg ttttccagt tcaaaatgcc ttatacaatc aagaggaaaa
2041  aaaattacac aatttcaggc aagctacgtt ttcctttgtt tcatctgctt cctctctcac
2101  cacccatct ccctctcttc cccagcaaga tgtcaattaa gcagtgtgaa ttctgactgc
2161  aataggcacc agtgcccaac acatacagcc ccaccatcat ccccttctca ttttataaac
2221  ctcaaagtgg attcactttc tgatagttaa cccccataaa tgtgcacgta cctgtgtctt
2281  atctatattt taacctggga gactgttgtc ctggcatgga gatgaccatg atgctgggt
2341  tacctcacag tccccaccct ttcaaagttg acatatggcc atcccattgg ccagaatcca
2401  cagacacacc taagcctgtg gcactgggac agaatagatt ttccatttga gaggcacttc
2461  ctgtgtcagt cttgtttgaa ggaggtggtg atggtggata gaggtgaagg aggtagggag
2521  tgccctccaa gtgcaaaaat aacaaatatg attattgacc atcggggaat tctcacacat
2581  tgatttgttt tttaagcaat tgccagaaac ccccttttttt agcttttgct tggggtgggg
2641  gtaggagtta aggtttattc aatcctgtcc tgggtagggc gaaagttaat ctagccatgt
2701  gattttttcag aaaagtaagt ggaacatgct gccacttttc aattctgtca gtgcttccac
2761  atggaaacaa aatgcaataa aattttttcca aaacctgttc tgatttagct ctctcttgag
2821  gtgttaccct tagtgggagg ccgactatcc acaatctact tgagttttct ctggttgggt
2881  gtttgtttca ttgctctgtc tcttgaatga ggatacttta tttttttgt tttaaaatgc
2941  atttatggtc cctctcttga accagcttgc cccaccaggc ctctttcctt tgctttctgc
3001  agcctgaatc aattcctttg tgctgatggg ctctcctaag agctttcctg agtcagttaa
3061  ctttaccctcg tgtctacggt gctattcatg cgatacgggc gaggctgaga tgctaagatt
3121  aaaagaaaa gaatgctgtt ttagatcaag ttgatagcat ttgttttcca tatgcttttt
3181  taaaattttt tcataacata cagctcagtt aggtgtatga aagaagtgtt attgtattaa
```

```
-continued
3241  ataactagag cagggctaca gctctggccc tcccctaggg ggaagagatt ggtaatactc
3301  catcttccag ggcatttttt aaagtgagcc aggttagctc ttttcccctg gcatttctca
3361  ggaatgcagt agatagtgct gaagatgcac tgactttttt ttagtcctaa aaatagaaac
3421  tcctccttta aagctgtgca tactatgctt atctttccaa tagagtgggg ttccttcaga
3481  tatcctatag gattctgcct ctggttttgt ataggccttg gctagaaaga gtcaatgttt
3541  ctgagctctc aaaccagttg ctctcagaag ataggaatac cccaaggttc ctggcatttt
3601  tcctatttca tttttgttca gactgatatt ttgccaagag cacaatgact gaggaatgta
3661  gccatcattt gcagggtagt gattggttcc cagcctggct tccacacagg acaggaaggg
3721  aaagcatccc tgagctctcc tcagtatttc cggatgtaat gaaagaggac atctttctac
3781  acaaagtcag ccccaacttt tggcttggtc acaggagttc tgatagtact gtttggtgca
3841  ctcatgggaa attgaaccag tcgtagccac agtctttcag agcctgggct ctggggagtg
3901  gaagtgaaaa ataaagatgt ggcttgttgg attgtgatcc ccagcttgct ttccttctgt
3961  caactctgtc aggtttgtgt tcatagcaac tagactgaat atgcaaaagg cttagatcca
4021  agcaaatcta taatctatgc atatttgcat gggcttggta atatcatgta cacaaaacac
4081  atttgggtag aagtgcatgt gctaaatctc cttttagtcc caccattttg tcttcttcat
4141  actgtacttc ctcttttttg tttgagacaa ggtcttgctc tgtcacccag gctggaatgc
4201  agtggcacaa ttagagctca ctgcagcctt gaactcctgg gctcaagtga ttcttgtgcc
4261  ttggcctcct gaatatccag ggctacaggc acgtactacc atgcctggct aattttttg
4321  tttttttaata gagtcagggt ctcactgtgt tgccctagct agtctcaaat gcccggcctc
4381  cagcaatttt cctgccttag cctcccaaag tcctgggatt acaggcgtga gccactgggc
4441  ccagccctgt acttcttgaa aaagccccaa gtattagctt ttgctcatct ggctaggcca
4501  cttaaatagt tagaatccac cgtcccctaa tgcagaaacc gtttaggtga ggtaaattaa
4561  caaacatttt aagccgggcg cggacacttc tcactgtgga catccctcac gcctgtaatc
4621  ccagcacttt gggaggccga ggcgggcaga tcacgaggtc aagagatcga gatcatcctg
4681  gctaacacgg tgaaaccctg tctctactaa aaatataaaa aaattagctg ggcgtggtgg
4741  caggcgtctg tagtcccagc tacttgggag gctgaggcag gagaatggcg tgaacccggg
4801  aagtggagct tgcagtgagc caagatcgca ccactgcact ccagcctggg cgacagagtg
4861  agactccgtc tcaaaaaaaa aaaacaaaca ttttaaacat gtatgtgagg ttggcattac
4921  acagaaactc ctctccgggt gggctgggat gggctttctc agccaggcta atgggtttta
4981  aatttctctc ttttcaagac ttgcagtgca tcagcttaaa gggtgagcca gccagtagag
5041  gggaaggcgc cccacctaga aggtgccctt agatatcaaa gaaatgtgaa aagagaaaga
5101  ttttgctaga atcctcctca aaggtgttct tgaggttgcc agaccagcaa cgtcaacatc
5161  agcatcacct gagaacttgt tagaaatgca cattctcggt ccccacccca ggctaccgaa
5221  ccagaaaccg agcggggccc agcagcccgt gtcttaacag ccctccaggt gattctgact
5281  atcaagtttg agaatccagt tggggctagc aggagtcccc cctcaggtgg tccctgatgc
5341  ctgctggtga tatgggtctt gtgtgctgct gggctcagca tagtgcagtt ggggtgtgct
5401  gattgtgaga caggcacgtg ttccctccgc ggagaagcca ctgagactgc cttccctcat
5461  aagctgcggc ctccccaaca aacaactgcc aagacatcaa agaaagtctg tatgaagcag
5521  atccaaatta ttagcctgcc caccactcct tgtgcatctc atcagtggaa cccatctcta
5581  gaccaagggc cctttgggtg aagaagcagc ccggaaggga aagagaaaag agtagaacca
5641  agggacctcc agatgggagc ggcggccggt gagtagtcta gagccagggg cattgtagca
```

-continued

```
5701  gcctggatac atgacctgaa cacgtcttga cctttgcttt ctacgtgtgg gtttcaacac
5761  ccatgtggct ttttcttgta ttctttaaat atgtatctgg cttaggatca cctcatagaa
5821  gagaaagaat tcacagtgaa gcagaaacaa gccactgacc agcgtactcc caacctgaac
5881  cttcttttc tcaccctctc cctcaagtaa acatcttgct gacttgagca gtgtgattgc
5941  cgtagcaaag cagagtggcc cccagggatc ccgctctgtt gggcccacag gaggagccga
6001  tgaagctgat ccaaggagtg aggacaagcg ctgcagaggg acgttcgcta aaagccttct
6061  aggggccgca catgctctaa cacggacata aggatgccct gaatttctgc agctgaggcc
6121  atatagtctg gtgaccaagt atttgggtcc tggcttcagt ctttggttga aatgtctgct
6181  tggctactta ttaccgcacc tactaccaaa atatgacctt gagcagtaac ttctttaagc
6241  ctcagttttt tcatctgaaa acgggaatga taatctaaat cacaaagtta atggaaggat
6301  taaatgaggg tgatgaatag gaatgtatag cgtctggccc tggtatggct ttataaatgt
6361  tagctgtgtt ggagctgtgc ttttcaaacc attggtcaca gccattcatg gtttgcaacc
6421  agcatgtttt tcaagaaaaa tgtttaatgc attacatatt gcaggataag tattgtttta
6481  tgaagcttag ggagttgtgt gtatatgtgt tctggaatgc aacagaaaaa tgtttcctct
6541  tgtgggttac aatatagagg tatgaaatct ctgatgagga gagacagtgt tatctggccc
6601  gctatgaaga gacacatttg cataggctgc tccctgaggc tctggctttc tacatctgat
6661  gatacaggga gcagggaaca gcctgttctc gttctgtggg gctcagctga gtctgttctg
6721  cacagactct tccttcctcg ggagccttag tcctaataca ttcattttgg agtgttggtg
6781  agtttgttca cagatcacag ctcatgtgtc acccagactg acctgggcca aaaggcccat
6841  cacacaccct gcaagagctt ctggtgtcga ctatgacccc cttaccaggc atcaaccatt
6901  tttgttcgtt ctcttgagcc tgaagctact attactgctc ctctgcaaac ctcaagctta
6961  agaactttgc ctgcaggatc cctttaaatc cacacaaaac tcaaaattga gtcctaccag
7021  gaaaaagcag ccctcagccc attttatac atcggatttg tttgcaatat tttctttcta
7081  gactcaaaag tcaacactcc ctgaaagttt gtcgactta ctgctgaaga cctctggtag
7141  acaggccagg ctctgtctgg aatactttat gaggttggtg aggaggttga gtataatcca
7201  agagtgccta tctgggagca tgccacatga atggcaaata atcatcctgt gggctcttgg
7261  cttcattccc cttctctctg actgagctca gcctgggcac agtggtgatt tgcagtagaa
7321  ctggaaacct gttgggcaga aaaaaagaca ctagttctgg ttccagttct gatacataac
7381  aagctagatg agccttggcc accgtcatgg cctcttggaa cttctgtttc ttccccatct
7441  gccaatcatc aatactcata cccacctcct cacaaggagg ccataaaaac ctatggtcat
7501  ggctttgagt ccaagtcagt gtggatgcag ccagtctgtc attttgggt gtttcctctg
7561  tagccgggtc tgccatatgg tgatgtccca gctctcgtgc tatgaagtta aagcctcttt
7621  ctcaacaggc tgcagatgat cacccaggaa gagaatgcag aatgcccaaa gcaaaccatc
7681  tcagctggtc actgcttctg tgccaagaag ggaggcctgg cgaggggcca gtcaggaagc
7741  agcatggcat cacatgctca tgacccacat gaaggtccct ttagacttgt gtcaacaaga
7801  tccatttct gaaacaacta ttttgttct gattataaaa gtaacattgg ctcattggta
7861  aaacttggat tgtgtgagaa gtctacagaa ataaatacaa atcctctaga attccatccc
7921  caaaagtaac cactcagaca aatgttctaa tgtcatgtaa aaccatatta aaccatcttt
7981  tctagctgca tagtgttata gaatcatttg cttaaccatc attattgggc atttctcatt
8041  tccagctttg cattattata attcagtgtt caagtttgta ttgcataaat ctttgtctca
```

```
8101  gattattgat tatttttaaa cttttttgtga aatcagactt acaaaaatgt gacaaaaaca
8161  gtacaaagag ttcccatgta cctttcagtc agtctcacca aaggtaaaca ttttatacaa
8221  ccataataca aatataaaac cctggacatt ggcaacacca taccttaac taatgtatgt
8281  accttattca catttctcca gttgtcccat taacacccctt ttctgttcca ggatcccaca
8341  ctgcatcatt tgcgatgtct ccttagtctc ctccagtttg tgacagttcc tcagtcttcc
8401  tttgtctttc atgaccttga ccctttttaa aaatcgaggt gaaattcctg taacacaaaa
8461  ttagccattt taaagtgtac atttaatgca ttcacaatgt tttgtaaccca ccaggtctgt
8521  ctggttccaa aatcttttca tcaatctttg accctttttga agattgtagg gcaggtattc
8581  tgtaggctgt ccttcagatt gtgttttga tgttttttctc atgattagat tgaggttagg
8641  catttggggc aggagcactg ctgaagcaat gtgtcctcgt tgcaccgtat caggaggcat
8701  atggtgttga tacgtttcat tattgtgatg ttaactttga tcattgggtg aaggtggtac
8761  gtgcaatgtt tcttccctgc tattaaggta ctgttttccc ctttgtaatt gataagtatc
8821  ttatgaggat atacttttga gatccaattt ttttaactta gaatttattc aaaagtcaag
8881  aatcttaaat ctctgaaatg gcgtgggaag aaaagtgct agatacacag agatctttct
8941  tgagtcatgt gaaggagcag tgcccaagcc cagcaaaccc acagcaaatt cccttggctt
9001  ccagaagaga tggagaaagc agtgccccca gtggagggtc aaaggcctct gtgcagggtg
9061  ttgtgggcct ggagagctgg cctggccatg tctttacctc ctctgggcat ctccccaccc
9121  caacacccctt tctgtggcct ggtggctgag ttgcagccga cacccagagg caggtgagtt
9181  gacagcttgg aagaggctgc agggtggatc tgctgcatga gcaggcctga gcccagcctt
9241  acctccccac agtggtcctg tgtgccctcc ggctgcctaa tgcatgttgg cacttgctgt
9301  acgagcaccc gcttcttcac ctcgcatgct gtttgtgtcc tgcactcctt ccttaacccc
9361  atcgtccttc tgctgtgttt gcagcccta tctaccctgg tgggagtggc caaaaatatt
9421  taggagggga tcaccagttt gtagtggcct cagaggatgt gtggtccccc ttatgcctca
9481  gccactcatc agcctagccc ctgcccatca tctggcattg cacttgtgga aggaaagaag
9541  gggagggctg ggtggtgggt ggagaacacg tcagtccacc aggcgggccc tgcttgctgt
9601  gttcctccac gctgctgtcc acccacaccc cagcagtcct ctgagggacc tcccgggggt
9661  gacctgggcc acaacagact gcccactcag accccatctt acccatgccg tggacacccc
9721  gcccccccccc ccgccactgc tatgctatag ctgggggtgt ctatgtgagc tgtacagccc
9781  agcaccacgc tgacgatgtt cttcatcccc ttctccctgc agggcatcga gcgcctcaaa
9841  cgaaagaacc agcccaggga gcacatgggg agctggcagt cagtaaagga gacctttggt
9901  ggggacttct ccctgaactg gttcaacccc ttctccagac cgtgtcagcc agagatcccc
9961  agtgacaaag acatggtgcg gcaggtgaca tcgctgtcag acaccgaaac aatggaggat
10021 ccatcagagg agacaaagga cgaggactct gtggaggtga cagatgaata gatgctgctg
10081 tggggagaga agcaaacact aaaaagtgct gtcaaccttc atcctggggt tttggctaaa
10141 ggggcttatg gcatggtgc gctcccagca ccccccagtgc ttcccttagc cactcgcttg
10201 gccttgccat ttcccctcct tcttctctcc atgttgggcc aggtctgggg gtcgggagta
10261 ggctggggac atcagaggag gatgggggct ttctcagagt tcatctaaga agagtctgca
10321 ctgagacggc tcatcaagaa ccgttctcca agactgggtg ctttcacat tctccgccca
10381 gcaaagggag cttttgaaca gggcatccca ggggcagaaa agagcttgcc tttggctttc
10441 cccaggattt ctgtcttctc ttgggaaggc tgggcccctg gctcctggct ttgagaagta
10501 aggttgtgac agaaggaccg ggcagggctt gccttgggga cctggttgg gacactgaca
```

-continued

```
10561  tcagggaga  ctagcctgga  aagactgcag  agctgccagc  tactccctgg  aaagggcttc
10621  cccatgctgc  ctgccgaaat  taggaggtag  aggtggctgc  cacatctacc  tgcaagggcc
10681  aggcatggtt  caaagaggac  cctgcattaa  gctctacaca  cacatgtgca  ggacatgtcc
10741  agcatggaca  gagccagagt  taagacagta  gcaccgaaaa  tgagccccca  ttccacagac
10801  actggagtct  tcactgagcg  agacagctgg  gagctgtcct  gcctgtggct  acatatctag
10861  ccattcacag  atgtggatat  gggaaggacc  tctttggagc  tactggggac  tccctaacca
10921  ctcgcatgag  aacttaattg  aatgttacct  cttggaggga  gtctaataac  acatgtaggt
10981  agaactgacc  ataaaccctg  cctgtgtgtt  tgaaaaggcc  agttctccca  aattggtgcc
11041  catcttgtct  ctgaaaagat  gggtgatggc  cagggtctgc  tgattgatga  atcagatgaa
11101  tcaggaagat  agacaaacac  acacacacac  acacacaccc  caccaggatg  agtctgccct
11161  ctattcaccc  catttgaagc  ctgtggtgtc  tgtgaccact  gctgaaggtc  tgagcagcgt
11221  tctggtgctc  ctaaacccca  ttccagtggt  gctgaagca  gcatcttctg  cacaaagccc
11281  aacagaaggg  ttcttatccc  cgtttggtat  aagaagtgga  ttcaccaccc  actccctcca
11341  cgtgcctttg  ttcctctctt  tggcccattt  ccccagcgtc  tactggcgtc  aggattggca
11401  ggagcacagg  cactcagcag  agcatgcccc  tgcaagacct  cagtgttagg  gccccccttc
11461  cagctccagg  caaaagggca  tgagtcctgg  ccccaagggg  cctgtggctg  cagttcagag
11521  gagaagaagg  tcagtgtttg  gaggtgcagc  ctcaggatgc  tgagaaagga  aactggcgac
11581  cgtgagaaag  aaaagagcca  agcagcatcc  tggttcttgg  acagcatctt  tggacactct
11641  gtgaagggca  acgatcctgc  cagagaccgt  ctctctacaa  ctgatgaccc  actagggcct
11701  ggggttaatt  gctcaaaggg  cccagtgttc  acaaagccac  ctctgcccta  acccttgcca
11761  gagctctcca  actatgaccc  acgagagggg  tgatggtggg  attctaacat  caacagagca
11821  accagaaaga  cattgggcct  cccacactca  ggctgcaggc  ccactttctt  ggtccttatc
11881  agctttaata  tttattaatg  acgacatagg  agcccgagtc  agctgtaaag  gccattaact
11941  tgcaatctgg  acaggaagtt  gacgctcacc  actttgggta  agagctgctc  tgactgtagg
12001  gcccccctatt  tgttgtccta  acccagaagc  agctctgggc  tgccaggatg  gtggatggaa
12061  taccagagag  ttcacactag  ggaggaagca  atgcctgccc  cctggagtct  cctaggggc
12121  agcagttaga  ataagggaag  aggatttgct  ggtcactgtt  tgctgacatg  ggtttccatg
12181  gtgagttcag  gcctgaggac  agcagtgtct  gcaaaaccac  atggcccttg  agaaatgtcc
12241  ttgcacattg  ggcttcaaac  tcctcttcta  gggaatccat  cttggcctga  aagcagaggt
12301  acaacaccag  ccccaaaggc  aattctgttt  tcagattggt  tgctctggaa  aggaaggctg
12361  gggtgagggg  gcattttact  tgcacagagg  ctgaccctgc  ctcccctctt  cactgacccc
12421  atctccaagg  tagacctcag  ccatgtcagt  ccctgttctg  ggaggtgctg  ggctgggcca
12481  cagccagggt  tatgtaggta  attaacctgt  ccaaccctga  gcctcgcctc  cccacaccag
12541  caacacagtg  gtctctctgt  ggtgaccatt  cacagcataa  cattctgctt  agcctcagac
12601  tgaaagcatt  gcaactgatg  tcaaaaccag  atgagatctt  acagggagag  agattgggtg
12661  caatttgcct  cttctctttga  ataaaaagct  ctttgctcac  cctca
```

An exemplary human CMTM6 amino acid sequence is set forth below (SEQ ID NO: 3; GenBank Accession No: NP_060271. Version NP_060271.1, incorporated herein by reference):

```
  1 mengavyspt teedpgparg prsglaayff mgrlpllrrv lkglqlllsl laficeevvs
 61 qctlcgglyf fefvscsafl lslliliyyc tpfyervdtt kvkssdfyit lgtgcvflla
121 siifvsthdr tsaeiaaivf gfiasfmfll dfitmlyekr qesqlrkpen ttraealtep
181 lna
```

An exemplary human CMTM6 nucleic acid sequence is set forth below (SEQ ID NO: 4; GenBank Accession No: NM_017801, Version NM_017801.2, incorporated herein by reference):

```
   1 aggggcggg gcgggccaag ggcggggggcg ggaaggggcg gagtcaggcg gaagccgggg
  61 agaaggccca ggaagtgacg gccgcctccc ggctaccggg gacttctgga gtccgagaag
 121 tcaacggcgc ggttgctgcg gccgccgcgc tccccggccc gaggcgatgg agaacggagc
 181 ggtgtacagc cccactacgg aggaggaccc gggcccccgcc agaggccccc ggagcggcct
 241 cgctgcctac tttttcatgg gccggctccc attgctccgg cgcgttctca agggcttgca
 301 gctgttgctg tctctgctgg ccttcatctg tgaagaagtt gtatcacaat gtactttatg
 361 tggaggactt tatttttttg agtttgtaag ctgcagtgcc tttcttctga gtctccttat
 421 actgattgtg tattgcactc cattttatga gagagttgat accacaaaag taaaatcatc
 481 ggatttttat attactttgg gaacaggatg tgtgttttg ttggcatcca tcattttgt
 541 ttccacacat gacaggactt cagctgagat tgctgcaatt gtgtttggat ttatagcaag
 601 ttttatgttc tacttgact ttatcactat gctgtatgaa aaacgacagg agtcccagct
 661 gagaaaacct gaaaatacca ctagggctga agccctcact gagccactta atgcctaaag
 721 actctgggga gcagatgtta cctaaggtag tgaccctgca ttgtggtgcc tgagccctgg
 781 cagaagctct tgtaaaattt gttaattgtt taaaccactt cttttggaga gcaagggaa
 841 ggtcaagaag gcagttttat caatattgtg tcagtcacca caaagtaggc cagataagtt
 901 aaaaaaaatt ttttttaaa taataattga aacttatctc aaatggagat tttggtggga
 961 ggaggagaaa acaattgttt ttaaatcaca cagctcaacg gttgataaat gattctgtca
1021 ttctgttaca ggtcattctt ttactaggct tagcttccaa attatgcttt atagctgtat
1081 aaacatcgtg attatattca tctacttaga aattgtttta tttttaaatt aatttgctta
1141 gctgtttgtt ttgatgctta gattatgttc tgttaatggg aatttaacat atttaagaaa
1201 ccaatattta aaatgttggt ctaggttttt ttccttaaca tatattacca ggcttactg
1261 tatttcactc agccttaaat gttataatat ttttggataa cggttattaa ttctttgaga
1321 ccttcgtata gcctataaaa tgtatgggag atgttggtat tttatgtgta taaaagcaac
1381 aatatcagca acttcgtgtt tatactgcac cttggttgtt gatgtcaagt aaaaaaaaga
1441 ttgttttgta acacatazaaa aaatgaaga aactgatacc acacctaagg accaaagata
1501 agaaagactt tttgcccaag acagtgaaag taattataaa aacaagcttt gaccacttac
1561 caagtatctg aagagatgag ttcatactat gatttagaaa gtggttcaat tcccctgttg
1621 gcatatgatt atttttacta aaattaatac agctctgtgg gtcttcctta gtgttttctt
1681 tgaagccaat ctgtttttttt taggacacca gcctttggtt tttcatctgt tcgagatgcc
1741 tcttctctgt ctccttatca gatagaaatg gagtcatgtg ctgctgcttc atctagcaga
```

```
1801  ggttggcctc tggctctgac acttttttgtc agttgtcttt aggtggtcct gaatcttggg 1861  cccttttgat tgtgaatact gtgtagcagg atcttgagag tccttgttct tacataggca 1921  ttgctctagt ttgtctttgg caaaaaaaaa aaaaaaaaaa agtaaatatc cagggaaccc 1981  tgcccagact aatactgttg gtggcataag agaatcaagc cattctcaag agataacttc 2041  ataaccagaa ttgtctgttg gctagcagct gtcacagata ggcagggcac ttgggatatg 2101  acctttctgt ccaggtgatt cacagactag acctttctta tcctcctcct agagttttga 2161  cttgggactc tagtgttaag atgatgagcc cgtgcatcag gtccttctgc actttggtgg 2221  aagtctccca gggtaggttt cctatttgaa acagtggaat catgtttcca gtgataaagt 2281  ttaatgacct catccttttt ttttttttctc atctgccatt tgtgtgtctt agatgggttt 2341  taattgcatg aatgtggcta atgtggttct cagaaattgg tcagtatggc caacatagc 2401  ttctgctctg tcttactgac tcaataccat taggatttgt atcagagttt ggatactagt 2461  gttagtggtg gtgtcaccac tacttaattg ggagataatg aaaccaatca tggatgctgt 2521  ttttattggg catgtcatct aagagaggag aaatagctgg gttttgggtc taattatgaa 2581  taaggactga ttcagaaaac gagtttatgg taggtagact aaagtttcac atcagactgt 2641  accattgtga tttagaccta tctaaaattc agagcatatc atctgggcta cctcagggtc 2701  accacccatg tattgggctt agtcaggatt gacagataca ttctcagctg gcctgtcata 2761  taaaacatac tgtcattgag cttaagctcc gcttgttctg aggtttcacc tccatgtgtt 2821  tcattggtgc aaaagtggat ctcttagttg gtcacttaat tctttctttt tcagaaagat 2881  agtatgttca ctggtatatt tggtcactct tagaaccttc cttcacattg tttttatgg 2941  gacccatgaa tggttagcct ttcttttcta ttgtagaagg aaataaatag gagtaaaaag 3001  accattgtag taaataagtt caaggggaac ttgggaccag aaaccactgt tatgtacaaa 3061  aaaatggcaa attcaataaa ctcaaattta aaataatttt taaattaaca gttatgataa 3121  attttatatt ttatacaaat agattgctta gaatggttct caagaattat aagagaaatg 3181  aactcacagt acaaaaattt tataattact atacttgtgt tttgtttggg ggctgggaaa 3241  tgtatttta cattgtagcc aatcattta tatttgtcaa tttaaatctt atgggtcttt 3301  tttttttatc tctcttgatg tcagatttta tagtcttttt aaataaatcc atttaattaa 3361  aacgttaaaa aaaaaaaaaa aaaa
```

An exemplary human PD-L1 amino acid sequence is set forth below (SEQ ID NO: 5; GenBank Accession No: AAP13470, Version AAP13470.1, incorporated herein by reference):

```
  1  mrifavfifm tywhllnaft vtvpkdlyvv eygsnmtiec kfpvekqldl aalivyweme 61  dkniiqfvhg eedlkvqhss yrqrarllkd qlslgnaalq itdvklqdag vyrcmisygg 121  adykritvkv napynkinqr ilvvdpvtse heltcqaegy pkaeviwtss dhqvlsgktt 181  ttnskreekl fnvtstlrin ttneifyct frrldpeenh taelvipelp lahppnerth 241  lvilgaillc lgvaltfifr lrkgrmmdvk kcgiqdtnsk kqsdthleet
```

An exemplary human PD-L1 nucleic acid sequence is set forth below (SEQ ID NO: 6; GenBank Accession No: AY254342, Version AY254342.1, incorporated herein by reference):

```
  1    atgaggatat ttgctgtctt tatattcatg acctactggc atttgctgaa cgcatttact 61    gtcacggttc ccaaggacct atatgtggta gagtatggta gcaatatgac aattgaatgc 121    aaattcccag tagaaaaaca attagacctg gctgcactaa ttgtctattg ggaaatggag 181    gataagaaca ttattcaatt tgtgcatgga gaggaagacc tgaaggttca gcatagtagc 241    tacagacaga gggcccggct gttgaaggac cagctctccc tgggaaatgc tgcacttcag 301    atcacagatg tgaaattgca ggatgcaggg gtgtaccgct gcatgatcag ctatggtggt 361    gccgactaca agcgaattac tgtgaaagtc aatgccccat acaacaaaat caaccaaaga 421    attttggttg tggatccagt cacctctgaa catgaactga catgtcaggc tgagggctac 481    cccaaggccg aagtcatctg gacaagcagt gaccatcaag tcctgagtgg taagaccacc 541    accaccaatt ccaagagaga ggagaagctt ttcaatgtga ccagcacact gagaatcaac 601    acaacaacta atgagatttt ctactgcact tttaggagat tagatcctga ggaaaaccat 661    acagctgaat tggtcatccc agaactacct ctggcacatc ctccaaatga aaggactcac 721    ttggtaattc tgggagccat cttattatgc cttggtgtag cactgacatt catcttccgt 781    ttaagaaaag ggagaatgat ggatgtgaaa aaatgtggca tccaagatac aaactcaaag 841    aagcaaagtg atacacattt ggaggagacg taa
```

DHHC3 Regulation of Adaptive Immunity

PD-L1, a molecule of some significance in the immune checkpoint blockade arena, appears on the surface of many cancer cells and triggers the inactivation of anti-cancer T cells. It was recently identified that a membrane protein called CMTM6 is needed for continued expression of PD-L1 (Burr et al., 2017 Nature, 549:101-105, incorporated herein by reference; Mezzadra et al., 2017 Nature, 549: 106-110, incorporated herein by reference). As described herein, knockdown of the protein acyltransferase DHHC3 also causes a marked decrease in PD-L1 expression. Notably, as described in detail below, palmitoylation of CMTM6 is largely dependent on DHHC3 being present. These results indicate that DHHC3 ablation causes a deficiency in CMTM6 palmitoylation, which renders it unable to support expression of PD-L1.

DHHC3 Regulation of Innate Immunity

When DHHC3 is ablated from breast and prostate tumor cells, in vivo growth and metastasis are markedly diminished in xenograft models (i.e. using immunocompromised mice). Available evidence (Sharma et al., 2017 Cancer Research, 77(24): 6880-6890) indicates that decreased in vivo growth is due to increased oxidative stress, leading to elevated senescence in tumor cells, which leads to clearance by the innate immune system.

The results presented herein provide an alternative approach towards diminishing PD-L1 expression, which is known to enhance anti-tumor immunity. Targeting of DHHC3 may combine the effects of enhancing adaptive immunity (i.e. through diminished expression of PD-L1) with effects of enhancing clearance of senescent tumor cells by the innate immune system.

DHHC3 knockout mice are relatively normal, indicating that the enzyme may not be needed for normal physiological processes. DHHC3 is an enzyme, and as described herein, can be inhibited by small molecules. As described herein, targeting of DHHC3 enhances anti-tumor immunity. Elevated DHHC3 expression may be a biomarker for poor patient outcome in several cancers. Accordingly, DHHC3 expression informs a method to overcome the immune checkpoint blockade.

DHHC3 Regulates Breast Tumor Growth

Included herein is evidence for DHHC3 having a key role in human breast cancer. Also, data are provided suggesting that DHHC3 enables tumor expansion in vivo, by a mechanism requiring an active enzyme palmitoylation site, and involving down-modulation of oxidative stress and senescence in cancer cells. Prior to the invention described herein, DHHC3 was not known to function in breast cancer or other cancers. Furthermore, neither DHHC3, nor other mammalian DHHC enzymes were known to control oxidative stress or senescence.

As described herein, elevated ZDHHC3 gene expression correlates with significantly reduced human breast cancer patient survival. Furthermore, DHHC3 protein levels were elevated in malignant breast cancer, and even more in metastatic breast cancer. These results, combined with ZDHHC3 ablation effects on ectopic and orthotopic tumor xenograft size and metastatic lung colony size, strongly indicate a surprising pro-breast tumor growth role for DHHC3.

Notably, ZDHHC3 gene upregulation correlated with reduced patient survival in six other human cancers. Also, DHHC3 protein expression was elevated in most breast cancer subtypes, and in prostate and colon cancers (Lukk et al., 2010 Nat Biotechnol, 28:322-4). In addition, ZDHHC3 ablation reduced prostate cancer xenograft growth. Hence, DHHC3 contributes to growth of multiple cancer types. Upregulation of ZDHHC7, closest homologue to ZDHHC3, correlated with reduced patient survival in 2/7 human cancers. By contrast, upregulation of other potentially oncogenic DHHC enzymes (i.e. ZDHHC5 (Ducker et al., 2004 Oncogene, 23:9230-7) and ZDHHC17 (Tian et al., 2015 Mol Cancer Res, 13:784-94)) was, with one exception, not significantly correlated with reduced human survival in the same seven cancers. Other DHHC-type enzymes have been suggested to show cancer expression correlations, or palmitoylate cancer-related substrates (Greaves J and Chamberlain L H, 2014 J Pathol, 233:4-6; Yeste-Velasco et al., 2015 Biochim Biophys Acta, 1856:107-20), but prior to the invention described herein, definitive cancer links remained to be established.

The Role of DHHC3 in Oxidative Stress

ZDHHC3 ablation minimally affected cell proliferation or soft agar growth in vitro, or cell proliferation, angiogenesis, or apoptosis in vivo. However, unbiased DNA array analysis results (for 12/52 genes with significantly altered expression) strongly suggested oxidative stress upregulation in ZDHHC3-ablated tumors. Upregulation of six genes (GTF2i, TXNIP, AVIL, FKBP11, SETD6 and SETX) and downregulation of six other genes (S100A4, PDE4B, HNMT, NUDT2, AKR1C1 and GSTZ1) is consistent with increased oxidative stress in ZDHHC3-ablated MDA-MB-231 xenograft tumor cells. Upregulation of TXNIP is particularly notable. TXNIP (thioredoxin inhibitory protein) binds to, and inhibits antioxidant function of thioredoxin protein TRX-1, thus enhancing oxidative stress (Cadenas et al., 2010 Breast Cancer Res, 12:R44; Mahmood et al., 2013 Antioxid Redox Signal, 19:1266-303).

Increased oxidative stress in ZDHHC3-ablated cells was confirmed, in multiple cell types, by measuring increased reactive oxygen species (ROS) levels. Both direct and indirect effects of oxidative stress were substantially reversed by oxidative stress inhibitors (N-acetyl cysteine (NAC), α-lipoic acid (α-LA), atorvastatin) or by knockdown of TXNIP, a major oxidative stress-inducing gene upregulated in ZDHHC3-ablated cells. Increased oxidative stress was further confirmed by typical downstream oxidative stress-dependent events, such as induced senescence (next section), and diminished phosphatase activity (Tanner et al., 2011 Antioxid Redox Signal, 15:77-97). The latter is manifested as a) increased tyrosine phosphorylation (of FAK and STAT3), and b) diminished time-dependent loss of tyrosine phosphorylation (of FAK).

Elevated FAK and STAT3 tyrosine phosphorylation may also contribute to deficiencies seen in ZDHHC3-ablated tumor cells. FAK hyper-phosphorylation caused by diminished tyrosine phosphatase activity may interfere with FAK turnover, resulting in diminished FAK function (Yu et al., 1998 J Biol Chem, 273:21125-31; Manes et al., 1999 Mol Cell Biol, 19:3125-35), which would adversely affect tumor cell invasion and dissemination. Regarding STAT3, elevated tyrosine phosphorylation is not only oncogenic, but also may be suppressive by multiple potential mechanisms ((Zhang et al., 2016 Clin Cancer Res, 22:691-703) and references within), including induction of cell senescence (Leung et al., 2017 Mol Cell Biol, 37; Lee et al., 2014 Cell Death Dis, 5:e1537).

Although the transcription factor, NRF2, has been termed the "master regulator" of antioxidant responses (Gorrini et al., 2013 Nat Rev Drug Discov, 12:931-47), NRF2 expression was only slightly upregulated (1.2-fold) in ZDHHC3-ablated cells. Furthermore, expression levels of 22 different redox-related genes known to be controlled by NRF2 (Gorrini et al., 2013 Nat Rev Drug Discov, 12:931-47) were only minimally altered in ZDHHC3-ablated cells. Hence, NRF2 does not appear to play a role in DHHC3-regulated redox-related events.

Elevated Oxidative Stress Leads to Senescence

Increased oxidative stress, coupled with other tumor microenvironment stresses, can limit tumor survival by triggering apoptosis (Ueda et al. 1998 J Immunol, 161:6689-95). However, instead of increased apoptosis in DHHC3-ablated tumors, oxidative stress-dependent induction of senescence was observed (Panieri et al., 2013 Free Radic Biol Med, 57:176-87; Dasari et al., 2006 Cancer Res, 66:10805-14). Evidence for increased senescence includes 10 upregulated senescence-linked genes (PIP5K1b, COL6A3, TXNIP, AMY1A, RSRPI, ITSN2, KLHL28, ATM, TRIM38, and COL13A1) and downregulation of 8 genes typically diminished during senescence (BCL2A1, ANAPC15, PF4, HePTP, CDKN3, CENPN, LIPA, HCLS1). Also significantly altered were CDKN2A, PAI-1, HLA-DRB4, TJPI, RBBP6, IGFBP7, Smurf2, Askl, THBS1, CBX1, GRP170, CDKN2C and CCNA2 genes (Table 4), which either support senescence or are senescence markers. Additional genes (Esm1, PDGFB, MAPKAPK2, PDGFC, TP53, and FGF5) showed altered expression (Table 4), not quite meeting criteria for inclusion in Table 3, but nonetheless consistent with enhanced senescence.

Multiple ZDHHC3-ablated cell lines showed increased β-galactosidase activity, indicative of senescence (Debacq-Chainiaux et al., 2009 Nat Protoc, 4:1798-806). Selective upregulation of specific chemokine proteins (MCP-1, GROa, CXCL16, IL-8), characteristic of SASP (senescence-activated secreted protein) responses was also demonstrated (Coppe et al, 2008 PLoS Biol, 6:2853-68). Increased senescence, measured by β-galactosidase activity and/or SASP marker MCP-1, was substantially reversed by oxidative stress inhibitors (NAC, α-LA, atorvastatin). Senescence in ZDHHC3-ablated cells was also substantially reversed upon knockdown of TXNIP, which supports both oxidative stress and senescence (Mahmood et al., 2013 Antioxid Redox Signal, 19:1266-303, Riahi et al., 2015 J Cell Mol Med, 19:1887-99). These results further reinforce a mechanism of ZDHHC3 ablation→diminished palmitoylation of key substrates→TXNIP upregulation→oxidative stress→senescence (see summary scheme in FIG. 12C).

Consistent with an SASP response (Xue W et al., 2007 Nature, 445:656-60), increased recruitment of anti-tumor "M1-like" macrophages and NK cells was observed. Furthermore, it was confirmed that conditioned media from ZDHHC3-ablated MDA-MB-231 cells (containing SASP elements MCP-1 and IL8) indeed can recruit anti-tumor "M1-like" macrophages in an in vitro model system. These results are consistent with SASP-dependent clearance of ZDHHC3-ablated tumors by innate immune cells. Diminished recruitment of pro-tumor "M2-like" macrophages (Mantovani A and Sica A, 2010 Curr Opin Immunol, 22:231-7) may further reduce in vivo growth of DHHC3-ablated tumors.

Reconstitution and a Requirement for the DHHC3 Active Site

Reconstitution with wild type ZDHHC3 reversed ZDHHC3 knockdown effects on TXNIP protein levels, oxidative stress, senescence and in vivo tumor growth. These results, plus similar results obtained using multiple RNAi targeting sequences, effectively rule out off-target shRNA/siRNA effects. A conserved 'DHHC' (Asp-His-His-Cys (SEQ ID NO: 7)) motif is required for palmitoyl transferase activity of DHHC3 and other DHHC enzymes (Mitchell et al., 2006 J Lipid Res, 47:1118-27). Hence, ZDHHC3-ablated cells were reconstituted with two DHHC (Asp-His-His-Cys (SEQ ID NO: 7)) active site disabled mutants. Both mutants failed to reverse ZDHHC3 ablation effects on oxidative stress, senescence, TXNIP expression or related events. Furthermore, the $D3^{C/S}$ mutant failed to restore tumor growth in vivo. Hence, DHHC3 palmitoylation activity is needed for reconstituted functions. Although overexpressed DHHC3/GODZ was claimed previously to mediate $Ca^{2+}$ transport (Hines et al., 2010 J Biol Chem, 285:4621-8), ZDHHC3 ablation did not alter calcium levels in the cells.

DHHC3 Palmitoylation Activity

Figure 7A:
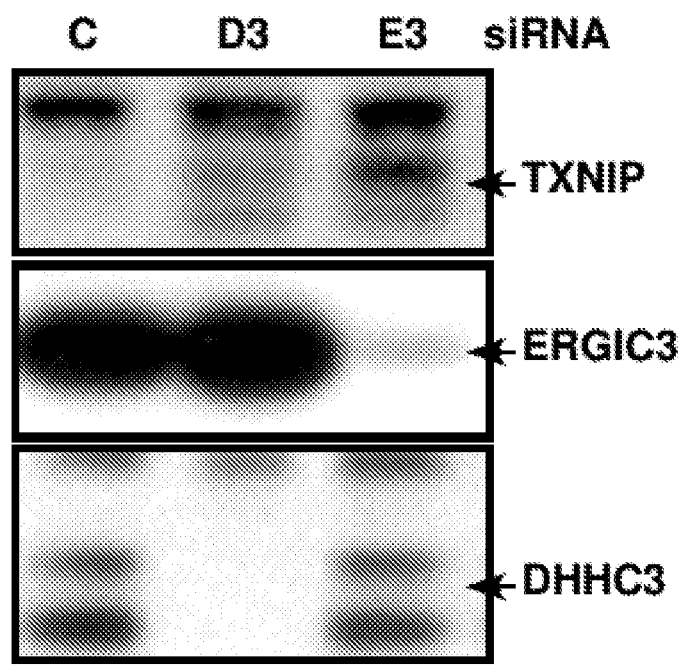
FIG. 7A-FIG. 7C is a series of photographs of immunoblots and a series of photomicrographs showing DHHC3 ablation effects on ERGIC3.

The requirement for the DHHC3 palmitoylation active site focused attention on potentially important DHHC3 substrates. Among ~50 putative protein substrates palmitoylated by DHHC3 (manuscript in preparation), ERGIC3 was focused on, because disruption of ERGIC3 is a known trigger of ER stress (Hong et al., 2016 Oncotarget, 7:65335-47), which leads to upregulation of TXNIP (Oslowski et al., 2012 Cell Metab, 16:265-73). It was confirmed that ERGIC3 ablation upregulates TXNIP, and that ZDHHC3 ablation markedly diminishes ERGIC3 palmitoylation, stimulates ER stress and considerably alters ERGIC3 subcellular distribution. Hence, diminished ERGIC3 palmitoylation and altered ERGIC3 distribution (and presumably also function) appear to be key mechanistic consequences of DHHC3 ablation (FIG. 7). Loss of DHHC3 also caused reduced palmitoylation of several other proteins, including a few antioxidant-type proteins. As described herein, this additionally contributes to oxidative stress, which can further enhance ER stress (Verfaillie et al. 2012 Cell Death Differ, 19:1880-91), and could then further amplify TXNIP upregulation (Step 3, FIG. 12C).

Although GABA(A) receptor (Keller et al., 2004 J Neurosci, 24:5881-91), integrin α6 and β4 subunits (Sharma et al., 2012 Cell Mol Life Sci, 69:2233-44), G protein α subunit (Tsutsumi et al., 2009 Mol Cell Biol, 29:435-47), regulator of G-protein signaling 4 (RGS4) (Wang et al., 2010 FEBS Lett, 584:4570-4) and phosphatidylinositol 4-kinase IIα (PI4KIIα) (Lu D et al., 2012 J Biol Chem, 287:21856-65) are reported to be DHHC3 substrates, it's unclear that diminished palmitoylation of these few proteins would cause diminished in vivo tumor growth, oxidative stress and/or senescence. Ablation of ZDHHC3 diminished α6β4 integrin palmitoylation, and partially reduced integrin expression (Sharma et al., 2012 Cell Mol Life Sci, 69:2233-44). However, this may not be relevant to current results because α6β4 ablation in MDA-MB-231 cells did not diminish oxidative stress, senescence or TXNIP expression.

Taken together, the results presented herein demonstrate that DHHC3 promotes in vivo breast tumor growth, by a mechanism involving palmitoylation of key substrate proteins such as ERGIC3. ZDHHC3 ablation not only diminishes in vivo breast tumor growth, but also promotes oxidative stress and senescence. This may explain reduced tumor growth because oxidative stress can diminish tumor growth and/or metastasis (Trachootham et al., 2009 Nat Rev Drug Discov, 8:579-91; Gorrini et al., 2013 Nat Rev Drug Discov, 12:931-47; Woditschka et al., 2014 J Natl Cancer Inst, 106) and senescence can lead to tumor clearance by immune cells (Perez-Mancera et al., 2014 Nat Rev Cancer, 14:547-58; Ben-Porath I and Weinberg R A, 2005 Int J Biochem Cell Biol, 37:961-7648). As a key supporter of breast tumor growth, the results presented herein indicate that DHHC3 is a useful cancer target. Furthermore, targeting DHHC3, which enhances oxidative stress, markedly improves sensitivity to a variety of oxidative stress-dependent anti-cancer drug types (Trachootham et al., 2009 Nat Rev Drug Discov, 8:579-91; Kim et al., 2016 Exp Mol Med, 48:e269).

Solutions to Overarching Challenges

Described herein is the identification of drivers of breast cancer growth, and methods of inhibiting breast cancer. Also described herein are revolutionized treatment regimens that are more effective, less toxic, and positively impact survival. Breast cancer growth is at least partly driven by the capability of tumor cells to express PD-L1, which triggers inhibition of the adaptive immune system. Described herein is a methodology to inhibit PD-L1 (indirectly by removing DHHC3), which enables re-activation of adaptive immunity, thereby resulting in diminished tumor growth. Removal of DHHC3 also activates innate immune cells, which further contribute to diminished tumor growth. Thus, as described herein, targeting DHHC3 is an effective means for treatment of breast cancer.

Accordingly, the results presented herein suggest that the presence of the DHHC3 enzyme, elevated in multiple types of breast cancer, contributes to the inhibition of both adaptive immunity and innate immunity. As described in detail herein, removal of DHHC3 unleashes both adaptive and innate anti-breast tumor immunity, leading to substantially reduced breast tumor growth. Because DHHC3 expression is elevated in breast cancer and some other cancers, but not needed for the survival of normal cells or mice, and not elevated in non-cancerous tissue, it appears that targeting of DHHC3 has minimal side effects.

The results presented herein describe whether DHHC3 ablation causes loss of PD-L1 expression by a mechanism involving loss of CMTM6 palmitoylation. Also, described herein is a determination of whether there exists a positive correlation between DHHC3 expression and elevated PD-L1 in human breast cancer tissue samples, which would further emphasize the relevance of the DHHC3-CMTM6-PD-L1 link identified herein. The results demonstrate clearly that DHHC3 ablation markedly enhances adaptive immunity, leading to diminished breast cancer growth in vivo. Also, the results confirm that DHHC3 ablation is acting almost entirely through a mechanism involving loss of CMTM6 palmitoylation, to cause diminished PD-L1 expression. Finally, the results demonstrate that benefits of DHHC3 ablation are most obvious when both adaptive and innate immunity are enhanced. These results all point to the therapeutic benefits of targeting DHHC3.

The unexpected results presented herein support the idea that targeting a single molecule (i.e., DHHC3) markedly enhances both adaptive and innate anti-breast cancer immunity. The results motivate the development of specific tools for use in targeting DHHC3. As described herein, DHHC3 is targeted using an RNAi strategy, as the potential for localized RNAi delivery is progressing rapidly. In addition, DHHC3 is also amenable to small molecule inhibition. Targeting of DHHC3 markedly inhibits aggressive and metastatic breast cancer either as a single agent, or in combination which other anti-cancer agents. As such, described herein are methods of early determination of which breast cancers are more likely to be aggressive and/or metastatic, and therefore in need of more aggressive treatment. Finally, as described herein, DHHC3 ablation disables antioxidant protections and enhances the potency of various chemotherapeutic agents.

Breast Cancer

Breast cancer develops in breast tissue. Signs of breast cancer include a lump in the breast, a dimpling of the skin, a change in breast shape, fluid exuding from the breast nipple, and/or a red, scaly patch of skin. Risk factors for developing breast cancer include being female, obesity, lack of physical exercise, drinking alcohol, hormone replacement therapy during menopause, ionizing radiation, early age at first menstruation, having children late or not at all, older age, and family history. About 5-10% of cases are due to inherited genes, including, e.g., breast cancer 1 (BRCA1) and BRCA2.

The most common types of breast cancer are ductal carcinoma, invasive ductal carcinoma, and invasive lobular carcinoma. Breast cancer most commonly develops in cells from the lining of milk ducts (i.e., in situ or invasive ductal carcinomas) and the lobules that supply the ducts with milk (i.e., in situ or invasive lobular carcinomas). Less common breast cancers include sarcomas, phyllodes tumors of the breast, Paget disease of the nipple, and angiosarcomas. Ductal carcinoma in situ (DCIS) is a non-invasive breast cancer where abnormal cells have not spread beyond the lining of the breast milk duct. By contrast, with invasive ductal carcinoma, abnormal cells that originated in the lining of the breast milk duct have invaded surrounding tissue. Triple negative breast cancer refers to tumor cells that are negative for progesterone, estrogen, and HER2/neu receptors. Inflammatory breast cancer often affects the skin and may not develop a tumor. Metastatic breast cancer refers to cancer that has spread beyond the breast, e.g., into lungs, bones, or brain. Other, less common, types of breast cancer include medullary carcinoma, tubular carcinoma, and mucinous carcinoma.

The diagnosis of breast cancer is confirmed by taking a biopsy of the concerning lump or tissue. Once the diagnosis is made, further tests are performed to determine if the cancer has spread beyond the breast. Treatment of breast cancer includes surgery, radiation therapy, chemotherapy, hormone therapy, targeted therapy. For example, chemotherapy may be used before surgery (neoadjuvant chemotherapy), after surgery (adjuvant chemotherapy), or for advanced breast cancer. The most common drugs for neoadjuvant and adjuvant chemotherapy include anthracyclines, such as doxorubicin and epirubicin, taxes, such as paclitaxel and docetaxel, 5-fluorouracil (5-Fu), cyclophosphamide, and carboplatin, or combinations thereof. Chemotherapy for advanced breast cancer includes taxanes, such as paclitaxel, docetaxel, and albumin-bound paclitaxel, anthracyclines, such as doxorubicin, pegylated liposomal doxorubicin, and epirubicin, platinum agents, vinorelbine, capecitabine, gemcitabine, ixabepilone, albumin-bound paclitaxel, and eribulin, or combinations thereof.

Pharmaceutical Therapeutics

For therapeutic uses, the compositions or agents described herein may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia, i.e., the melanoma. Generally, amounts will be in the range of those used for other agents used in the treatment of other diseases associated with neoplasia, although in certain instances lower amounts will be needed because of the increased specificity of the compound. For example, a therapeutic compound is administered at a dosage that is cytotoxic to a neoplastic cell.

Formulation of Pharmaceutical Compositions

The administration of a compound or a combination of compounds for the treatment of a neoplasia, e.g., a melanoma, may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other cases, this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other aspects, it is envisaged that doses may be in the range of about 5 mg compound/Kg body to about 20 mg compound/Kg body. In other embodiments, the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic (i.e., cancer) cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Combination Therapies

In some cases, the DHHC3 inhibitors of the invention are administered in combination with any other standard therapy; such methods are known to the skilled artisan and described in Remington's Pharmaceutical Sciences by E. W. Martin. For example, the DHHC3 inhibitors of the invention are administered with an anti-PD-L1 inhibitor, e.g., an anti-PD-L1 antibody, or any other anti-neoplastic therapy, including but not limited to immunotherapy, therapeutic antibodies, targeted therapy, surgery, radiation therapy, or chemotherapy.

Kits or Pharmaceutical Systems

The present compositions may be assembled into kits or pharmaceutical systems for use in ameliorating a neoplasia (e.g., breast cancer). Kits or pharmaceutical systems according to this aspect of the invention comprise a carrier means, such as a box, carton, tube or the like, having in close confinement therein one or more container means, such as vials, tubes, ampoules, or bottles. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Materials and Methods

The following materials and methods were utilized in generating the results presented herein.

Cell Culture, Other Reagents and Western Blotting

Human breast cancer (MDA-MB-231, MCF-7, ZR-75, BT549, BT474) and kidney (HEK 293) cell lines were obtained from American Type Culture Collection (ATCC; Manassas, Va.) without further authentication. After 10-20 passages, frozen cells were newly thawed. *Mycoplasma* was tested using the MycoAlert kit (Lonza Biologics, Portsmouth, N.H.). Cells were cultured in DMEM and/or RPMI medium (Invitrogen, Grand Island, N.Y.) containing 10% FBS (Sigma, Mo.), HEPES and 1% penicillin-streptomycin (Invitrogen, Grand Island, N.Y.). Antibodies to DHHC3 (pAb) and MCP-1 (pAb) were from Abcam, (Cambridge, Mass.), and antibodies to p-FAK (pAb), total FAK (pAb), VEGF (pAb), total STAT3 (pAb) and IL-8 (pAb) were from Santa Cruz Biotechnology, Inc. (Dallas, Tex.). Antibodies to p-STAT3 (mAb), p-ERK (pAb), and total ERK (mAb) were from Cell Signaling technology (Danvers, Mass.), anti-TXNIP (mAb) was from MBL International (Woburn, Mass.), 4G10 (mAb) was from Millipore (Billerica, Mass.), and anti-EGFR (mAb) was from BD Biosciences (San Jose, Calif.). Dyes for measuring oxidative stress (CellROX) and cellular senescence (C12FDG) were from Invitrogen (Carlsbad, Calif.). Oxidative stress inhibitors, N-acetyl cysteine (NAC) and α-lipoic acid (α-LA) were from Sigma (Saint Louis, Mo.), and atorvastatin was from Cayman Chemicals (Ann Arbor, Mich.). Chemokine array analysis kit was from R&D systems (Minneapolis, Minn.). Cultured cells were lysed in 1% Triton X-100, and total protein was quantified using BCA protein estimation kit. Western blotting and relative band intensity densitometry were described previously (Sharma et al., 2012 Cell Mol Life Sci, 69:2233-44).

Gene Ablation and Reconstitution

Transient and stable, control and ZDHHC3 ablations were performed as described (Sharma et al., 2012 Cell Mol Life Sci, 69:223344). TXNIP was ablated using two different siRNA's from OriGene (Rockville, Md.). For ZDHHC3 reconstitution, ZDHHC3 cDNA was mutated to escape shRNA targeting ($D3^R$) and two "DHHC" palmitoylation site mutations were made ($D3^{R+DH/AA}$ & $D3^{R+C/S}$). These three cDNA's were cloned into lentiviral plasmids downstream of DHHC3 shRNA, and followed by DNA coding for C-terminal 2A linker peptide and GFP tag. These lentiviral plasmids were transfected into HEK293 cells along with pCMV-dR8.91 and VSV-G packaging plasmids, to produce lentiviral particles, which were subsequently used to infect target cells (MDA-MB-231) for stable expression. Plasmid expression in target cells was verified by GFP analysis and GFP positive cells were sorted by flow cytometry.

Mouse Xenograft Growth and Lung Metastasis Assays

For in vivo tumor growth experiments, control and ZDHHC3-ablated MDA-MB-231 cells were injected into female nude mice on both flanks either ectopically ($1.0 \times 10^6$ cells, s.c.) or orthotopically ($0.5 \times 10^6$ cells, into mammary fat pads), with 5 mice/group. Starting at day 5 post injection, tumors were measured using calipers and tumor volumes were calculated (length×width$^2$×0.5). Mice were sacrificed when tumor size reached 2 cm, and tumors were excised, weighed and portions were fixed and embedded in paraffin sections for immunohistochemical staining, while remaining portions were frozen and used for RNA isolation and DNA array analysis. For lung metastasis, control and ZDHHC3-ablated MDA-MB-231 ($1.0 \times 10^6$ cells) were injected into tail veins of SCID Beige mice (3 mice/group). After 5 weeks, mice were sacrificed and lungs were perfused with India Ink, excised and fixed with Fekete's solution. Tumor colonies (white) on lung surfaces were counted using a stereomicroscope. Paraffin embedded lung sections were H&E stained to assess colony size (using light microscope; 2× magnification).

Measurement of Oxidative Stress and Senescence

To assess oxidative stress/reactive oxygen species (ROS), control and ZDHHC3-ablated tumor cells were trypsinized and suspended in complete medium. After PBS wash, cells were loaded with 2 μM CellROX dye in complete medium (37° C., 30 min). Cells were then washed twice with IX PBS, incubated in complete media (37° C., 30 min), washed twice again with 1×PBS, and then analyzed by flow cytometry. Similarly, senescence was measured by loading suspended control and ZDHHC3 ablated cells with C12FDG dye (30 min, 37° C.) in complete medium. The C12FDG dye is converted by intracellular β-galactosidase (elevated in senescent cells) to produce fluorescence, which was quantitated by flow cytometry.

Chemokine Assay

As per array kit instructions (ARY017 Kit, R & D Systems), 500 μl of supernatant was collected from MDA-MB-231 cells (after 30 h in DMEM media with 1% BSA), and mixed with detection antibody (biotinylated) cocktail. Next nitrocellulose membranes (in duplicate) containing immobilized antibodies to 31 human chemokines were incubated overnight at 4° C. with supernatant/antibody mix. Membranes were then incubated with streptavidin-HRP solution followed by Chemi reagent mix and autoradiography detection. Signal intensities for each chemokine were estimated from pixel densities (Image Quant, version 5.2 software, GE Healthcare).

Immunohistochemical Staining

Human malignant and metastatic breast tumor microarray slides and normal controls (BR2082, BR10010a) were from US Biomax Inc. (Rockville, Md., USA), and stained for DHHC3 using Alkaline Phosphatase immunohistochemistry Detection kit (ZYAGEN, San Diego, USA). Briefly, slides were deparaffinized, rehydrated, boiled in 10 mmol/L citrate buffer (pH 6.0, 15 min), followed by blocking in serum (1 hr). Next, slides were incubated with 1:75 dilution of anti-DHHC3 antibody, Sigma (Saint Louis, Mo.) at 4° C. overnight, and then with biotinylated secondary antibody (1 hr) and streptavidin-alkaline phosphatase (AP) conjugate (30 min). Finally, slides were incubated with fast red solution and counterstained for hematoxylin. Staining intensity was analyzed by light microscopy and scoring (from 0=no staining to 3=high staining) was performed, in an unbiased and blinded fashion, by a pathology expert at Brigham and Women's Hospital, Boston.

Microarray Analysis

RNA was isolated using RNeasy kit (Qiagen, Germantown, Md.) from mammary fat pad derived xenograft tumors from control and ZDHHC3 ablated MDA-MB-231 cells. RNA was analyzed from two tumors of each group using U133A 2.0 Affymetrix gene chip array at Dana-Farber Cancer Institute, Microarray Core facility. Microarray data were processed using dChip software. Results were submitted to the GEO database and assigned accession number GSE102776.

Patient Survival and Tissue Expression Data

Data used for FIG. 1A and Table 1 were gathered from publicly available TCGA (The Cancer Genome Atlas) data accessed through the cbioportal.org database (Cerami et al., 2012 Cancer Discov, 2:4014; Gao et al., 2013 Sci Signal, 6:11). Survival curves and logrank tests were performed using the cBioPortal "survival" tool. Breast cancer patient samples are from non-identifiable patients, from a publicly available commercial source (US Biomax). As shown in Table 1, elevated DHHC3 gene expression correlates with diminished patient survival in multiple cancers.

Differential Protein Palmitoylation

Using described procedures (Yang et al., 2010 Mol Cell Proteomics, 9:54-70), protein lysates from MDA-MB-231 cells were subjected to TCEP [tris(2-carboxyethyl)phosphine]treatment to selectively reduce all disulfide bonds, followed by irreversible alkylation with NEM (N-ethylmaleimide) to block all free sulfhydryl moieties. Then, proteins were subjected to hydroxylamine (HA) treatment to cleave thioester bonds and newly freed SH moieties subsequently were biotinylated using BMCC-biotin reagent. Finally, biotinylated proteins were immunoprecipitated using neutrAvidin agarose beads, and transferred to nylon membrane for blotting.

TABLE 1

Correlation between elevated gene expression and diminished patient survival$_a$

| Type of Cancer | # of samples | ZDHHC3 | ZDHHC7 | ZDHHC5 | ZDHHC17 |
|---|---|---|---|---|---|
| Breast Invasive Carcinoma | 817 | $0.01^b$ | 0.03 | 0.38 | 0.66 |
| Thyroid Carcinoma | 509 | 0.01 | 0.46 | 0.45 | 0.37 |
| Skin Cutaneous Melanoma | 472 | 0.01 | 0.04 | $9.6e^{-4}$ | 0.38 |
| Uterine Corpus Endometrial Carcinoma | 333 | $3.1e^{-4}$ | 0.65 | 0.21 | 0.41 |
| Sarcoma | 263 | 0.02 | 0.20 | 0.09 | 0.57 |
| Bladder Urothelial Carcinoma | 129 | 0.04 | 0.2 | 0.09 | 0.2 |
| Papillary Thyroid Carcinoma | 486 | 0.04 | 0.32 | 0.45 | 0.5 |

$_a$Elevated gene expression is defined as Z score ≥2 (data from cBioPortal (14, 15)).
$^b$Numbers in last four columns represent P values (log rank test) from Kaplan Meier overall survival graphs.

Statistics

For evaluation of statistical significance, unpaired t tests were used unless otherwise indicated.

Example 2: DHHC3 Upregulation and Cancer Patient Survival

Figure 1B:
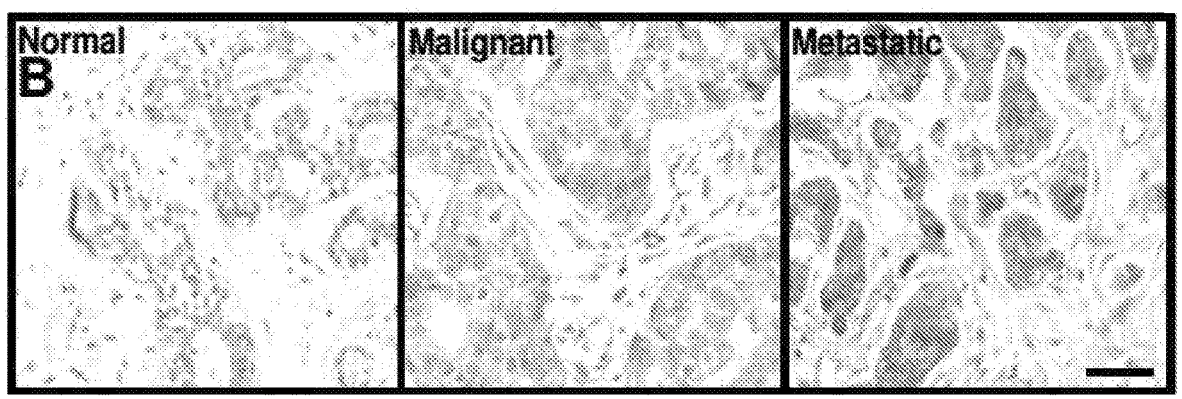
Figure 1C:
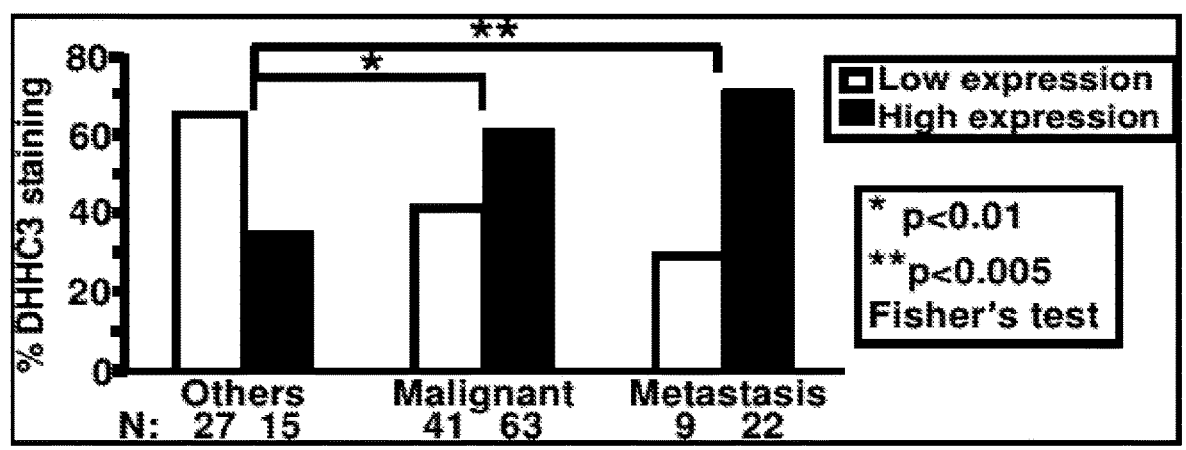
Figure 8A:
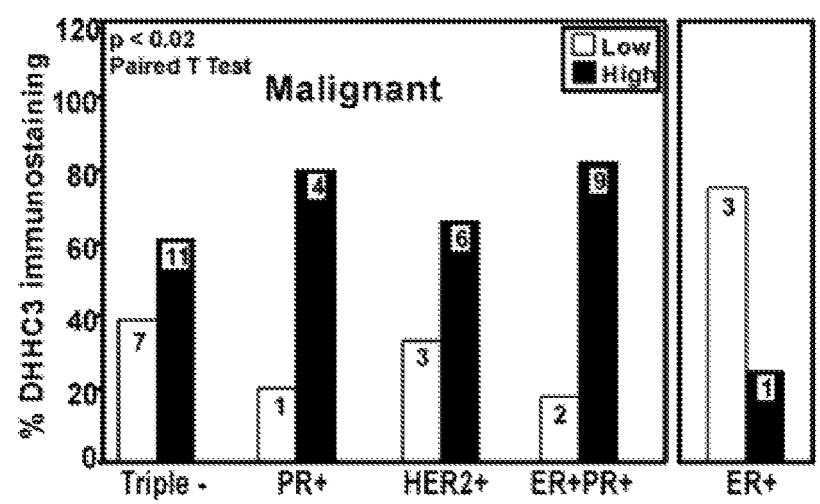
FIG. 8A-FIG. 8F is a series of bar graphs line graphs, and photographs showing that DHHC3 expression in malignant and metastatic human breast cancer subtypes and effects on breast tumor growth.
Figure 8B:
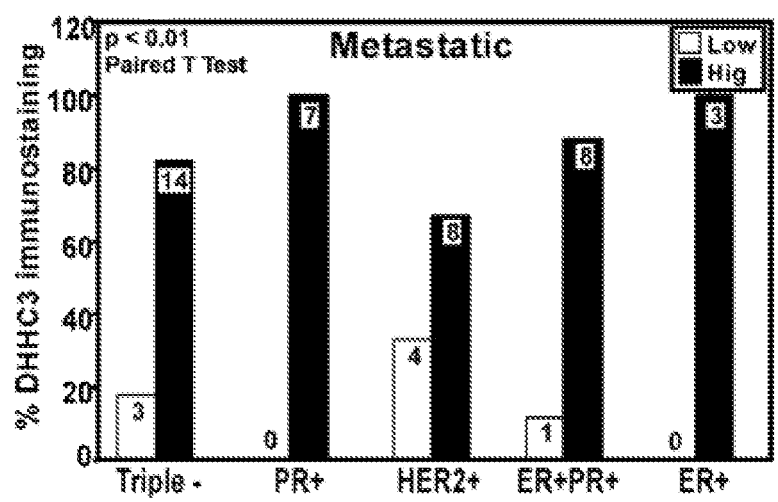

As described in detail below, DHHC3 expression correlates with patient survival and supports breast xenograft growth. Specifically, analysis of publicly available human breast invasive carcinoma patient data, from the cBioPortal TCGA database, indicated that elevated ZDHHC3 gene expression significantly correlated with diminished patient overall survival (FIG. 1A). Furthermore, DHHC3 protein expression was upregulated significantly in malignant human breast cancer and even more in metastatic breast cancer samples, in comparison to non-cancerous breast tissue (FIG. 1B and FIG. 1C). DHHC3 protein was also significantly upregulated in 4/5 major malignant primary breast cancer subtypes and 5/5 major metastatic breast cancer subtypes (FIG. 8A, FIG. 8B).

Upregulated ZDHHC3 gene expression correlated with significantly diminished overall patient survival in six other cancer types (Table 1). Upregulation of ZDHHC7, the protein acyl transferase with most sequence similarity to ZDHHC3, correlated with significantly diminished overall survival in 2/7 cancers (Table 1). By contrast, upregulation of other DHHC genes (ZDHHC5 and ZDHHC17), though previously linked to tumor xenograft growth, did not correlate with survival of these patients, except for ZDHHC5 in melanoma (Table 1).

Example 3: DHHC3 Supports Breast Cancer Xenograft Growth

Figure 8C:
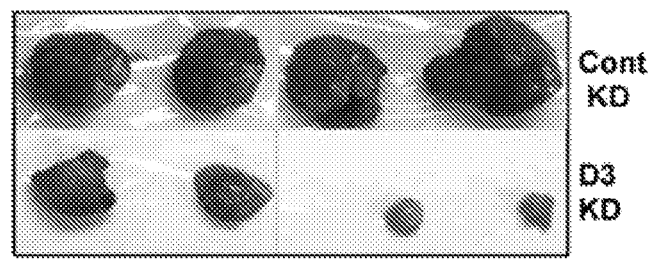
Figure 8D:
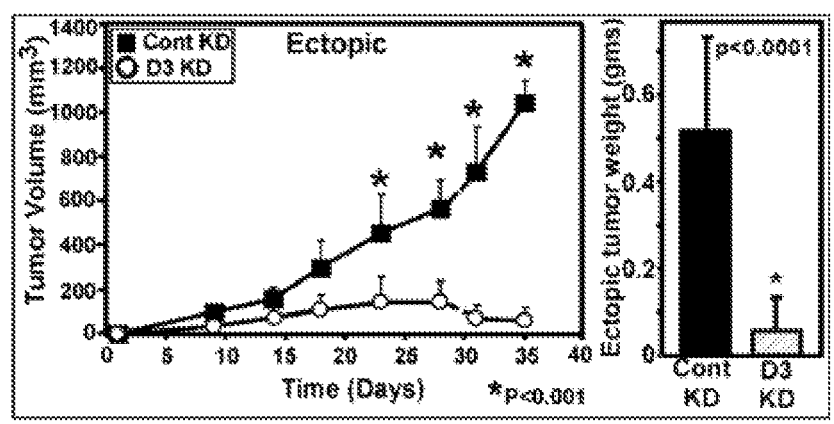
Figure 8E:
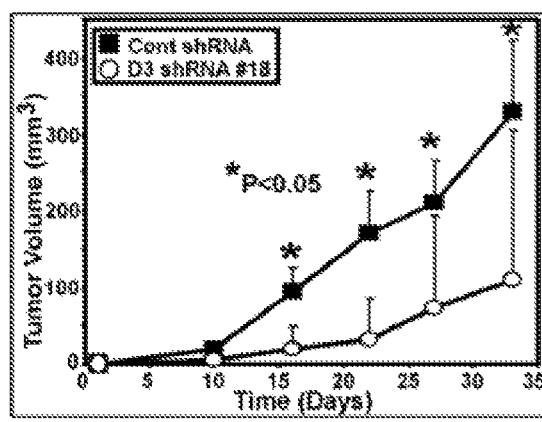
Figure 8F:
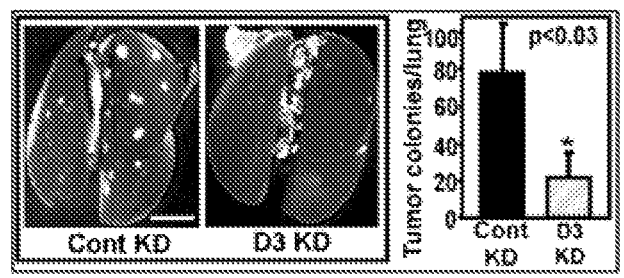
Figure 9A:
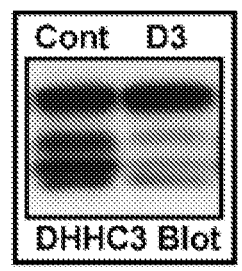
FIG. 9A-FIG. 9F is a series of photographs and bar charts showing validation of shRNA knockdown and DHHC3 ablation effects on mammary tumor cell growth and invasion.
Figure 9B:
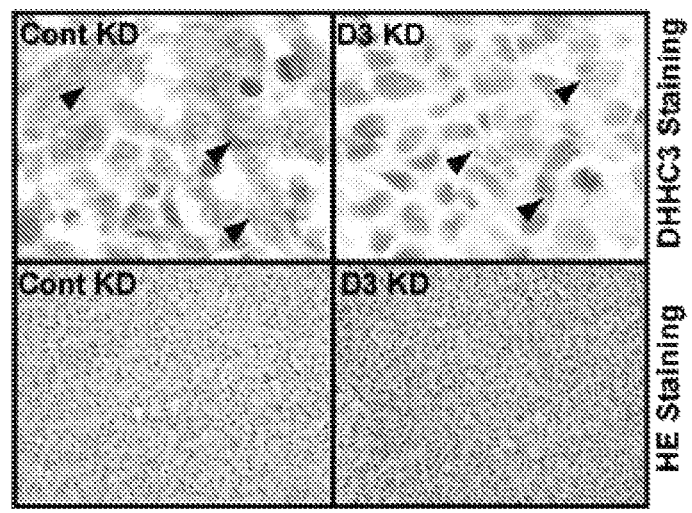

MDA-MB-231 human breast cancer cells stably ablated for ZDHHC3 (D3) yielded significantly reduced xenograft growth in female nude mice, whether in mammary fat pads (FIG. 1D and FIG. 8C) or at a subcutaneous site (FIG. 8D). Diminished ZDHHC3-ablated tumor growth was independently confirmed using another shRNA targeting sequence (FIG. 8E). After injection of ZDHHC3-ablated MDA-MB-231 cells into SCID mice tail veins, H&E-stained lung sections (4 weeks) showed significant reductions in colony size (FIG. 1E) and colony number (FIG. 8F), compared to control shRNA-injected cells. ZDHHC3 knockdown efficiency was >90%, as shown by DHHC3 immunoblotting (FIG. 9A) and by immunohistochemically stained xenograft tumor sections (FIG. 9B).

Example 4: Mechanistic Insights into Effects of DHHC3 Ablation

Figure 9C:
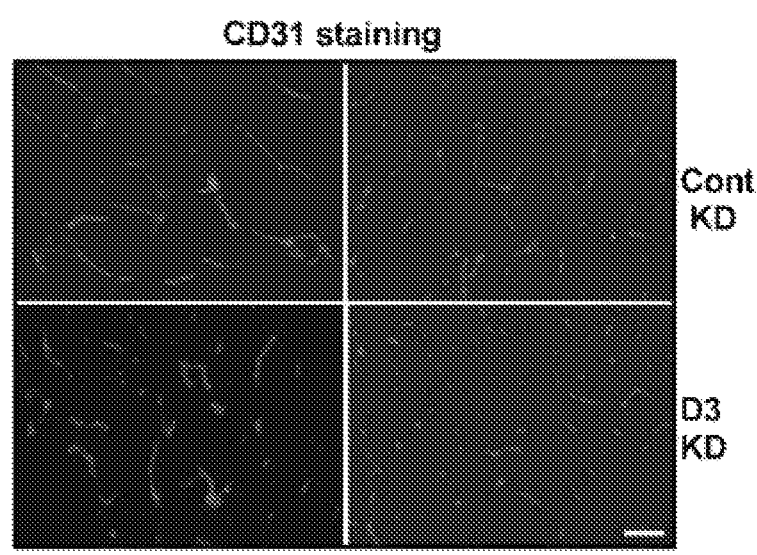
Figure 9D:
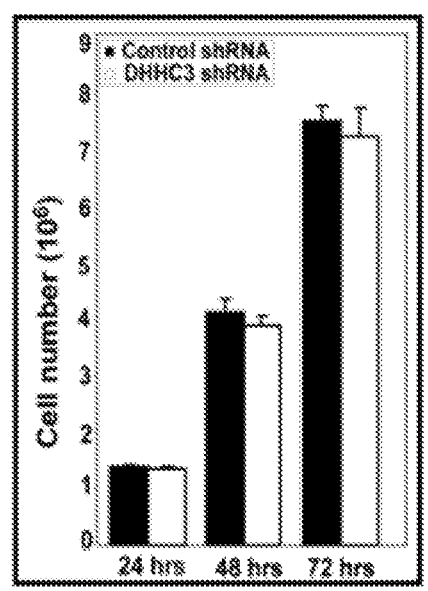
Figure 9E:
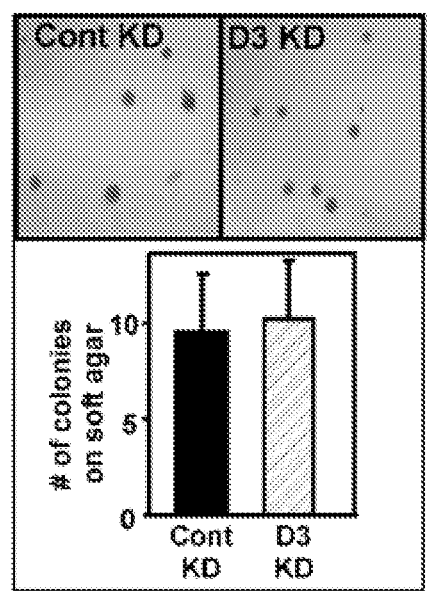
Figure 9F:
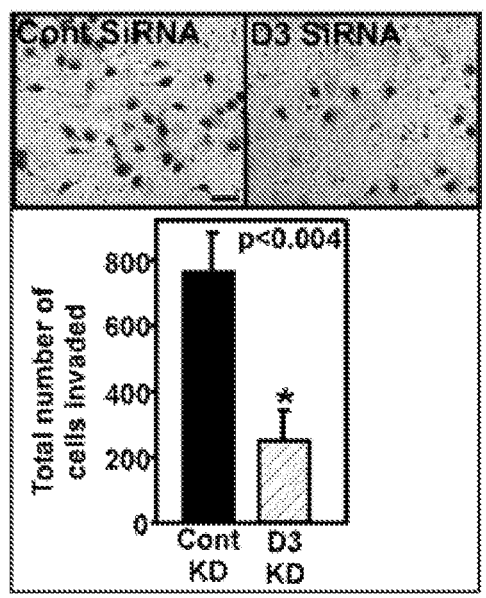

ZDHHC3 ablation minimally affected primary tumor xenograft angiogenesis (CD31 staining; FIG. 9C), cell proliferation (Ki67 staining), or apoptosis (TUNEL assay, caspase 3 cleavage). Furthermore, ZDHHC3 ablation minimally affected in vitro cell proliferation (up to 72 hr) or 3D soft agar growth (14 days) (FIG. 9D and FIG. 9E). However, invasion through Matrigel was significantly reduced (FIG. 9F), which may partly explain reduced lung colony numbers (FIG. 8F).

For unbiased mechanistic insight, DNA microarray analysis was performed on ZDHHC3-ablated orthotopic xenograft tumor samples. The complete list of results (Table 2) included 25 upregulated and 27 downregulated genes (>1.5-fold increase or decrease; P<0.05; Table 3). ZDHHC3 itself topped the list of downregulated genes. Importantly, changes in 29/52 genes (55.8%; Table 3) are consistent with increased oxidative stress and/or senescence. Altered expression of 21 additional genes typically linked to senescence, but not quite meeting rigorous criteria for inclusion in Table 3, are indicated in Table 4. Tumor suppressor genes VGLL3 and TXNIP were also upregulated in ZDHHC3-ablated samples (Table 3).

TABLE 2

DNA array results for control and ZDHHC3 ablated MDA-MB-231 cells

| | probe set | gene | Accession | EntrezGene | Description |
|---|---|---|---|---|---|
| 1 | Supplemental Table S2. DNA array results for control and ZDHHC3 ablated MDA-MB-231 cells | | | | |
| 2 | probe set | gene | Accession | EntrezGene | Description |
| 3 | 201008_s_at | thioredoxin interacting protein | NM_006472 | 10628 | Consensus includes gb: AA812232/FEA = EST/ DB_XREF = gi: 2881843/DB_XREF = est: ob84h09.s1/ CLONE = IMAGE: 1338113/UG = Hs.179526 |

TABLE 2-continued

DNA array results for control and ZDHHC3 ablated MDA-MB-231 cells

| | | | | | |
|---|---|---|---|---|---|
| 4 | 201368_at | zinc finger protein 36, C3H type-like 2 | AI356398 | 678 | upregulated by 1,25-dihydroxyvitamin D-3/ FL = gb: NM_006472.1 gb: S73591.1 Consensus includes gb: U07802/DEF = Human Tis11d gene, complete cds/FEA = mRNA/ DB_XREF = gi: 984508/UG = Hs.78909 butyrate response factor 2 (EGF-response factor 2)/ FL = gb: BC005010.1 gb: NM_006887.1 |
| 5 | 201438_at | collagen, type VI, alpha 3 | NM_004369 | 1293 | gb: NM_004369.1/DEF = *Homo sapiens* collagen, type VI, alpha 3 (COL6A3), mRNA./FEA = mRNA/ GEN = COL6A3/PROD = collagen, type VI, alpha 3/ DB_XREF = gi: 4758027/UG = Hs.80988 collagen, type VI, alpha 3/FL = gb: NM_004369.1 |
| 6 | 201711_x_at | RAN binding protein 2 | AI681120 | 5903 | gb: AI681120/DB_XREF = gi: 4891302/ DB_XREF = tx44b06.x1/CLONE = IMAGE: 2272403/ FEA = FLmRNA/CNT = 183/TID = Hs.199179.0/ TIER = Stack/STK = 9/UG = Hs.199179/LL = 5903/ UG_GENE = RANBP2/UG_TITLE = RAN binding protein 2/FL = gb: NM_006267.2 gb: D42063.1 |
| 7 | 201847_at | lipase A, lysosomal acid, cholesterol esterase (Wolman disease) | NM_000235 | 3988 | gb: NM_000235.1/DEF = *Homo sapiens* lipase A, lysosomal acid, cholesterol esterase (Wolman disease) (LIPA), mRNA./FEA = mRNA/GEN = LIPA/ PROD = lipase A precursor/DB_XREF = gi: 4557720/ UG = Hs.85226 lipase A, lysosomal acid, cholesterol esterase (Wolman disease)/FL = gb: M74775.1 gb: NM_000235.1 gb: U08464.1 |
| 8 | 201965_s_at | senataxin | NM_015046 | 23064 | gb: NM_015046.1/DB_XREF = gi: 7662211/ GEN = KIAA0625/FEA = FLmRNA/CNT = 233/ TID = Hs.154919.0/TIER = FL + Stack/STK = 39/ UG = Hs.154919/LL = 23064/DEF = *Homo sapiens* KIAA0625 protein (KIAA0625), mRNA./ PROD = KIAA0625 protein/FL = gb: NM_015046.1 |
| 9 | 202149_at | neural precursor cell expressed, developmentally down-regulated 9 | AL136139 | 4739 | gb: AL136139/DB_XREF = gi: 8217463/FEA = FLmRNA/ CNT = 161/TID = Hs.80261.0/TIER = Stack/STK = 41/ UG = Hs.80261/LL = 10543/UG_GENE = HEF1/ UG_TITLE = enhancer of filamentation 1 (cas-like docking: Crk-associated substrate related)/ DEF = Human DNA sequence from clone RP4-761I2 on chromosome 6 Contains 3 part of the gene for enhancer of filamentation (HEF1), ESTs, STSs and CpG islands/FL = gb: U64317.1 gb: NM_006403.1 gb: L43821.1 |
| 10 | 202279_at | chromosome 14 open reading frame 2 | NM_004894 | 9556 | gb: NM_004894.1/DEF = *Homo sapiens* chromosome 14 open reading frame 2 (C14ORF2), mRNA./ FEA = mRNA/GEN = C14ORF2/PROD = chromosome 14 open reading frame 2/DB_XREF = gi: 4758939/ UG = Hs.109052 chromosome 14 open reading frame 2/FL = gb: BC000429.1 gb: BC001944.1 gb: AF054175.1 gb: NM_004894.1 |
| 11 | 202481_at | dehydrogenase/ reductase (SDR family) member 3 | NM_004753 | 9249 | gb: NM_004753.1/DEF = *Homo sapiens* short-chain dehydrogenasereductase 1 (SDR1), mRNA./ FEA = mRNA/GEN = SDR1/PROD = short-chain dehydrogenasereductase 1/DB_XREF = gi: 4759083/ UG = Hs.17144 short-chain dehydrogenasereductase 1/FL = gb: BC002730.1 gb: AF061741.1 gb: NM_004753.1 |
| 12 | 202554_s_at | glutathione S-transferase M3 (brain) | AL527430 | 2947 | gb: AL527430/DB_XREF = gi: 12790923/ DB_XREF = AL527430/CLONE = CS0DC021YF13 (5 prime)/FEA = FLmRNA/CNT = 157/TID = Hs.2006.0/ TIER = Stack/STK = 54/UG = Hs.2006/LL = 2947/ UG_GENE = GSTM3/UG_TITLE = glutathione S-transferase M3 (brain)/FL = gb: NM_000849.1 gb: BC000088.1 gb: J05459.1 |
| 13 | 202759_s_at | A kinase (PRKA) anchor protein 2/// PALM2-AKAP2 protein | BE879367 | 11217/// 445815 | Consensus includes gb: BE879367/FEA = EST/ DB_XREF = gi: 10328143/DB_XREF = est: 601484628F1/ CLONE = IMAGE: 3887262/UG = Hs.42322 A kinase (PRKA) anchor protein 2/FL = gb: AB023137.1 gb: NM_007203.1 |
| 14 | 202957_at | hematopoietic cell-specific Lyn substrate 1 | NM_005335 | 3059 | gb: NM_005335.1/DB_XREF = gi: 4885404/ GEN = HCLS1/FEA = FLmRNA/CNT = 140/ TID = Hs.14601.0/TIER = FL + Stack/STK = 59/ UG = Hs.14601/LL = 3059/DEF = *Homo sapiens* hematopoietic cell-specific Lyn substrate 1 (HCLS1), mRNA./PROD = hematopoietic cell-specific Lyn substrate 1/FL = gb: NM_005335.1 |
| 15 | 203186_s_at | S100 calcium binding | NM_002961 | 6275 | gb: NM_002961.2/DEF = *Homo sapiens* S100 calcium-binding protein A4 (calcium protein, calvasculin, |

TABLE 2-continued

DNA array results for control and ZDHHC3 ablated MDA-MB-231 cells

| | | | | | |
|---|---|---|---|---|---|
| | | protein A4 (calcium protein, calvasculin, metastasin, murine placental homolog) | | | metastasin, murine placental homolog) (S100A4), transcript variant 1, mRNA./FEA = mRNA/ GEN = S100A4/PROD = S100 calcium-binding protein A4/DB_XREF = gi: 9845514/UG = Hs.81256 S100 calcium-binding protein A4 (calcium protein, calvasculin, metastasin, murine placental homolog)/ FL = gb: NM_002961.2 gb: NM_019554.1 |
| 16 | 203568_s_at | tripartite motif-containing 38 | NM_006355 | 10475 | gb: NM_006355.1/DB_XREF = gi: 5454013/ GEN = RNF15/FEA = FLmRNA/CNT = 108/ TID = Hs.59545.0/TIER = FL + Stack/STK = 16/ UG = Hs.59545/LL = 10475/DEF = Homo sapiens ring finger protein 15 (RNF15), mRNA./PROD = ring finger protein 15/FL = gb: U90547.1 gb: NM_006355.1 |
| 17 | 204151_x_at | aldo-keto reductase family 1, member C1 (dihydrodiol dehydrogenase 1; 20-alpha (3-alpha)-hydroxysteroid dehydrogenase) | NM_001353 | 1645 | gb: NM_001353.2/DB_XREF = gi: 5453542/ GEN = AKR1C1/FEA = FLmRNA/CNT = 107/ TID = Hs.306098.0/TIER = FL + Stack/STK = 25/ UG = Hs.306098/LL = 1645/DEF = Homo sapiens aldo-keto reductase family 1, member C1 (dihydrodiol dehydrogenase 1; 20-alpha (3-alpha)-hydroxysteroid dehydrogenase) (AKR1C1), mRNA./PROD = aldo-keto reductase family 1, member C1(dihydrodiol dehydrogenase 1; 20-alpha(3-alpha)-hydroxysteroid dehydrogenase)/FL = gb: NM_001353.2 gb: M86609.1 gb: U05684.1 |
| 18 | 204218_at | chromosome 11 open reading frame 51 | NM_014042 | 25906 | gb: NM_014042.1/DB_XREF = gi: 7661621/ GEN = DKFZP564M082/FEA = FLmRNA/CNT = 67/ TID = Hs.38044.0/TIER = FL + Stack/STK = 18/ UG = Hs.38044/LL = 25906/DEF = Homo sapiens DKFZP564M082 protein (DKFZP564M082), mRNA./ PROD = DKFZP564M082 protein/FL = gb: AF077206.1 gb: BC005156.1 gb: AL080071.1 gb: NM_014042.1 gb: BC005393.1 |
| 19 | 204387_x_at | mitochondrial ribosomal protein 63 | NM_024026 | 78988 | gb: NM_024026.1/DEF = Homo sapiens hypothetical protein MGC3243 (MGC3243), mRNA./FEA = mRNA/ GEN = MGC3243/PROD = hypothetical protein MGC3243/DB_XREF = gi: 13128969/UG = Hs.182695 hypothetical protein MGC3243/FL = gb: BC000002.1 gb: NM_024026.1 |
| 20 | 204461_x_at | RAD1 homolog (S. pombe) | NM_002853 | 5810 | gb: NM_002853.1/DEF = Homo sapiens RAD1 (S. pombe) homolog (RAD1), mRNA./FEA = mRNA/ GEN = RAD1/ PROD = RAD1 (S. pombe) homolog/ DB_XREF = gi: 4506384/UG = Hs.7179 RAD1 (S. pombe) homolog/FL = gb: AF058392.1 gb: AF073524.1 gb: AF074717.1 gb: AF011905.1 gb: AF084512.1 gb: AF030933.1 gb: AF076841.1 gb: NM_002853.1 |
| 21 | 204525_at | PHD finger protein 14 | NM_014660 | 9678 | gb: NM_014660.1/DB_XREF = gi: 7662303/ GEN = KIAA0783/FEA = FLmRNA/CNT = 49/ TID = Hs.156276.0/TIER = FL/STK = 4/UG = Hs.156276/ LL = 9678/DEF = Homo sapiens KIAA0783 gene product (KIAA0783), mRNA./PROD = KIAA0783 gene product/FL = gb: AB018326.1 gb: NM_014660.1 |
| 22 | 204852_s_at | protein tyrosine phosphatase, non-receptor type 7 | NM_002832 | 5778 | gb: NM_002832.1/DEF = Homo sapiens protein tyrosine phosphatase, non-receptor type 7 (PTPN7), mRNA./FEA = mRNA/GEN = PTPN7/PROD = protein tyrosine phosphatase, non-receptor type7/ DB_XREF = gi: 4506298/UG = Hs.35 protein tyrosine phosphatase, non-receptor type 7/ FL = gb: BC001746.1 gb: M64322.1 gb: NM_002832.1 |
| 23 | 204860_s_at | baculoviral IAP repeat-containing 1/// similar to Baculoviral IAP repeat-containing protein 1 (Neuronal apoptosis inhibitory protein)/// similar to Baculoviral IAP repeat-containing protein 1 (Neuronal | AI817801 | 4671/// 648984/// 653371 | gb: AI817801/DB_XREF = gi: 5436880/ DB_XREF = wk40d12.x1/CLONE = IMAGE: 2417879/ FEA = FLmRNA/CNT = 49/TID = Hs.79019.0/ TIER = Stack/STK = 10/UG = Hs.79019/LL = 4671/ UG_GENE = BIRC1/UG_TITLE = baculoviral IAP repeat-containing 1/FL = gb: NM_004536.1 gb: U19251.1 |

TABLE 2-continued

DNA array results for control and ZDHHC3 ablated MDA-MB-231 cells

| | | | | | |
|---|---|---|---|---|---|
| | | apoptosis inhibitory protein) | | | |
| 24 | 205362_s_at | prefoldin subunit 4 | NM_002623 | 5203 | gb: NM_002623.2/DEF = *Homo sapiens* prefoldin 4 (PFDN4), mRNA./FEA = mRNA/GEN = PFDN4/ PROD = prefoldin 4/DB_XREF = gi: 12408676/ UG = Hs.91161 prefoldin 4/FL = gb: NM_002623.2 gb: U41816.1 |
| 25 | 205511_at | hypothetical protein FLJ10038 | NM_017976 | 55056 | gb: NM_017976.1/DEF = *Homo sapiens* hypothetical protein FLJ10038 (FLJ10038), mRNA./FEA = mRNA/ GEN = FLJ10038/PROD = hypothetical protein FLJ10038/DB_XREF = gi: 8922197/UG = Hs.181202 hypothetical protein FLJ10038/FL = gb: NM_017976.1 |
| 26 | 205539_at | advillin | NM_006576 | 10677 | gb: NM_006576.1/DB_XREF = gi: 5729735/GEN = AVIL/ FEA = FLmRNA/CNT = 32/TID = Hs.47344.0/TIER = FL/ STK = 0/UG = Hs.47344/LL = 10677/DEF = *Homo sapiens* advillin (AVIL), mRNA./ PROD = advillin/FL = gb: AF041449.1 gb: NM_006576.1 |
| 27 | 205681_at | BCL2-related protein A1 | NM_004049 | 597 | gb: NM_004049.1/DB_XREF = gi: 4757839/ GEN = BCL2A1/FEA = FLmRNA/CNT = 32/ TID = Hs.227817.0/TIER = FL + Stack/STK = 11/ UG = Hs.227817/LL = 597/DEF = *Homo sapiens* BCL2-related protein A1 (BCL2A1), mRNA./PROD = BCL2-related protein A1/FL = gb: U27467.1 gb: U29680.1 gb: NM_004049.1 |
| 28 | 205741_s_at | dystrobrevin, alpha | NM_001392 | 1837 | gb: NM_001392.1/DB_XREF = gi: 4503410/ GEN = DTNA/FEA = FLmRNA/CNT = 26/ TID = Hs.54435.0/TIER = FL + Stack/STK = 15/ UG = Hs.54435/LL = 1837/DEF = *Homo sapiens* dystrobrevin, alpha (DTNA), mRNA./ PROD = dystrobrevin, alpha/FL = gb: NM_001392.1 gb: BC005300.1 |
| 29 | 205871_at | plasminogen-like B2/// plasminogen-like B1/// plasminogen-like A1 | BC005379 | 285189/// 5342/// 5343 | gb: BC005379.1/DB_XREF = gi: 13529238/ FEA = FLmRNA/CNT = 46/TID = Hs.262869.0/TIER = FL/ STK = 2/UG = Hs.262869/LL = 5342/UG_GENE = PLGL/ DEF = *Homo sapiens*, Similar to plasminogen, clone MGC: 12496, mRNA, complete cds./ PROD = Similar to plasminogen/FL = gb: NM_002665.1 gb: M93143.2 gb: BC005379.1 |
| 30 | 205888_s_at | janus kinase and microtubule interacting protein 2 | AI962693 | 9832 | Consensus includes gb: AI962693/FEA = EST/ DB_XREF = gi: 5755406/DB_XREF = est: wq55a09.x1/ CLONE = IMAGE: 2475160/UG = Hs.43107 KIAA0555 gene product/FL = gb: AB011127.1 gb: NM_014790.1 |
| 31 | 206659_at | hypothetical protein FLJ14082 | NM_025024 | 80092 | gb: NM_025024.1/DB_XREF = gi: 13376542/ GEN = FLJ14082/FEA = FLmRNA/CNT = 10/ TID = Hs.287622.0/TIER = FL/STK = 1/UG = Hs.287622/ LL = 80092/DEF = *Homo sapiens* hypothetical protein FLJ14082 (FLJ14082), mRNA./PROD = hypothetical protein FLJ14082/FL = gb: NM_025024.1 |
| 32 | 207487_at | hypothetical protein FLJ11996 | NM_024976 | 80041 | gb: NM_024976.1/DB_XREF = gi: 13376475/ GEN = FLJ11996/FEA = FLmRNA/CNT = 4/ TID = Hs.287473.0/TIER = FL/STK = 0/UG = Hs.287473/ LL = 80041/DEF = *Homo sapiens* hypothetical protein FLJ11996 (FLJ11996), mRNA./PROD = hypothetical protein FLJ11996/FL = gb: NM_024976.1 |
| 33 | 207598_x_at | X-ray repair complementing defective repair in Chinese hamster cells 2 | NM_005431 | 7516 | gb: NM_005431.1/DB_XREF = gi: 4885656/ GEN = XRCC2/FEA = FLmRNA/CNT = 5/ TID = Hs.129727.0/TIER = FL/STK = 0/UG = Hs.129727/ LL = 7516/DEF = *Homo sapiens* X-ray repair complementing defective repair in Chinese hamster cells 2 (XRCC2), mRNA./PROD = X-ray repair cross complementing protein 2/FL = gb: AF035587.1 gb: NM_005431.1 |
| 34 | 207730_x_at | Hepatoma-derived growth factor-related protein 2 | NM_017932 | 84717 | gb: NM_017932.1/DB_XREF = gi: 8923629/ GEN = FLJ20700/FEA = FLmRNA/CNT = 3/ TID = Hs.272222.0/TIER = FL/STK = 0/UG = Hs.272222/ LL = 55021/DEF = *Homo sapiens* hypothetical protein FLJ20700 (FLJ20700), mRNA./PROD = hypothetical protein FLJ20700/FL = gb: NM_017932.1 |
| 35 | 207829_s_at | BCL2/ adenovirus E1B 19 kDa interacting protein 1 | NM_013978 | 662 | gb: NM_013978.1/DB_XREF = gi: 7524347/GEN = BNIP1/ FEA = FLmRNA/CNT = 4/TID = Hs.77572.2/ TIER = FL/STK = 0/UG = Hs.77572/LL = 662/DEF = *Homo sapiens* BCL2adenovirus E1B 19 kD-interacting protein 1 (BNIP1), transcript variant BNIP1-a, mRNA./ PROD = BCL2adenovirus E1B 19 kD-interacting protein 1, isoform BNIP1-a/FL = gb: NM_013978.1 gb: AF083956.1 |

TABLE 2-continued

DNA array results for control and ZDHHC3 ablated MDA-MB-231 cells

| 36 | 208154_at | mesenchymal stem cell protein DSCD28 | NM_016646 | 51336 | gb: NM_016646.1/DB_XREF = gi: 7706197/ GEN = LOC51336/FEA = FLmRNA/CNT = 2/ TID = Hs.272416.0/TIER = FL/STK = 0/UG = Hs.272416/ LL = 51336/DEF = *Homo sapiens* mesenchymal stem cell protein DSCD28 (LOC51336), mRNA./ PROD = mesenchymal stem cell protein DSCD28/ FL = gb: NM_016646.1 gb: AF242772.1 |
| --- | --- | --- | --- | --- | --- |
| 37 | 208185_x_at | gb: NM_016415.1/ DB_XREF = gi: 10047109/ GEN = LOC51216/ FEA = FLmRNA/ CNT = 2/ TID = Hs.277887.0/ TIER = ConsEnd/ STK = 0/ UG = Hs.277887/ LL = 51216/ DEF = *Homo sapiens* clone FLB3816 (LOC51216), mRNA./ PROD = clone FLB3816/ FL = gb: NM_016415.1 gb: AF113685.1 | NM_016415 | | gb: NM_016415.1/DB_XREF = gi: 10047109/ GEN = LOC51216/FEA = FLmRNA/CNT = 2/ TID = Hs.277887.0/TIER = ConsEnd/STK = 0/ UG = Hs.277887/LL = 51216/DEF = *Homo sapiens* clone FLB3816 (LOC51216), mRNA./PROD = clone FLB3816/FL = gb: NM_016415.1 gb: AF113685.1 |
| 38 | 208238_x_at | gb: NM_013344.1/ DB_XREF = gi: 7106350/ GEN = LZLP/ FEA = FLmRNA/ CNT = 2/ TID = Hs.278952.0/ TIER = FL/ STK = 0/ UG = Hs.278952/ LL = 29932/ DEF = *Homo sapiens* leucine zipper-like protein (LZLP), mRNA./ PROD = leucine zipper-like protein/FL = gb: NM_013344.1 gb: AF159055.1 | NM_013344 | | gb: NM_013344.1/DB_XREF = gi: 7106350/ GEN = LZLP/ FEA = FLmRNA/CNT = 2/TID = Hs.278952.0/TIER = FL/ STK = 0/UG = Hs.278952/LL = 29932/DEF = *Homo sapiens* leucine zipper-like protein (LZLP), mRNA./PROD = leucine zipper-like protein/ FL = gb: NM_013344.1 gb: AF159055.1 |
| 39 | 208386_x_at | DMC1 dosage suppressor of mck1 homolog, meiosis-specific homologous recombination (yeast) | NM_007068 | 11144 | gb: NM_007068.1/DB_XREF = gi: 5901995/ GEN = DMC1/FEA = FLmRNA/CNT = 4/TID = Hs.37181.0/ TIER = FL/STK = 0/UG = Hs.37181/LL = 11144/ DEF = *Homo sapiens* DMC1 (dosage suppressor of mck1, yeast homolog) meiosis-specific homologous recombination (DMC1), mRNA./PROD = DMC1 (dosage suppressor of mck1, yeast homolog)meiosis-specific homologous recombination/ FL = gb: NM_007068.1 gb: D64108.1 gb: D63882.1 |
| 40 | 208498_s_at | amylase, alpha 1A; salivary/// amylase, alpha 1B; salivary/// amylase, alpha 1C; salivary/// amylase, alpha 2A; pancreatic/// amylase, alpha 2B (pancreatic)/// similar to Pancreatic alpha-amylase precursor (PA) | NM_004038 | 276/// 277/// 278/// 279/// 280/// 647537/// 648759 | gb: NM_004038.1/DB_XREF = gi: 4757749/ GEN = AMY1A/FEA = FLmRNA/CNT = 2/ TID = Hs.274376.0/TIER = FL/STK = 0/UG = Hs.274376/ LL = 276/DEF = *Homo sapiens* amylase, alpha 1A; salivary (AMY1A), mRNA./PROD = amylase, alpha 1A; salivary/FL = gb: NM_004038.1 |

TABLE 2-continued

DNA array results for control and ZDHHC3 ablated MDA-MB-231 cells

| | | | | | |
|---|---|---|---|---|---|
| | | (1,4-alpha-D-glucan glucanohydrolase)/// similar to Salivary alpha-amylase precursor (1,4-alpha-D-glucan glucanohydrolase) | | | |
| 41 | 208760_at | Ubiquitin-conjugating enzyme E2I (UBC9 homolog, yeast) | AL031714 | 7329 | gb: AL031714/DB_XREF = gi: 4775608/FEA = FLmRNA/ CNT = 328/TID = Hs.84285.0/TIER = Stack/STK = 30/ UG = Hs.84285/LL = 7329/UG_GENE = UBE2I/ UG_TITLE = ubiquitin-conjugating enzyme E2I (homologous to yeast UBC9)/DEF = Human DNA sequence from clone LA16-358B7 on chromosome 16 Contains the UBE2I gene for ubiquitin-conjugating enzyme E2I (homologous to yeast UBC9), and an RPS20 (40S Ribosomal protein S20) pseudogene. Contains ESTs, STSs. GSSs and a putative CpG is . . ./FL = gb: U31933.1 gb: U66867.1 gb: U38785.1 gb: U66818.1 gb: NM_003345.1 gb: BC000427.1 gb: BC004429.1 gb: U31882.1 gb: U45328.1 gb: U29092.1 |
| 42 | 209006_s_at | chromosome 1 open reading frame 63 | AF247168 | 57035 | gb: AF247168.1/DB_XREF = gi: 12005626/ GEN = NPD014/FEA = FLmRNA/CNT = 237/ TID = Hs.8084.0/TIER = FL + Stack/STK = 13/ UG = Hs.8084/LL = 57035/DEF = Homo sapiens NPD014 (NPD014) mRNA, complete cds./ PROD = NPD014/ FL = gb: AF247168.1 gb: AF267856.1 |
| 43 | 209012_at | triple functional domain (PTPRF interacting) | AV718192 | 7204 | gb: AV718192/DB_XREF = gi: 10815344/ DB_XREF = AV718192/CLONE = FHTAABE08/ FEA = FLmRNA/CNT = 235/TID = Hs.171957.1/ TIER = Stack/STK = 47/UG = Hs.171957/LL = 7204/ UG_GENE = TRIO/UG_TITLE = triple functional domain (PTPRF interacting)/FL = gb: AF091395.1 |
| 44 | 209531_at | glutathione transferase zeta 1 (maleylacetoacetate isomerase) | BC001453 | 2954 | gb: BC001453.1/DB_XREF = gi: 12655190/ FEA = FLmRNA/ CNT = 127/TID = Hs.26403.0/ TIER = FL + Stack/STK = 54/ UG = Hs.26403/LL = 2954/UG_GENE = GSTZ1/ DEF = Homo sapiens, glutathione transferase zeta 1 (maleylacetoacetate isomerase), clone MGC: 2029, mRNA, complete cds./ PROD = glutathione transferase zeta 1(maleylacetoacetate isomerase)/ FL = gb: NM_001513.1 gb: BC001453.1 gb: U86529.1 |
| 45 | 209689_at | coiled-coil domain containing 93 | BC005078 | 54520 | gb: BC005078.1/DB_XREF = gi: 13477224/ FEA = FLmRNA/CNT = 76/TID = Hs.26118.0/ TIER = FL + Stack/STK = 41/UG = Hs.26118 /DEF = Homo sapiens, clone MGC: 13033, mRNA, complete cds./PROD = Unknown (protein for MGC: 13033)/FL = gb: BC005078.1 |
| 46 | 209714_s_at | cyclin-dependent kinase inhibitor 3 (CDK2-associated dual specificity phosphatase) | AF213033 | 1033 | gb: AF213033.1/DB_XREF = gi: 12734643/ FEA = FLmRNA/CNT = 87/TID = Hs.84113.0/TIER = FL/ STK = 0/UG = Hs.84113/LL = 1033/UG_GENE = CDKN3/ DEF = Homo sapiens isolate BX-01 cyclin-dependent kinase associated protein phosphatase mRNA, complete cds./PROD = cyclin-dependent kinase associated proteinphosphatase/FL = gb: L27711.1 gb: L25876.1 gb: AF213037.1 gb: AF213041.1 gb: AF213052.1 gb: AF213033.1 gb: AF213039.1 gb: AF213036.1 gb: AF213046.1 gb: AF213053.1 gb: AF213040.1 gb: AF213048.1 gb: AF213044.1 gb: AF213049.1 gb: AF213042.1 gb: AF213051.1 gb: AF213038.1 gb: AF213047.1 gb: AF213050.1 gb: AF213034.1 gb: AF213035.1 gb: NM_005192.1 gb: U02681.1 |
| 47 | 209907_s_at | intersectin 2 | AF182198 | 50618 | gb: AF182198.1/DB_XREF = gi: 7329075/GEN = ITSN2/ FEA = FLmRNA/CNT = 34/TID = Hs.166184.2/TIER = FL/ STK = 4/UG = Hs.166184/LL = 50618/DEF = Homo sapiens intersectin 2 long isoform (ITSN2) mRNA, complete cds./PROD = intersectin 2 long isoform/ FL = gb: AF182198.1 |
| 48 | 210528_at | major histocompatibility complex, class I-related | AF010447 | 3140 | gb: AF010447.1/DB_XREF = gi: 4102223/GEN = MR1C/ FEA = FLmRNA/CNT = 4/TID = Hs.101840.2/TIER = FL/ STK = 2/UG = Hs.101840/LL = 3140/DEF = Homo sapiens MHC class I related protein 1 isoform C (MR1C) mRNA, complete cds./PROD = MHC class I related protein 1 isoform C/FL = gb: AF010447.1 |
| 49 | 210534_s_at | B9 protein | BC002944 | 27077 | gb: BC002944.1/DB_XREF = gi: 12804172/ FEA = FLmRNA/CNT = 4/TID = Hs.11955.1/TIER = FL/ |

TABLE 2-continued

*DNA array results for control and ZDHHC3 ablated MDA-MB-231 cells*

| | | | | | |
|---|---|---|---|---|---|
| | | | | | STK = 0/UG = Hs.11955/LL = 27077/UG_GENE = B9/ DEF = *Homo sapiens*, Similar to B9 protein, clone MGC: 11339, mRNA, complete cds./PROD = Similar to B9 protein/FL = gb: BC002944.1 |
| 50 | 210598_at | gb: AF130051.1/ DEF = *Homo sapiens* clone FLB3535 PRO0898 mRNA, complete cds./ FEA = mRNA/ PROD = PRO0898/ DB_XREF = gi: 11493408/ UG = Hs.306960 *Homo sapiens* clone FLB3535 PRO0898 mRNA, complete cds/ FL = gb: AF130051.1 | AF130051 | | gb: AF130051.1/DEF = *Homo sapiens* clone FLB3535 PRO0898 mRNA, complete cds./FEA = mRNA/ PROD = PRO0898/DB_XREF = gi: 11493408/ UG = Hs.306960 *Homo sapiens* clone FLB3535 PRO0898 mRNA, complete cds/FL = gb: AF130051.1 |
| 51 | 210892_s_at | general transcription factor II, i | BC004472 | 2969 | gb: BC004472.1/DB_XREF = gi: 13325321/ FEA = FLmRNA/CNT = 2/TID = Hs.278589.2/ TIER = FL/STK = 0/UG = Hs.278589/LL = 2969/ UG_GENE = GTF2I/DEF = *Homo sapiens*, Similar to general transcription factor II, i, clone MGC: 10428, mRNA, complete cds./PROD = Similar to general transcription factor II, i/FL = gb: BC004472.1 |
| 52 | 211114_x_at | survival of motor neuron protein interacting protein 1 | AB037702 | 8487 | gb: AB037702.1/DEF = *Homo sapiens* SIP1-gamma mRNA for SMN interacting protein 1-gamma, complete cds./FEA = mRNA/GEN = SIP1-gamma/ PROD = SMN interacting protein 1-gamma/ DB_XREF = gi: 9650994/UG = Hs.102456 survival of motor neuron protein interacting protein 1/ FL = gb: AB037702.1 |
| 53 | 211115_x_at | survival of motor neuron protein interacting protein 1 | AB037703 | 8487 | gb: AB037703.1/DEF = *Homo sapiens* SIP1-delta mRNA for SMN interacting protein 1-delta, complete cds./FEA = mRNA/GEN = SIP1-delta/PROD = SMN interacting protein 1-delta/DB_XREF = gi: 9650996/ UG = Hs.102456 survival of motor neuron protein interacting protein 1/FL = gb: AB037703.1 |
| 54 | 211302_s_at | phosphodiesterase 4B, cAMP-specific (phosphodiesterase E4 dunce homolog, *Drosophila*) | L20966 | 5142 | gb: L20966.1/DEF = Human phosphodiesterase mRNA, complete cds./FEA = mRNA/ PROD = phosphodiesterase/DB_XREF = gi: 347121/ UG = Hs.188 phosphodiesterase 4B, cAMP-specific (dunce (*Drosophila*)-homolog phosphodiesterase E4)/ FL = gb: L20966.1 |
| 55 | 211732_x_at | histamine N-methyltransferase/// histamine N-methyltransferase | BC005907 | 3176 | gb: BC005907.1/DB_XREF = gi: 13543496/ FEA = FLmRNA/CNT = 1/TID = HsAffx.900754.434/ TIER = FL/STK = 0/DEF = *Homo sapiens*, Similar to histamine N-methyltransferase, clone MGC: 14500, mRNA, complete cds./PROD = Similar to histamine N-methyltransferase/FL = gb: BC005907.1 |
| 56 | 211796_s_at | T cell receptor beta variable 21-1/// T cell receptor beta variable 19/// T cell receptor beta variable 5-4/// T cell receptor beta variable 3-1/// T cell receptor beta constant 1/// similar to T-cell receptor beta chain V region CTL-L17 precursor | AF043179 | 28566/// 28568/// 28611/// 28619/// 28639/// 647353 | gb: AF043179.1/DB_XREF = gi: 3002924/ GEN = TCRBV13S1-TCRBJ2S1/FEA = FLmRNA/CNT = 3/ TID = Hs.303157.6/TIER = FL/STK = 0/UG = Hs.303157/ LL = 6957/DEF = *Homo sapiens* T cell receptor beta chain (TCRBV13S1-TCRBJ2S1) mRNA, complete cds./ PROD = T cell receptor beta chain/ FL = gb: AF043179.1 |
| 57 | 211809_x_at | collagen, type XIII, alpha 1 | M59217 | 1305 | gb: M59217.1/DEF = Human collagen type XIII alpha-1 mRNA, complete cds./FEA = CDS/GEN = COL13A1/ PROD = alpha-1 type XIII collagen/ DB_XREF = gi: 178319/UG = Hs.211933 collagen, type XIII, alpha 1/FL = gb: M59217.1 |
| 58 | 211929_at | heterogeneous nuclear | BF195526 | 220988 | Consensus includes gb: AA527502/FEA = EST/ DB_XREF = gi: 2269571/DB_XREF = est: ng41f10.s1/ |

TABLE 2-continued

DNA array results for control and ZDHHC3 ablated MDA-MB-231 cells

| | | | | | |
|---|---|---|---|---|---|
| | | ribonucleoprotein A3 | | | CLONE = IMAGE: 937387/UG = Hs.249247 heterogeneous nuclear protein similar to rat helix destabilizing protein |
| 59 | 211980_at | collagen, type IV, alpha 1 | AI922605 | 1282 | gb: AI922605/DB_XREF = gi: 5658569/ DB_XREF = wm90c05.x1/CLONE = IMAGE: 2443208/ FEA = FLmRNA/CNT = 492/TID = Hs.119129.0/ TIER = Stack/STK = 55/UG = Hs.119129/LL = 1282/ UG_GENE = COL4A1/UG_TITLE = collagen, type IV, alpha 1/FL = gb: NM_001845.1 |
| 60 | 212156_at | vacuolar protein sorting 39 (yeast) | AA812224 | 23339 | gb: AA812224/DB_XREF = gi: 2881835/ DB_XREF = ob84g11.s1/CLONE = IMAGE: 1338116/ FEA = mRNA/CNT = 170/TID = Hs.9452.0/TIER = Stack/ STK = 11/UG = Hs.9452/LL = 23339/ UG_GENE = KIAA0770/UG_TITLE = KIAA0770 protein |
| 61 | 212162_at | kinase D-interacting substance of 220 kDa | AK022873 | 57498 | gb: AK022873.1/DB_XREF = gi: 10434518/ FEA = mRNA/CNT = 204/TID = Hs.9873.0/TIER = Stack/ STK = 11/UG = Hs.9873/LL = 57498/ UG_GENE = KIAA1250/UG_TITLE = likely homolog of rat kinase D-interacting substance of 220 kDa; KIAA1250 protein/DEF = *Homo sapiens* cDNA FLJ12811 fis, clone NT2RP2002475. |
| 62 | 212248_at | CDNA FLJ41088 fis, clone ASTRO2002459/// Metadherin | AI886796 | 92140 | gb: AI886796/DB_XREF = gi: 5591960/ DB_XREF = wk20b07.x1/CLONE = IMAGE: 2412853/ FEA = mRNA/CNT = 189/TID = Hs.243901.0/ TIER = Stack/STK = 19/UG = Hs.243901/ UG_TITLE = *Homo sapiens* cDNA FLJ20738 fis, clone HEP08257 |
| 63 | 212538_at | dedicator of cytokinesis 9 | AL576253 | 23348 | Consensus includes gb: AL576253/FEA = EST/ DB_XREF = gi: 12938214/DB_XREF = est: AL576253/ CLONE = CS0DI073YM22 (3 prime)/UG = Hs.8021 KIAA1058 protein |
| 64 | 212556_at | scribbled homolog (*Drosophila*) | AI469403 | 23513 | gb: AI469403/DB_XREF = gi: 4331493/ DB_XREF = tm08c12.x1/CLONE = IMAGE: 2155990/ FEA = mRNA/CNT = 120/TID = Hs.239784.0/ TIER = Stack/STK = 50/UG = Hs.239784/LL = 23513/ UG_GENE = KIAA0147/UG_TITLE = human homolog of *Drosophila* Scribble |
| 65 | 212655_at | zinc finger, CCHC domain containing 14 | AB011151 | 23174 | gb: AB011151.1/DB_XREF = gi: 3043681/ GEN = KIAA0579/FEA = mRNA/CNT = 135/ TID = Hs.81505.0/TIER = Stack/STK = 51/ UG = Hs.81505/LL = 23174/DEF = *Homo sapiens* mRNA for KIAA0579 protein, partial cds./ PROD = KIAA0579 protein |
| 66 | 212672_at | ataxia telangiectasia mutated (includes complementation groups A, C and D) | U82828 | 472 | gb: U82828/DB_XREF = gi: 2304970/FEA = mRNA/ CNT = 113/TID = Hs.194382.2/TIER = Stack/STK = 42/ UG = Hs.194382/LL = 472/UG_GENE = ATM/ UG_TITLE = ataxia telangiectasia mutated (includes complementation groups A, C and D)/DEF = *Homo sapiens* ataxia telangiectasia (ATM) gene, complete cds |
| 67 | 212921_at | SET and MYND domain containing 2 | AF070592 | 56950 | Consensus includes gb: AF070592.1/DEF = *Homo sapiens* clone 24503 mRNA sequence./FEA = mRNA/ DB_XREF = gi: 3387967/UG = Hs.66170 HSKM-B protein |
| 68 | 213383_at | Full-length cDNA clone CS0DF026YC16 of Fetal brain of *Homo sapiens* (human) | AW593269 | | Consensus includes gb: AW593269/FEA = EST/ DB_XREF = gi: 7280527/DB_XREF = est: hg11h06.x1/ CLONE = IMAGE: 2945339/UG = Hs.296406 KIAA0685 gene product |
| 69 | 213478_at | kazrin | AB028949 | 23254 | gb: AB028949.1/DB_XREF = gi: 5689388/ GEN = KIAA1026/FEA = mRNA/CNT = 40/ TID = Hs.27742.0/TIER = Stack/STK = 23/ UG = Hs.27742/LL = 23254/DEF = *Homo sapiens* mRNA for KIAA1026 protein, partial cds./ PROD = KIAA1026 protein |
| 70 | 214005_at | gamma-glutamyl carboxylase | BE326952 | 2677 | gb: BE326952/DB_XREF = gi: 9200728/ DB_XREF = hr68a04.x1/CLONE = IMAGE: 3133614/ FEA = EST/CNT = 23/TID = Hs.77719.1/TIER = Stack/ STK = 18/UG = Hs.77719/LL = 2677/UG_GENE = GGCX/ UG_TITLE = gamma-glutamyl carboxylase |
| 71 | 214097_at | ribosomal protein S21 | AW024383 | 6227 | gb: AW024383/DB_XREF = gi: 5877913/ DB_XREF = wv03e06.x1/CLONE = IMAGE: 2528482/ FEA = EST/CNT = 16/TID = Hs.1948.1/TIER = Stack/ STK = 8/UG = Hs.1948/LL = 6227/UG_GENE = RPS21/ UG_TITLE = ribosomal protein S21 |
| 72 | 214415_at | plasminogen-like A1 | N58120 | 285189 | gb: N58120/DB_XREF = gi: 1202010/ DB_XREF = yv65a07.s1/CLONE = IMAGE: 247572/ |

TABLE 2-continued

DNA array results for control and ZDHHC3 ablated MDA-MB-231 cells

| | | | | | |
|---|---|---|---|---|---|
| | | | | | FEA = EST/CNT = 20/TID = Hs.262869.1/TIER = Stack/ STK = 11/UG = Hs.262869/LL = 5342/UG_GENE = PLGL/ UG_TITLE = plasminogen-like |
| 73 | 214670_at | zinc finger with KRAB and SCAN domains 1 | AA653300 | 7586 | gb: AA653300/DB_XREF = gi: 2589471/ DB_XREF = ag65c10.s1/CLONE = IMAGE: 1127826/ FEA = mRNA/CNT = 54/TID = Hs.132390.1/ TIER = ConsEnd/STK = 1/UG = Hs.132390/LL = 7586/ UG_GENE = ZNF36/UG_TITLE = zinc finger protein 36 (KOX 18) |
| 74 | 214715_x_at | zinc finger protein 160 | AK024789 | 90338 | gb: AK024789.1/DB_XREF = gi: 10437175/ FEA = mRNA/CNT = 37/TID = Hs.206882.0/ TIER = ConsEnd/STK = 0/UG = Hs.206882/ UG_TITLE = Homo sapiens mRNA for FLJ00032 protein, partial cds/DEF = Homo sapiens cDNA: FLJ21136 fis, clone CAS07469. |
| 75 | 214719_at | hypothetical protein LOC283537 | AK026720 | 283537 | gb: AK026720.1/DB_XREF = gi: 10439638/ FEA = mRNA/CNT = 79/TID = Hs.117167.0/ TIER = ConsEnd/STK = 0/UG = Hs.117167/ UG_TITLE = Homo sapiens cDNA: FLJ23067 fis, clone LNG04993/DEF = Homo sapiens cDNA: FLJ23067 fis, clone LNG04993. |
| 76 | 214753_at | Phosphonoformate immuno-associated protein 5 | AW084068 | 10443 | gb: AW084068/DB_XREF = gi: 6039220/ DB_XREF = xc26c06.x1/CLONE = IMAGE: 2585386/ FEA = mRNA/CNT = 22/TID = Hs.110630.0/ TIER = ConsEnd/STK = 1/UG = Hs.110630/ UG_TITLE = Human BRCA2 region, mRNA sequence CG006 |
| 77 | 214778_at | multiple EGF-like-domains 8 | AB011541 | 1954 | Consensus includes gb: AB011541.1/DEF = Homo sapiens mRNA for MEGF8, partial cds./FEA = mRNA/ GEN = MEGF8/PROD = MEGF8/DB_XREF = gi: 3449307/UG = Hs.158200 EGF-like-domain, multiple 4 |
| 78 | 214808_at | MRNA; cDNA DKFZp762N156 (from clone DKFZp762N156) | AU147851 | | gb: AU147851/DB_XREF = gi: 11009372/ DB_XREF = AU147851/CLONE = MAMMA1001878/ FEA = mRNA/CNT = 19/TID = Hs.183819.0/ TIER = ConsEnd/STK = 1/UG = Hs.183819/ UG_TITLE = Homo sapiens cDNA FLJ12304 fis, clone MAMMA1001878 |
| 79 | 214829_at | aminoadipate-semialdehyde synthase | AK023446 | 10157 | gb: AK023446.1/DB_XREF = gi: 10435383/FEA = mRNA/ CNT = 18/TID = Hs.323091.0/TIER = ConsEnd/STK = 0/ UG = Hs.323091/UG_TITLE = Homo sapiens cDNA FLJ13384 fis, clone PLACE1001062, highly similar to Homo sapiens mRNA for lysine-ketoglutarate reductasesaccharopine dehydrogenase/DEF = Homo sapiens cDNA FLJ13384 fis, clone PLACE1001062, highly similar to Homo sapiens mRNA for lysine-ketoglutarate reductasesaccharopine dehydrogenase. |
| 80 | 214917_at | protein kinase, AMP-activated, alpha 1 catalytic subunit | AK024252 | 5562 | gb: AK024252.1/DB_XREF = gi: 10436581/ FEA = mRNA/CNT = 9/TID = Hs.288546.0/ TIER = ConsEnd/STK = 0/UG = Hs.288546/ UG_TITLE = Homo sapiens cDNA FLJ14190 fis, clone NT2RP2006534, moderately similar to 5-AMP-ACTIVATED PROTEIN KINASE, CATALYTIC ALPHA-1 CHAIN (EC 2.7.1.—)/DEF = Homo sapiens cDNA FLJ14190 fis, clone NT2RP2006534, moderately similar to 5-AMP-ACTIVATED PROTEIN KINASE, CATALYTIC ALPHA-1 CHAIN (EC 2.7.1.—). |
| 81 | 215067_x_at | peroxiredoxin 2 | AU147942 | 7001 | Consensus includes gb: AU147942/FEA = EST/ DB_XREF = gi: 11009463/DB_XREF = est: AU147942/ CLONE = MAMMA1002198/ UG = Hs.287517 Homo sapiens cDNA FLJ12333 fis, clone MAMMA1002198, highly similar to THIOREDOXIN PEROXIDASE 1 |
| 82 | 215233_at | phosphatidylserine receptor | AA351360 | 23210 | Consensus includes gb: AA351360/FEA = EST/ DB_XREF = gi: 2003690/DB_XREF = est: EST59093/ UG = Hs.72660 phosphatidylserine receptor |
| 83 | 215268_at | hypothetical LOC643314 | AW663712 | 643314 | Consensus includes gb: AW663712/FEA = EST/ DB_XREF = gi: 7456250/DB_XREF = est: hj12e06.x1/ CLONE = IMAGE: 2981602/UG = Hs.159183 KIAA0754 protein |
| 84 | 215287_at | ELISC-1 | AA975427 | | Consensus includes gb: AA975427/FEA = EST/ DB_XREF = gi: 3151219/DB_XREF = est: oq28g02.s1/ CLONE = IMAGE: 1587698/UG = Hs.128434 Homo sapiens ELISC-1 mRNA, partial cds |

TABLE 2-continued

DNA array results for control and ZDHHC3 ablated MDA-MB-231 cells

| | | | | | |
|---|---|---|---|---|---|
| 85 | 215314_at | Ankyrin 3, node of Ranvier (ankyrin G) | AU146646 | 288 | Consensus includes gb: AU146646/FEA = EST/ DB_XREF = gi: 11008167/DB_XREF = est: AU146646/ CLONE = HEMBB1001096/UG = Hs.179752 *Homo sapiens* cDNA FLJ10270 fis, clone HEMBB1001096 |
| 86 | 215359_x_at | zinc finger protein 44 | AI758888 | 51710 | Consensus includes gb: AI758888/FEA = EST/ DB_XREF = gi: 5152613/DB_XREF = est: ty94c12.x1/ CLONE = IMAGE: 2286742/UG = Hs.278480 zinc finger protein 44 (KOX 7) |
| 87 | 215385_at | Fatso | AK022473 | 79068 | Consensus includes gb: AK022473.1/ DEF = *Homo sapiens* cDNA FLJ12411 fis, clone MAMMA1002964./FEA = mRNA/DB_XREF = gi: 10433882/UG = Hs.296722 *Homo sapiens* cDNA FLJ12411 fis, clone MAMMA1002964 |
| 88 | 215447_at | Consensus includes gb: AL080215.1/ DEF = *Homo sapiens* mRNA; cDNA DKFZp586J0323 (from clone DKFZp586J0323)./ FEA = mRNA/ DB_XREF = gi: 5262706/ UG = Hs.102301 *Homo sapiens* mRNA; cDNA DKFZp586J0323 (from clone DKFZp586J0323) | AL080215 | | Consensus includes gb: AL080215.1/DEF = *Homo sapiens* mRNA; cDNA DKFZp586J0323 (from clone DKFZp586J0323)./FEA = mRNA/ DB_XREF = gi: 5262706/UG = Hs.102301 *Homo sapiens* mRNA; cDNA DKFZp586J0323 (from clone DKFZp586J0323) |
| 89 | 215595_x_at | Glucosaminyl (N-acetyl) transferase 2, I-branching enzyme (I blood group) | AK023918 | 2651 | Consensus includes gb: AK023918.1/DEF = *Homo sapiens* cDNA FLJ13856 fis, clone THYRO1000988./ FEA = mRNA/DB_XREF = gi: 10436003/ UG = Hs.288489 *Homo sapiens* cDNA FLJ13856 fis, clone THYRO1000988 |
| 90 | 215599_at | SMA4/// region containing SMA4; hypothetical protein LOC153561/// region containing hypothetical protein LOC153561; SMA4/// SMA4/// similar to Beta-glucuronidase precursor | X83300 | 11039/// 643367/// 643373/// 652924/// 653869 | Consensus includes gb: X83300.1/ DEF = *H. sapiens* SMA4 mRNA./FEA = mRNA/ GEN = SMA4/DB_XREF = gi: 603028/ UG = Hs.289103 SMA4 |
| 91 | 215648_at | NudC domain containing 3 | AU144324 | 23386 | Consensus includes gb: AU144324/FEA = EST/ DB_XREF = gi: 11005845/DB_XREF = est: AU144324/ CLONE = HEMBA1001570/UG = Hs.306599 *Homo sapiens* cDNA FLJ11461 fis, clone HEMBA1001570 |
| 92 | 215907_at | BTB and CNC homology 1, basic leucine zipper transcription factor 2 | AK027193 | 60468 | Consensus includes gb: AK027193.1/DEF = *Homo sapiens* cDNA: FLJ23540 fis, clone LNG08239./ FEA = mRNA/DB_XREF = gi: 10440262/ UG = Hs.293931 *Homo sapiens* cDNA: FLJ23540 fis, clone LNG08239 |
| 93 | 216187_x_at | Kinesin 2 | AF222691 | 3831 | Consensus includes gb: AF222691.1/DEF = *Homo sapiens* Alu repeat (LNX1) mRNA sequence./ FEA = mRNA/DB_XREF = gi: 12655850/UG = Hs.307008 *Homo sapiens* Alu repeat (LNX1) mRNA sequence |
| 94 | 216527_at | HLA complex group 18 | AL049252 | 414777 | Consensus includes gb: AL049252.1/DEF = *Homo sapiens* mRNA; cDNA DKFZp564D193 (from clone DKFZp564D193)./FEA = mRNA/DB_XREF = gi: 4499993/UG = Hs.302048 *Homo sapiens* mRNA; cDNA DKFZp564D193 (from clone DKFZp564D193) |
| 95 | 216698_x_at | olfactory receptor, family 7, subfamily E, member 47 pseudogene/// olfactory receptor, family 7, | AF065854 | 26628/// 26636/// 390885/// 391632/// 441453 | Consensus includes gb: AF065854/DEF = *Homo sapiens* OR7E12P pseudogene, complete sequence/ FEA = CDS/DB_XREF = gi: 3831591/UG = Hs.120017 olfactory receptor, family 7, subfamily E, member 12 pseudogene |

TABLE 2-continued

DNA array results for control and ZDHHC3 ablated MDA-MB-231 cells

| | | | | | |
|---|---|---|---|---|---|
| | | subfamily E, member 37 pseudogene/// olfactory receptor, family 7, subfamily E, member 18 pseudogene/// olfactory receptor, family 7, subfamily E, member 35 pseudogene/// similar to olfactory receptor, family 7, subfamily A, member 17 | | | |
| 96 | 216751_at | CMT1A duplicated region transcript 4 | AK024879 | 284040 | Consensus includes gb: AK024879.1/DEF = *Homo sapiens* cDNA: FLJ21226 fis, clone COL00721./ FEA = mRNA/DB_XREF = gi: 10437291/UG = Hs.306715 *Homo sapiens* cDNA: FLJ21226 fis, clone COL00721 |
| 97 | 216859_x_at | Consensus includes gb: AL080112.1/ DEF = *Homo sapiens* mRNA; cDNA DKFZp586H0722 (from clone DKFZp586H0722)./ FEA = mRNA/ DB_XREF = gi: 5262539/ UG = Hs.332731 *Homo sapiens* mRNA; cDNA DKFZp586H0722 (from clone DKFZp586H0722) | AL080112 | | Consensus includes gb: AL080112.1/DEF = *Homo sapiens* mRNA; cDNA DKFZp586H0722 (from clone DKFZp586H0722)./FEA = mRNA/DB_XREF = gi: 5262539/UG = Hs.332731 *Homo sapiens* mRNA; cDNA DKFZp586H0722 (from clone DKFZp586H0722) |
| 98 | 217191_x_at | Consensus includes gb: AF042163/ DEF = *Homo sapiens* cytochrome c oxidase subunit VIc (COX6CP1) pseudogene, complete sequence/ FEA = CDS/ DB_XREF = gi: 3861484/ UG = Hs.248205 cytochrome c oxidase subunit VIc pseudogene 1 | AF042163 | | Consensus includes gb: AF042163/DEF = *Homo sapiens* cytochrome c oxidase subunit VIc (COX6CP1) pseudogene, complete sequence/FEA = CDS/ DB_XREF = gi: 3861484/UG = Hs.248205 cytochrome c oxidase subunit VIc pseudogene 1 |
| 99 | 217477_at | phosphatidylinositol-4-phosphate 5-kinase, type I, beta | U78581 | 8395 | Consensus includes gb: U78581.1/DEF = Human type I phosphatidylinositol-4-phosphate 5-kinase beta (STM7) mRNA, partial cds./FEA = mRNA/GEN = STM7/ PROD = type I phosphatidylinositol-4-phosphate 5-kinasebeta/DB_XREF = gi: 1743882/UG = Hs.78406 phosphatidylinositol-4-phosphate 5-kinase, type I, beta |
| 100 | 217503_at | Consensus includes gb: AA203487/ FEA = EST/ DB_XREF = gi: 1799460/ DB_XREF = est: zx53d03.r1/ CLONE = IMAGE: 446213/ UG = Hs.314363 ESTs | AA203487 | | Consensus includes gb: AA203487/FEA = EST/ DB_XREF = gi: 1799460/DB_XREF = est: zx53d03.r1/ CLONE = IMAGE: 446213/UG = Hs.314363 ESTs |
| 101 | 217536_x_at | Transcribed locus | M78162 | | Consensus includes gb: M78162/FEA = EST/ DB_XREF = gi: 273899/DB_XREF = est: EST01755/ |

TABLE 2-continued

DNA array results for control and ZDHHC3 ablated MDA-MB-231 cells

| | | | | | |
|---|---|---|---|---|---|
| | | | | | CLONE = HHCPN60/UG = Hs.314534 ESTs, Moderately similar to ALU5_HUMAN ALU SUBFAMILY SC SEQUENCE CONTAMINATION WARNING ENTRY *H. sapiens* |
| 102 | 217586_x_at | Consensus includes gb: N35922/ FEA = EST/ DB_XREF = gi: 1157064/ DB_XREF = est: yy28g05.s1/ CLONE = IMAGE: 272600/ UG = Hs.269852 ESTs, Weakly similar to ALU1_HUMAN ALU SUBFAMILY J SEQUENCE CONTAMINATION WARNING ENTRY *H. sapiens* | N35922 | | Consensus includes gb: N35922/FEA = EST/ DB_XREF = gi: 1157064/DB_XREF = est: yy28g05.s1/ CLONE = IMAGE: 272600/UG = Hs.269852 ESTs, Weakly similar to ALU1_HUMAN ALU SUBFAMILY J SEQUENCE CONTAMINATION WARNING ENTRY *H. sapiens* |
| 103 | 217610_at | hypothetical protein LOC641807 | AL047879 | 641807 | Consensus includes gb: AL047879/FEA = EST/ DB_XREF = gi: 4728067/ DB_XREF = est: DKFZp586N1222_s1/ CLONE = DKFZp586N1222/UG = Hs.194251 ESTs, Weakly similar to ALU2_HUMAN ALU SUBFAMILY SB SEQUENCE CONTAMINATION WARNING ENTRY *H. sapiens* |
| 104 | 217653_x_at | similar to Ribosome biogenesis protein BMS1 homolog/// similar to Ribosome biogenesis protein BMS1 homolog | AW150065 | 653471/// 654000 | Consensus includes gb: AW150065/FEA = EST/ DB_XREF = gi: 6197971/DB_XREF = est: xg48a10.x1/ CLONE = IMAGE: 2630778/UG = Hs.271957 ESTs |
| 105 | 217679_x_at | Consensus includes gb: AI683552/ FEA = EST/ DB_XREF = gi: 4893734/ DB_XREF = est: tx67h02.x1/ CLONE = IMAGE: 2274675/ UG = Hs.201605 ESTs, Moderately similar to ALU8_HUMAN ALU SUBFAMILY SX SEQUENCE CONTAMINATION WARNING ENTRY *H. sapiens* | AI683552 | | Consensus includes gb: AI683552/FEA = EST/ DB_XREF = gi: 4893734/DB_XREF = est: tx67h02.x1/ CLONE = IMAGE: 2274675/UG = Hs.201605 ESTs, Moderately similar to ALU8_HUMAN ALU SUBFAMILY SX SEQUENCE CONTAMINATION WARNING ENTRY *H. sapiens* |
| 106 | 218078_s_at | zinc finger, DHHC-type containing 3 | NM_016598 | 51304 | gb: NM_016598.1/DEF = *Homo sapiens* DHHC1 protein (LOC51304), mRNA./FEA = mRNA/GEN = LOC51304/ PROD = DHHC1 protein/DB_XREF = gi: 7706132/ UG = Hs.14896 DHHC1 protein/FL = gb: AF247703.1 gb: NM_016598.1 |
| 107 | 218609_s_at | nudix (nucleoside diphosphate linked moiety X)- type motif 2 | NM_001161 | 318 | gb: NM_001161.1/DEF = *Homo sapiens* nudix (nucleoside diphosphate linked moiety X)-type motif 2 (NUDT2), mRNA./FEA = mRNA/GEN = NUDT2/ PROD = nudix (nucleoside diphosphate linked moietyX)-type motif 2/DB_XREF = gi: 4502124/ UG = Hs.14142 nudix (nucleoside diphosphate linked moiety X)-type motif 2/FL = gb: BC004926.1 gb: NM_001161.1 |

TABLE 2-continued

DNA array results for control and ZDHHC3 ablated MDA-MB-231 cells

| | | | | | |
|---|---|---|---|---|---|
| 108 | 219117_s_at | FK506 binding protein 11, 19 kDa | NM_016594 | 51303 | gb: NM_016594.1/DEF = *Homo sapiens* FK506 binding protein precursor (LOC51303), mRNA./FEA = mRNA/GEN = LOC51303/PROD = FK506 binding protein precursor/DB_XREF = gi: 7706130/UG = Hs.24048 FK506 binding protein precursor/FL = gb: AF238079.1 gb: NM_016594.1 |
| 109 | 219186_at | zinc finger and BTB domain containing 7A | NM_020224 | 51341 | gb: NM_020224.1/DEF = *Homo sapiens* hypothetical protein DKFZp547O146 (DKFZp547O146), mRNA./FEA = mRNA/GEN = DKFZp547O146/PROD = hypothetical protein DKFZp547O146/DB_XREF = gi: 9910203/UG = Hs.91246 hypothetical protein DKFZp547O146/FL = gb: NM_020224.1 |
| 110 | 219232_s_at | egl nine homolog 3 (*C. elegans*) | NM_022073 | 112399 | gb: NM_022073.1/DEF = *Homo sapiens* hypothetical protein FLJ21620 (FLJ21620), mRNA./FEA = mRNA/GEN = FLJ21620/PROD = hypothetical protein FLJ21620/DB_XREF = gi: 11545786/UG = Hs.18878 hypothetical protein FLJ21620/FL = gb: NM_022073.1 |
| 111 | 219555_s_at | chromosome 16 open reading frame 60 | NM_018455 | 55839 | gb: NM_018455.1/DEF = *Homo sapiens* uncharacterized bone marrow protein BM039 (BM039), mRNA./FEA = mRNA/GEN = BM039/PROD = uncharacterized bone marrow protein BM039/DB_XREF = gi: 8922096/UG = Hs.283532 uncharacterized bone marrow protein BM039/FL = gb: AF217515.1 gb: NM_018455.1 |
| 112 | 219610_at | Rho-guanine nucleotide exchange factor/// similar to Rho-guanine nucleotide exchange factor (Rho-interacting protein 2) (RhoGEF) (RIP2) | NM_022448 | 64283/// 643607 | gb: NM_022448.1/DEF = *Homo sapiens* hypothetical protein FLJ21817 similar to Rhoip2 (FLJ21817), mRNA./FEA = mRNA/GEN = FLJ21817/PROD = hypothetical protein FLJ21817 similar to Rhoip2/DB_XREF = gi: 11967978/UG = Hs.33254 hypothetical protein FLJ21817 similar to Rhoip2/FL = gb: NM_022448.1 |
| 113 | 219648_at | dilute suppressor | NM_018000 | 55686 | gb: NM_018000.1/DEF = *Homo sapiens* hypothetical protein FLJ10116 (FLJ10116), mRNA./FEA = mRNA/GEN = FLJ10116/PROD = hypothetical protein FLJ10116/DB_XREF = gi: 8922236/UG = Hs.79741 hypothetical protein FLJ10116/FL = gb: NM_018000.1 |
| 114 | 219751_at | SET domain containing 6 | NM_024860 | 79918 | gb: NM_024860.1/DEF = *Homo sapiens* hypothetical protein FLJ21148 (FLJ21148), mRNA./FEA = mRNA/GEN = FLJ21148/PROD = hypothetical protein FLJ21148/DB_XREF = gi: 13376287/UG = Hs.193300 hypothetical protein FLJ21148/FL = gb: NM_024860.1 |
| 115 | 219763_at | DENN/MADD domain containing 1A | NM_024820 | 57706 | gb: NM_024820.1/DEF = *Homo sapiens* KIAA1608 protein (KIAA1608), mRNA./FEA = mRNA/GEN = KIAA1608/PROD = hypothetical protein FLJ21129/DB_XREF = gi: 13449264/UG = Hs.300842 KIAA1608 protein/FL = gb: NM_024820.1 |
| 116 | 220071_x_at | centrosomal protein 27 kDa | NM_018097 | 55142 | gb: NM_018097.1/DEF = *Homo sapiens* hypothetical protein FLJ10460 (FLJ10460), mRNA./FEA = mRNA/GEN = FLJ10460/PROD = hypothetical protein FLJ10460/DB_XREF = gi: 8922429/UG = Hs.14347 hypothetical protein FLJ10460/FL = gb: NM_018097.1 |
| 117 | 220227_at | cadherin 4, type 1, R-cadherin (retinal) | NM_024883 | 1002 | gb: NM_024883.1/DEF = *Homo sapiens* hypothetical protein FLJ22202 (FLJ22202), mRNA./FEA = mRNA/GEN = FLJ22202/PROD = hypothetical protein FLJ22202/DB_XREF = gi: 13376328/UG = Hs.217754 hypothetical protein FLJ22202/FL = gb: NM_024883.1 |
| 118 | 220327_at | vestigial like 3 (*Drosophila*) | NM_016206 | 389136 | gb: NM_016206.1/DEF = *Homo sapiens* colon carcinoma related protein (LOC51159), mRNA./FEA = mRNA/GEN = LOC51159/PROD = colon carcinoma related protein/DB_XREF = gi: 7705882/UG = Hs.23142 colon carcinoma related protein/FL = gb: AF099505.1 gb: NM_016206.1 |
| 119 | 220374_at | BTB (POZ) domain containing 5 | NM_017658 | 54813 | gb: NM_017658.1/DEF = *Homo sapiens* hypothetical protein FLJ20081 (FLJ20081), mRNA./FEA = mRNA/GEN = FLJ20081/PROD = hypothetical protein FLJ20081/DB_XREF = gi: 8923089/UG = Hs.126219 hypothetical protein FLJ20081/FL = gb: NM_017658.1 |
| 120 | 220575_at | family with sequence similarity 106, member A | NM_024974 | 80039 | gb: NM_024974.1/DEF = *Homo sapiens* hypothetical protein FLJ11800 (FLJ11800), mRNA./FEA = mRNA/GEN = FLJ11800/PROD = hypothetical protein FLJ11800/DB_XREF = gi: 13376473/UG = Hs.287456 hypothetical protein FLJ11800/FL = gb: NM_024974.1 |

TABLE 2-continued

DNA array results for control and ZDHHC3 ablated MDA-MB-231 cells

| | | | | | |
|---|---|---|---|---|---|
| 121 | 220940_at | KIAA1641 | NM_025190 | 57730 | gb: NM_025190.1/DEF = *Homo sapiens* KIAA1641 protein (KIAA1641), mRNA./FEA = mRNA/ GEN = KIAA1641/PROD = hypothetical protein FLJ21281/DB_XREF = gi: 13449272/UG = Hs.44566 KIAA1641 protein/FL = gb: NM_025190.1 |
| 122 | 220954_s_at | paired immunoglobin-like type 2 receptor beta | NM_013440 | 29990 | gb: NM_013440.1/DEF = *Homo sapiens* paired immunoglobulin-like receptor beta (PILR(BETA)), mRNA./FEA = mRNA/GEN = PILR(BETA)/ PROD = paired immunoglobulin-like receptor beta/ DB_XREF = gi: 7305386/UG = Hs.9408 paired immunoglobulin-like receptor beta/ FL = gb: AF161081.1 gb: NM_013440.1 |
| 123 | 220967_s_at | zinc finger protein 696/// zinc finger protein 696 | NM_030895 | 79943 | gb: NM_030895.1/DEF = *Homo sapiens* hypothetical protein FLJ14129 (FLJ14129), mRNA./FEA = mRNA/ GEN = FLJ14129/PROD = hypothetical protein FLJ14129/DB_XREF = gi: 13569857/ FL = gb: NM_030895.1 |
| 124 | 221499_s_at | syntaxin 16 | AK026970 | 8675 | Consensus includes gb: AK026970.1/DEF = *Homo sapiens* cDNA: FLJ23317 fis, clone HEP12062, highly similar to AF008936 *Homo sapiens* syntaxin-16B mRNA./FEA = mRNA/DB_XREF = gi: 10439960/ UG = Hs.102178 syntaxin 16/FL = gb: AF008936.1 |
| 125 | 221531_at | WD repeat domain 61 | AF309553 | 80349 | gb: AF309553.1/DEF = *Homo sapiens* meiotic recombination protein REC14 mRNA, complete cds./ FEA = mRNA/PROD = meiotic recombination protein REC14/DB_XREF = gi: 11139241/UG = Hs.296242 recombination protein REC14/FL = gb: AF309553.1 gb: NM_025234.1 |
| 126 | 221879_at | calmodulin-like 4 | AA886335 | 91860 | Consensus includes gb: AA886335/FEA = EST/ DB_XREF = gi: 3001443/DB_XREF = est: oj23g02.s1/ CLONE = IMAGE: 1493042/UG = Hs.239812 *Homo sapiens* serologically defined breast cancer antigen NY-BR-20 mRNA, partial cds |
| 127 | 222104_x_at | general transcription factor IIH, polypeptide 3, 34 kDa | AI569458 | 2967 | Consensus includes gb: AI569458/FEA = EST/ DB_XREF = gi: 4532832/DB_XREF = est: tn87c02.x1/ CLONE = IMAGE: 2176514/UG = Hs.90304 general transcription factor IIH, polypeptide 3 (34 kD subunit)/ FL = gb: NM_001516.1 |
| 128 | 222149_x_at | golgi autoantigen, golgin subfamily a, 8G/// golgi autoantigen, golgin subfamily a, 8D/// golgi autoantigen, golgin subfamily a, 8E/// golgi autoantigen, golgin subfamily a, 8C/// golgi autoantigen, golgin subfamily a, 8F | AL137398 | 283768/// 388080/// 390535/// 400304/// 440244 | Consensus includes gb: AL137398.1/DEF = *Homo sapiens* mRNA; cDNA DKFZp434K052 (from clone DKFZp434K052)./FEA = mRNA/DB_XREF = gi: 6807944/ UG = Hs.169639 *Homo sapiens* mRNA; cDNA DKFZp434K052 (from clone DKFZp434K052) |
| 129 | 222266_at | Chromosome 19 open reading frame 2 | BF796940 | 8725 | Consensus includes gb: BF796940/FEA = EST/ DB_XREF = gi: 12101994/DB_XREF = est: 602258153F1/CLONE = IMAGE: 4341588/ UG = Hs.294100 ESTs |
| 130 | 222267_at | hypothetical protein FLJ14803 | BE619220 | 84928 | Consensus includes gb: BE619220/FEA = EST/ DB_XREF = gi: 9890158/DB_XREF = est: 601472975F1/ CLONE = IMAGE: 3875730/UG = Hs.267245 ESTs, Weakly similar to cDNA EST EMBL: T02216 comes from this gene *C. elegans* |
| 131 | 222372_at | Membrane associated guanylate kinase, WW and PDZ domain containing 1 | AW971248 | 9223 | Consensus includes gb: AW971248/FEA = EST/ DB_XREF = gi: 8161093/DB_XREF = est: EST383337/ UG = Hs.291289 ESTs, Weakly similar to ALU1_HUMAN ALU SUBFAMILY J SEQUENCE CONTAMINATION WARNING ENTRY *H. sapiens* |
| 132 | 222375_at | Peptidylprolyl isomerase G (cyclophilin G) | AW970944 | 9360 | Consensus includes gb: AW970944/FEA = EST/ DB_XREF = gi: 8160789/DB_XREF = est: EST383027/ UG = Hs.291839 ESTs |
| 133 | 37226_at | BCL2/ adenovirus | U15172 | 662 | Cluster Incl. U15172: *Homo sapiens* BCL2/ adenovirus E1B 19 kD-interacting protein 1 (BNIP1) |

TABLE 2-continued

DNA array results for control and ZDHHC3 ablated MDA-MB-231 cells

| | | | | | |
|---|---|---|---|---|---|
| | | | E1B 19 kDa interacting protein 1 | | mRNA, complete cds/cds = (10,696)/gb = U15172/ gi = 558841/ug = Hs.77572/len = 1100 |
| 134 | 38918_at | SRY (sex determining region Y)- box 13 | AF083105 | 9580 | Cluster Incl. AF083105: *Homo sapiens* HMG box factor SOX-13 mRNA, complete cds/cds = (111,2783)/ gb = AF083105/gi = 3982828/ug = Hs.201671/ len = 3583 |
| 135 | 39582_at | Cylindromatosis (turban tumor syndrome) | AL050166 | 1540 | Cluster Incl. AL050166: *Homo sapiens* mRNA; cDNA DKFZp586D1122 (from clone DKFZp586D1122)/ cds = UNKNOWN/gb = AL050166/gi = 4884381/ ug = Hs.26295/len = 2654 |
| 136 | 51228_at | RNA binding motif protein 12B | N36928 | 389677 | Cluster Incl. N36928: yy38e06.s1 *Homo sapiens* cDNA, 3 end/clone = IMAGE-273538/clone_end = 3'/ gb = N36928/gi = 1158070/ug = Hs.33540/len = 582 |
| 137 | 60815_at | hypothetical protein MGC13098 | AA601208 | 84820 | Cluster Incl. AA601208: no14c12.s1 *Homo sapiens* cDNA, 3 end/clone = IMAGE-1100662/clone_end = 3'/ gb = AA601208/gi = 2434833/ug = Hs.220255/ len = 488 |
| 138 | 63825_at | abhydrolase domain containing 2 | AI557319 | 11057 | Cluster Incl. AI557319: PT2.1_16_F08.r *Homo sapiens* cDNA, 3 end/clone_end = 3'/gb = AI557319/ gi = 4489682/ug = Hs.21921/len = 876 |
| 139 | 78383_at | NADH dehydrogenase (ubiquinone) 1 beta subcomplex, 6, 17 kDa | AI150117 | 4712 | Cluster Incl. AI150117: qf44e06.x1 *Homo sapiens* cDNA, 3 end/clone = IMAGE-1752898/clone_end = 3'/ gb = AI150117/gi = 3678586/ug = Hs.121573/len = 482 |

| 1 | | | baseline | | | experiment | fold | lower bound | upper bound | t | | filter- |
|---|---|---|---|---|---|---|---|---|---|---|---|---|
| 2 | V_10L | V_30L | mean | C3_0R | C3_30R_ | mean | change | of FC | of FC | statistic | P value | ed |
| 3 | 922.09 | 905.33 | 915.94 | 2376.17 | 2317.29 | 2350.47 | 2.57 | 2.35 | 2.81 | 17.879 | 0.007152 | * |
| 4 | 1977.44 | 2035.84 | 2002.8 | 4045.53 | 3752.24 | 3896.24 | 1.95 | 1.77 | 2.14 | 10.501 | 0.023083 | * |
| 5 | 264.5 | 329.5 | 294.1 | 913 | 940.36 | 926.42 | 3.15 | 2.56 | 4.06 | 13.672 | 0.011321 | * |
| 6 | 208.07 | 230.43 | 216.04 | 380.57 | 384.02 | 382.4 | 1.77 | 1.52 | 2.1 | 7.065 | 0.030743 | * |
| 7 | 2242.95 | 2162.92 | 2201.44 | 1312.67 | 1338.47 | 1326 | −1.66 | −1.54 | −1.79 | −10.423 | 0.020539 | * |
| 8 | 382.23 | 418.38 | 396.41 | 724.2 | 703.19 | 716.23 | 1.81 | 1.58 | 2.1 | 8.479 | 0.022197 | * |
| 9 | 506.86 | 456.97 | 480.44 | 909.97 | 862.13 | 886.76 | 1.85 | 1.65 | 2.07 | 9.753 | 0.010555 | * |
| 10 | 1610.05 | 1558.89 | 1589.33 | 875.12 | 882.45 | 878.23 | −1.81 | −1.67 | −1.97 | −13.16 | 0.00579 | * |
| 11 | 149.85 | 140.45 | 145.03 | 72.21 | 70.62 | 71.44 | −2.03 | −1.62 | −2.63 | −5.622 | 0.030218 | * |
| 12 | 2456.05 | 2311.02 | 2384.72 | 1192.69 | 1157.87 | 1175.42 | −2.03 | −1.88 | −2.19 | −13.879 | 0.013846 | * |
| 13 | 1354.59 | 1498.64 | 1425.34 | 2364.53 | 2338.21 | 2352.89 | 1.65 | 1.5 | 1.83 | 9.812 | 0.01469 | * |
| 14 | 276.3 | 289.72 | 283.27 | 167.59 | 174.15 | 170.59 | −1.66 | −1.5 | −1.84 | −8.362 | 0.015621 | * |
| 15 | 9350.78 | 8746.29 | 9051.77 | 4264.6 | 4313.27 | 4286.89 | −2.11 | −1.92 | −2.32 | −11.563 | 0.024141 | * |
| 16 | 447.5 | 463.45 | 453.66 | 765.95 | 776.01 | 770.82 | 1.7 | 1.51 | 1.92 | 8.083 | 0.015627 | * |
| 17 | 521.02 | 540.73 | 529.66 | 306.54 | 301.46 | 304.32 | −1.74 | −1.54 | −1.99 | −7.745 | 0.016304 | * |
| 18 | 680.26 | 686.6 | 682.9 | 308.13 | 330.83 | 319.39 | −2.14 | −1.9 | −2.44 | −13.247 | 0.009657 | * |
| 19 | 274.29 | 334.24 | 310.51 | 578.65 | 597.89 | 591.41 | 1.9 | 1.54 | 2.46 | 5.786 | 0.043153 | * |
| 20 | 3602.07 | 4101.87 | 3849.03 | 6669.78 | 6815.24 | 6744.54 | 1.75 | 1.57 | 1.98 | 9.844 | 0.028837 | * |
| 21 | 97.47 | 111.44 | 104.62 | 53.94 | 47.9 | 51.72 | −2.02 | −1.61 | −2.6 | −5.208 | 0.039098 | * |
| 22 | 287.8 | 277.18 | 281.99 | 149.05 | 152.57 | 150.12 | −1.88 | −1.57 | −2.26 | −5.582 | 0.043939 | * |
| 23 | 74.37 | 64.26 | 70.56 | 179.84 | 179.58 | 179.7 | 2.55 | 1.85 | 3.95 | 5.786 | 0.032902 | * |
| 24 | 1582.39 | 1577.16 | 1580.32 | 771.31 | 780.11 | 774.53 | −2.04 | −1.89 | −2.21 | −17.65 | 0.003266 | * |
| 25 | 108.73 | 123.59 | 115.93 | 227.96 | 201.82 | 214.81 | 1.85 | 1.51 | 2.3 | 4.881 | 0.047614 | * |
| 26 | 82.88 | 97.26 | 90.69 | 181.6 | 212.25 | 197.53 | 2.18 | 1.74 | 2.78 | 5.585 | 0.042766 | * |
| 27 | 1096.03 | 1206.74 | 1151.65 | 484.03 | 478.94 | 480.83 | −2.4 | −2.1 | −2.74 | −10.009 | 0.02495 | * |
| 28 | 329.91 | 286.17 | 307.74 | 151.94 | 130.46 | 141.57 | −2.17 | −1.74 | −2.76 | −5.643 | 0.042982 | * |
| 29 | 162.35 | 137.17 | 150.42 | 479.5 | 436.65 | 458.78 | 3.05 | 2.45 | 3.92 | 8.81 | 0.020509 | * |
| 30 | 49.28 | 34.36 | 41.9 | 114.41 | 127.69 | 121.57 | 2.9 | 1.99 | 4.98 | 5.402 | 0.032606 | * |
| 31 | 235.64 | 169.28 | 201.33 | 481.6 | 421.47 | 451.29 | 2.24 | 1.65 | 3.32 | 4.841 | 0.040923 | * |
| 32 | 38.38 | 29.43 | 34.16 | 65.15 | 73.37 | 69.37 | 2.03 | 1.53 | 2.91 | 4.55 | 0.049665 | * |
| 33 | 140.4 | 138.9 | 139.32 | 265.79 | 276.08 | 270.84 | 1.94 | 1.64 | 2.37 | 7.138 | 0.02134 | * |
| 34 | 301.78 | 266.57 | 283.99 | 518.19 | 567.56 | 542.73 | 1.91 | 1.66 | 2.23 | 7.774 | 0.016833 | * |
| 35 | 510.11 | 563.35 | 536.81 | 292.3 | 320.86 | 304.15 | −1.76 | −1.51 | −2.06 | −5.886 | 0.040511 | * |
| 36 | 29.08 | 43.01 | 36.19 | 98.95 | 84.13 | 91.5 | 2.53 | 1.73 | 4.29 | 4.496 | 0.046118 | * |
| 37 | 29.3 | 58.84 | 44.48 | 133.46 | 164.48 | 149.22 | 3.35 | 2.03 | 8.17 | 4.629 | 0.043683 | * |
| 38 | 1117.13 | 1171.35 | 1148.76 | 2386.54 | 2203.36 | 2304.12 | 2.01 | 1.79 | 2.26 | 9.277 | 0.023096 | * |
| 39 | 1840.87 | 2041.63 | 1912.33 | 3895.74 | 3397.03 | 3646.44 | 1.91 | 1.62 | 2.25 | 6.062 | 0.045441 | * |
| 40 | 69.79 | 50.92 | 59.63 | 157.76 | 143.53 | 150.76 | 2.53 | 1.8 | 3.97 | 4.988 | 0.037992 | * |
| 41 | 1131 | 964.37 | 1048.96 | 2077.94 | 1882.18 | 1979.93 | 1.89 | 1.61 | 2.25 | 6.744 | 0.02224 | * |
| 42 | 375.47 | 328.08 | 353.16 | 901.16 | 792.75 | 847.14 | 2.4 | 1.98 | 2.94 | 7.332 | 0.030732 | * |
| 43 | 1911.61 | 1787.67 | 1854.59 | 4005.01 | 3593.72 | 3804.02 | 2.05 | 1.81 | 2.31 | 8.174 | 0.048745 | * |
| 44 | 939.25 | 1004.2 | 974.01 | 570.04 | 555.72 | 563.82 | −1.73 | −1.57 | −1.91 | −8.878 | 0.018512 | * |
| 45 | 155.5 | 126.19 | 141.27 | 265.4 | 300.42 | 283.74 | 2.01 | 1.62 | 2.56 | 5.583 | 0.031407 | * |
| 46 | 4123.2 | 3983.46 | 4062.81 | 2196.2 | 2458.44 | 2322.76 | −1.75 | −1.58 | −1.95 | −10.232 | 0.013555 | * |

TABLE 2-continued

DNA array results for control and ZDHHC3 ablated MDA-MB-231 cells

| 47 | 394.53 | 394.66 | 394.58 | 765.84 | 755.65 | 761.58 | 1.93 | 1.73 | 2.18 | 11.007 | 0.008959 | * |
|---|---|---|---|---|---|---|---|---|---|---|---|---|
| 48 | 125.44 | 136.96 | 130.05 | 247.76 | 238.43 | 243.84 | 1.88 | 1.66 | 2.14 | 10.059 | 0.013322 | * |
| 49 | 559.7 | 498.27 | 529.82 | 287.78 | 256.19 | 272.55 | −1.94 | −1.62 | −2.34 | −5.912 | 0.039153 | * |
| 50 | 74.95 | 89.43 | 82.42 | 174.23 | 166.4 | 170.81 | 2.07 | 1.61 | 2.82 | 5.468 | 0.036898 | * |
| 51 | 31.43 | 29.14 | 29.96 | 84.96 | 84.52 | 84.71 | 2.83 | 2.16 | 3.97 | 7.403 | 0.01798 | * |
| 52 | 962.36 | 948.38 | 955.24 | 589.3 | 570.6 | 581.65 | −1.64 | −1.51 | −1.79 | −9.931 | 0.011366 | * |
| 53 | 1583.78 | 1438.1 | 1512.03 | 879.86 | 850.67 | 864.44 | −1.75 | −1.58 | −1.93 | −7.798 | 0.049299 | * |
| 54 | 333.81 | 354.44 | 342.93 | 167.97 | 198.82 | 182 | −1.88 | −1.56 | −2.34 | −6.081 | 0.027406 | * |
| 55 | 937.02 | 900.54 | 921.86 | 535.58 | 458.27 | 497.34 | −1.85 | −1.55 | −2.28 | −6.151 | 0.027594 | * |
| 56 | 157.52 | 146.54 | 152.01 | 25.39 | 50.42 | 38.29 | −3.97 | −2.46 | −9.74 | −6.647 | 0.02684 | * |
| 57 | 1242.62 | 1216.9 | 1230.79 | 2064.14 | 1969.67 | 2015.81 | 1.64 | 1.52 | 1.76 | 10.549 | 0.017822 | * |
| 58 | 1699.94 | 1456.25 | 1575.73 | 3352.79 | 3121.47 | 3234.52 | 2.05 | 1.77 | 2.42 | 8.783 | 0.012805 | * |
| 59 | 1865.06 | 2197.36 | 2022.32 | 4104.56 | 3691.08 | 3896.55 | 1.93 | 1.63 | 2.31 | 6.557 | 0.025411 | * |
| 60 | 90.05 | 111.55 | 102.68 | 193 | 198.35 | 195.05 | 1.9 | 1.52 | 2.49 | 5.33 | 0.042904 | * |
| 61 | 303.43 | 409.95 | 356.09 | 754.1 | 752.58 | 753.41 | 2.12 | 1.67 | 2.86 | 6.29 | 0.044228 | * |
| 62 | 3130.1 | 3118.14 | 3124.47 | 4942.08 | 4890.82 | 4919.33 | 1.57 | 1.52 | 1.64 | 18.837 | 0.006053 | * |
| 63 | 830.03 | 898.32 | 857.29 | 1431.81 | 1480.78 | 1452.25 | 1.69 | 1.51 | 1.9 | 7.827 | 0.018039 | * |
| 64 | 1273.64 | 1256.49 | 1267.2 | 2206.84 | 2032.64 | 2123.3 | 1.68 | 1.51 | 1.85 | 7.282 | 0.049006 | * |
| 65 | 673.39 | 574.35 | 622.41 | 1216.07 | 1115.91 | 1168.18 | 1.88 | 1.58 | 2.27 | 6.269 | 0.024787 | * |
| 66 | 483.95 | 455.96 | 467.93 | 814.81 | 790.73 | 802.13 | 1.71 | 1.53 | 1.93 | 8.304 | 0.014221 | * |
| 67 | 133.19 | 113.53 | 124.58 | 320.16 | 288.18 | 304.64 | 2.45 | 1.99 | 3.07 | 7.363 | 0.024709 | * |
| 68 | 179.27 | 202.81 | 193.07 | 403.43 | 354.73 | 380.07 | 1.97 | 1.62 | 2.41 | 5.609 | 0.042866 | * |
| 69 | 24.72 | 15.01 | 20.44 | 75.8 | 69.48 | 72.78 | 3.56 | 2.18 | 9.18 | 5.797 | 0.04036 | * |
| 70 | 1074.28 | 987.37 | 1031.48 | 522.55 | 537.86 | 530.16 | −1.95 | −1.75 | −2.16 | −9.078 | 0.035694 | * |
| 71 | 1742.37 | 1648.31 | 1693.44 | 866.28 | 886.21 | 876.12 | −1.93 | −1.78 | −2.11 | −12.502 | 0.011245 | * |
| 72 | 134.02 | 109.87 | 121.71 | 513.82 | 483.3 | 498.97 | 4.1 | 3.3 | 5.33 | 13.202 | 0.008424 | * |
| 73 | 462.24 | 522.52 | 492.56 | 865.07 | 885.7 | 874.64 | 1.78 | 1.57 | 2.04 | 8.866 | 0.026287 | * |
| 74 | 919.47 | 804.23 | 862.51 | 1468.96 | 1643.67 | 1556.38 | 1.8 | 1.55 | 2.12 | 6.17 | 0.032323 | * |
| 75 | 147.08 | 138.31 | 142.97 | 263.51 | 276.57 | 269.75 | 1.89 | 1.61 | 2.24 | 6.785 | 0.021848 | * |
| 76 | 238.73 | 336.16 | 286.79 | 707.71 | 620.22 | 665.82 | 2.32 | 1.73 | 3.35 | 5.076 | 0.037084 | * |
| 77 | 78.35 | 97.43 | 87.52 | 180.85 | 204.78 | 192.44 | 2.2 | 1.61 | 3.23 | 4.368 | 0.049735 | * |
| 78 | 178.94 | 203.94 | 193.12 | 555.59 | 500.12 | 527.64 | 2.73 | 2.17 | 3.59 | 7.906 | 0.017721 | * |
| 79 | 312.14 | 324.62 | 317.9 | 662.04 | 699.51 | 679.96 | 2.14 | 1.93 | 2.38 | 12.692 | 0.008363 | * |
| 80 | 194.69 | 207.7 | 200.23 | 354.63 | 342.37 | 349.33 | 1.74 | 1.51 | 2.03 | 6.307 | 0.029152 | * |
| 81 | 254.54 | 252.42 | 253.74 | 515.94 | 586.25 | 550.54 | 2.17 | 1.82 | 2.59 | 6.622 | 0.045646 | * |
| 82 | 60.33 | 53.62 | 57.5 | 104.95 | 113.75 | 109.06 | 1.9 | 1.56 | 2.38 | 5.907 | 0.030233 | * |
| 83 | 62.05 | 78.2 | 69.69 | 179.74 | 155.79 | 167.98 | 2.41 | 1.79 | 3.49 | 5.245 | 0.035335 | * |
| 84 | 148.44 | 147.45 | 148.11 | 354.12 | 341.37 | 349.18 | 2.36 | 2.05 | 2.74 | 11.338 | 0.008322 | * |
| 85 | 38.99 | 41.04 | 40.08 | 136.75 | 130.56 | 133.97 | 3.34 | 2.65 | 4.49 | 12.99 | 0.011444 | * |
| 86 | 445.86 | 391.27 | 417.7 | 722.78 | 760.46 | 740.91 | 1.77 | 1.57 | 2.03 | 8.635 | 0.015805 | * |
| 87 | 130.29 | 155.57 | 141.23 | 313.19 | 320.06 | 317.04 | 2.24 | 1.87 | 2.8 | 9.03 | 0.020409 | * |
| 88 | 286.21 | 414.54 | 348.29 | 985.82 | 995.05 | 990.4 | 2.84 | 2.16 | 4.16 | 9.225 | 0.049506 | * |
| 89 | 131.42 | 110.91 | 122.78 | 247.45 | 223.32 | 236.79 | 1.93 | 1.53 | 2.54 | 5.004 | 0.038821 | * |
| 90 | 112.61 | 137.23 | 125.04 | 293.85 | 321.31 | 307.79 | 2.46 | 2.04 | 3.05 | 9.093 | 0.011966 | * |
| 91 | 53.05 | 57.31 | 55.25 | 108.42 | 115.51 | 112.36 | 2.03 | 1.68 | 2.51 | 6.466 | 0.024294 | * |
| 92 | 157.78 | 135.22 | 145.47 | 310.51 | 342.11 | 327.58 | 2.25 | 1.83 | 2.87 | 7.123 | 0.019178 | * |
| 93 | 2419.57 | 2525.23 | 2473 | 4412.4 | 4840.91 | 4619.04 | 1.87 | 1.69 | 2.06 | 8.867 | 0.042128 | * |
| 94 | 215.76 | 186.58 | 201.09 | 401.49 | 418.78 | 409.73 | 2.04 | 1.7 | 2.51 | 7.604 | 0.021132 | * |
| 95 | 437.27 | 409.44 | 423.12 | 228.06 | 248.67 | 238.97 | −1.77 | −1.57 | −2 | −7.614 | 0.025043 | * |
| 96 | 123.92 | 107.89 | 115.29 | 225.21 | 221.88 | 223.4 | 1.94 | 1.6 | 2.42 | 6.515 | 0.027006 | * |
| 97 | 612.78 | 576.59 | 595.48 | 1096.59 | 1000 | 1048.84 | 1.76 | 1.59 | 1.95 | 7.943 | 0.043916 | * |
| 98 | 1748.38 | 1703.42 | 1726.52 | 1036.42 | 966.07 | 999.33 | −1.73 | −1.6 | −1.87 | −13.819 | 0.008998 | * |
| 99 | 9.69 | 13.76 | 11.28 | 43.94 | 37.02 | 40.77 | 3.61 | 2.04 | 11.81 | 4.351 | 0.049011 | * |
| 100 | 461.12 | 486.8 | 474.07 | 202.43 | 201.6 | 201.94 | −2.35 | −2.15 | −2.57 | −15.536 | 0.009759 | * |
| 101 | 25.16 | 20.62 | 22.17 | 57.02 | 58.29 | 57.55 | 2.6 | 1.74 | 4.65 | 4.461 | 0.047383 | * |
| 102 | 312 | 350.96 | 337.07 | 576.04 | 626.6 | 606.13 | 1.8 | 1.53 | 2.14 | 5.92 | 0.031648 | * |
| 103 | 62.62 | 88.28 | 77.98 | 244.94 | 233.31 | 238.98 | 3.06 | 2.23 | 4.71 | 6.949 | 0.020111 | * |
| 104 | 1475.25 | 1551.27 | 1509.99 | 2951.15 | 2813.6 | 2885.76 | 1.91 | 1.79 | 2.04 | 15.344 | 0.010397 | * |
| 105 | 1367.45 | 1501.79 | 1437.52 | 2718.02 | 2697.74 | 2708.16 | 1.88 | 1.73 | 2.06 | 15.464 | 0.009932 | * |
| 106 | 970.89 | 853.71 | 912.25 | 239.75 | 263.56 | 250.51 | −3.64 | −3.1 | −4.29 | −10.546 | 0.040834 | * |
| 107 | 986.93 | 896.21 | 941.85 | 495.03 | 549.02 | 520.07 | −1.81 | −1.56 | −2.11 | −6.563 | 0.027917 | * |
| 108 | 374.15 | 401.85 | 385.58 | 814.69 | 731.24 | 775.62 | 2.01 | 1.72 | 2.36 | 6.656 | 0.044234 | * |
| 109 | 363.89 | 434.04 | 398.95 | 772.24 | 701.41 | 737.44 | 1.85 | 1.57 | 2.2 | 6.638 | 0.02207 | * |
| 110 | 387.41 | 362.67 | 376.24 | 209.07 | 214.57 | 211.27 | −1.78 | −1.53 | −2.09 | −6.247 | 0.028515 | * |
| 111 | 2366.93 | 2270.57 | 2317.53 | 1349.62 | 1427.98 | 1389.5 | −1.67 | −1.5 | −1.85 | −7.705 | 0.027981 | * |
| 112 | 452.15 | 409.67 | 432.83 | 800.92 | 746.29 | 773.68 | 1.79 | 1.55 | 2.08 | 7.041 | 0.019802 | * |
| 113 | 1530.91 | 1468.46 | 1498.36 | 894.5 | 938.85 | 912.04 | −1.64 | −1.51 | −1.8 | −10.283 | 0.009669 | * |
| 114 | 175.96 | 159.11 | 167.68 | 336.43 | 308.35 | 322.49 | 1.92 | 1.6 | 2.33 | 5.835 | 0.037189 | * |
| 115 | 142.21 | 150 | 146.13 | 76.02 | 79.16 | 77.39 | −1.89 | −1.63 | −2.22 | −7.348 | 0.018732 | * |
| 116 | 2454 | 2941.95 | 2697.31 | 5067.12 | 4950.76 | 5011.42 | 1.86 | 1.61 | 2.19 | 8.533 | 0.033698 | * |
| 117 | 167.3 | 203.1 | 187.65 | 354.17 | 353.2 | 353.7 | 1.88 | 1.57 | 2.34 | 6.871 | 0.046797 | * |
| 118 | 22.44 | 11.02 | 17.07 | 66.74 | 58.4 | 62.61 | 3.67 | 2.07 | 12.35 | 4.527 | 0.045678 | * |
| 119 | 128.87 | 113.17 | 121.31 | 224.26 | 244.11 | 233.04 | 1.92 | 1.61 | 2.35 | 6.606 | 0.022576 | * |
| 120 | 83.91 | 72.84 | 77.62 | 203.18 | 171.35 | 186.99 | 2.41 | 1.86 | 3.21 | 5.457 | 0.046675 | * |
| 121 | 289.94 | 429.56 | 360.03 | 962.21 | 1149.02 | 1054.8 | 2.93 | 2.11 | 4.47 | 5.818 | 0.032936 | * |
| 122 | 140.37 | 119.62 | 131.47 | 275.34 | 241.37 | 257.7 | 1.96 | 1.55 | 2.54 | 4.865 | 0.043266 | * |
| 123 | 109.7 | 119.64 | 115.46 | 228.47 | 214.51 | 221.46 | 1.92 | 1.58 | 2.38 | 5.821 | 0.028482 | * |
| 124 | 1036.33 | 1114.29 | 1073.98 | 1860.83 | 1808.33 | 1835.09 | 1.71 | 1.57 | 1.86 | 11.087 | 0.008285 | * |

TABLE 2-continued

DNA array results for control and ZDHHC3 ablated MDA-MB-231 cells

| 125 | 1415.81 | 1386.03 | 1402.49 | 738.95 | 832.69 | 786.02 | −1.78 | −1.61 | −2 | −11.284 | 0.021506 | * |
|---|---|---|---|---|---|---|---|---|---|---|---|---|
| 126 | 58.55 | 53.83 | 56.45 | 113.47 | 117.94 | 115.68 | 2.05 | 1.64 | 2.67 | 5.752 | 0.029238 | * |
| 127 | 1150.48 | 1436.97 | 1294.46 | 2663.89 | 2541.9 | 2601.29 | 2.01 | 1.65 | 2.53 | 7.023 | 0.030687 | * |
| 128 | 1054.35 | 830.59 | 942.89 | 2033.33 | 1950.52 | 1985.61 | 2.11 | 1.72 | 2.69 | 7.727 | 0.042502 | * |
| 129 | 390.8 | 361.45 | 376.33 | 737.14 | 762.16 | 749.59 | 1.99 | 1.79 | 2.24 | 11.194 | 0.008077 | * |
| 130 | 70.14 | 87.27 | 79.02 | 167.2 | 170.58 | 169.01 | 2.14 | 1.72 | 2.8 | 7.272 | 0.042197 | * |
| 131 | 223.18 | 283.83 | 251.19 | 557.31 | 493.51 | 526.69 | 2.1 | 1.63 | 2.83 | 5.277 | 0.034132 | * |
| 132 | 23.65 | 25.36 | 24.6 | 88.17 | 84.37 | 86.44 | 3.51 | 2.4 | 5.98 | 6.011 | 0.033103 | * |
| 133 | 528.19 | 530.43 | 529.26 | 311.58 | 313.24 | 312.31 | −1.69 | −1.58 | −1.83 | −12.373 | 0.006947 | * |
| 134 | 143.92 | 128.72 | 135.94 | 255.75 | 231.23 | 243.63 | 1.79 | 1.52 | 2.13 | 5.786 | 0.033891 | * |
| 135 | 124.49 | 118.76 | 121.6 | 225.26 | 210.25 | 218.32 | 1.8 | 1.51 | 2.15 | 5.539 | 0.039085 | * |
| 136 | 338.22 | 288.47 | 313.31 | 579.08 | 631.22 | 604.1 | 1.93 | 1.62 | 2.34 | 6.713 | 0.021482 | * |
| 137 | 136.2 | 162.96 | 149.84 | 376.54 | 333.88 | 356.47 | 2.38 | 1.93 | 2.99 | 6.872 | 0.029495 | * |
| 138 | 492.44 | 604.79 | 548.42 | 997.44 | 1113.6 | 1055.22 | 1.92 | 1.58 | 2.39 | 5.861 | 0.028089 | * |
| 139 | 837.23 | 813.65 | 825.88 | 464.11 | 453.91 | 459.35 | −1.8 | −1.68 | −1.93 | −13.104 | 0.014148 | * |

TABLE 3

Genes altered due to DHHC3 ablation

| Gene Name | Fold Change | Links (reference)[a] |
|---|---|---|
| Up-regulated | | |
| Vestigial like 3 (VGLL3) | 3.67 | TS (1) |
| Phosphatidylinositol-4-phosphate 5-kinase, type I, beta (PIP5K1b) | 3.61 | Sen (2) |
| Collagen, type VI, alpha 3 (COL6A3) | 3.15 | Sen (3) |
| General transcription factor II, i (GTF2i) | 2.83 | OS (4, 5) |
| Thioredoxin interacting protein (TXNIP) | 2.57 | OS, Sen, TS (6, 7) |
| Amylase, alpha 1A (AMY1A) | 2.53 | Sen (8) |
| Chromosome 1 open reading frame 63, C1orf63 (RSRP1) | 2.4 | Sen (9) |
| Advillin (AVIL) | 2.18 | ES (10) |
| Kinase D-interacting substance of 220 kDa (KIDINS220) | 2.12 | — |
| FK506 binding protein 11, 19 kDa (FKBP11) | 2.01 | OS (11) |
| X-ray repair complementing defective repair in Chinese hamster cells 2 (XRCC2) | 1.94 | — |
| Intersectin 2 (ITSN2) | 1.93 | Sen (12) |
| SET domain containing 6 (SETD6) | 1.92 | OS (13) |
| BTB (POZ) domain containing 5 (KLHL28)[b] | 1.92 | Sen |
| DMC1 dosage suppressor of mck1 homolog (DMC1) | 1.91 | — |
| Mitochondrial ribosomal protein 63 (MRPL57) | 1.90 | — |
| Major histocompatibility complex, class I-related (MR1) | 1.88 | — |
| Zinc finger, CCHC domain containing 14 (KIAA0579) | 1.88 | — |
| Centrosomal protein 27 kDa, CEP27 (HAUS2) | 1.86 | — |
| Senataxin (SETX) | 1.81 | OS (14) |
| S.RY (sex determining region Y)-box 13 (SOX13) | 1.79 | — |
| RAD1 homolog (RAD1) | 1.7.5 | — |
| Ataxia telangiectasia mutated (ATM) | 1.71 | Sen (15) |
| Tripartite motif-containing 38 (TRIM38) | 1.7 | Sen (16) |
| Collagen, type XIII, alpha 1 (COL13A1) | 1.64 | Sen (3) |
| Downregulated | | |
| ZDHHC3 | −3.64 | — |
| BCL2-related protein A1 (BCL2A1) | −2.4 | Sen (17) |
| Dystobrevin, alpha (DTNA) | −2.17 | — |
| Chromosome II open reading frame 51 (ANAPC15) | −2.14 | Sen (18) |
| S100A4 protein (S100A4) | −2.11 | Onc. OS (19) |
| Prefoldin subunit 4 (PFDN4) | −2.04 | Sen (20) |
| Dehydrogenase/reductase (SDR family) member 3 (DHRS3) | −2.03 | — |
| PHD finger protein 14 (PHF14) | −2.02 | — |
| B9 protein (B9D1) | −1.94 | — |
| DENN/MADD domain containing 1A (DENND1A) | −1.89 | — |
| Protein tyrosine phosphatase, non-receptor type 7 (HePTP) | −1.88 | Sen (21) |
| Phosphodiesterase 4B, cAMP-specific (PDE4B) | −1.88 | OS (22) |
| Histamine N-methyltransferase (HNMT)[c] | −1.85 | OS |
| Nudix (nucleoside diphosphate linked moietyX)-type motif 2 (NUDT2) | −1.81 | OS (23) |
| Chromosome 14 open reading frame 2 (C14orf2) | −1.81 | — |
| WD repeat domain 61 (WDR61) | −1.78 | — |
| Egl nine homolog 3 (EGLN3) | −1.78 | — |
| BCL2/adenovirus E1B 19 kDa interacting protein 1 (BNIP1) | −1.76 | — |
| Cyclin-dependent kinase inhibitor 3 (CDKN3) | −1.75 | Sen (24) |
| SMN interacting protein 1-delta (GEMIN2) | −1.74 | — |
| Aldo-keto reductase family 1, member C1 (AKR1C1) | −1.74 | OS (25) |
| Glutathione transferase zeta 1 (GSTZ1) | −1.73 | OS (26) |

TABLE 3-continued

Genes altered due to DHHC3 ablation

| Gene Name | Fold Change | Links (reference)[a] |
|---|---|---|
| Chromosome 16 open reading frame 60 (CENPN) | −1.67 | Sen (9) |
| Lipase A, lysosomal acid, cholesterol esterase (Wolman disease) | −1.66 | Sen (27) |
| Hematopoietic cell specific Lyn substrate 1 (HCLS1) | −1.66 | Sen (28) |
| SMN interacting protein 1-gamma (GEMIN2) | −1.64 | — |
| Dilute suppressor (MREG) | −1.64 | — |

[a]OS = oxidative stress; Sen = senescent; Onc = oncogenic; Ts = Tumor suppressor; ES = ER stress
[b]predicted functional partner of RGN (senescence marker protein-30) (//string-db.org/cgi/network.pl?taskId=4OrMQuLACUrH)
[c]Enhancing HNMT enzyme levels is a suggested therapy for oxidative stress related disorders (U.S. Pat. No. 8,709,406 B2)

TABLE 4

Additional list of senescence related genes from human microarray analysis of D3 xenograft tumors

| S#[a] Gene name | Fold | P value | Reference |
|---|---|---|---|
| 1. Cyclin-dependent kinase inhibitor 2A (melanoma, p16, inhibits CDK4), (CDKN2A) | 16 | 0.008 | (29) |
| 2. Serpin peptidase inhibitor, clade E (nexin, plasminogen activator inhibitor type 1), (PAI-1) | 2.87 | 0.04 | (30) |
| 3. Major histocompatibility complex, class II, DR beta 1, (HLA-DRB4)[b] | 1.81 | 0.005 | |
| 4. Tight junction protein 1 (zona occludens 1), (TJP1) | 1.63 | 0.0008 | (31) |
| 5. Retinoblastoma binding protein 6, (RBBP6) | 1.6 | 0.03 | (32) |
| 6. Insulin-like growth factor binding protein 7, (IGFBP7) | 1.5 | 0.03 | (33) |
| 7. SMAD specific E3 ubiquitin protein ligase 2, (Smurf2) | 1.45 | 0.04 | (34) |
| 8. Mitogen-activated protein kinase kinase kinase 5, (Ask1) | 1.41 | 0.03 | (35) |
| 9. Thrombospondin 1, (THBS1) | 1.4 | 0.02 | (36) |
| 10. Chromobox homolog 1 (HP1 beta homolog Drosophila), (CBX1) | 1.3 | 0.001 | (37) |
| 11. Hypoxia up-regulated 1/ORP150, (GRP170) | 1.3 | 0.04 | (38) |
| 12. Cyclin-dependent kinase inhibitor 2C (p18, inhibits CDK4), (CDKN2C) | −1.4 | 0.008 | (29) |
| 13. Cyclin A2, (CCNA2) | −1.32 | 0.01 | (39) |
| 14. Endothelial cell-specific molecule 1, (Esm1) | 3.83 | 0.09 | (40) |
| 15. Platelet-derived growth factor beta polypeptide, (PDGFB) | 1.93 | 0.09 | (41) |
| 16. Mitogen-activated protein kinase-activated protein kinase 2 | 1.6 | 0.08 | (42) |
| 17. Platelet derived growth factor C, (PDGFC) | 1.22 | 0.07 | (43) |
| 18. Tumor protein p53 (Li-Fraumeni syndrome), (TP53) | 1.2 | 0.07 | (44) |
| 19. Fibroblast growth factor 5 (FGF5) | −1.4 | 0.1 | (45) |

[a]Althought the top six genes in this list apparently do meet fold change and P value criteria, they were not selected by the array analysis program due to erroneous false probe results, and thus do not appear in Table 2.
[b]suggested as human senescence gene (//liweilab.genetics.ac.en/tm/search.php?st=gn&gn=human%20senescence%20gene&ti=9606&tn=1105&sot=&pg=6)

The following references were cited in Table 3 and Table 4.
(1) Gambaro et al., 2013 Mol Oncol, 7:513-30.
(2) Ischebeck et al., 2013 Plant Cell, 25:4894-911.
(3) Larsson et al., 2004 Cancer Res, 64:482-9.
(4) Inberg A and Linial M. 2010 J Biol Chem, 285:25686-98.
(5) Hassona et al, 2013 Carcinogenesis, 34:1286-95.
(6) Mahmood et al, 2013 Antioxid Redox Signal, 19:1266-303.
(7) Riahi et al., 2015 J Cell Mol Med, 19:1887-99.
(8) Jie et al., 2009 BMB Rep, 42:101-5.
(9) Chechlinska et al., 2009 BMC Genomics, 10:261.
(10) Wang et al., 1998 EMBO J, 17:3619-30.
(11) Laybutt et al., 2007 Diabetologia, 50:752-63.
(12) Rajarajacholan et al., 2013 PLoS Biol, 11:e1001502.
(13) Chen et al., 2016 Biochim Biophys Acta, 1859:420-7.
(14) Suraweera et al., 2009 Hum Mol Genet, 18:3384-96.
(15) Zhan et al., 2010 J Biol Chem, 285:29662-70.
(16) Santos J and Gil J. 2014 Immunol Lett, 162:281-9.
(17) Makpol et al., 2012 Oxid Med Cell Longev, 2012:785743.
(18) Mansfeld et al., 2011 Nat Cell Biol, 13:1234-43.
(19) Dmytriyeva et al., 2012 Nat Commun, 3:1197.
(20) Iijima et al., 1996 Acta Med Okayama, 50:73-7.
(21) Sergienko et al., 2012 ACS Chem Biol, 7:367-77.
(22) Kashiwagi et al., 2012 Prostate, 72:741-51.
(23) Ogawa et al., 2009 Plant J, 57:289-301.
(24) Krizhanovsky et al., 2008 Cell, 134:657-67.
(25) Burczynski et al., 2001 J Biol Chem, 276:2890-7.
(26) Blackburn et al., 2006 Mol Pharmacol, 69:650-7.
(27) Kojima et al., 2013 Hepatol Res, 43:1361-7.
(28) Marthandan et al., 2015 Biomed Res Int, 2015:731938.
(29) Gagrica et al., 2012 Cancer Res, 72:165-75.
(30) Kortlever et al., 2006 Nat Cell Biol, 8:877-84.
(31) Dabrowska et al., 2011 Tumour Biol, 32:965-76.
(32) Deschenes-Simard et al., 2014 Cell Cycle, 13:1840-58.
(33) Benatar et al., 2012 Breast Cancer Res Treat, 133:563-73.
(34) Zhang H and Cohen S N. 2004 Genes Dev, 18:302840.
(35) Yokoi et al., 2006 Diabetes, 55:1660-5.
(36) Acosta et al., 2013 Nat Cell Biol, 15:978-90.
(37) Adams P D. 2007 Gene, 397:84-93.
(38) Kretowski et al., 2014 Biomed Res Int, 2014:196249.
(39) Gopinathan et al., 2014 Cancer Res, 74:3870-9.
(40) Sousa-Victor et al., 2014 Nature, 506:316-21.
(41) Vindrieux et al., 2013 Aging (Albany N.Y.), 5:531-8.
(42) Herranz et al., 2015 Nat Cell Biol, 17:1205-17.

(43) Alessio et al., 2013 Cell Mol Life Sci, 70:1637-51.
(44) Lujambio et al., 2013 Cell, 153:449-60.
(45) Matsunaga et al., 1999 Mol Vis, 5:39.

Example 5: DHHC3 Ablation Promotes Oxidative Stress

Figure 2A:
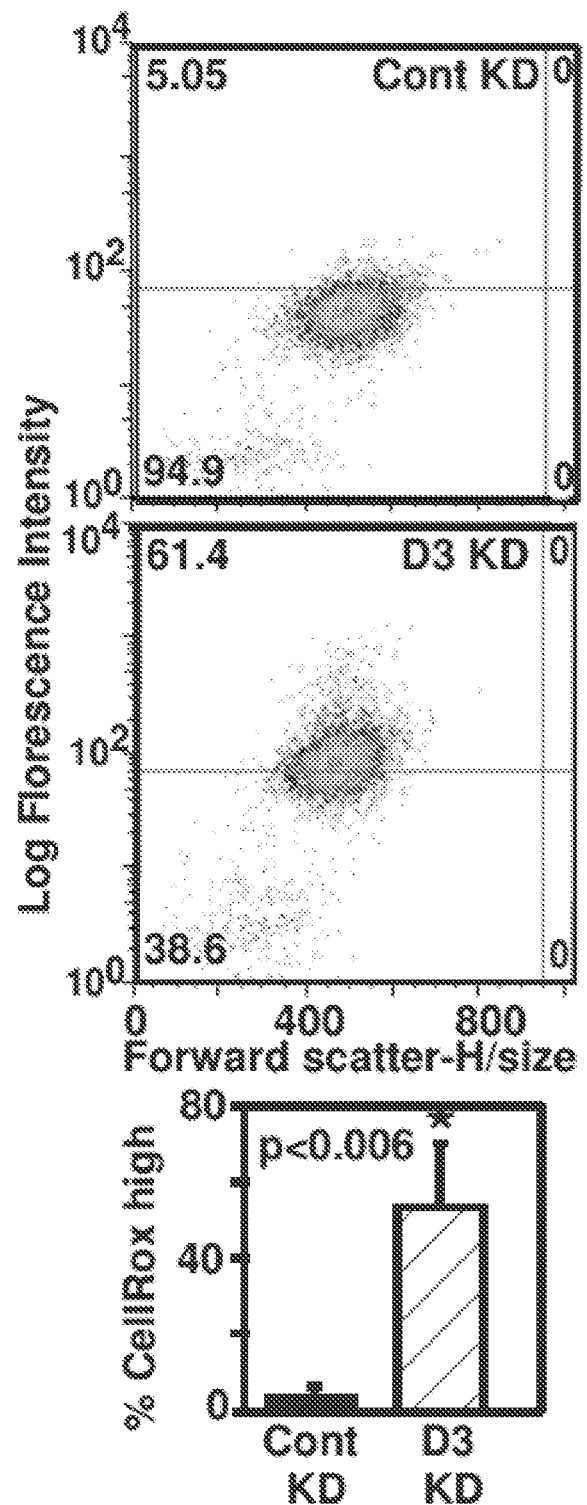
FIG. 2A-FIG. 2C is a series of flow cytometry plots, bar charts, and photographs of immunoblots showing that DHHC3 ablation promotes oxidative stress.
Figure 2B:
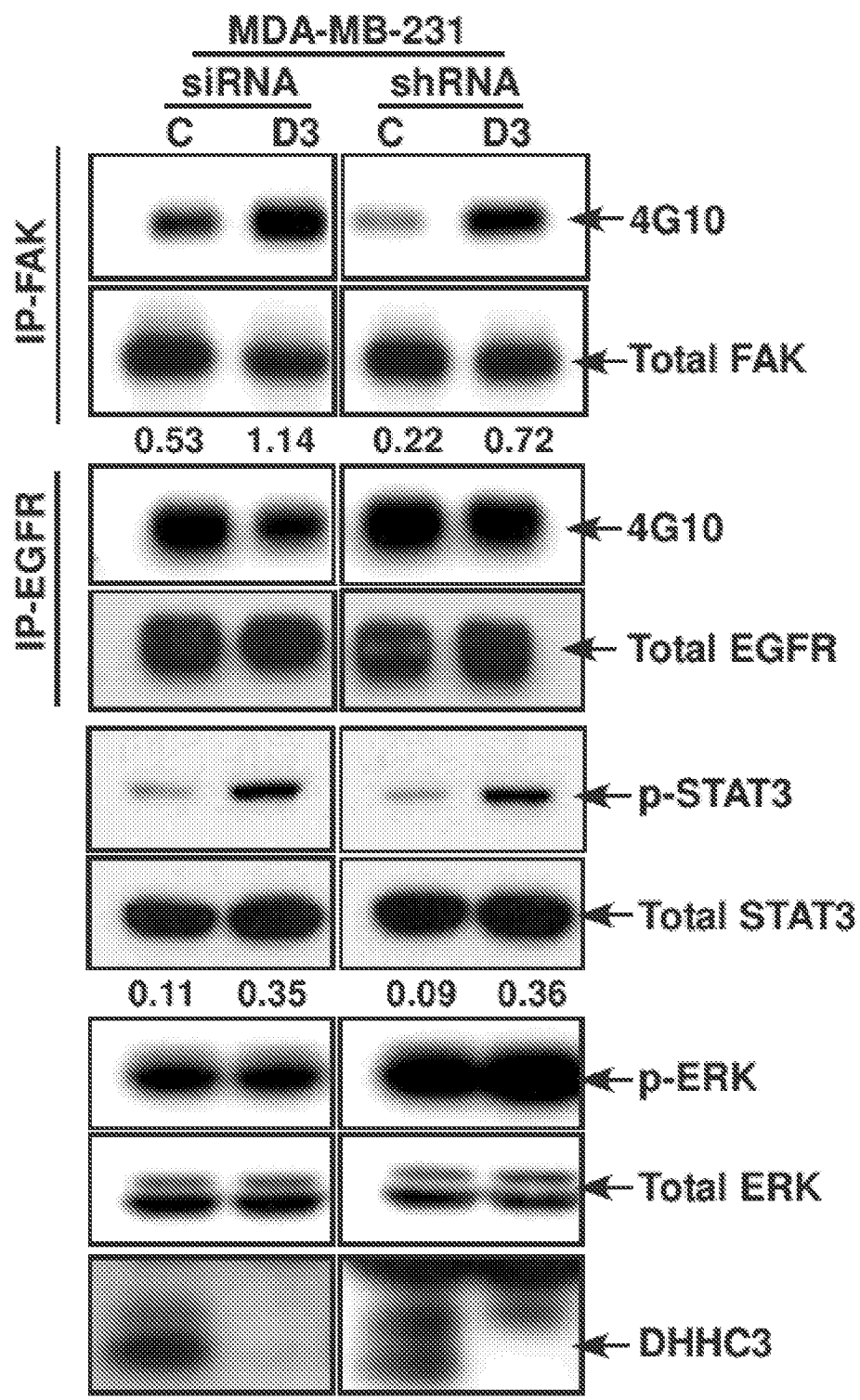
Figure 2C:
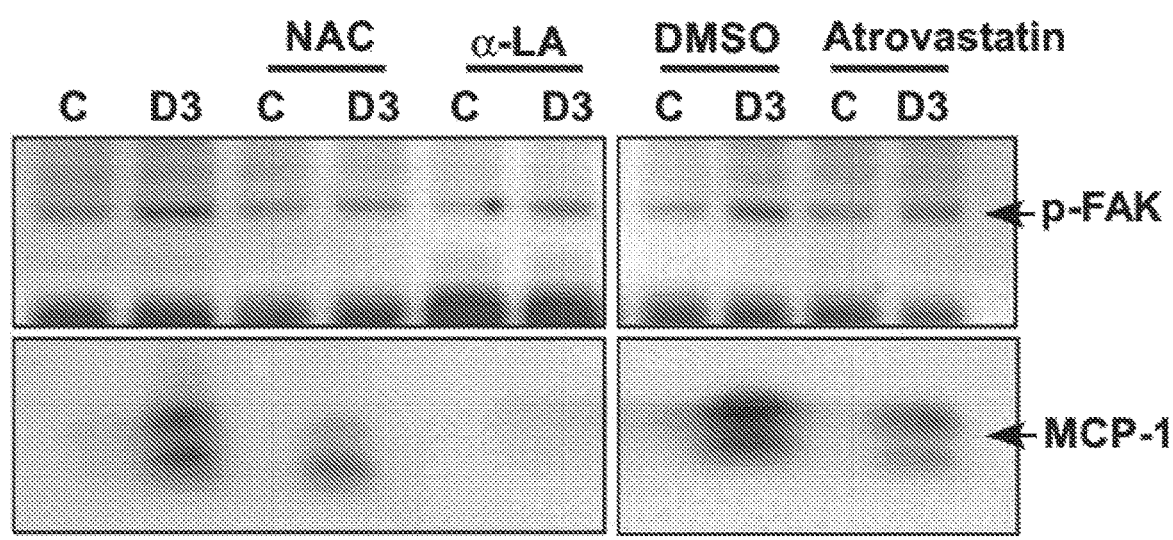
Figure 10A:
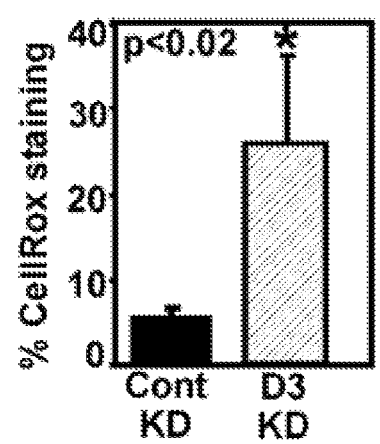
FIG. 10A-FIG. 10E is a series of photographs of immunoblots, bar graphs, and scatter plots showing that DHHC3 ablation affects oxidative stress and senescence.
Figure 10B:
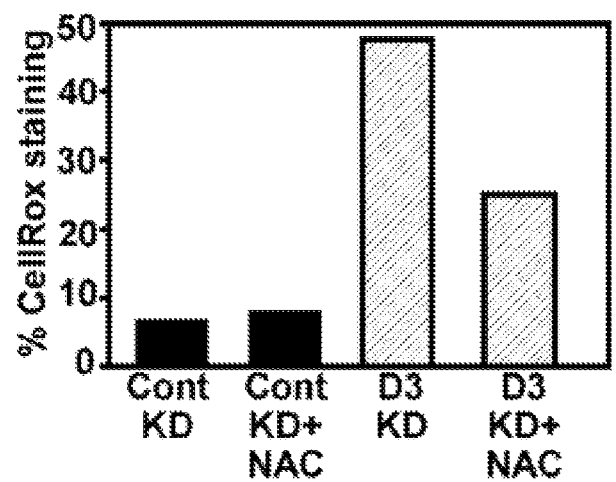
Figure 10C:
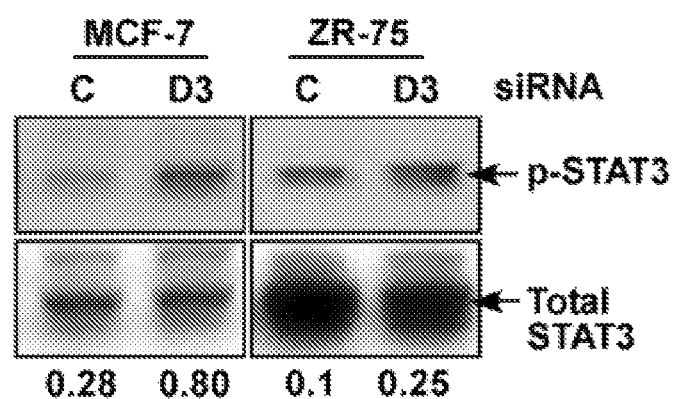
Figure 10D:
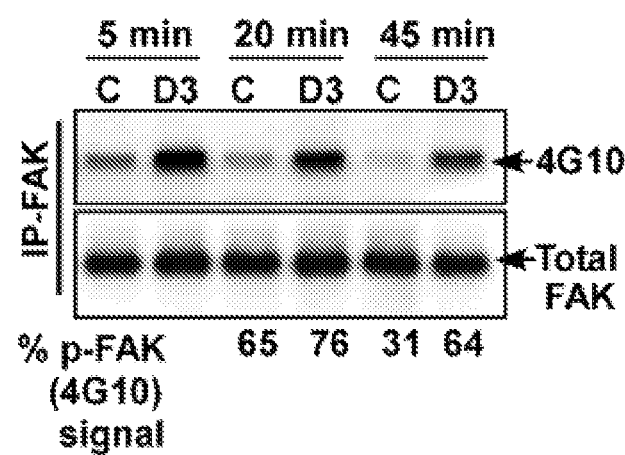

A fluorescent dye conversion assay confirmed that oxidative stress/ROS is significantly elevated in stable ZDHHC3-ablated MDA-MB-231 (FIG. 2A), and in siRNA ZDHHC3-ablated MCF-7 cells (FIG. 10A). Oxidative stress inhibitors NAC (N-acetyl cysteine; FIG. 10B) and α-LA (α-lipoic acid) substantially prevented ZDHHC3 ablation effects. Increased oxidative stress can decrease tyrosine phosphatase activities (Tanner et al., 2011 Antioxid Redox Signal, 15:77-97), which can elevate tyrosine phosphorylation of focal adhesion kinase (FAK) and STAT3 proteins (Carballo et al., 1999 J Biol Chem, 274:17580-6; Ben et al., 2000 IUBMB Life, 50:291-9). Accordingly, siRNA or shRNA ablation of ZDHHC3 markedly increased tyrosine phosphorylation of FAK and STAT3 in MDA-MB-231 (FIG. 2B), and STAT3 in MCF-7 and ZR-75 mammary cells (FIG. 10C). These results are consistent with diminished phosphatase activity. By contrast, tyrosine phosphorylation of EGFR protein, not known to be affected by oxidative stress, was unaltered (FIG. 2B). In addition, serine phosphorylation of ERK (as another negative control) was unchanged (FIG. 2B). As further evidence for diminished phosphatase activity, ZDHHC3 ablation diminished time-dependent FAK dephosphorylation in suspended MDA-MB-231 cells (FIG. 10D). Oxidative stress inhibitors NAC, α-LA and atorvastatin substantially prevented effects of ZDHHC3 ablation on FAK tyrosine phosphorylation (FIG. 2C, upper panels). Together these results support ZDHHC3-ablation diminishing tyrosine phosphatase activity due to increased oxidative stress.

Example 6: DHHC3 Ablation Enhances Cellular Senescence

Figure 3A:
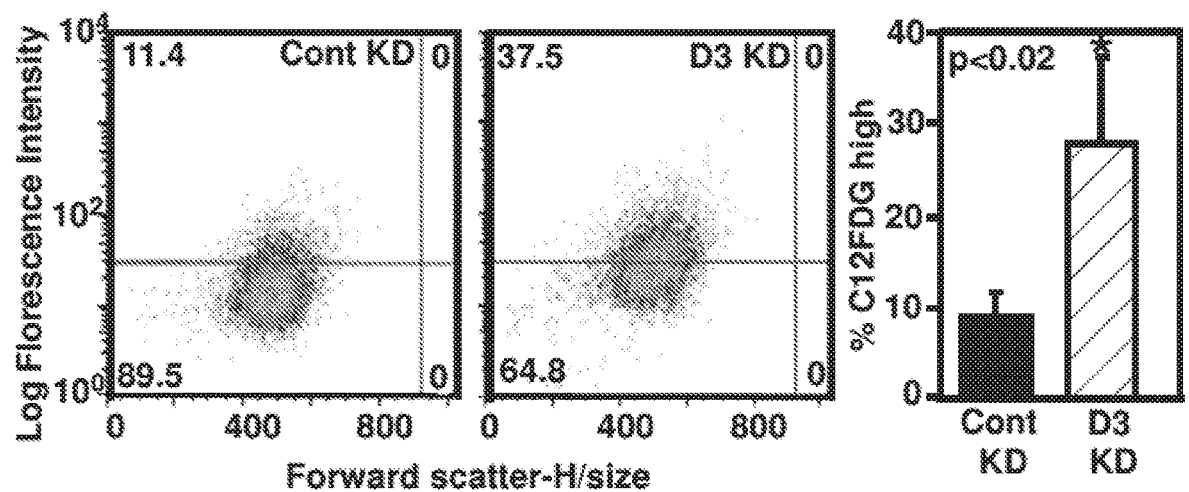
FIG. 3A-FIG. 3D is a series of flow cytometry graphs, bar charts and photographs of immunoblots showing that DHHC3 ablation enhances cellular senescence.
Figure 3B:
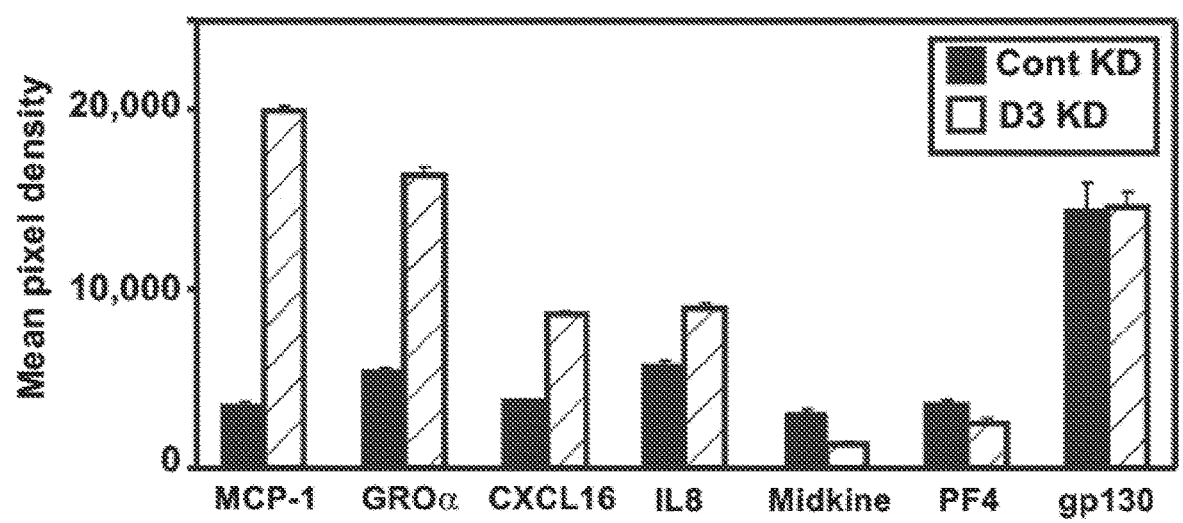
Figure 3C:
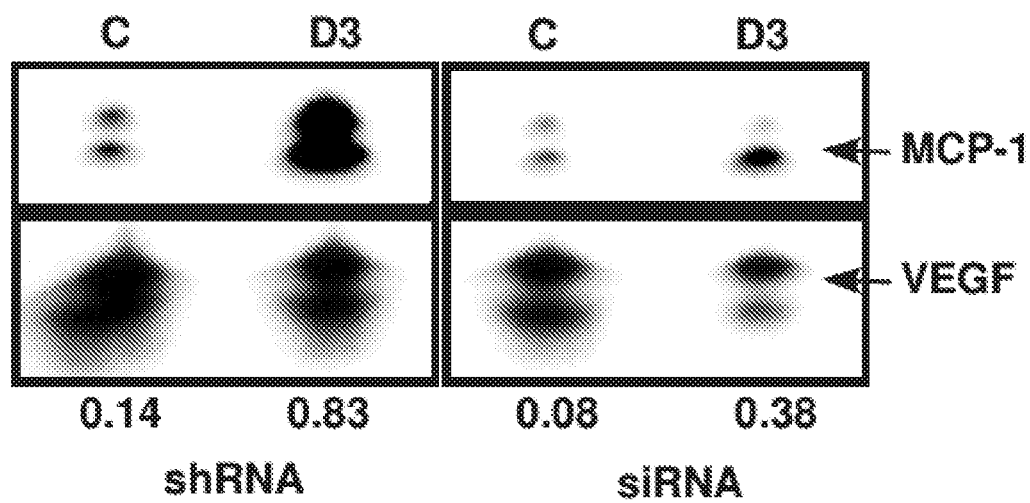
Figure 3D:
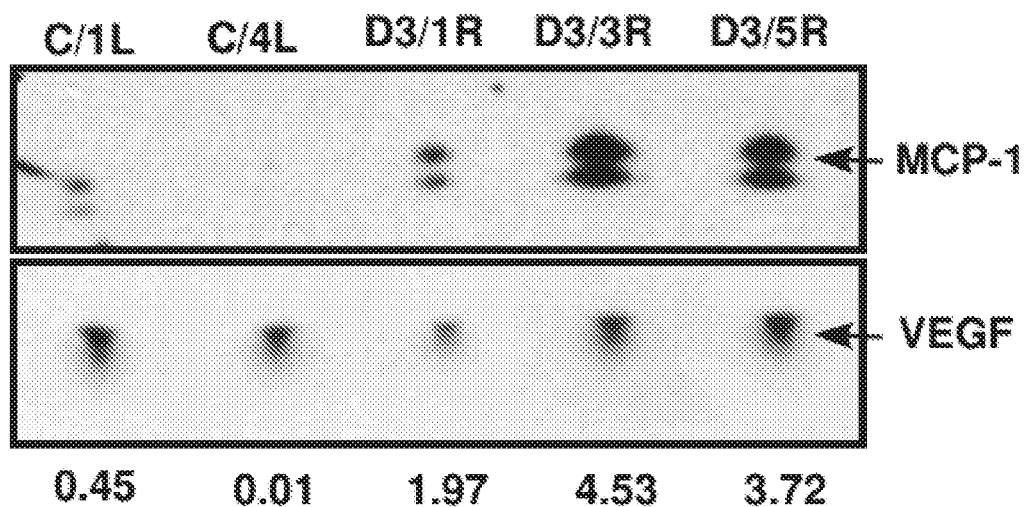
Figure 10E:
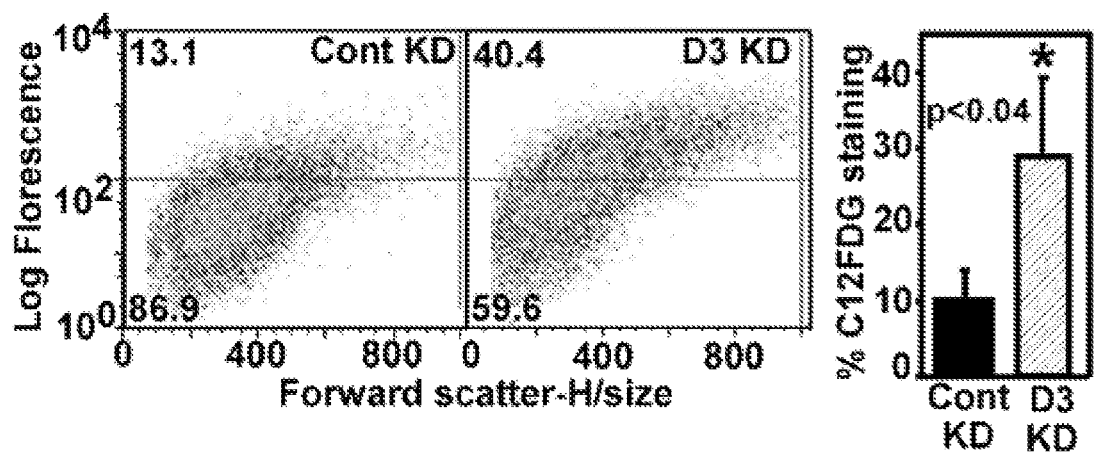

Increased oxidative stress often triggers senescence (Hwang et al., 2013 Free Radic Biol Med, 61:95-110; Mahmood et al., 2013 Antioxid Redox Signal, 19:1266-303; Panieri et al., 2013 Free Radic Biol Med, 57:176-87). Consistent with this (and with results in Table 3), ZDHHC3 ablation markedly elevated senescence-associated 1-galactosidase (SA-β-Gal) activity in MDA-MB-231 (FIG. 3A) and MCF-7 cells (FIG. 10E). Furthermore, ZDHHC3-ablated MDA-MB-231 cells increased secretion (FIG. 3B) of proteins (MCP-1, GROα, CXCL16 and IL-8) linked to senescence (Coppe et al, 2008 PLoS Biol, 6:2853-68). Secretion of three other proteins was not increased (FIG. 3B), and 24 other chemokines were absent or barely detectable. Enhanced MCP-1 secretion was confirmed by western blotting (FIG. 3C, upper panels), whereas VEGF control protein was not upregulated (FIG. 3C, lower panels). Increased secretion of MCP-1 (but not VEGF) was further validated in 3/3 ex vivo tumor cell lines derived from ZDHHC3-ablated xenograft tumors, compared to two control (i.e. non-ablated) tumor-derived cell lines (FIG. 3D). Oxidative stress inhibitors (NAC, α-LA, Atorvastatin) markedly diminished MCP-1 upregulation in ZDHHC3-ablated cells (FIG. 2C, bottom panel), consistent with senescence being triggered by oxidative stress.

Example 7: Recruitment of Innate Immune Cells—Further Evidence for Senescence As shown herein, DHHC3 ablation induces cellular senescence and senescence-associated secretory phenotype (SASP). Specifically, the upregulated chemokine pattern (FIG. 3B) emulates a SASP response, which triggers innate immune cell recruitment, and facilitates tumor clearance (Perez-Mancera et al., 2014 Nat Rev Cancer, 14:547-58).

Figure 4A:
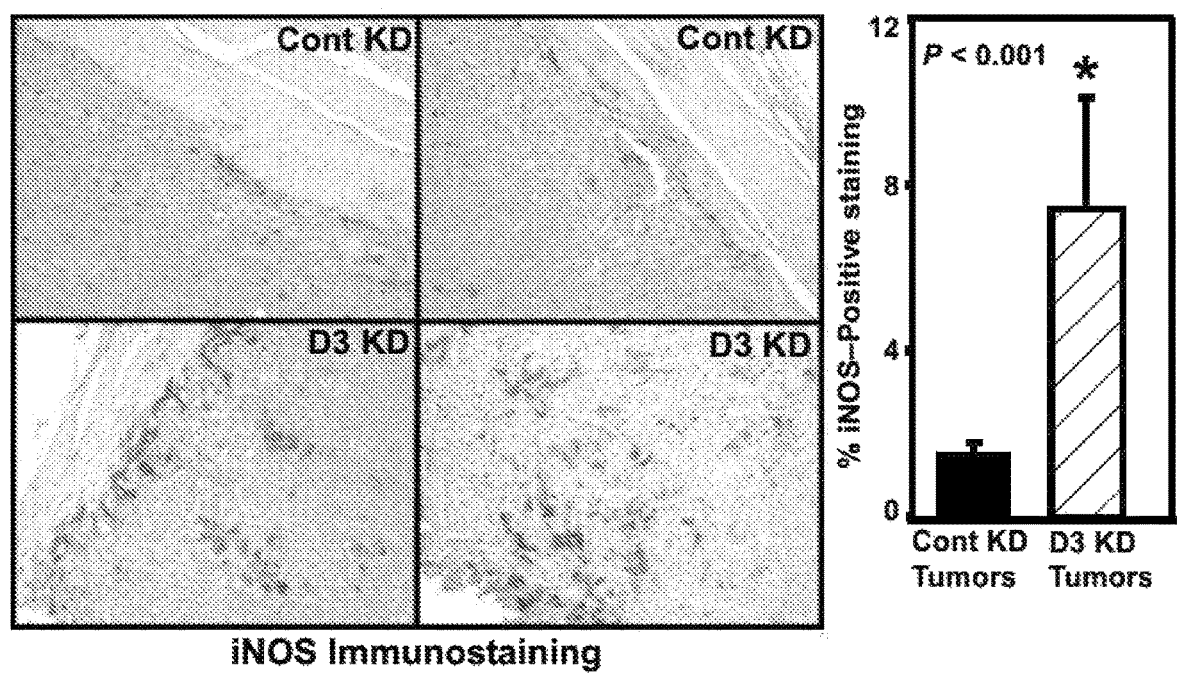
FIG. 4A-FIG. 4E is a series of photomicrographs and bar charts showing that DHHC3 ablation affects tumor recruitment of immune cells.
Figure 4B:
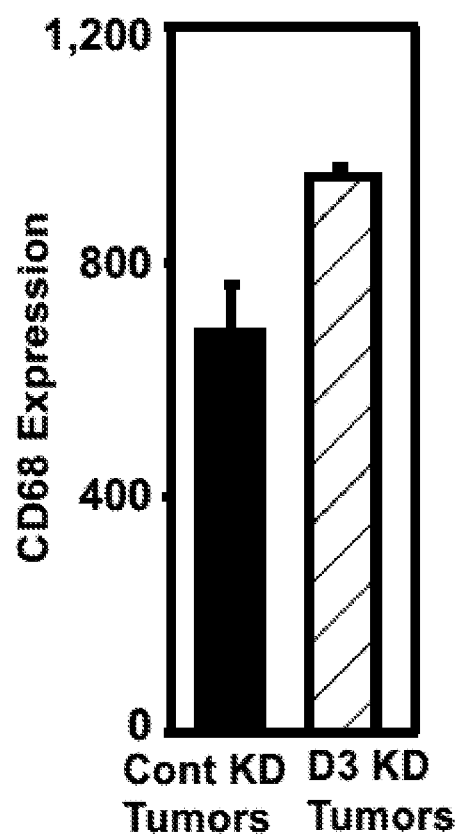
Figure 4C:
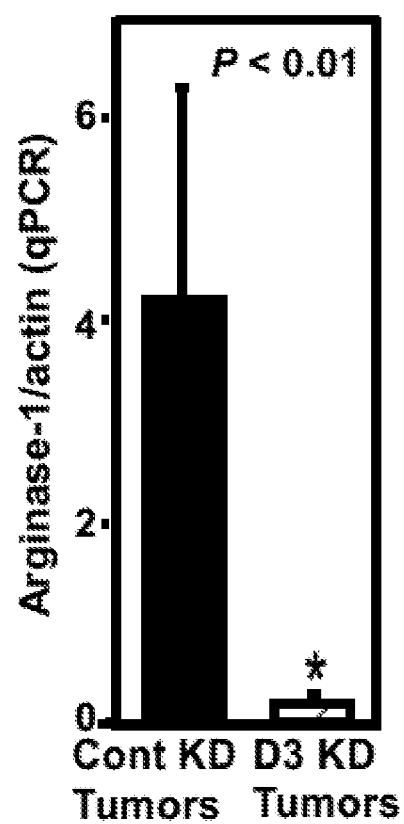
Figure 4D:
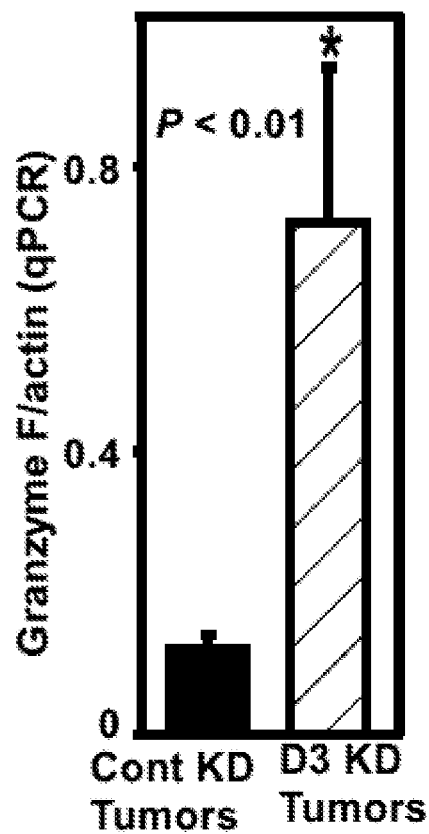
Figure 4E:
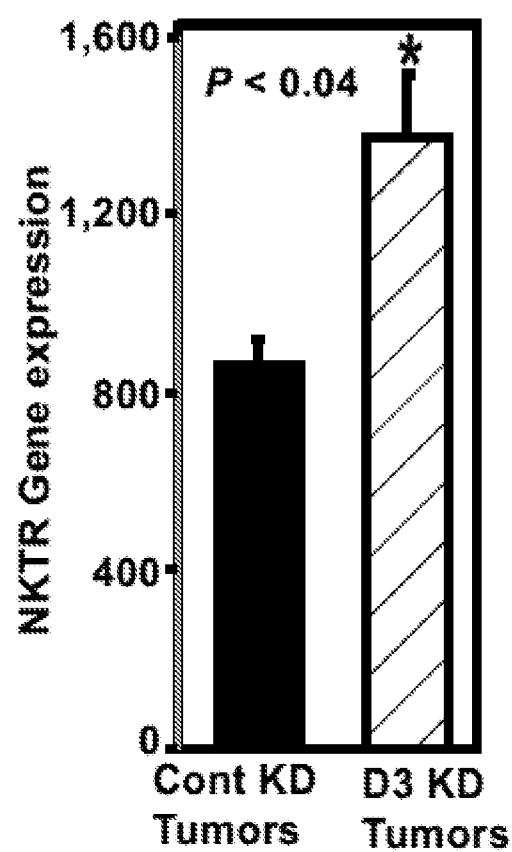

As described herein, DHHC3 effects innate immunity. Indeed, ZDHHC3-ablated xenografts showed enhanced iNOS staining, indicative of anti-tumor "M1-like" macrophages (FIG. 4A) and moderate upregulation of pan-macrophage marker CD68 (FIG. 4B). Conversely, diminished expression of Arginase 1 indicates fewer pro-tumor "M2-like" macrophages (FIG. 4C). Furthermore, elevated Granzyme F levels (FIG. 4D) indicate increased NK cell recruitment into tumors of reduced size (as in FIG. 1D, FIG. 8D). Notably, of five ZDHHC3-ablated tumors, the one with least Granzyme F elevation had the largest tumor volume. Another NK cell marker, NKTR (Natural Killer Cell Triggering Receptor), also showed significant upregulation in ZDHHC3-ablated tumors (FIG. 4E). These results are consistent with the innate immune system contributing to reduced tumor appearance.

Figure 11A:
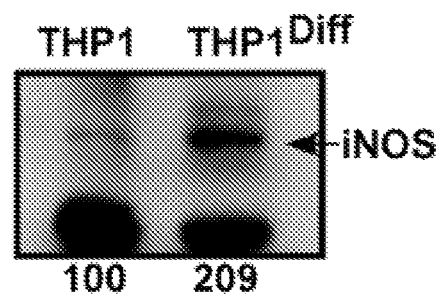
FIG. 11A-FIG. 11E is a series of photographs of immunoblots and a bar chart showing that conditioned media from DHHC3 ablated cells chemoattracts model M1 macrophages and DHHC3 ablation alters TXNIP protein levels.
Figure 11B:
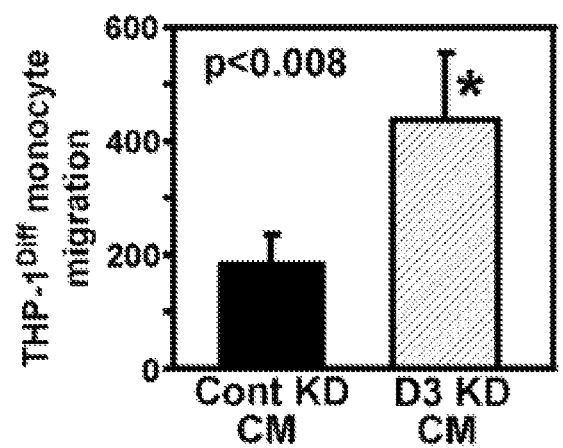
Figure 11C:
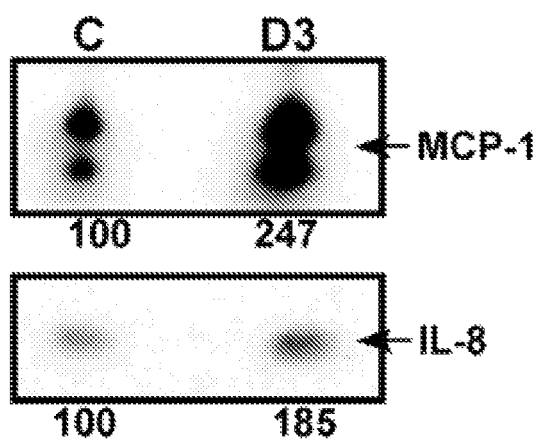

In an in vitro model system, THP1 cells were stimulated by LPS and IFN-γ to differentiate into iNOS-positive "M1-like" macrophages (FIG. 11A). Conditioned media was then collected from control and ZDHHC3-ablated MDA-MB-231 breast cancer cells, to use in a transwell migration assay as a chemoattractant. As indicated (FIG. 11B), THP1-derived "M1-like" macrophages showed significant preferential migration towards conditioned media from ZDHHC3-ablated breast cancer cells. ZDHHC3-ablation increased secretion of chemoattractant proteins MCP-1 and IL-8 (FIG. 11C), consistent with enhanced "M1-like" macrophage chemoattraction. In another control assay, undifferentiated THP1 cells showed essentially no transwell migration.

Example 8: TXNIP Contributes to the DHHC3 Ablation Phenotype

Figure 5A:
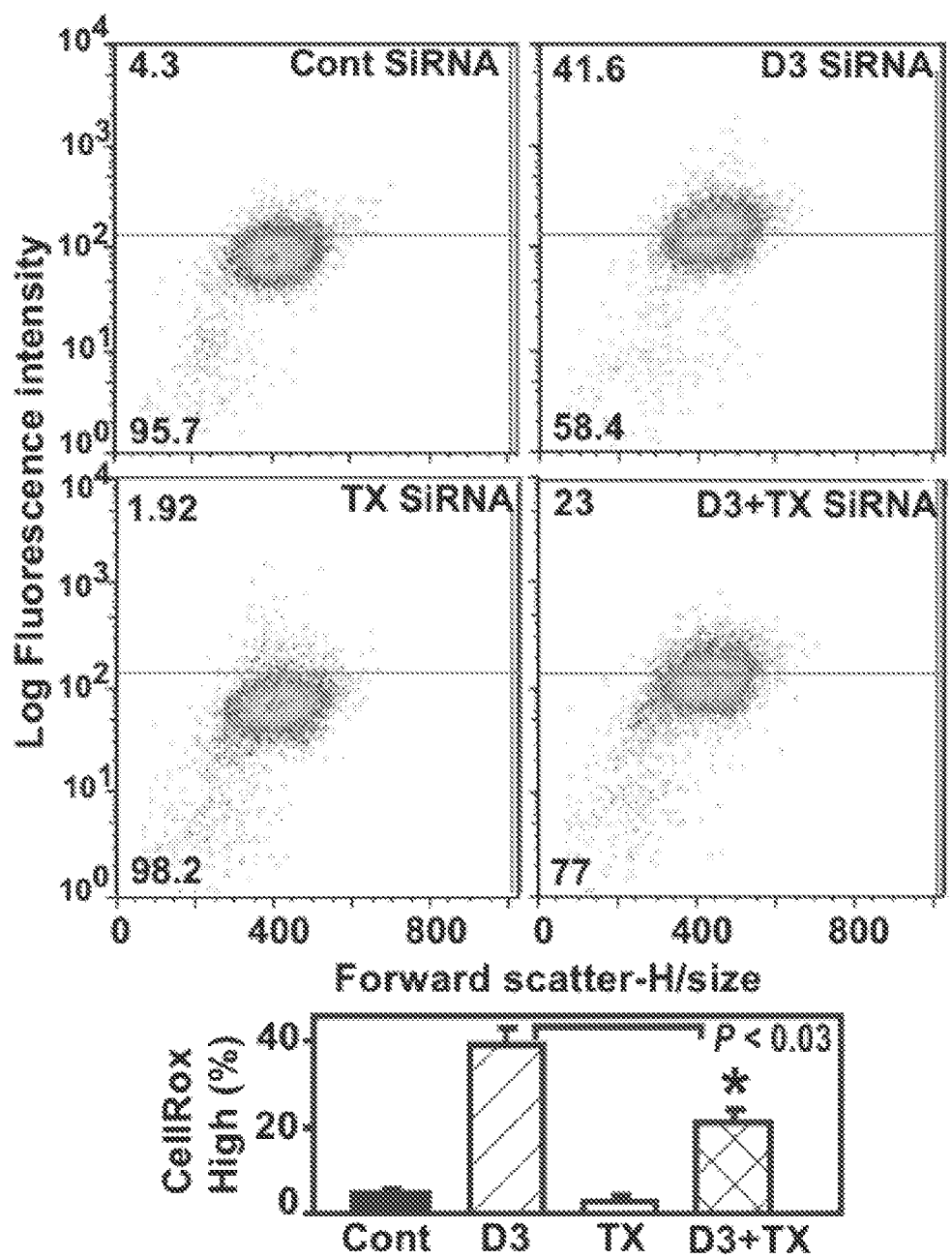
FIG. 5A-FIG. 5D is a series of flow cytometry graphs, photographs of immunoblots, and bar graphs showing TXNIP contributions to DHHC3 ablation phenotype. MDA-MB-231 cells were transiently transfected with control, DHHC3, TXNIP siRNA, and DHHC3+TXNIP siRNA. After 60 hrs, cells were analyzed.
Figure 5B:
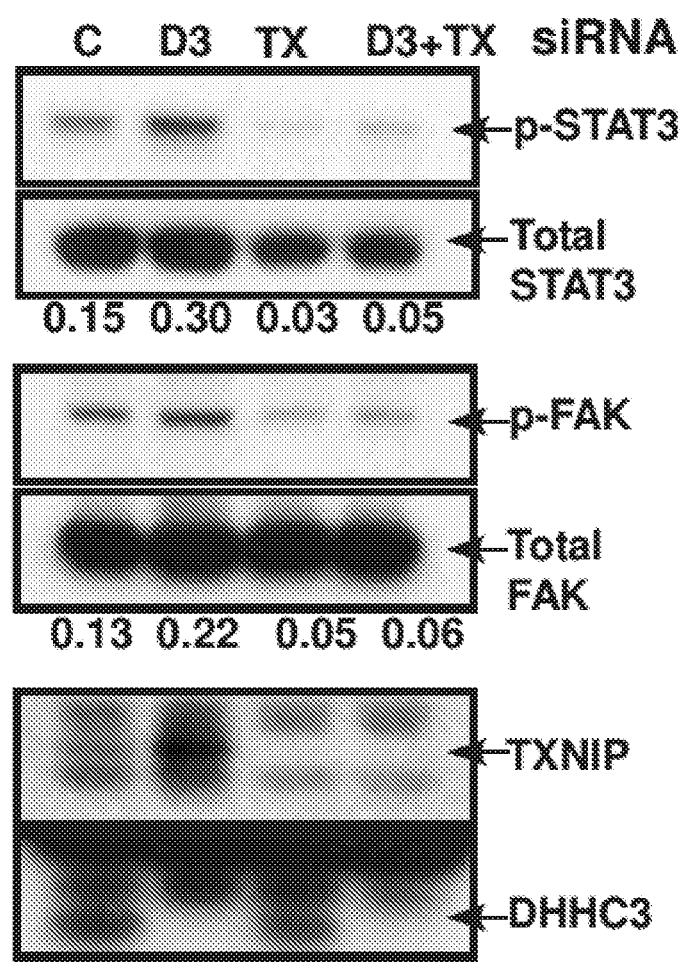
Figure 5C:
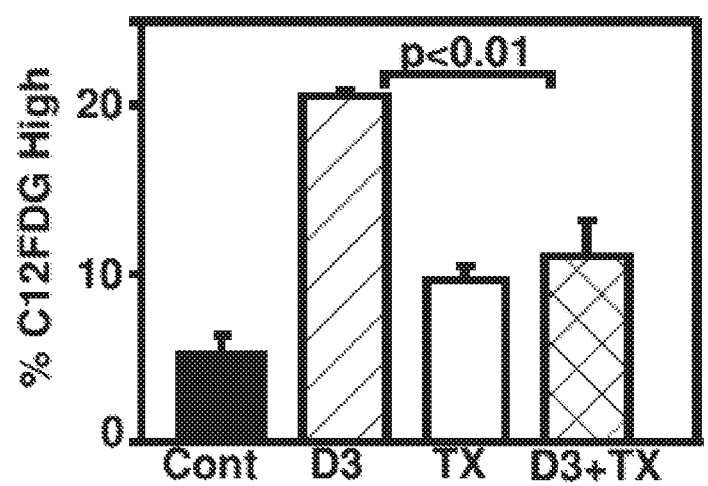
Figure 5D:
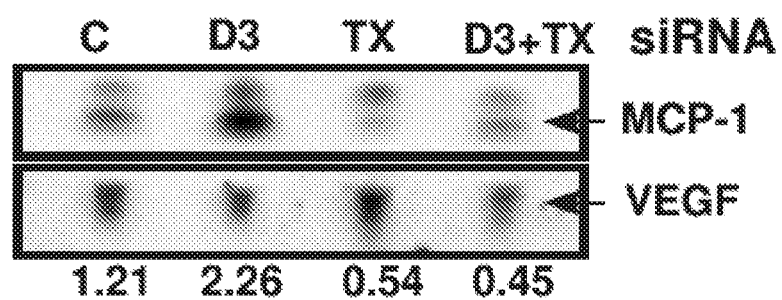
Figure 11D:
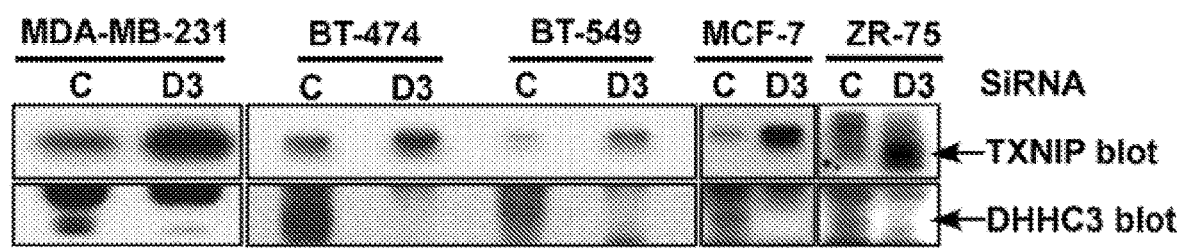
Figure 11E:
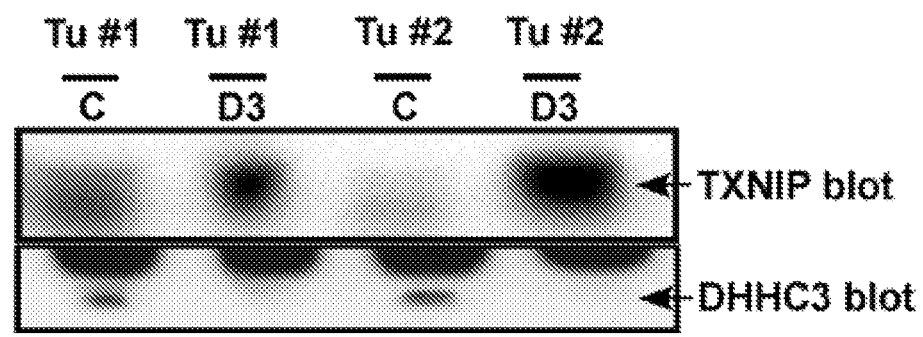

Among genes with expression altered by ZDHHC3 ablation, TXNIP (#5 in Table 3), which is linked to oxidative stress, senescence, and tumor suppression was focused on (Mahmood et al., 2013 Antioxid Redox Signal, 19:1266-303; Riahi et al., 2015 J Cell Mol Med, 19:1887-99; Morrison et al., 2014 Mol Cancer, 13:62). Enhanced TXNIP protein expression was validated in multiple breast cancer lines (FIG. 11D) and in tumor xenograft-derived cells (FIG. 11E). Notably, TXNIP removal from MDA-MB-231 cells partially but significantly reversed oxidative stress (FIG. 5A) and almost completely reversed ZDHHC3 ablation effects on oxidative stress-dependent STAT3 and FAK tyrosine phosphorylation (FIG. 5B). DHHC3 and TXNIP protein knockdowns were >90% (FIG. 5B, bottom panels). TXNIP removal also largely reversed senescence upregulation (colorimetric senescence assay, FIG. 5C: senescence-associated MCP-1, FIG. 5D). Again, ZDHHC3 ablation did not upregulate control VEGF protein (FIG. 5D).

Figure 6A:
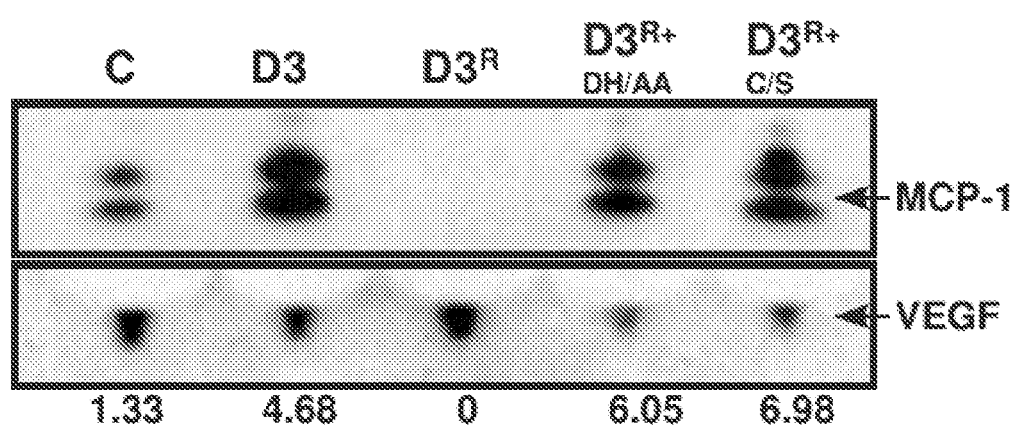
FIG. 6A-FIG. 6D is a series of graphs showing reversal of DHHC3 ablation effects by wild type and mutant DHHC3 re-expression. MDA-MB-231 cells stably expressing control shRNA (C), DHHC3 shRNA (D3), DHHC3 rescue vector ($D3^R$) unmutated or with palmitoylation site mutations ($D3^{R+DH/AA}$ and $D3^{R+C/S}$), were analyzed by western blotting.
Figure 6B:
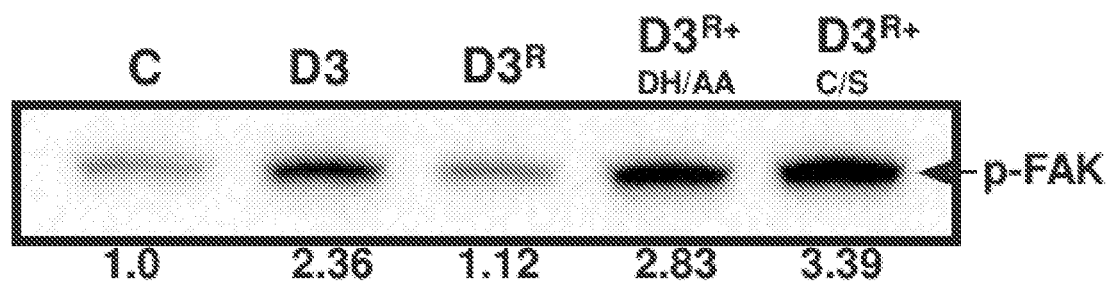
Figure 6C:
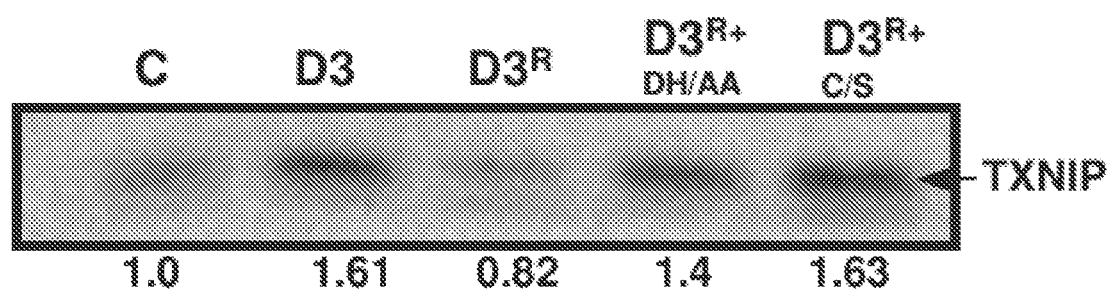
Figure 12A:
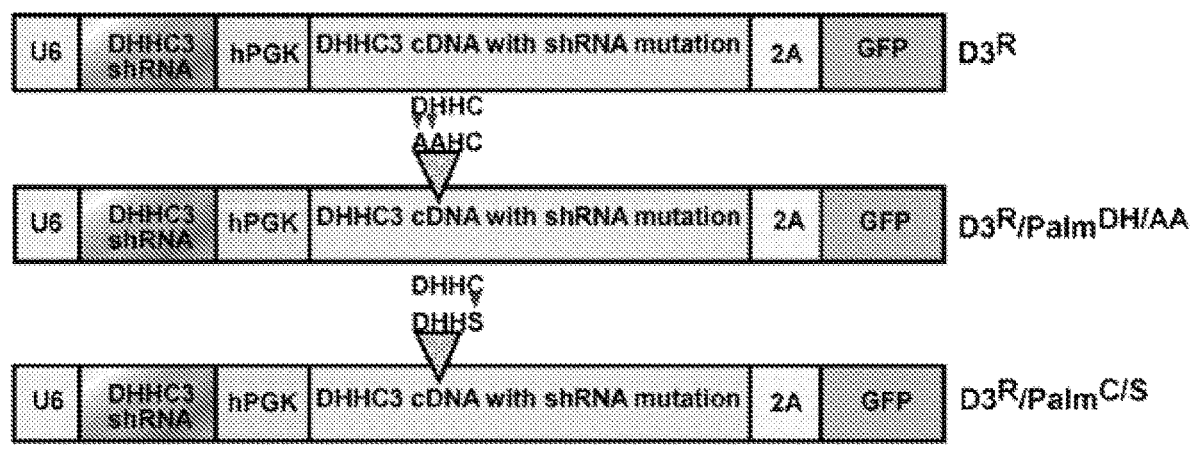
FIG. 12A-FIG. 12C is a series of schematics and a flow cytometry graph showing DHHC3 reconstitution lentiviral vectors, expression in stably infected MDA-MB-231 cells, and an overview of effects of DHHC3 ablation.
Figure 12B:
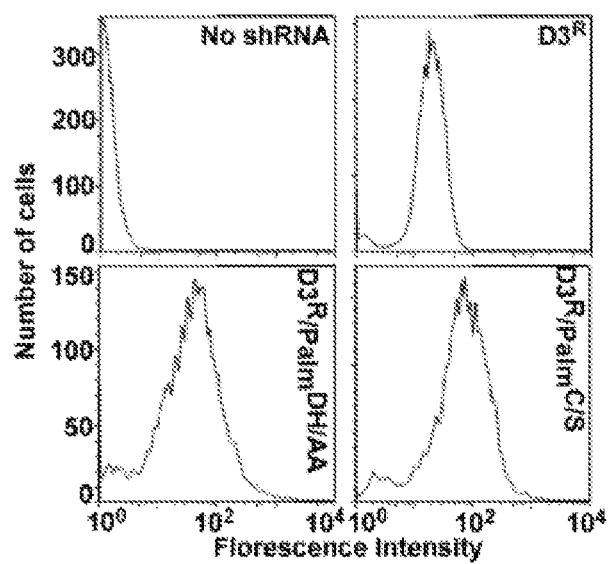
Figure 12C:
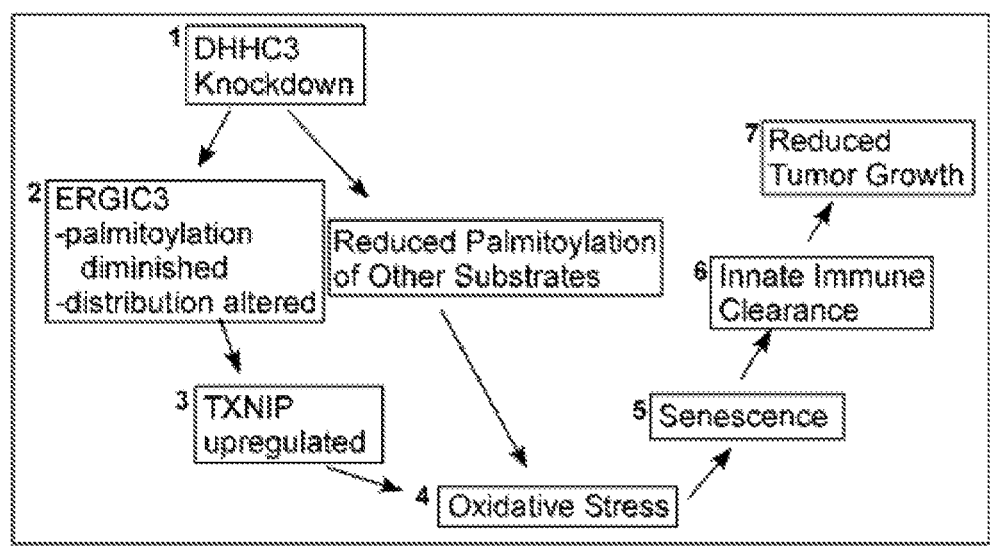

Example 9: DHHC3 Ablation Effects are Specific and Require the Enzyme Active Site To confirm ZDHHC3 ablation specificity, rescue vector $D3^R$, containing ZDHHC3 knockdown shRNA, ZDHHC3 cDNA resistant to the shRNA, 2A peptide linker, and GFP tag was designed (FIG. 12A). Reconstitution vectors $D3^{R+}_{DH/AA}$ and $D3^{R+C/S}$ contained DHHC3 active site mutations (DHHC (Asp-His-His-Cys (SEQ ID NO: 7))→AAHC (Ala-Ala-His-Cys (SEQ ID NO: 8)); DHHC (Asp-His-His-Cys (SEQ ID NO: 7))→DHHS (Asp-His-His-Ser (SEQ ID NO:

9))) that abolish palmitoylation activity (Mitchell et al., 2006 J Lipid Res, 47:1118-27; Politis et al., 2005 J Biol Chem, 280:10156-63). By GFP analysis (FIG. 12B), all three vectors are well expressed in MDA-MB-231 cells, with $D3^{R+DH/AA}$ and $D3^{R+C/S}$ present at somewhat higher levels than $D3^R$. Importantly, $D3^R$ expression completely reversed ZDHHC3 ablation effects, with respect to increased MCP-1 (indicative of senescence), FAK tyrosine phosphorylation (indicative of oxidative stress) and TXNIP (indicative of oxidative stress and senescence) (FIG. 6A-C). Protein levels for $D3^R$ are ~2-fold greater than endogenous DHHC3 in non-ablated control cells. This helps to explain why MCP-1 (FIG. 6A) and TXNIP (FIG. 6C) drop below control levels (compare control "C" and "$D3^R$" results). By contrast, reconstitution with active site mutants ($D3^{R+DH/AA}$ and $D3^{R+C/S}$) failed to reverse ZDHHC3 knockdown effects on oxidative stress and senescence (FIG. 6A-C, compare lanes 4 and 5 with lane 2 in each of the three panels).

Figure 1D:
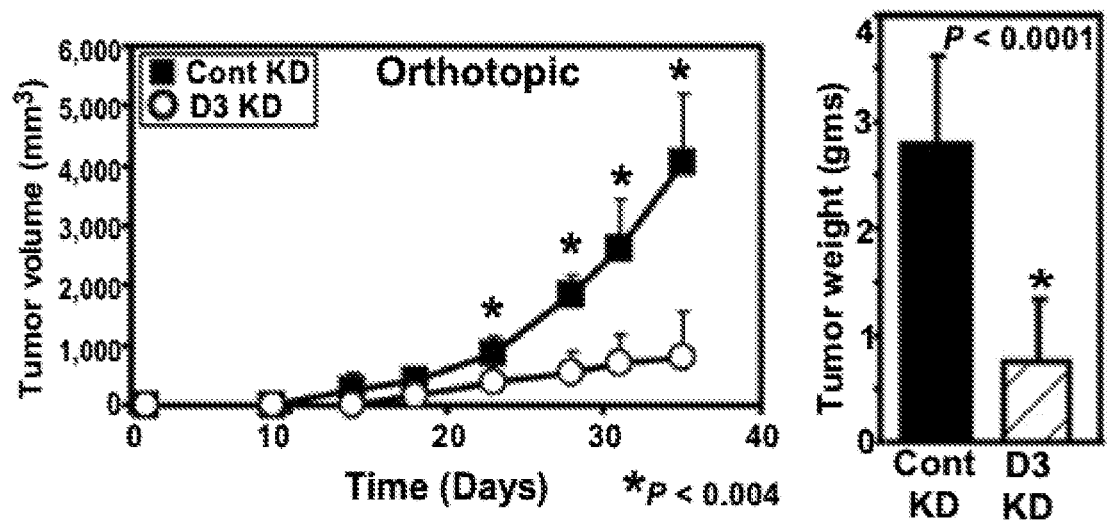
Figure 1E:
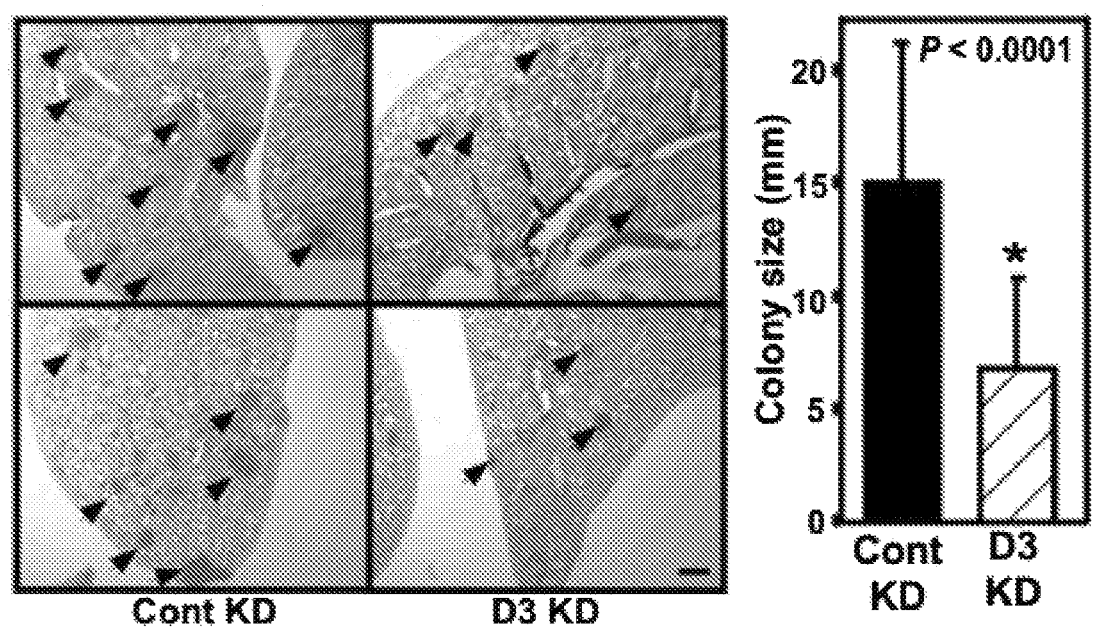
Figure 6D:
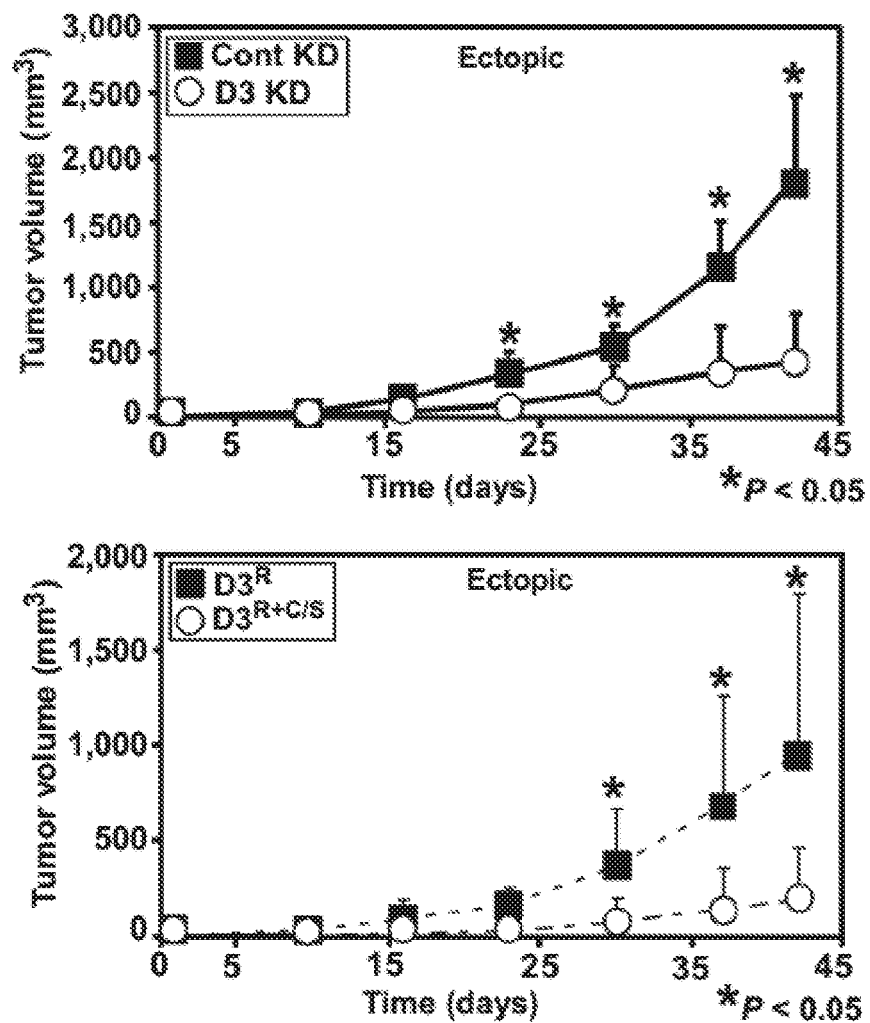

Recapitulating FIG. 1D results, stable ZDHHC3 ablation significantly reduced in vivo MDA-MB-231 tumor xenograft growth (FIG. 6D, top panel). In the same experiment, tumor xenograft growth was almost completely restored upon ZDHHC3 reconstitution, using rescue vector $D3^R$ (FIG. 6D, bottom panel). As expected, reconstitution with the $D3^{R+C/S}$ negative control mutant did not reverse the diminished tumor xenograft growth that was caused by ZDHHC3 ablation (FIG. 6D, bottom panel).

Example 10: Disruption of ERGIC3 Upregulates TXNIP

Figure 7B:
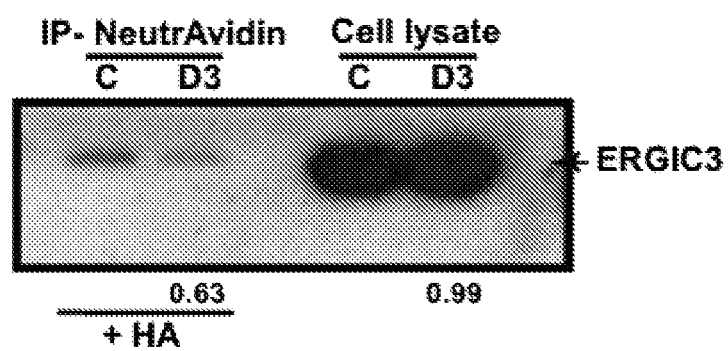
Figure 7C:
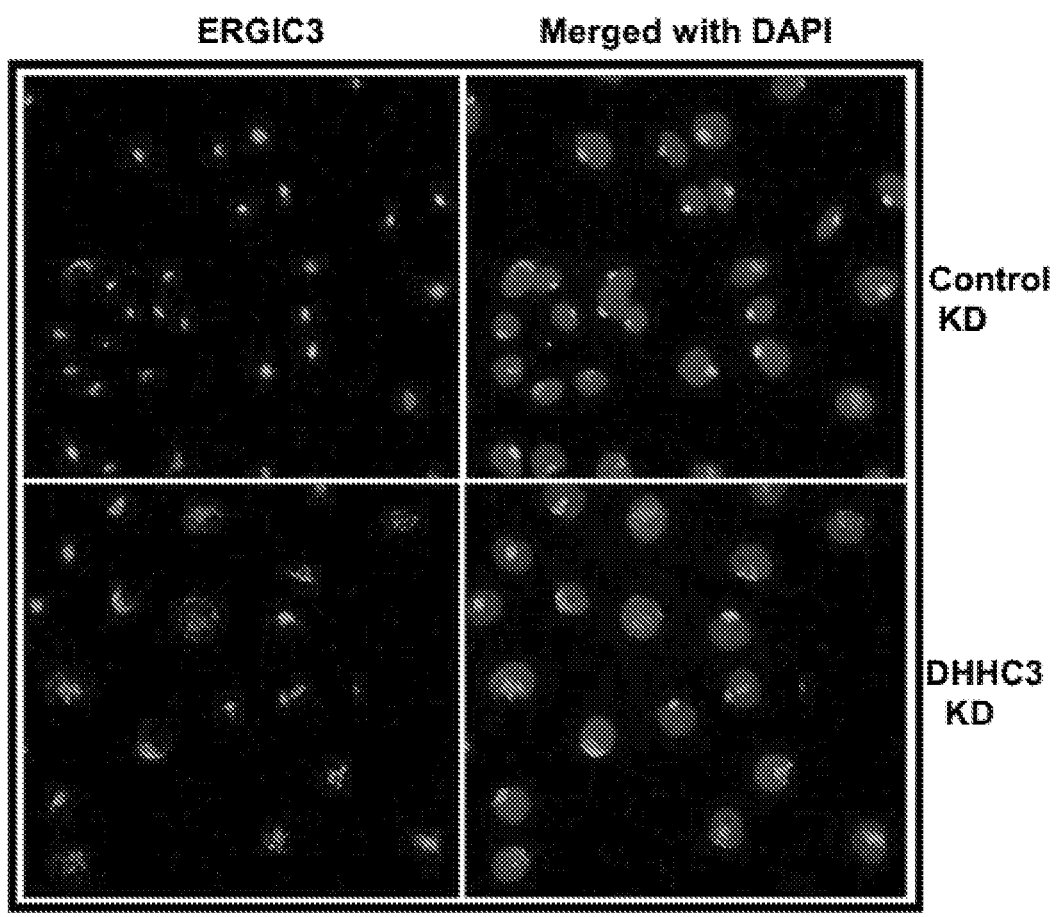

To understand how ZDHHC3-ablation might upregulate TXNIP, disruption of ERGIC3 (endoplasmic reticulum Golgi intermediate compartment-3) protein, which is known to cause ER stress (Hong et al., 2016 Oncotarget, 7:65335-47), which then upregulates TXNIP was examined (Oslowski et al., 2012 Cell Metab, 16:265-73). First, it was confirmed again that ZDHHC3 ablation in MDA-MB-231 cells upregulates TXNIP (FIG. 7A, top panel, lane 2) and then showed that ERGIC3 ablation upregulates TXNIP to an even greater extent (lane 3). Second, it was established that ZDHHC3 ablation causes a marked decrease in ERGIC3 palmitoylation (FIG. 7B), accompanied by ERGIC3 subcellular distribution becoming considerably less punctate (FIG. 7C). In a control experiment, DHHC3 ablation did not alter the amount of total ERGIC3 protein in the cell lysate (FIG. 7B).

Example 11: DHHC3 Regulates CMTM6 Palmitoylation and PD-L1 Expression

Described herein is the identification of drivers of breast cancer growth, and methods of inhibiting breast cancer. Also described herein are revolutionized treatment regimens that are more effective, less toxic, and positively impact survival.

As described herein, DHHC3 affects breast tumor growth and metastasis. Prior to the invention described herein, it was unknown which of several putative DHHC3 substrates might be important for tumor regulation.

Figures 13A, 13B:
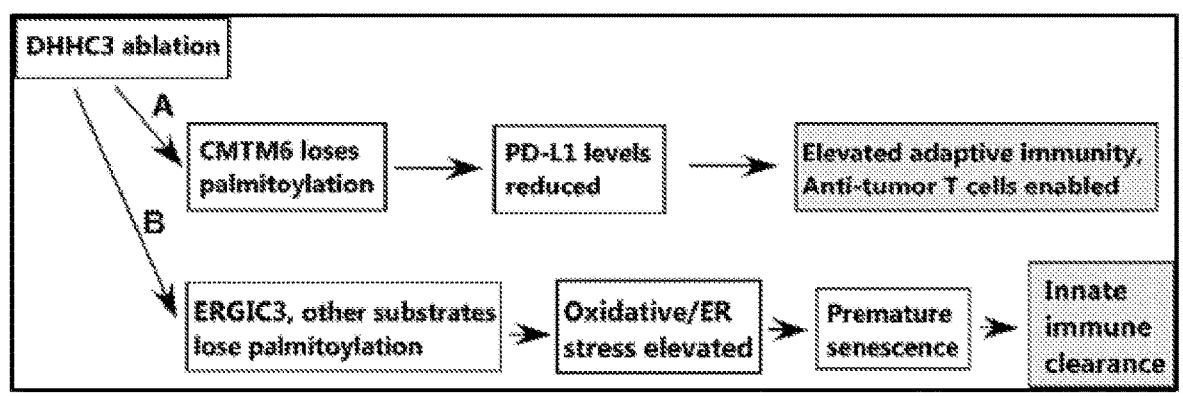
FIG. 13A and FIG. 13B are schematics showing the dual effects of DHHC3 ablation on tumor growth and a proposed model for DHHC3 function.

Direct inhibition of the immune checkpoint molecule, PD-L1, has considerable potential in the treatment of breast cancer (Bertucci F, Goncalves A. 2017 Curr Oncol Rep, 19:64) and other cancers (Homet M B, Ribas A. 2015 Br J Cancer, 112:1421-7). However, because this approach has limitations, alternative and combinatorial approaches are described herein. Described herein is an approach towards simultaneously amplifying a) adaptive anti-tumor immunity, by indirectly down-regulating PD-L1; and b) innate anti-tumor immunity, by promoting premature tumor cell senescence (FIG. 13A-FIG. 13C). The Golgi-resident protein acyl transferase DHHC3 (GODZ) is a member of the "DHHC" (Asp-His-His-Cys (SEQ ID NO: 7)) enzyme family that palmitoylates several substrate proteins in mammals (Mitchell et al., 2006 J Lipid Res, 47:1118-27). It was recently found that a) DHHC3 expression is upregulated in multiple human breast cancer subtypes; b) upregulated zDHHC3 expression correlates with diminished survival in human breast cancer patients; and c) ablation of zDHHC3 results in diminished breast cancer growth and metastasis in xenograft models (Sharma et al., 2017 Cancer Research, 77(24): 6880-6890). These results point to DHHC3 being a potentially interesting breast cancer target, but potential effects on adaptive immunity have not been explored and prior to the invention described herein, a mechanistic understanding regarding the role of DHHC3 substrates was lacking.

It was recently found that cell surface protein, CMTM6, is needed for maintenance of PD-L1 on tumor cells (Mezzadra et al., 2017 Nature, 549:106-10; Burr et al., 2017 Nature, 549:101-5). However, prior to the invention described herein, relatively little was known regarding the properties of CMTM6 and factors that regulate its expression and function. It was identified that CMTM6 is a DHHC3 substrate. As described herein, ablation of the protein acyl transferase, DHHC3, causes a loss of CMTM6 palmitoylation and altered subcellular distribution, thus leading to a marked decrease in PD-L1 expression on breast tumor cells. These results suggest an elevated anti-tumor immunity response (FIG. 13A). In addition, it was found that DHHC3 ablation leads to tumor cell senescence, which triggers tumor clearance by innate immune cells (Sharma et al., 2017 Cancer Research, 77(24): 6880-6890) (FIG. 1B). Because DHHC3 ablation may simultaneously amplify both adaptive and innate anti-tumor immunity, targeting of DHHC3 is particularly effective in breast cancer.

The data described herein indicate that DHHC3 ablation should enhance 1) adaptive immunity; and 2) innate immunity; and 3) that DHHC3 is a biomarker/target in human breast cancer. Specifically, it was identified that a) DHHC3 expression is upregulated in multiple human breast cancer subtypes; b) upregulated zDHHC3 expression correlates with diminished survival in human breast cancer patients; and c) ablation of zDHHC3 results in diminished breast cancer growth and metastasis in xenograft models. For these reasons, and because DHHC3 ablation simultaneously amplifies both adaptive and innate anti-tumor immunity, targeting of DHHC3 is particularly effective in breast cancer.

DHHC3 and Adaptive Immunity

Figure 19:
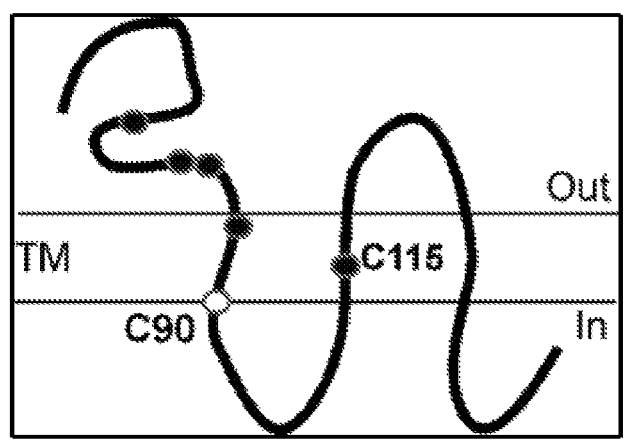
FIG. 19 is a schematic showing the likely palmitoylation site within CMTM6. Transmembrane domain probabilities described elsewhere (Mezzadra et al., 2017 Nature, 549: 106-10) suggest a topological model in which CMTM6 contains at least 3 transmembrane domains. The six cysteine residues are indicated (red circles), including C90, which appears most likely to undergo palmitoylation.

It was identified that CMTM6, a membrane protein, contains at least 1 intracellular membrane-proximal cysteine that is likely be palmitoylated (FIG. 19). DHHC3 is a protein acyl transferase that palmitoylates multiple transmembrane proteins (Sharma et al., 2017 Cancer Research, 77(24): 6880-6890; Sharma et al., 2012 Cell Mol Life Sci, 69:2233-44).

Figure 14A:
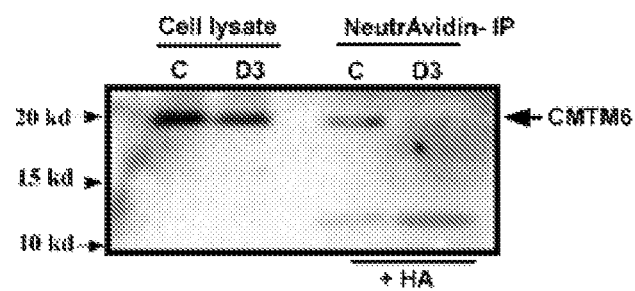
FIG. 14A-FIG. 14C is a series of photographs of immunoblots showing that DHHC3 regulates CMTM6 palmitoylation and PD-L1 expression.

As described in detail below, the effects of DHHC3 ablation on CMTM6 palmitoylation were examined. The results show that DHHC3 ablation reduced CMTM6 palmitoylation. Specifically, it was determined that it is ~90% diminished (FIG. 14A, lane 4). At the same time, overall expression of CMTM6 was partly diminished (FIG. 14A, lane 2). Consistent with the recently discovered requirement for CMTM6 to maintain PD-L1 expression (Mezzadra et al., 2017 Nature, 549:106-10; Burr et al., 2017 Nature, 549:101-5), PD-L1 levels were also substantially diminished (FIG.

Figure 14B:
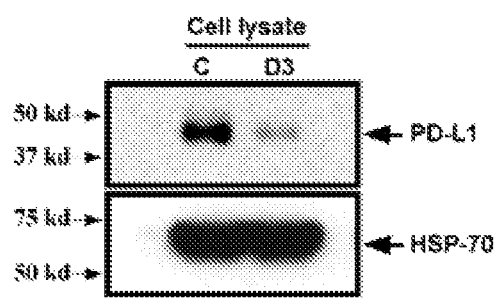
Figure 14C:
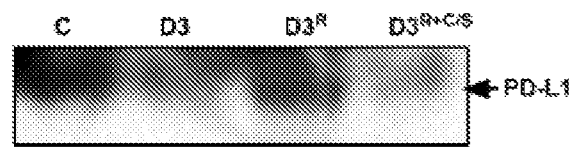

14B). PD-L1 expression, elevated due to treatment of MDA-MB-231 cells with 50 ng/ml IFN-γ for 48 h, was again substantially diminished upon DHHC3 ablation. Upon reconstitution of DHHC3 knockdown cells with non-mutated DHHC3, PD-L1 expression was restored (FIG. 14C, lane 3). However, reconstitution with active site-deficient DHHC3 (DHHC (Asp-His-His-Cys (SEQ ID NO: 7)) changed to DHHS (Asp-His-His-Ser (SEQ ID NO: 9))) failed to restore PD-L1 expression (FIG. 14C, lane 4).

Figure 15:
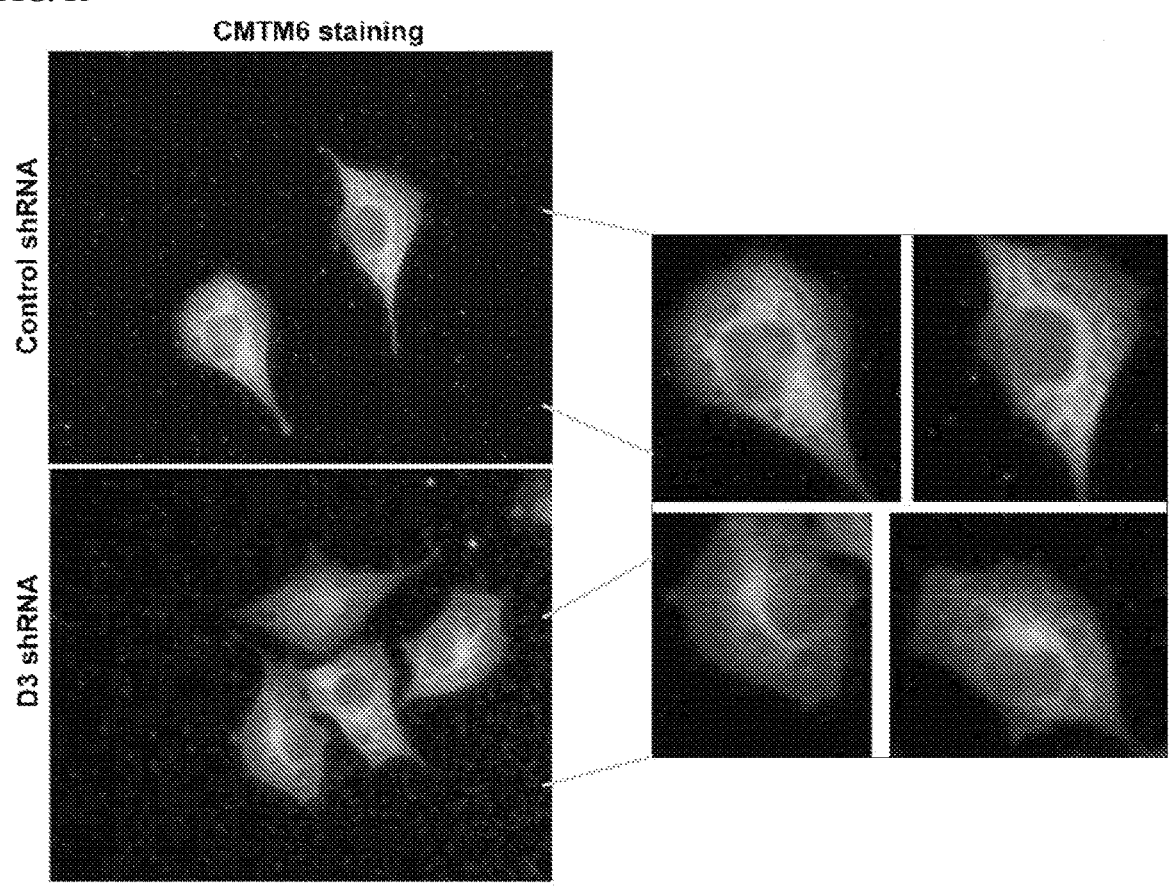
FIG. 15 is a photomicrograph showing that DHHC3 ablation affects subcellular distribution of CMTM6. MDA-MB-231 cells±DHHC3 ablation were cultured on glass slides, fixed (4% PFA, 10 min), permeabilized (0.25% Tween-20, 10 min), blocked (0.3M Glycine, 5% BSA, 1 hr), incubated with anti-CMTM6 antibody (Thermo Fisher Scientific, Cat #PA5-34744; overnight at 40° C.), washed, then incubated with Alexa-594-conj rabbit antibody (1 hr, RT). After 5× washing with PBS, slides were mounted with proLong Gold antifade with DAPT, and photos were taken using a Nikon Eclipse TE 300 microscope.

To understand how loss of CMTM6 palmitoylation might affect its role in PD-L1 modulation, effects of DHHC3 ablation on CMTM6 subcellular distribution were analyzed in MDA-MB-231 cells. As indicated (FIG. 15), control cell CMTM6 staining is brighter and more evenly distributed throughout the peri-nuclear cell body. By contrast, staining in DHHC3-ablated cells is overall dimmer and more diffuse, except for being concentrated in a single peri-nuclear location. Thus, DHHC3 palmitoylates CMTM6 and regulates its cellular localization.

Taken together, the results presented herein suggest that CMTM6 palmitoylation is needed for proper localization and support of PD-L1 expression, and that palmitoylation is dependent on an intact active site within the DHHC3 enzyme. Hence, DHHC3 ablation in tumor cells diminishes tumor growth at least in part due to removal of PD-L1, thus enhancing adaptive immunity.

DHHC3 and Innate Immunity

Figure 16:
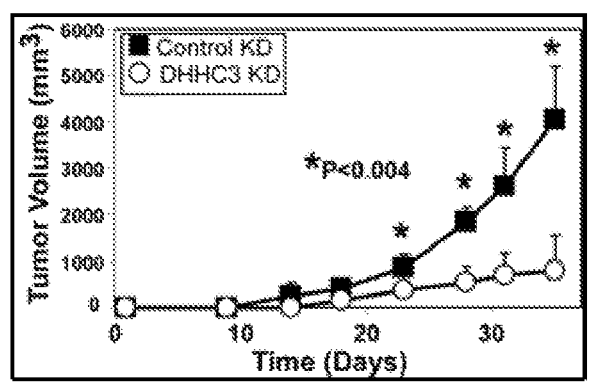
FIG. 16 is a line graph showing the DHHC3 effects on tumor cell growth, wherein MDA-MB-231 cells ($1\times10^6$) stably ablated for DHHC3 (using shRNA) were injected into mammary fat pads of nude mice (N=10) and tumor volume was monitored. Results in FIG. 16 and FIGS. 17A and 17B have been confirmed using multiple independent RNAi targeting sequences.
Figure 17A:
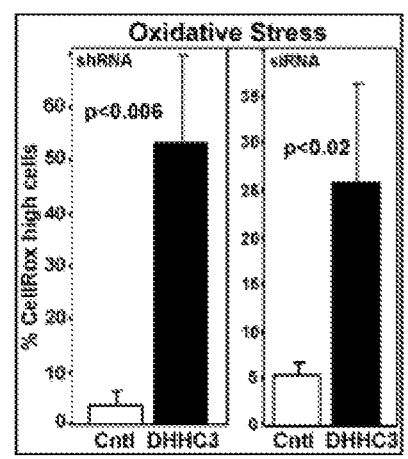
FIG. 17A and FIG. 17B is a series of bar charts showing that DHHC3 ablation increases oxidative stress and senescence. DHHC3 was ablated in triple negative MDA-MB-231 cells (FIG. 17A, left.
Figure 17B:
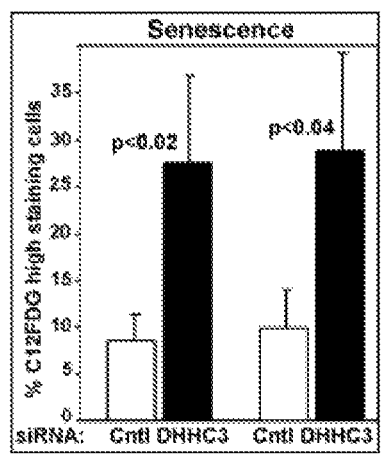

In vivo xenograft models showed that zDHHC3-ablation causes significant reductions in breast cancer growth in vivo (FIG. 16) and fewer, smaller metastatic colonies (Sharma et al., 2017 Cancer Research, 77(24): 6880-6890). zDHHC3-ablation didn't affect cell proliferation or soft agar colony growth in vitro (or ex vivo), but tumor cell oxidative stress and senescence were increased in two different breast cancer cell lines (FIG. 17A and FIG. 17B), and there were changes in expression of >18 senescence indicator genes (Sharma et al., 2017 Cancer Research, 77(24): 6880-6890). Also, zDHHC3-ablated cells acquired a senescence-associated secretory phenotype (SASP; Coppe et al., 2008 PLoS Biol, 6:2853-68), with secretion of characteristic chemokines (e.g., MCP-1, Groα, CXCL16, IL8) (Sharma et al., 2017 Cancer Research, 77(24): 6880-6890). Accordingly, recruitment was enhanced for innate immune cells (M1-like macrophages, NK cells; (Sharma et al., 2017 Cancer Research, 77(24): 6880-6890) that clear senescent tumor cells (Xue et al., 2007 Nature, 445:656-60). Effects of zDHHC3 ablation (decreased tumor growth, increased oxidative stress/senescence) were reversed by reconstitution with wild type, but not active site-deficient DHHC3, thus showing a key role for DHHC3 enzyme activity (Sharma et al., 2017 Cancer Research, 77(24): 6880-6890).

DHHC3 Relevance to Human Breast Cancer

Figure 18A:
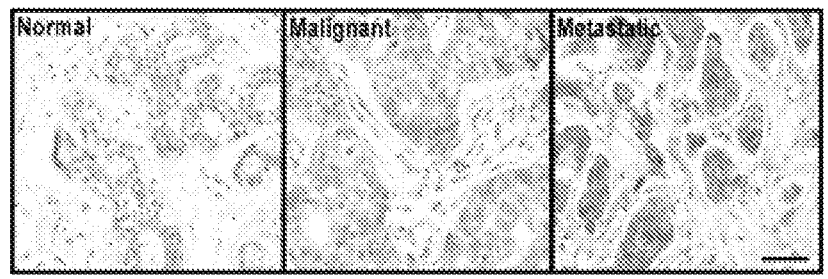
FIG. 18A-FIG. 18C is a series of photomicrographs, a bar chart, and a survival curve showing that DHHC3 ablation increases oxidative stress and senescence.
Figure 18B:
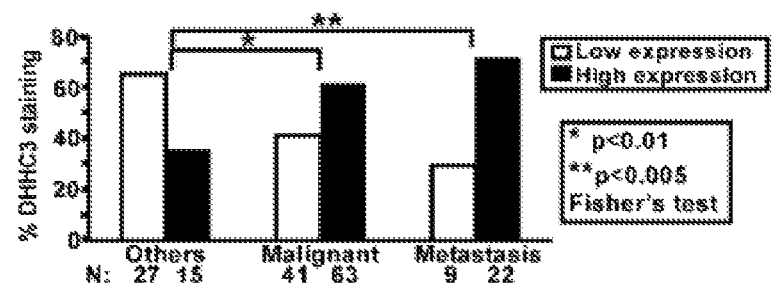

As evidence for DHHC3 having an important role in human breast cancer, and as described in detail herein, DHHC3 expression was upregulated in human malignant and metastatic breast cancer samples, as seen by immunohistochemistry staining (FIG. 18A). Quantitation of results showed significant elevation in malignant samples, and even higher elevation in metastatic samples (including those of the triple negative subtype) in comparison to non-cancerous tissue (FIG. 18B). Consistent with these results, DHHC3 gene expression is markedly upregulated in malignant breast cancer cell lines and breast adenocarcinoma (data from EMBL-ATLAS). DHHC3 protein was also significantly upregulated in 4/5 major malignant primary breast cancer subtypes and 5/5 major metastatic breast cancer subtypes (Sharma et al., 2017 Cancer Research, 77(24): 6880-6890).

Figure 18C:
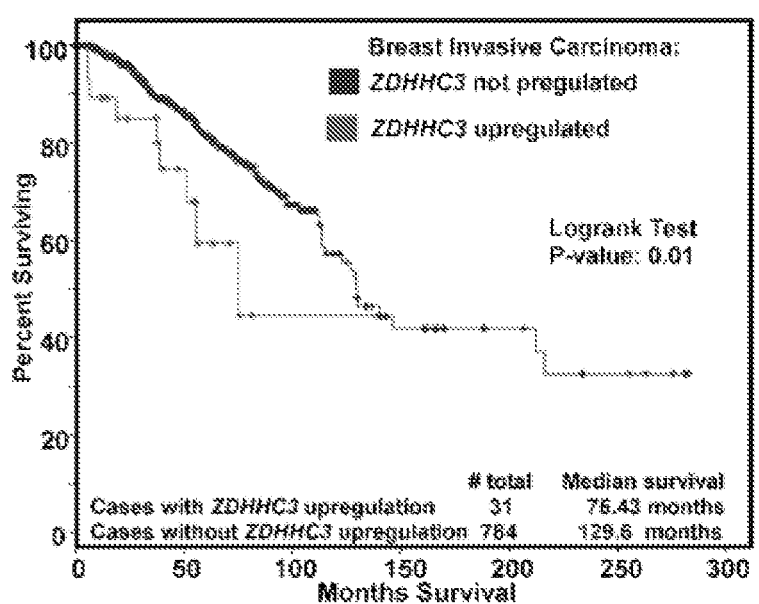

Furthermore, analysis of TCGA data showed that zDHHC3 upregulation correlates with significantly diminished overall survival of patients with breast cancer (FIG. 18C). Together, these results point to DHHC3 as a marker for aggressive, metastatic breast cancer and also a potential therapeutic target. Accordingly, DHHC3 is a target for inhibition in women with triple negative-type breast cancer, as well as HER2+ and ER+ patients.

The data described herein indicate that ablation of protein acyl transferase, DHHC3, in breast tumor cells may diminish tumor growth by two distinct mechanisms. First, the absence of DHHC3 promotes adaptive immunity, e.g., by causing loss of CMTM6 palmitoylation, leading to diminished expression of PD-L1 on cancer cells, thus enabling the effector functions of antigen-specific $CD8^+$ T cells. DHHC3 ablation causes diminished palmitoylation of CMTM6, resulting in diminished expression of PD-L1 on cancer cells, which is well known to enhance anti-tumor T cell functions. Second, the absence of DHHC3 causes tumor cell senescence, leading to tumor clearance by innate immune cells. The experiments described herein determine the biochemical and cell biological links between DHHC3 ablation, CMTM6 palmitoylation and function, and PD-L1 expression and function, leading to anti-tumor T cell amplification. Also, the individual and combined effects of DHHC3 ablation on adaptive and innate anti-cancer immunity are examined.

In vitro studies are carried out to determine the biochemical and cell biological mechanisms linking DHHC3 ablation and loss of CMTM6 palmitoylation to A) diminished PD-L1 expression and altered subcellular localization; and B) to diminished PD-L1 functions, as well as amplified T cell function. This is achieved using RNAi knockdowns (of DHHC3, CMTM6), palmitoylation, co-immunoprecipitation, cellular co-localization, and functional studies dependent on PD1 (counterreceptor for PD-L1). Finally, a potential correlation between DHHC3 and PD-L1 upregulation is examined in human breast cancer samples.

In vivo consequences of DHHC3 ablation on tumor growth in mice are investigated to determine the extent to which reduced breast tumor growth in mice is due to loss of CMTM6 and PD-L1 expression and/or functions, leading to enhanced adaptive immunity. The effects of DHHC3 ablation on adaptive and innate anti-tumor immunity are compared.

In Vitro Links Between DHHC3. CMTM6 and PD-L1

To assess cell biological and functional links between DHHC3, CMTM6 palmitoylation, PD-L1, and adaptive immunity, the following strategies are employed: RNAi knockdown of DHHC3 and CMTM6; reconstitution with palmitoylation-deficient mutant CMTM6; co-immunoprecipitation, cellular c-localization, and functional studies dependent upon PD1 (counterreceptor for PD-L1). Also, it is determined whether there is a correlation between DHHC3 and PD-L1 upregulation in human breast cancer samples.

Results show that PD-L1 expression depends on presence of CMTM6 (Mezzadra et al., 2017 Nature, 549:106-10; Burr et al., 2017 Nature, 549:101-5). The results provided herein show that CMTM6 palmitoylation (and to some extent, expression) depends on DHHC3. Consistent with disruption of CMTM6, it was also observed that DHHC3 ablation causes a decrease in PD-L1 expression (FIG. 14A-FIG. 14C).

As described in detail below, it is determined whether decreased PD-L1 in DHHC3-ablated cells is entirely due to disrupted CMTM6. To test this, the following is examined:

a) Subcellular distribution and PD-L1 maintenance. In MDA-MB-231 cells (±DHHC3 ablation; ±IFNγ treatment) subcellular and cell surface distributions and co-localization of CMTM6 and PD-L1 are analyzed individually and together, using red and green-conjugated 2nd antibodies as described (Burr et al., 2017 Nature, 549:101-5). Also, PD-L1 is analyzed using standard cell surface internalization and recycling assays (Burr et al., 2017 Nature, 549:101-5) to confirm that effects of DHHC3 ablation mimic effects of CMTM6 ablation (i.e., enhanced PD-L1 internalization, diminished recycling).

b) Co-immunoprecipitation. MDA-MB-231 cells (±DHHC3 ablation; ±chloroquine or bafilomycin A1 to prevent lysosomal degradation of PD-L1) are lysed in digitonin (Burr et al., 2017 Nature, 549:101-5) or another appropriately mild detergent (e.g. Brij 99), while taking care to remove all insoluble materials (both heavy and light) by centrifuging lysates at ~100,000 g. Then, CMTM6 with PD-L1 are reciprocally co-immunoprecipitated.

c) Mutation of CMTM6 palmitoylation site. Of 6 cysteines present in the CMTM6 sequence, 4 are possibly extracellular and 1 appears to be buried within the $2^{nd}$ TM domain (FIG. 19). However, C90 appears to be intracellular and membrane-proximal, like other known DHHC3 substrates (Sharma et al., 2012 Cell Mol Life Sci, 69:2233-44). C90 is mutated to alanine, and endogenous CMTM6 in MDA-MB-231 cells are stably ablated and replaced with non-mutated CMTM6 or CMTM6-C90A mutant. CMTM6 (and CMTM6-C90A) cDNA is mutated to escape shRNA targeting, and cloned, with C-terminal 2A linker peptide and GFP tag sequences, into lentiviral plasmids downstream of CMTM6 shRNA, using a strategy that was described for DHHC3 reconstitution (Sharma et al., 2017 Cancer Research, 77(24): 6880-6890). Then, it is confirmed that CMTM6-C90A is not palmitoylated, using the exposed free-cysteine chemical derivatization approach used in FIG. 14A (and Sharma et al., 2017 Cancer Research, 77(24): 6880-6890).

d) Determine whether effects of DHHC3 ablation on PD-L1 are dependent on altered CMTM6. MDA-MB-231 cells lacking CMTM6, or reconstituted with mutant or non-mutant CMTM6 are treated±DHHC3 ablation. Cells are then compared, using approaches described herein, with respect to PD-L1 expression, subcellular distribution, internalization, recycling, and co-immunoprecipitation with CMTM6.

e) Additional controls and confirmatory experiments. DHHC2 is used as a negative enzyme control and MHC-1 is used as a negative cell surface protein control. MHC-1 neither co-localizes nor co-immunoprecipitates with CMTM6, nor is affected by DHHC3 ablation, and knockdown of DHHC2 does not affect CMTM6 or PD-L1 cell biology or functions. Also, all key experiments performed using MDA-MB-231 cells are repeated using a mouse mammary carcinoma cell line, EMT6 (Jiao et al., 2017 Clin Cancer Res, 23:3711-20). It has been confirmed that available anti-mouse DHHC3 and DHHC2 antibodies are adequate for the proposed experiments.

DHHC3 Affects PD-L1-Dependent Functions In Vitro.

Diminished PD-L1 expression, due to DHHC3 ablation, is accompanied by diminished PD-L1-dependent functions. The following is examined:

a) Jurkat cell co-culture assays. MDA-MB-231 cells, ±DHHC3 ablation and pretreated with IFNγ, are co-cultured with PD-1$^+$ Jurkat T cells (pre-activated overnight with PHA and PMA). After 48 and 72 h, levels of IL-2 secreted into the supernatant are detected as described (Mezzadra et al., 2017 Nature, 549:106-10).

b) Effects of rPD1. MDA-MB-231 cells, ±DHHC3 ablation and pretreated with IFNγ, are incubated with recombinant soluble PD1 protein (rPD1, 10 μg/ml), and effects on activation of ERK and mTOR are assessed as described (Black et al., 2016 Oncotarget, 7:10557-67).

c) Cytotoxicity assays. Tumor-specific CTLs are generated by injecting mitomycin-C-treated mouse mammary carcinoma cell line EMT6 intraperitoneally into BALB/c mice. After 2 weeks, CD3+ lymphocytes are isolated and expanded by coculture with mitomycin-C-treated EMT6 cells using standard methods (Barsoum et al., 2014 Cancer Res, 74:7185-90). CTLs are incubated with EMT6 cells, ±DHHC3 ablation, using various E:T ratios, and cytotoxicity is assessed using a LIVE/DEAD cytotoxicity/cell viability assay (Invitrogen).

d) Determine whether effects DHHC3 ablation are dependent on loss of CMTM6 palmitoylation. To address this question, the assays above are repeated, except that MDA-MB-231 and/or EMT6 cells stably ablated for CMTM6, ±reconstitution with non-mutated CMTM6 or palmitoylation deficient CMTM6-C90A are used.

Determine Whether DHHC3 and PD-L1 Levels Correlate in Human Breast Cancer

Both PD-L1 and DHHC3 (FIG. 18A and FIG. 18B) are variably upregulated in human breast cancer. Since DHHC3 ablation diminishes PD-L1 levels (FIG. 14B and FIG. 14C), it is identified whether DHHC3 and PD-L1 are upregulated in parallel in human breast cancer. To test this, human breast cancer samples, from multiple breast cancer subtypes, are obtained from US Biomax, processed, stained for PD-L1 and DHHC3 (e.g., see, FIG. 18A-FIG. 18C), and given blinded semi-quantitative H-scores. If a correlation is observed, breast cancer samples are stained for CMTM6, to assure that sufficient amounts are present to maintain PD-L1 levels.

The results indicate that DHHC3 ablation mimic effects of CMTM6 ablation on PD-L1 internalization and recycling and also markedly diminish the co-localization and co-immunoprecipitation of CMTM6 with PD-L1. Results suggest that altered CMTM6 distribution makes it less available for direct interaction and PD-L1 stabilization. It is also possible that absence of palmitoylation may more directly contribute to diminished CMTM6 association, but this is difficult to prove if altered distribution prevents opportunity for association. It is expected that the CMTM6-C90A mutant loses nearly all palmitoylation. If this does not occur, a C115A mutation is made (see, FIG. 19). It is expected that cells lacking CMTM6 or expressing CMTM6-C90A show similar alterations to PD-L1 distribution, expression, internalization, and recycling as in DHHC3 ablated cells. The results show that responses to Jurkat coculture, rPD1, and anti-tumor CTLs are markedly and similarly altered, consistent with diminished PD-L1. Such results affirm the importance of CMTM6 palmitoylation during CMTM6-dependent maintenance of PD-L1. In absence of CMTM6 (or presence of CMTM6-C90A), PD-L1 expression and function is already diminished, and DHHC3 ablation has no further effect on PD-L1-dependent functions. Such results again confirm that effects of DHHC3 ablation on PD-L1 are almost entirely dependent on DHHC3-mediated palmitoylation of CMTM6.

In Vivo Consequences of DHHC3 Ablation

The consequences of DHHC3 removal on tumor growth in mice are examined. Also, it is determined the extent to which reduced breast tumor growth in mice is due to loss of CMTM6 and diminished PD-L1 expression, leading to enhanced adaptive immunity. Finally, as described herein, the removal of DHHC3 is most effective when it can stimulate the anti-tumor activity of both innate and adaptive immunity.

Accordingly, EMT6 mouse carcinoma cells, +/− DHHC3 ablation, are used to grow tumors in mice containing both adaptive and innate immunity, or innate immunity alone. The removal of PD-L1 or CMTM6 or reconstitution with palmitoylation-deficient CMTM6 is analyzed with respect to mimicking DHHC3 ablation.

Although DHHC3 ablation was shown herein to promote enhanced innate anti-tumor immunity in mouse xenograft models, prior to the invention described herein, the effects of DHHC3 ablation were not analyzed in fully immunocompetent mouse models. Due to indirect effects of DHHC3 ablation on PD-L1 levels, adaptive tumor immunity is amplified.

Tumors are established by injecting EMT6 mouse mammary carcinoma cells, ±DHHC3 stable knockdown, into BALB/c mice. Injected cells express luciferase-neomycin phosphotransferase (neo) fusion protein (EMT6-LucNeo cells). Mice are then monitored for primary tumor size every 3 days, from day 15-40, by quantitative bioluminescence imaging (Rice et al., 2001 J Biomed Opt, 6:432-40; Rehemtulla et al., 2000 Neoplasia, 2:491-5) (IVIS™ System, Xenogen Co.) as previously described (Kolesnikova et al., 2009 Neoplasia, 11:77-86). Mice are sacrificed if moribund, or tumors reach 2 cm in diameter, or after 40 days. After 40 days, tumor sections are stained for expression of PD-L1 and CMTM6, and for markers of oxidative stress (Toyokuni et al., 1997 Lab Invest, 76:365-74; Toyokuni et al., 1995 FEBS Lett, 359:189-91) and senescence (Althubiti et al., 2014 Cell Death Dis, 5:e1528). Also, tumors are analyzed for infiltration of T cells, NK cells, M1-like macrophages, and MDSC's as described (Sharma et al., 2017 Cancer Research, 77(24): 6880-6890).

Determine to What Extent Diminished Growth of DHHC3-Ablated Tumors is Due to Effects on CMTM6 and PD-L1

The results presented herein suggest that DHHC3 ablation amplifies anti-tumor adaptive immunity due to loss of CMTM6 palmitoylation, leading to diminished PD-L1 expression. To confirm, two populations of EMT6 tumor cells (with or without DHHC3 ablation) are each treated ±PD-L1 ablation, or ±CMTM6 ablation, or reconstituted with CMTM6 or CMTM6-C90A. Cells are injected into BALB/c mice, and then primary tumor growth is monitored, and tumor sections are analyzed as described above.

Determine to What Extent DHHC3 Ablation Diminishes Growth, Independent of Effects on Adaptive Immunity As seen previously (Sharma et al., 2017 Cancer Research, 77(24): 6880-6890), DHHC3 ablation enhanced innate immune clearance of senescent tumor cells. To assess the relative magnitude of enhanced innate immunity (compared to innate plus adaptive immunity described above), EMT6 cells±DHHC3 ablation, are be injected into Rag2-null mice, which lack adaptive immunity. Also, EMT6 cells ablated for CMTM6 are prepared and reconstituted with mutant or non-mutant CMTM6. These cells, ±DHHC3 ablation, are injected and tested for tumor growth (which should not be affected by CMTM6 alterations). Tumors are analyzed for infiltration of NK cells, M1-macrophages, and MDSCs, to provide evidence for innate immune cell clearance. Also, tumor sections are stained for oxidative stress (Toyokuni et al., 1997 Lab Invest, 76:365-74; Toyokuni et al., 1995 FEBS Lett, 359:189-91) and senescence markers (Althubiti et al., 2014 Cell Death Dis, 5:e1528).

The results demonstrate that tumor growth and metastasis arising from EMT6 cell injection are substantially reduced, when DHHC3 is ablated, to an extent greater than seen previously (Sharma et al., 2017 Cancer Research, 77(24): 6880-6890). Reduced tumor growth is accompanied by diminished PD-L1 staining, and enhanced T lymphocyte infiltration, consistent with enhanced adaptive immunity. Also, there is enhanced infiltration of innate immune cells (e.g. NK, M1-like macrophages, MDSCs) together with elevated markers for oxidative stress and senescence. The relative amounts of infiltrated cell types (adaptive vs innate) are consistent with the relative magnitudes of these two effects.

When PD-L1 or CMTM6 is ablated, or tumor cells are reconstituted with CMTM6-C90A, adaptive immunity is constitutively amplified, and not further enhanced by DHHC3 ablation. However, enhanced innate immunity is still evident (see, FIG. 20, middle panel). Such results establish that effects on adaptive immunity are perhaps almost entirely through a CMTM6-PD-L1 dependent mechanism.

Figure 20:
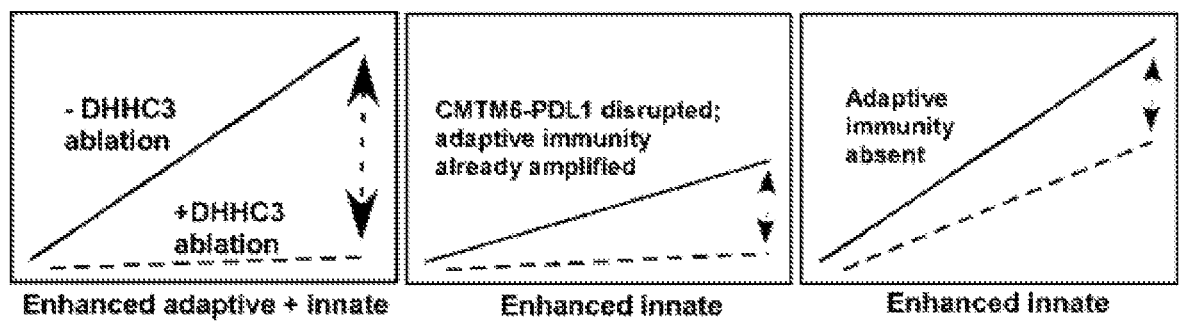
FIG. 20 is a schematic showing predicted in vivo tumor growth results. Specifically, DHHC3 ablation should enhance both adaptive and innate immunity, innate only—with adaptive constitutively active; or innate only—with adaptive absent.

Tumor growth and metastasis in Rag2-null mice are reduced somewhat upon DHHC3 ablation, due to enhanced innate immunity. However, overall growth of DHHC3-ablated tumors remains partly elevated, due to the absence of adaptive immunity (FIG. 20, right panel). Effects may be comparable to those seen previously when DHHC3-ablated tumor cells were grown in immunocompromised mice (Sharma et al., 2017 Cancer Research, 77(24): 6880-6890). The magnitude of DHHC3-ablation effects should be similar, since in both cases only innate immunity may be enhanced. However, if a greater magnitude is seen regardless of adaptive immunity, it might suggest that DHHC3 ablation could affect adaptive immunity by an additional mechanism not involving CMTM6-PD-L1. In summary, the results show DHHC3 ablation having the largest anti-tumor impact when it can enhance both adaptive and innate immunity. Such results further validate DHHC3 as a worthy target for anti-cancer therapy.

Statistical Considerations

For quantitative experiments described above, mean±S.D. is determined for N≥3 samples, and significance is determined using unpaired two-tailed t tests. For correlation studies described above, Pearson's Correlation Coefficients is determined, with r≥0.4 considered as a strong positive correlation. For examining the in vivo consequences of DHHC3 ablation on tumor growth in mice, 6 mice are initially be used in each experimental group (3M, 3F). 6 mice/group have >80% power to detect 2-standard deviation difference between groups, testing at 0.05, two-sided level of significance. Sample sizes are adjusted accordingly as more data becomes available. Analysis of variance techniques compare 30-day measures (e.g. tumor volume, tumor weight).

Implications of the Results Presented Herein

The results presented herein 1) establish a means to indirectly target PD-L1 to overcome this immune checkpoint molecule; 2) show the relative effects of DHHC3 ablation on the enhancement of adaptive and innate immunity; and 3) establish the value of DHHC3, which is upregulated in most types of breast cancer, as a useful target for breast cancer therapy. In this regard, DHHC3 is selectively upregulated on malignant and metastatic breast cancer tissue, but is neither upregulated on normal tissue, nor needed for normal mammalian development.

The results, showing a method to diminish PD-L1 levels, amplify anti-tumor adaptive immunity. Additive (or possibly synergistic) enhancement of both adaptive and innate anti-tumor immunity, due to DHHC3 ablation, emphasizes the value of targeting DHHC3 for therapeutic benefit. Because DHHC3 is an enzyme, it is an excellent candidate for small molecule targeting, which is actively being pursued for various other enzymes in the DHHC protein acyltransferase family (Jennings et al., 2009 J Lipid Res, 50:233-420. DHHC3 ablation has minimal effects on normal mouse cells and on whole animal physiology (Kilpatrick et al., 2016 J Biol Chem, 291:27371-86), thus pointing to the 'tumor-specific' potential of DHHC3 targeting. Finally, the results presented herein link DHHC3 to breast cancer growth, PD-L1 levels, adaptive immunity, senescence and innate immunity. Other DHHC enzymes (e.g., DHHC13, DHHC5) have also been linked to tumor malignancy (Perez et al., 2015 J Invest Dermatol, 135:3133-43; Tian et al., 2015 Mol Cancer Res, 13:784-94).

Figure 21A:
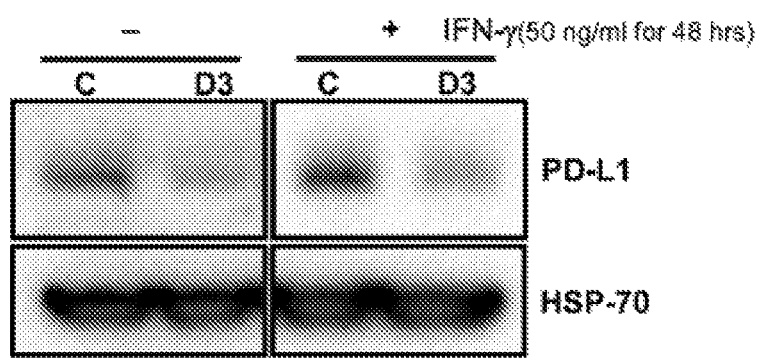
FIG. 21A is a photograph of an immunoblot showing that DHHC3 ablation reduces PD-L1 expression on cancer cells both in the presence and absence of interferon-gamma. Lysates from MDA-MB-231 cells (±DHHC3 ablation and ±IFN-γ) were blotted for PD-1 and HSP-70 (loading control) proteins.
Figure 21B:
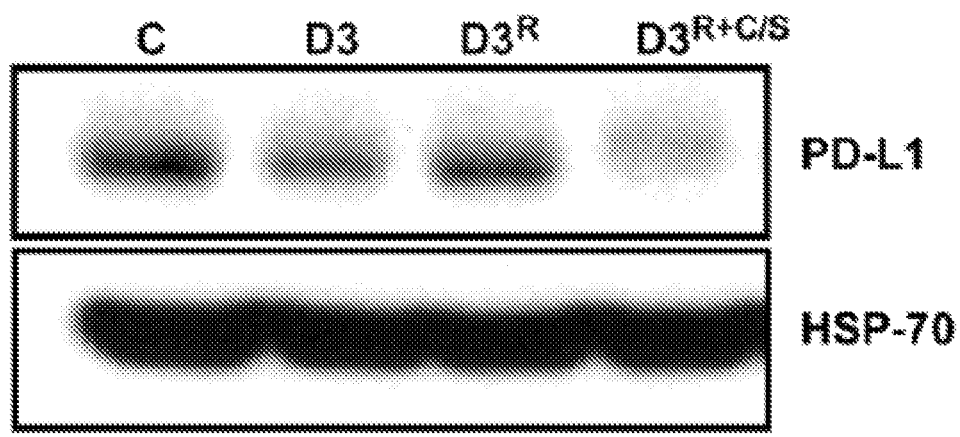
FIG. 21B is a photograph of an immunoblot, wherein lysates from MDA-MB-231 cells stably expressing control shRNA (c), DHHC3 shRNA (D3), DHHC3 rescue vector ($D3^R$) unmutated or with palmitoylation site mutations ($D3^{R+C/S}$), were blotted for PD-L1 and HSP-70 (loading control) proteins.

Example 12: DHHC3 Ablation Causes Diminished PD-L1 Expression on Cancer Cells Both in Presence and Absence of Interferon-Gamma To determine if DHHC3 inhibition could diminish PD-L1 in physiologically-relevant concentrations of interferon gamma (IFN-γ), human breast carcinoma MDA-MB-231 cells were selected to express control shRNA (C), or shRNA (D3) that stably ablated DHHC3 expression. Subsequently, cells were treated with or without IFN-γ (50 ng/ml) for 48 hrs. Thereafter, cell lysates were prepared, proteins separated on SDS-PAGE, and transferred onto nylon membrane. Finally, PD-L1 and HSP-70 proteins were detected by blotting the membrane with specific antibodies. As shown in FIG. 21A and FIG. 21B, PD-L1 expression changes in MDA-MB-231 cells +/− DHHC3, after IFN-γ treatment, i.e., DHHC3 ablation caused diminished PD-L1 expression on cancer cells both in the presence and absence of IFN-γ.

Example 13: DHHC3 Ablation Causes Increased Apoptotic Cell Death in Cells Exposed to Chemotherapeutic Agents DHHC3 ablation enhanced sensitivity to chemotherapeutic agents. Efficacy of anti-cancer chemotherapeutic agents is decreased by protective antioxidant proteins in cancer cells in response to increased oxidation. Because zDHHC3 ablation disables palmitoylation and proper function of several antioxidant proteins, it was determined whether zDHHC3 ablation increases sensitivity to chemotherapeutic agents.

Figure 22:
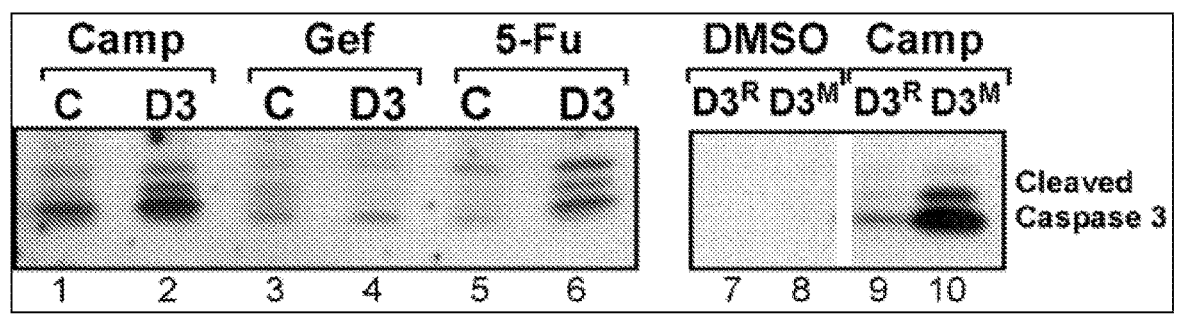
FIG. 22 is a series of photographs of immunoblots showing that DHHC3 ablation causes increased apoptotic cell death in cells exposed to chemotherapeutic agents.

As shown in FIG. 22, DHHC3 ablation increases drug sensitivity. Specifically, human breast carcinoma MDA-MB-231 cells were treated with Camptothecin (2 μM), Gefitinib (50 μM), 5-Fluorouracil (10 μg/ml), or DMSO (vehicle control), for 25 hr, lysed, then blotted for caspase-3, to assess apoptotic cell death. C=control shRNA; D3=stable DHHC3 ablation; $D3^R$=shRNA knockdown cells reconstituted with wild type DHHC3; $D3^M$=mutant DHHC3 (inactivated by C→S active site mutation).

As shown in FIG. 22, MDA-MB-231 breast cancer cell sensitivity to camptothecin and 5-Fu is enhanced when zDHHC3 is ablated (FIG. 22, compare lanes 2, 6 with 1, 5). By comparison, cell death induced by Gefitinib (which does not trigger oxidative stress), was not enhanced by zDHHC3 ablation (lanes 3,4). In another experiment, zDHHC3-ablated MDA-MB-231 cells were reconstituted with fully functional DHHC3 (D3R), or active site-disabled DHHC3 (D3M). Again, sensitivity to camptothecin was markedly enhanced when DHHC3 was totally inactive (lane 10), compared to fully functional (lane 9). Vehicle control (DMSO) didn't induce cell death regardless of DHHC3 expression (lanes 7, 8). Hence, DHHC3 enzymatic activity is required for DHHC3 reversal of drug sensitization.

Significance

Because anti-cancer monotherapies have shown limited long-term success, attention has turned to combination therapies. The results presented herein suggest that maximal effects of zDHHC3-ablation include enhanced sensitivity to chemotherapeutic agents combined with enhanced innate and/or adaptive anti-cancer immunity.

Example 14: Protein Acyltransferase, DHHC3, and its Relevance to Cancer DHHC3 and Adaptive Immunity As described herein, ablation of the enzyme, DHHC3, from human mammary carcinoma MDA-MB-231 cells causes a marked decrease in expression of PD-L1, a major negative regulator of adaptive anti-cancer immunity (FIG. 14A-FIG. 14C). The PD-L1 protein does not undergo palmitoylation and, thus, would not be directly modified by DHHC3. Hence, as described herein, it was hypothesized that CMTM6, a protein needed to maintain PD-L1 expression, may be the direct target of DHHC3-mediated palmitoylation. Consistent with this, ablation of DHHC3 markedly diminished palmitoylation of CMTM6 (FIG. 14A) caused a marked alteration in CMTM6 distribution (FIG. 19).

As described herein, an over-expression system was used to further establish that DHHC3 indeed can palmitoylate CMTM6. Specifically, in FIG. 23A, wherein CMTM6 C90 is needed for DHHC3-mediated palmitoylation, HEK293 cells expressing FLAG-tagged DHHC3 (FIG. 23A, lanes 3-6) and/or Myc-tagged CMTM6 (mutant or wild type) were incubated in serum-free media for 2 h, in presence of $^3$[H]-palmitate. After immunoprecipitation from cell lysates with anti-Myc antibody, samples were visualized for $^3$[H]-palmitate using photographic film and an intensifying screen (top panel) or were blotted for Myc (bottom panel).

Figure 23A:
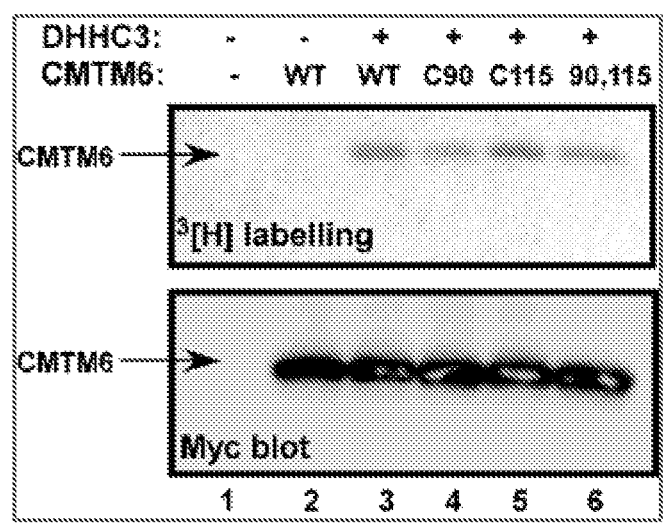
FIG. 23A-FIG. 23C is a series of immunoblots and photomicrographs showing protein acyltransferase DHHC3 and its relevance to cancer.

As shown herein, CMTM6 incorporates $^3$[H]-palmitate when DHHC3 is present (FIG. 23A, lane 3), but not when DHHC3 is absent (FIG. 23A, lane 2). This made the CMTM6 C90 amino acid a good candidate to undergo palmitoylation (FIG. 19). Indeed, mutation of C90 (C→S) caused palmitoylation to be diminished by ~50% (FIG. 23A, lane 4). By contrast, a C115 mutation did not diminish incorporation of $^3$[H]-palmitate (FIG. 23A, lane 5) and both mutations together (C90S+C115S) did not diminish palmitoylation (FIG. 23A, lane 6) more than C90S alone (FIG. 23A, lane 4). Because the C90S mutation only diminished palmitoylation by ~50% and C115 appears not to be involved, the four other CMTM6 cysteines (C76, C65, C52, C55) (FIG. 19) are perhaps responsible for the remaining palmitoylation. C76 and C55 are of particular interest because these are flanked by clusters of hydrophobic amino acids and DHHC3 may have preference for membrane-proximal cysteines.

DHHC3 Redox Regulation and Innate Immunity

As described herein, ablation of DHHC3 diminished palmitoylation of ERGIC3, a key regulator of oxidative stress/ER stress. Diminished palmitoylation was accompanied by substantial alteration in ERGIC3 subcellular distribution (FIG. 7C), consistent with altered function. The identification of ~50 additional DHHC3 substrates was done using a mass spectrometry approach.

Figure 23B:
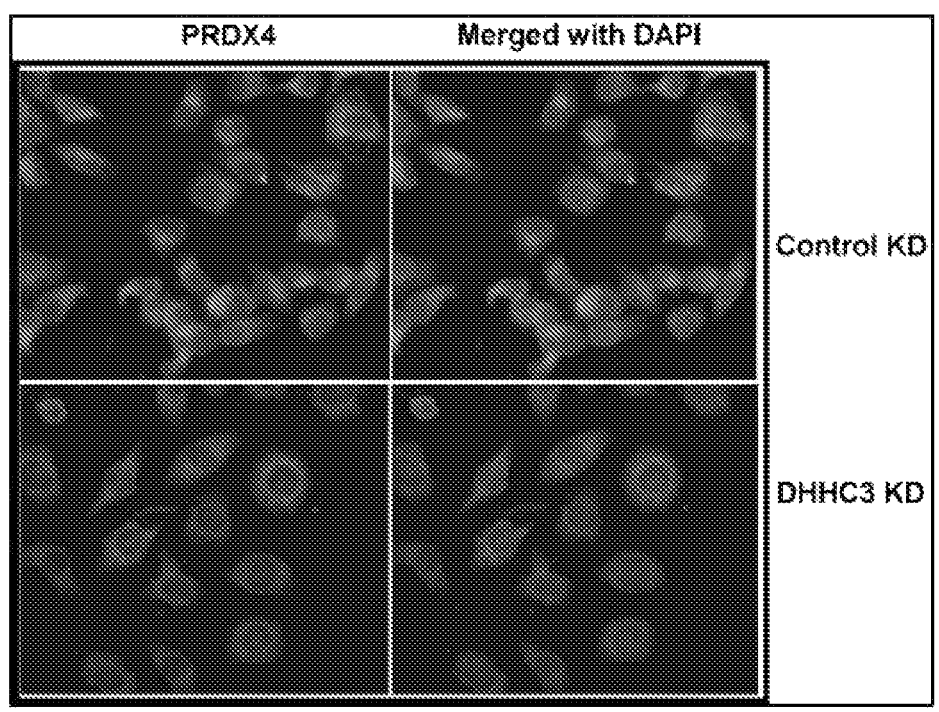
Figure 23C:
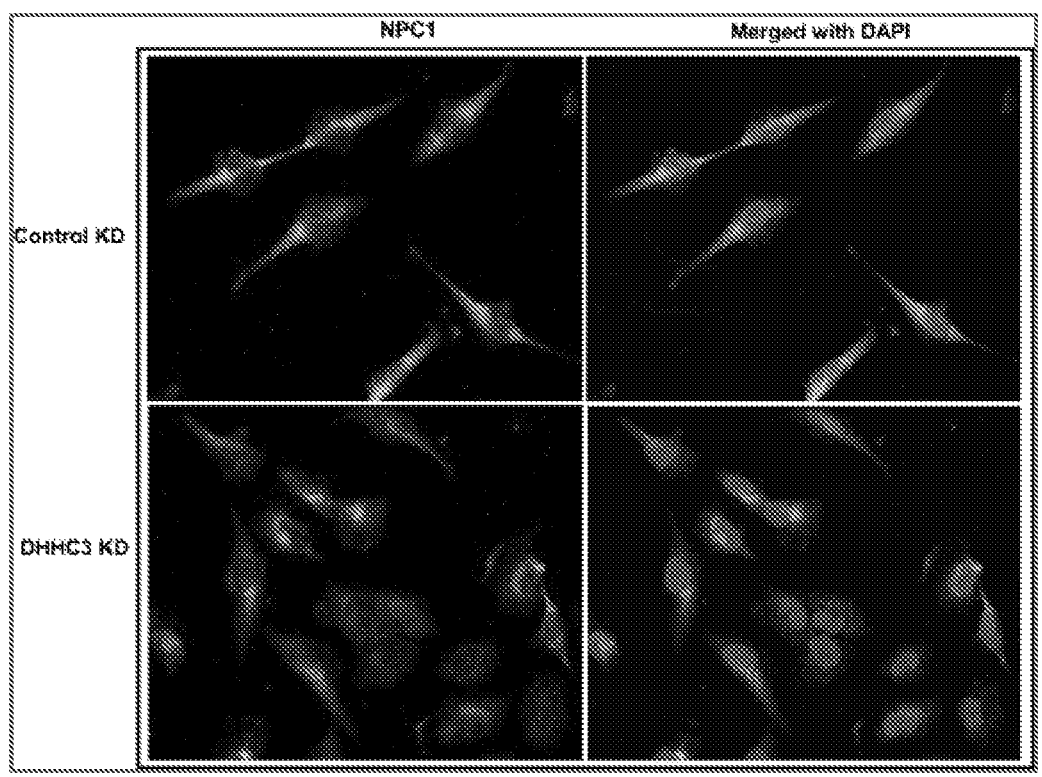

In FIG. 23B, which shows PRDX4 subcellular distribution, MDA-MB-231 cells DHHC3 ablation were cultured on slides, fixed, permeabilized, incubated with anti-PRDX4 antibody, and then Alexa-594-conj $2^{nd}$ antibody. Cells in the right panels were also stained with DAPI, to visualize nuclei. In FIG. 23C, which shows NPC1 subcellular distribution, MDA-MB-231 cells f DHHC3 ablation were cultured on slides, fixed, permeabilized, incubated with anti-NPC1 antibody, and then Alexa-594-conj $2^{nd}$ antibody. Cells in the right panels were also stained with DAPI, to visualize nuclei.

As shown, subcellular distributions of additional DHHC3 substrates involved in redox regulation (PRDX4 and Niemann-Pick C1 (NPC1)), are also markedly altered (FIG. 23B and FIG. 23C). As shown, ablation of DHHC3 causes PRDX4 to shift from an uneven and somewhat punctate distribution (FIG. 23B, top panels) to a more even and perinuclear localization (FIG. 23B, bottom panels). Similarly, NPC1 shifts from being diffuse throughout the cell body (FIG. 23C, top panels) to a more clustered perinuclear distribution (FIG. 23C, bottom panels). This suggests that altered distributions of PRDX4 and NPC1, due to diminished DHHC3-dependent palmitoylation, are consistent with diminished capability to protect cells from elevated oxidative stress.

Altogether, the results presented herein confirm that 4/4 putative DHHC3 substrates (ERGIC3, CMTM6, NPC1, transmembrane protein 192 (TMEM192)) lose substantial palmitoylation when DHHC3 is ablated. Also, 4/4 substrates (ERGIC3, CMTM6, NPC1, PRDX4) show markedly altered subcellular distribution when DHHC3 is ablated. Hence, ~50 of the DHHC3 substrates that have been identified using mass spectrometry are indeed likely to be valid DHHC3 substrates. As described herein, CMTM6 palmitoylation contributes to inhibition of adaptive immunity, whereas palmitoylation of several of the other substrates (especially those involved in redox regulation) contributes to inhibition of innate immunity.

Example 15: Targeting of DHHC3 on Tumor Cells Enhances Anti-Tumor Immunity

Protein palmitoylation affects protein localization, stability, molecular interactions and functions. Palmitoylation is typically mediated by protein acyl transferases containing conserved DHHC (Asp-His-His-Cys (SEQ ID NO: 7)) motifs, needed for enzymatic activity. As described herein, DHHC3 (one of 23 mammalian DHHC enzymes) is upregulated in malignant and metastatic human breast cancer, as well as prostate and colon carcinomas. Elevated zDHHC3 expression correlates with diminished survival in breast cancer and six other human cancers. Furthermore, zDHHC3 ablation in human MDA-MB-231 mammary cell xenografts reduced sizes of both primary tumors and metastatic lung colonies.

Effects on Innate Immunity

As described herein, in zDHHC3-ablated cells, oxidative stress and senescence were both elevated, as demonstrated by gene array data and fluorescence dye assays. Also, a consequence of elevated senescence was enhanced recruitment of innate immune cells (anti-tumor macrophages, NK cells) associated with clearance of senescent tumors. Anti-tumor effects of zDHHC ablation were reversed upon reconstitution with wild type, but not enzyme active site-deficient DHHC3.

Effects on Adaptive Immunity

As described herein, ablation of zDHHC3 causes a reduction in expression of immune checkpoint molecule, PD-L1, by ~90% in breast and prostate cancer cell lines, with or without stimulation by interferon gamma (INF-γ). Hence, it is determined whether zDHHC3 ablation markedly upregulates adaptive immunity.

In conclusion, DHHC3 is an important target in breast cancer and other cancers, because: i) it is upregulated in breast cancer and other cancers, ii) it is neither upregulated in normal tissue, nor needed for normal development, and iii) its removal elevates innate anti-tumor immunity and likely adaptive anti-tumor immunity.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting expression or activity of programmed death-ligand 1 (PD-L1) in a cell of a subject diagnosed with cancer or at risk of developing cancer comprising:
administering to the subject an effective amount of a palmitoyltransferase inhibitor, wherein the palmitoyltransferase inhibitor is selected from the group consisting of 1-Benzyl-4-(5-chloro-2-nitro-benzyl)-piperazine, 11-Methyl-4-(4-nitro-benzyl) 1,2,3,3a4,5,6,7-octahydro-[1,4]diazepino[3,2,1-jk]carbanzole, {2-[2-(4-Chloro-phenyl)-1,3a8-triaza-cyclopenta[a]inden-1-yl]ethyl}-diethyl-amine, and 2-(2-Hydroxy-5-nitro-benzylidene)-benzo[b]thiophen-3-one,
thereby inhibiting the expression or activity of PD-L1 in the subject.

2. The method of claim 1, wherein the palmitoyltransferase comprises an Asp-His-His-Cys (SEQ ID NO: 7) motif (DHHC)-type protein.

3. The method of claim 2, wherein the DHHC-type protein comprises DHHC3, DHHC5, DHHC7, or DHHC17.

4. The method of claim 3, wherein the DHHC-type protein comprises DHHC3.

5. The method of claim 1, wherein the palmitoyltransferase inhibitor decreases DHHC3-dependent palmitoylation of chemokine-like factor (CKLF)-like MARVEL transmembrane domain containing family member 6 (CMTM6).

6. The method of claim 5, wherein the palmitoyltransferase inhibitor decreases DHHC3-dependent palmitoylation of CMTM6 at an amino acid selected from the group consisting of C90, C76, C65, C52, and C55.

7. The method of claim 1, wherein the cancer is breast carcinoma, thyroid carcinoma, skin cutaneous melanoma, uterine corpus endometrial carcinoma, sarcoma, bladder urothelial carcinoma, papillary thyroid carcinoma, colon cancer, or prostate cancer.

8. The method of claim 7, wherein the breast cancer is selected from the group consisting of ductal carcinoma in situ, invasive ductal carcinoma, triple negative breast cancer, inflammatory breast cancer, metastatic breast cancer, medullary carcinoma, tubular carcinoma, mucinous carcinoma, human epidermal growth factor receptor 2 (HER2)+ breast cancer, and estrogen receptor (ER)+ breast cancer.

9. The method of claim 1, wherein the palmitoyltransferase inhibitor inhibits tumor growth and/or tumor metastasis of a tumor in the subject.

10. The method of claim 1, wherein the palmitoyltransferase inhibitor is administered orally, intramuscularly, subcutaneously or intravenously.

11. The method of claim 1, wherein the PD-L1 activity comprises reducing the infiltration or activity of tumor-specific cytotoxic lymphocytes (CTLs).

12. The method of claim 11, wherein infiltration or activity of tumor-specific cytotoxic lymphocytes (CTLs) is increased as compared to infiltration or activity of tumor-specific CTLs in the absence of the palmitoyltransferase inhibitor.

13. The method of claim 1, further comprising administering a PD-L1 inhibitor prior to, simultaneously with, or after administration of the palmitoyltransferase inhibitor, wherein the PD-L1 inhibitor comprises atezolizumab, avelumab, or durvalumab.

14. The method of claim 1, further comprising administering a chemotherapeutic agent prior to, simultaneously with, or after administration of the palmitoyltransferase inhibitor, wherein the chemotherapeutic agent is selected from the group consisting of camptothecin, 5-fluorouracil, cyclophosphamide, methotrexate, doxorubicin, paclitaxel, docetaxel, and epirubicin.

15. The method of claim 1, wherein the palmitoyltransferase inhibitor increases oxidative stress and/or tumor cellular senescence as compared to oxidative stress and/or tumor cellular senescence in the absence of the palmitoyltransferase inhibitor.

16. The method of claim 1, wherein the subject is a human.

17. A method of inhibiting intrinsic or acquired resistance to chemotherapy or increasing the potency of chemotherapy in a cell of a subject diagnosed with cancer or at risk of developing cancer comprising administering to the subject an effective amount of a palmitoyltransferase inhibitor, wherein the palmitoyltransferase inhibitor is selected from the group consisting of 1-Benzyl-4-(5-chloro-2-nitro-benzyl)-piperazine, 11-Methyl-4-(4-nitro-benzyl) 1,2,3,3a4,5,6,7-octahydro-[1,4]diazepino[3,2,1-jk]carbanzole, {2-[2-(4-Chloro-phenyl)-1,3a,8-triaza-cyclopenta[a]inden-1-yl]ethyl}-diethyl-amine, and 2-(2-Hydroxy-5-nitro-benzylidene)-benzo[b]thiophen-3-one, and wherein the palmitoyltransferase comprises DHHC3, thereby inhibiting intrinsic or acquired resistance to chemotherapy or increasing the potency of chemotherapy in a cell of a subject.

18. The method of claim 17, further comprising administering an oxidative stress-dependent anti-cancer agent selected from the group consisting of camptothecin and 5-Fluorouracil.

19. The method of claim 17, further comprising administering a chemotherapeutic agent selected from the group consisting of cyclophosphamide, methotrexate, doxorubicin, paclitaxel, docetaxel, and epirubicin.

20. The method of claim 17, further comprising administering a PD-L1 inhibitor prior to, simultaneously with, or after administration of the palmitoyltransferase inhibitor, wherein the PD-L1 inhibitor comprises atezolizumab, avelumab, or durvalumab.

21. The method of claim 17, wherein the subject has been diagnosed with breast cancer selected from the group consisting of ductal carcinoma in situ, invasive ductal carcinoma, triple negative breast cancer, inflammatory breast cancer, metastatic breast cancer, medullary carcinoma, tubular carcinoma, mucinous carcinoma, human epidermal growth factor receptor 2 (HER2)+ breast cancer, and estrogen receptor (ER)+ breast cancer.

22. A method of inhibiting a tumor or enhancing anti-tumor immunity in a subject diagnosed with cancer or at risk of developing cancer comprising administering to the subject an inhibitor of a DHHC-type palmitoyltransferase, wherein the palmitoyltransferase inhibitor is selected from the group consisting of 1-Benzyl-4-(5-chloro-2-nitro-benzyl)-piperazine, 11-Methyl-4-(4-nitro-benzyl) 1,2,3,3a4,5,6, 7-octahydro-[1,4]diazepino[3,2,1-jk]carbanzole, {2-[2-(4-Chloro-phenyl)-1.3a8-triaza-cyclopenta[a]inden-1-yl] ethyl}-diethyl-amine, and 2-(2-Hydroxy-5-nitro-benzylidene)-benzo[b]thiophen-3-one,
thereby inhibiting a tumor or enhancing anti-tumor immunity in a subject.

23. The method of claim 22, further comprising administering a PD-L1 inhibitor, wherein the PD-L1 inhibitor comprises atezolizumab, avelumab, or durvalumab.

24. The method of claim 22, further comprising administering a chemotherapeutic agent selected from the group consisting of camptothecin, gefitinib, 5-fluorouracil, cyclophosphamide, methotrexate, doxorubicin, paclitaxel, docetaxel, and epirubicin.

25. The method of claim 22, further comprising determining that the cancer is likely to metastasize if the expression level of the DHHC-type palmitoyltransferase in the test sample is higher as compared to the level of the DHHC-type palmitoyltransferase in the reference sample.

* * * * *

SEQUENCE LISTING

```
<160> NUMBER OF SEQ ID NOS: 9

<210> SEQ ID NO 1
<211> LENGTH: 299
<212> TYPE: PRT
<213> ORGANISM: Homo sapiens

<400> SEQUENCE: 1

Met Met Leu Ile Pro Thr His His Phe Arg Asn Ile Glu Arg Lys Pro
1               5                   10                  15
```

Glu Tyr Leu Gln Pro Glu Lys Cys Val Pro Pro Tyr Pro Gly Pro
        20                  25                  30

Val Gly Thr Met Trp Phe Ile Arg Asp Gly Cys Gly Ile Ala Cys Ala
            35                  40                  45

Ile Val Thr Trp Phe Leu Val Leu Tyr Ala Glu Phe Val Val Leu Phe
50                      55                  60

Val Met Leu Ile Pro Ser Arg Asp Tyr Val Tyr Ser Ile Ile Asn Gly
65                  70                  75                  80

Ile Val Phe Asn Leu Leu Ala Phe Leu Ala Leu Ala Ser His Cys Arg
                85                  90                  95

Ala Met Leu Thr Asp Pro Gly Ala Val Pro Lys Gly Asn Ala Thr Lys
            100                 105                 110

Glu Phe Ile Glu Ser Leu Gln Leu Lys Pro Gly Gln Val Val Tyr Lys
        115                 120                 125

Cys Pro Lys Cys Cys Ser Ile Lys Pro Asp Arg Ala His His Cys Ser
    130                 135                 140

Val Cys Lys Arg Cys Ile Arg Lys Met Asp His His Cys Pro Trp Val
145                 150                 155                 160

Asn Asn Cys Val Gly Glu Asn Asn Gln Lys Tyr Phe Val Leu Phe Thr
                165                 170                 175

Met Tyr Ile Ala Leu Ile Ser Leu His Ala Leu Ile Met Val Gly Phe
            180                 185                 190

His Phe Leu His Cys Phe Glu Glu Asp Trp Thr Lys Cys Ser Ser Phe
        195                 200                 205

Ser Pro Pro Thr Thr Val Ile Leu Leu Ile Leu Leu Cys Phe Glu Gly
    210                 215                 220

Leu Leu Phe Leu Ile Phe Thr Ser Val Met Phe Gly Thr Gln Val His
225                 230                 235                 240

Ser Ile Cys Thr Asp Glu Thr Gly Ile Glu Gln Leu Lys Lys Glu Glu
                245                 250                 255

Arg Arg Trp Ala Lys Lys Thr Lys Trp Met Asn Met Lys Ala Val Phe
            260                 265                 270

Gly His Pro Phe Ser Leu Gly Trp Ala Ser Pro Phe Ala Thr Pro Asp
        275                 280                 285

Gln Gly Lys Ala Asp Pro Tyr Gln Tyr Val Val
    290                 295

<210> SEQ ID NO 2
<211> LENGTH: 12705
<212> TYPE: DNA
<213> ORGANISM: Homo sapiens

<400> SEQUENCE: 2
agcgcgtcat caacctgcgc ggcggccgct cctgcagccg cggccgccgc cactgccggg     60
agagctcgat gggcttctcc tgcgcgccgc ccggtgtctg gccgagtcca gagagccgcg    120
gcgcctcgtt ccgaggagcc atcgccgaag cccgaggccg ggtcccgggt tggggactgc    180
aggggaaggc agcggcggcg gcggcggag ccccaccggg gtctgggact ggggaactgc     240
ctccggcttc acgggcacc taaaggaag acagcttgca gggttggact ttgccttcca      300
gggaaactga agaggtgaa gccggaagga tttcctccct aatgaaggca cagatgccag     360
tatggacaga atagcttatg atgcttatcc ccaccacca cttccgaaac attgagcgga     420
aaccagaata cctccagcca gagaagtgtg tcccaccccc ctaccctggt cctgtgggaa    480

```
ccatgtggtt tatccgtgac ggctgtggca tcgcctgtgc catcgttacc tggtttctgg      540
tcctctatgc ggagttcgtg gtcctctttg tcatgctgat ccatctcga gactacgtgt       600
atagcatcat caacggaatt gtgttcaacc tgctggcctt cttggccctg gcctcccact      660
gccgggccat gctgacggac cccggggcag tgcccaaagg aaatgccact aaagaattca      720
tcgagagttt acagttgaag cctgggcagg tggtgtacaa gtgccccaaa tgctgcagca      780
tcaagcccga ccgagcccac cactgcagtg tttgtaagcg gtgcattcgg aagatggacc      840
accactgtcc ctgggtcaac aactgtgtag gcgagaacaa ccagaagtac ttcgtcctgt      900
ttacaatgta catagctctc atttccttgc acgccctcat catggtggga ttccacttcc      960
tgcattgctt tgaagaagat tggacaaagt gcagctcctt ctctccaccc accacagtga     1020
ttctccttat cctgctgtgc tttgagggcc tgctcttcct cattttcaca tcagtgatgt     1080
ttgggaccca ggtgcactcc atctgcacag atgagacggg aatagaacaa ttgaaaaagg     1140
aagagagaag atgggctaaa aaacaaaat ggatgaacat gaaagccgtt tttggccacc      1200
ccttctctct aggctgggcc agcccctttg ccacgccaga ccaagggaag gcagaccgt      1260
accagtatgt ggtctgaagg accccgaccg gcatggccac tcagacacaa gtccacacca     1320
cagcactacc gtcccatccg ttctcatgaa tgtttaaatc gaaaaagcaa acaactact      1380
cttaaaactt tttttatgtc tcaagtaaaa tggctgagca ttgcagagaa aaaaaaagt      1440
ccccacattt tattttttaa aaaccatcct ttcgatttct tttggtgacc gaagctgctc     1500
tcttttcctt ttaaaatcac ttctctggcc tctggtttct ctctgctgtc tgtctggcat     1560
gactaatgta gagggcgctg tctcgcgctg tgcccattct actaactgag tgagacatga     1620
cgctgtgcgt ggatggaata gtctggacac ctggtgggg atgcatggga aagccaggag      1680
ggccctgacc tcccactgcc caggaggcag tggcgggctc cccgatggga cataaaacct     1740
caccgaagat ggatgcttac cccttgaggc ctgagaaggg caggatcaga agggaccttg     1800
gcacagcgac ctcatccccc aagtggacac ggtttgcctg ctaactcgca aagcaattgc     1860
ctgccttgta ctttatgggc ttggggtgtg tagaatgatt ttgcggggga gtggggagaa     1920
agatgaaaga ggtcttatt gtattctgaa tcagcaatta tattccctgt gattatttgg      1980
aagagtgtgt aggaaagacg ttttccagt tcaaaatgcc ttatacaatc aagaggaaaa      2040
aaaattacac aatttcaggc aagctacgtt ttcctttgtt tcatctgctt cctctctcac     2100
caccccatct ccctctcttc cccagcaaga tgtcaattaa gcagtgtgaa ttctgactgc     2160
aataggcacc agtgcccaac acatacagcc ccaccatcat ccccttctca ttttataaac     2220
ctcaaagtgg attcactttc tgatagttaa ccccccataaa tgtgcacgta cctgtgtctt    2280
atctatattt taacctggga gactgttgtc ctggcatgga gatgaccatg atgctggggt     2340
tacctcacag tccccaccct ttcaaagttg acatatggcc atcccattgg ccagaatcca     2400
cagacacacc taagcctgtg gcactgggac agaatagatt ttccatttga gaggcacttc     2460
ctgtgtcagt cttgtttgaa ggaggtgtg atggtggata gaggtgaagg aggtagggag      2520
tgccctccaa gtgcaaaaat aacaaatatg attattgacc atcggggaat tctcacacat     2580
tgatttgttt tttaagcaat tgccagaaac ccccttttt agcttttgct tggggtgggg      2640
gtaggagtta aggtttattc aatcctgtcc tgggtagggc gaaagttaat ctagccatgt     2700
gattttcag aaaagtaagt ggaacatgct gccacttttc aattctgtca gtgcttccac      2760
atggaaacaa aatgcaataa aatttttcca aaacctgttc tgatttagct ctctcttgag     2820
gtgttaccct tagtgggagg ccgactatcc acaatctact tgagttttct ctggttgggt     2880
```

```
gtttgtttca ttgctctgtc tcttgaatga ggatacttta tttttttgt tttaaaatgc    2940 atttatggtc cctctcttga accagcttgc cccaccaggc ctctttcctt tgctttctgc    3000
agcctgaatc aattcctttg tgctgatggg ctctcctaag agctttcctg agtcagttaa    3060
ctttacctcg tgtctacggt gctattcatg cgatacgggc gaggctgaga tgctaagatt    3120
aaaaagaaaa gaatgctgtt ttagatcaag ttgatagcat ttgttttcca tatgcttttt    3180
taaaattttt tcataacata cagctcagtt aggtgtatga agaagtgtt attgtattaa     3240 ataactagag cagggctaca gctctggccc tcccctaggg ggaagagatt ggtaatactc    3300
catcttccag ggcatttttt aaagtgagcc aggttagctc ttttcccctg gcatttctca    3360
ggaatgcagt agatagtgct gaagatgcac tgacttttt ttagtcctaa aaatagaaac     3420
tcctccttta aagctgtgca tactatgctt atctttccaa tagagtgggg ttccttcaga    3480
tatcctatag gattctgcct ctggttttgt ataggccttg gctagaaaga gtcaatgttt    3540
ctgagctctc aaaccagttg ctctcagaag ataggaatac cccaaggttc ctggcatttt    3600
tcctatttca tttttgttca gactgatatt ttgccaagag cacaatgact gaggaatgta    3660
gccatcattt gcagggtagt gattggttcc cagcctggct tccacacagg acaggaaggg    3720
aaagcatccc tgagctctcc tcagtatttc cggatgtaat gaaagaggac atctttctac    3780
acaaagtcag ccccaacttt tggcttggtc acaggagttc tgatagtact gtttggtgca    3840
ctcatgggaa attgaaccag tcgtagccac agtctttcag agcctgggct ctggggagtg    3900
gaagtgaaaa ataaagatgt ggcttgttgg attgtgatcc ccagcttgct ttccttctgt    3960
caactctgtc aggtttgtgt tcatagcaac tagactgaat atgcaaaagg cttagatcca    4020
agcaaatcta taatctatgc atatttgcat gggcttggta atatcatgta cacaaaacac    4080
atttgggtag aagtgcatgt gctaaatctc ctttttagtcc caccatttg tcttcttcat    4140 actgtacttc ctctttttg tttgagacaa ggtcttgctc tgtcacccag gctggaatgc    4200
agtggcacaa ttagagctca ctgcagcctt gaactcctgg gctcaagtga ttcttgtgcc    4260
ttggcctcct gaatatccag ggctacaggc acgtactacc atgcctggct aattttttg    4320 ttttttaata gagtcagggt ctcactgtgt tgccctagct agtctcaaat gcccggcctc    4380
cagcaatttt cctgcttag cctcccaaag tcctgggatt acaggcgtga gccactgggc     4440
ccagccctgt acttcttgaa aaagccccaa gtattagctt tgctcatct ggctaggcca     4500 cttaaatagt tagaatccac cgtcccctaa tgcagaaacc gtttaggtga ggtaaattaa    4560
caaacatttt aagccgggcg cggacacttc tcactgtgga catccctcac gcctgtaatc    4620
ccagcacttt gggaggccga ggcgggcaga tcacgaggtc aagagatcga gatcatcctg    4680
gctaacacgg tgaaaccctg tctctactaa aaatataaaa aaattagctg gcgtggtgg    4740 caggcgtctg tagtcccagc tacttggag gctgaggcag gagaatggcg tgaacccggg    4800
aagtggagct gcagtgagc caagatcgca ccactgcact ccagcctggg cgacagagtg    4860
agactccgtc tcaaaaaaaa aaaacaaaca ttttaaacat gtatgtgagg ttggcattac    4920
acagaaactc ctctccgggt gggctgggat gggctttctc agccaggcta atgggtttta    4980
aatttctctc ttttcaagac ttgcagtgca tcagcttaaa gggtgagcca gccagtagag    5040
gggaaggcgc cccacctaga aggtgccctt agatatcaaa gaaatgtgaa aagagaaaga    5100
ttttgctaga atcctcctca aaggtgttct tgaggttgcc agaccagcaa cgtcaacatc    5160
agcatcacct gagaacttgt tagaaaatgca cattctcggt ccccacccca ggctaccgaa    5220
```

```
ccagaaaccg agcggggccc agcagcccgt gtcttaacag ccctccaggt gattctgact    5280
atcaagtttg agaatccagt tggggctagc aggagtcccc cctcaggtgg tccctgatgc    5340
ctgctggtga tatgggtctt gtgtgctgct gggctcagca tagtgcagtt ggggtgtgct    5400
gattgtgaga caggcacgtg ttccctccgc ggagaagcca ctgagactgc cttccctcat    5460
aagctgcggc ctccccaaca acaactgcc aagacatcaa agaaagtctg tatgaagcag    5520
atccaaatta ttagcctgcc caccactcct tgtgcatctc atcagtggaa cccatctcta    5580
gaccaagggc cctttgggtg aagaagcagc ccggaaggga aagagaaaag agtagaacca    5640
agggacctcc agatgggagc ggcggccggt gagtagtcta gagccagggg cattgtagca    5700
gcctggatac atgacctgaa cacgtcttga cctttgcttt ctacgtgtgg gtttcaacac    5760
ccatgtggct ttttcttgta ttctttaaat atgtatctgg cttaggatca cctcatagaa    5820
gagaaagaat tcacagtgaa gcagaaacaa gccactgacc agcgtactcc caacctgaac    5880
cttcttttc tcaccctctc cctcaagtaa acatcttgct gacttgagca gtgtgattgc    5940
cgtagcaaag cagagtggcc cccagggatc ccgctctgtt gggcccacag gaggagccga    6000
tgaagctgat ccaaggagtg aggacaagcg ctgcagaggg acgttcgcta aaagccttct    6060
aggggccgca catgctctaa cacggacata aggatgccct gaatttctgc agctgaggcc    6120
atatagtctg gtgaccaagt atttgggtcc tggcttcagt cttttggttga aatgtctgct    6180
tggctactta ttaccgcacc tactaccaaa atatgacctt gagcagtaac ttctttaagc    6240
ctcagttttt tcatctgaaa acgggaatga taatctaaat cacaaagtta atggaaggat    6300
taaatgaggg tgatgaatag gaatgtatag cgtctggccc tggtatggct ttataaatgt    6360
tagctgtgtt ggagctgtgc ttttcaaacc attggtcaca gccattcatg gtttgcaacc    6420
agcatgtttt tcaagaaaaa tgtttaatgc attacatatt gcaggataag tattgttta    6480
tgaagcttag ggagttgtgt gtatatgtgt tctggaatgc aacagaaaaa tgtttcctct    6540
tgtgggttac aatatagagg tatgaaatct ctgatgagga gagacagtgt tatctggccc    6600
gctatgaaga gacacatttg cataggctgc tccctgaggc tctggctttc tacatctgat    6660
gatacaggga gcagggaaca gcctgttctc gttctgtggg gctcagctga gtctgttctg    6720
cacagactct tccttcctcg ggagccttag tcctaataca ttcattttgg agtgttggtg    6780
agtttgttca cagatcacag ctcatgtgtc acccagactg acctgggcca aaaggcccat    6840
cacacaccct gcaagagctt ctggtgtcga ctatgacccc cttaccaggc atcaaccatt    6900
tttgttcgtt ctcttgagcc tgaagctact attactgctc ctctgcaaac ctcaagctta    6960
agaactttgc ctgcaggatc cctttaaatc cacacaaaac tcaaaattga gtcctaccag    7020
gaaaaagcag ccctcagccc attttatac atcggatttg tttgcaatat ttctttcta    7080
gactcaaaag tcaacactcc ctgaaagttt gtcgacttta ctgctgaaga cctctggtag    7140
acaggccagg ctctgtctgg aatactttat gaggttggtg aggaggttga gtataatcca    7200
agagtgccta tctgggagca tgccacatga atggcaaata atcatcctgt gggctcttgg    7260
cttcattccc cttctctctg actgagctca gcctgggcac agtggtgatt gcagtagaa    7320
ctggaaacct gttgggcaga aaaaaagaca ctagttctgg ttccagttct gatacataac    7380
aagctagatg agccttggcc accgtcatgg cctcttggaa cttctgtttc ttccccatct    7440
gccaatcatc aatactccata cccacctcct cacaaggagg ccataaaaac ctatggtcat    7500
ggctttgagt ccaagtcagt gtggatgcag ccagtctgtc atttttgggt gtttcctctg    7560
tagccgggtc tgccatatgg tgatgtccca gctctcgtgc tatgaagtta aagcctcttt    7620
```

```
ctcaacaggc tgcagatgat cacccaggaa gagaatgcag aatgcccaaa gcaaaccatc   7680
tcagctggtc actgcttctg tgccaagaag ggaggcctgg cgaggggcca gtcaggaagc   7740
agcatggcat cacatgctca tgacccacat gaaggtccct ttagacttgt gtcaacaaga   7800
tccattttct gaaacaacta ttttttgttct gattataaaa gtaacattgg ctcattggta   7860
aaacttggat tgtgtgagaa gtctacagaa ataaatacaa atcctctaga attccatccc   7920
caaaagtaac cactcagaca aatgttctaa tgtcatgtaa aaccatatta aaccatcttt   7980
tctagctgca tagtgttata gaatcatttg cttaaccatc attattgggc atttctcatt   8040
tccagctttg cattattata attcagtgtt caagtttgta ttgcataaat ctttgtctca   8100
gattattgat tattttttaaa ctttttgtga aatcagactt acaaaaatgt gacaaaaaca   8160
gtacaaagag ttcccatgta cctttcagtc agtctcacca aaggtaaaca ttttatacaa   8220
ccataataca aatataaaac cctggacatt ggcaacacca tacccttaac taatgtatgt   8280
accttattca catttctcca gttgtcccat taacacccctt ttctgttcca ggatcccaca   8340
ctgcatcatt tgcgatgtct ccttagtctc ctccagtttg tgacagttcc tcagtcttcc   8400
tttgtctttc atgaccttga ccctttttaa aaatcgaggt gaaattcctg taacacaaaa   8460
ttagccattt taaagtgtac atttaatgca ttcacaatgt tttgtaacca ccaggtctgt   8520
ctggttccaa aatcttttca tcaatctttg acccttttga agattgtagg gcaggtattc   8580
tgtaggctgt ccttcagatt gtgttttga tgttttctc atgattagat tgaggttagg   8640
catttggggc aggagcactg ctgaagcaat gtgtcctcgt tgcaccgtat caggaggcat   8700
atggtgttga tacgtttcat tattgtgatg ttaactttga tcattgggtg aaggtggtac   8760
gtgcaatgtt tcttccctgc tattaaggta ctgttttttcc ctttgtaatt gataagtatc   8820
ttatgaggat atacttttga gatccaattt ttttaactta gaatttattc aaaagtcaag   8880
aatcttaaat ctctgaaatg gcgtgggaag aaaaagtgct agatacacag agatctttct   8940
tgagtcatgt gaaggagcag tgcccaagcc cagcaaaccc acagcaaatt cccttggctt   9000
ccagaagaga tggagaaagc agtgccccca gtggagggtc aaaggcctct gtgcagggtg   9060
ttgtgggcct ggagagctgg cctggccatg tctttacctc ctctgggcat ctccccaccc   9120 caacacccctt tctgtggcct ggtggctgag ttgcagccga cacccagagg caggtgagtt   9180
gacagcttgg aagaggctgc agggtggatc tgctgcatga gcaggcctga gcccagcctt   9240
acctccccac agtggtcctg tgtgccctcc ggctgcctaa tgcatgttgg cacttgctgt   9300
acgagcaccc gcttcttcac ctcgcatgct gttttgtgtcc tgcactcctt ccttaacccc   9360
atcgtccttc tgctgtgttt gcagccccta tctaccctgg tgggagtggc caaaaatatt   9420
taggagggga tcaccagttt gtagtggcct cagaggatgt gtggtccccc ttatgcctca   9480
gccactcatc agcctagccc ctgcccatca tctggcattg cacttgtgga aggaaagaag   9540
gggagggctg ggtggtgggt ggagaacacg tcagtccacc aggcgggccc tgcttgctgt   9600
gttcctccac gctgctgtcc acccacaccc cagcagtcct ctgagggacc tcccgggggt   9660
gacctgggcc acaacagact gcccactcag acccatcttt acccatgccg tggacacccc   9720 gcccccccc ccgccactgc tatgctatag ctggggggtgt ctatgtgagc tgtacagccc   9780
agcaccacgc tgacgatgtt cttcatcccc ttctccctgc agggcatcga gcgcctcaaa   9840
cgaaagaacc agcccaggga gcacatgggg agctggcagt cagtaaagga gacctttggt   9900
ggggacttct ccctgaactg gttcaacccc ttctccagac cgtgtcagcc agagatcccc   9960
```

```
agtgacaaag acatggtgcg gcaggtgaca tcgctgtcag acaccgaaac aatggaggat    10020
ccatcagagg agacaaagga cgaggactct gtggaggtga cagatgaata gatgctgctg    10080
tggggagaga agcaaacact aaaaagtgct gtcaaccttc atcctggggt tttggctaaa    10140
ggggcttatg ggcatggtgc gctcccagca cccccagtgc ttcccttagc cactcgcttg    10200
gccttgccat ttcccctcct tcttctctcc atgttgggcc aggtctgggg gtcgggagta    10260
ggctggggac atcagaggag gatggggggct ttctcagagt tcatctaaga agagtctgca   10320
ctgagacggc tcatcaagaa ccgttctcca agactgggtg gctttcacat tctccgccca    10380
gcaaagggag cttttgaaca gggcatccca ggggcagaaa agagcttgcc tttggctttc    10440
cccaggattt ctgtcttctc ttgggaaggc tgggcccctg gctcctggct ttgagaagta    10500
aggttgtgac agaaggaccg ggcagggctt gccttgggga cctgggttgg gacactgaca    10560 tcagggggaga ctagcctgga aagactgcag agctgccagc tactccctgg aaagggcttc   10620
cccatgctgc ctgccgaaat taggaggtag aggtggctgc cacatctacc tgcaagggcc    10680
aggcatggtt caaagaggac cctgcattaa gctctacaca cacatgtgca ggacatgtcc    10740
agcatggaca gagccagagt taagacagta gcaccgaaaa tgagcccca ttccacagac     10800 actggagtct tcactgagcg agacagctgg gagctgtcct gcctgtggct acatatctag    10860
ccattcacag atgtggatat gggaaggacc tctttggagc tactggggac tccctaacca    10920
ctcgcatgag aacttaattg aatgttacct cttggaggga gtctaataac acatgtaggt    10980
agaactgacc ataaaccctg cctgtgtgtt tgaaaaggcc agttctccca aattggtgcc    11040
catcttgtct ctgaaaagat gggtgatggc cagggtctgc tgattgatga atcagatgaa    11100
tcaggaagat agacaaacac acacacacac acacacaccc caccaggatg agtctgccct    11160
ctattcaccc catttgaagc ctgtggtgtc tgtgaccact gctgaaggtc tgagcagcgt    11220
tctggtgctc ctaaaccccca ttccagtggt tgctgaagca gcatcttctg cacaaagccc    11280
aacagaaggg ttcttatccc cgtttggtat aagaagtgga ttcaccaccc actccctcca    11340
cgtgcctttg ttcctctctt tggcccattt ccccagcgtc tactggcgtc aggattggca    11400
ggagcacagg cactcagcag agcatgcccc tgcaagacct cagtgttagg gccccccttc    11460
cagctccagg caaaagggca tgagtcctgg ccccaagggg cctgtggctg cagttcagag    11520
gagaagaagg tcagtgtttg gaggtgcagc ctcaggatgc tgagaaagga aactggcgac    11580
cgtgagaaag aaaagagcca agcagcatcc tggttcttgg acagcatctt tggacactct    11640
gtgaagggca acgatcctgc cagagaccgt ctctctacaa ctgatgaccc actagggcct    11700
ggggttaatt gctcaaaggg cccagtgttc acaaagccac ctctgcccta acccttgcca    11760
gagctctcca actatgaccc acgagagggg tgatggtggg attctaacat caacagagca    11820
accagaaaga cattgggcct cccacactca ggctgcaggc ccactttctt ggtccttatc    11880
agctttaata tttattaatg acgacatagg agcccgagtc agctgtaaag gccattaact    11940
tgcaatctgg acaggaagtt gacgctcacc actttgggta agagctgctc tgactgtagg    12000
gccccctatt tgttgtccta acccagaagc agctctgggc tgccaggatg gtggatggaa    12060
taccagagag ttcacactag ggaggaagca atgcctgccc cctggagtct cctagggggc    12120
agcagttaga ataagggaag aggatttgct ggtcactgtt tgctgacatg ggtttccatg    12180
gtgagttcag gcctgaggac agcagtgtct gcaaaccac atggcccttg agaaatgtcc     12240
ttgcacattg ggcttcaaac tcctcttcta gggaatccat cttggcctga aagcagaggt    12300
acaacaccag cccccaaggc aattctgttt tcagattggt tgctctggaa aggaaggctg    12360
```

-continued

```
gggtgagggg gcattttact tgcacagagg ctgaccctgc ctcccctctt cactgacccc    12420
atctccaagg tagacctcag ccatgtcagt ccctgttctg ggaggtgctg ggctgggcca    12480
cagccagggt tatgtaggta attaacctgt ccaaccctga gcctcgcctc cccacaccag    12540
caacacagtg gtctctctgt ggtgaccatt cacagcataa cattctgctt agcctcagac    12600
tgaaagcatt gcaactgatg tcaaaaccag atgagatctt acagggagag agattgggtg    12660
caatttgcct ctttctttga ataaaaagct ctttgctcac cctca                    12705
```

<210> SEQ ID NO 3
<211> LENGTH: 183
<212> TYPE: PRT
<213> ORGANISM: Homo sapiens

<400> SEQUENCE: 3

```
Met Glu Asn Gly Ala Val Tyr Ser Pro Thr Thr Glu Glu Asp Pro Gly
1               5                   10                  15

Pro Ala Arg Gly Pro Arg Ser Gly Leu Ala Ala Tyr Phe Phe Met Gly
                20                  25                  30

Arg Leu Pro Leu Leu Arg Arg Val Leu Lys Gly Leu Gln Leu Leu Leu
            35                  40                  45

Ser Leu Leu Ala Phe Ile Cys Glu Glu Val Val Ser Gln Cys Thr Leu
        50                  55                  60

Cys Gly Gly Leu Tyr Phe Phe Glu Phe Val Ser Cys Ser Ala Phe Leu
65                  70                  75                  80

Leu Ser Leu Leu Ile Leu Ile Val Tyr Cys Thr Pro Phe Tyr Glu Arg
                85                  90                  95

Val Asp Thr Thr Lys Val Lys Ser Ser Asp Phe Tyr Ile Thr Leu Gly
                100                 105                 110

Thr Gly Cys Val Phe Leu Leu Ala Ser Ile Ile Phe Val Ser Thr His
            115                 120                 125

Asp Arg Thr Ser Ala Glu Ile Ala Ala Ile Val Phe Gly Phe Ile Ala
        130                 135                 140

Ser Phe Met Phe Leu Leu Asp Phe Ile Thr Met Leu Tyr Glu Lys Arg
145                 150                 155                 160

Gln Glu Ser Gln Leu Arg Lys Pro Glu Asn Thr Thr Arg Ala Glu Ala
                165                 170                 175

Leu Thr Glu Pro Leu Asn Ala
            180
```

<210> SEQ ID NO 4
<211> LENGTH: 3384
<212> TYPE: DNA
<213> ORGANISM: Homo sapiens

<400> SEQUENCE: 4

```
agggggcggg gcgggccaag ggcgggggcg ggaaggggcg gagtcaggcg gaagccgggg     60
agaaggccca ggaagtgacg gccgcctccc ggctaccggg gacttctgga gtccgagaag    120
tcaacggcgc ggttgctgcg gccgccgcgc tccccggccc gaggcgatgg agaacggagc    180
ggtgtacagc cccactacgg aggaggaccc gggccccgcc agaggccccc ggagcggcct    240
cgctgcctac ttttttcatg ggccggctcc cattgctccg gcgcgttctca agggcttgca    300 gctgttgctg tctctgctgg ccttcatctg tgaagaagtt gtatcacaat gtactttatg    360
tggaggactt tattttttg agtttgtaag ctgcagtgcc tttcttctga gtctccttat    420
```

-continued

```
actgattgtg tattgcactc cattttatga gagagttgat accacaaaag taaaatcatc    480
ggattttat  attactttgg gaacaggatg tgtgttttg  ttggcatcca tcattttgt     540
ttccacacat gacaggactt cagctgagat tgctgcaatt gtgtttggat ttatagcaag    600
ttttatgttc ctacttgact ttatcactat gctgtatgaa aaacgacagg agtcccagct    660
gagaaaacct gaaaatacca ctagggctga agccctcact gagccactta atgcctaaag    720
actctgggga gcagatgtta cctaaggtag tgaccctgca ttgtggtgcc tgagccctgg    780
cagaagctct tgtaaaattt gttaattgtt taaaccactt cttttggaga gcaaggggaa    840
ggtcaagaag gcagttttat caatattgtg tcagtcacca caaagtaggc cagataagtt    900
aaaaaaaatt ttttttaaa  taataattga aacttatctc aaatggagat tttggtggga    960
ggaggagaaa acaattgttt ttaaatcaca cagctcaacg gttgataaat gattctgtca   1020
ttctgttaca ggtcattctt ttactaggct tagcttccaa attatgcttt atagctgtat   1080
aaacatcgtg attatattca tctacttaga aattgtttta tttttaaatt aatttgctta   1140
gctgtttgtt ttgatgctta gattatgttc tgttaatggg aatttaacat atttaagaaa   1200
ccaatattta aaatgttggt ctaggttttt ttccttaaca tatattacca ggctttactg   1260
tatttcactc agcctaaaat gttataatat ttttggataa cggttattaa ttctttgaga   1320
ccttcgtata gcctataaaa tgtatgggag atgttggtat tttatgtgta taaaagcaac   1380
aatatcagca acttcgtgtt tatactgcac cttggttgtt gatgtcaagt aaaaaaaaga   1440
ttgttttgta acacataaaa aaatggaaga aactgatacc acacctaagg accaaagata   1500
agaaagactt tttgcccaag acagtgaaag taattataaa aacaagcttt gaccacttac   1560
caagtatctg aagagatgag ttcatactat gatttagaaa gtggttcaat tcccctgttg   1620
gcatatgatt attttactac aaattaatac agctctgtgg gtcttcctta gtgttttctt   1680
tgaagccaat ctgtttttt  taggacacca gcctttggtt tttcatctgt tcgagatgcc   1740
tcttctctgt ctccttatca gatagaaatg gagtcatgtg ctgctgcttc atctagcaga   1800
ggttggcctc tggctctgac acttttttgtc agttgtcttt aggtggtcct gaatcttggg   1860
cccttttgat tgtgaatact gtgtagcagg atcttgagag tccttgttct tacataggca   1920
ttgctctagt ttgtctttgg caaaaaaaaa aaaaaaaaa  agtaaatatc cagggaaccc   1980
tgcccagact aatactgttg gtggcataag agaatcaagc cattctcaag agataacttc   2040
ataaccagaa ttgtctgttg gctagcagct gtcacagata ggcagggcac ttgggatatg   2100
acctttctgt ccaggtgatt cacagactag acctttctta tcctcctcct agagttttga   2160
cttgggactc tagtgttaag atgatgagcc cgtgcatcag gtccttctgc actttggtgg   2220
aagtctccca gggtaggttt cctatttgaa acagtggaat catgtttcca gtgataaagt   2280
ttaatgacct catcctttt  tttttttctc atctgccatt tgtgtgtctt agatgggttt   2340
taattgcatg aatgtggcta atgtggttct cagaaattgg tcagtatggc ccaacatagc   2400
ttctgctctg tcttactgac tcaataccct taggatttgt atcagagttt ggatactagt   2460
gttagtggtg gtgtcaccac tacttaattg ggagataatg aaaccaatca tggatgctgt   2520
ttttattggg catgtcatct aagagaggag aaatagctgg gttttgggtc taattatgaa   2580
taaggactga ttcagaaaac gagtttatgg taggtagact aaagtttcac atcagactgt   2640
accattgtga tttagaccta tctaaaattc agagcatatc atctgggcta cctcagggtc   2700
accacccatg tattgggctt agtcaggatt gacagataca ttctcagctg gcctgtcata   2760
taaaacatac tgtcattgag cttaagctcc gcttgttctg aggtttcacc tccatgtgtt   2820
```

-continued

```
tcattggtgc aaaagtggat ctcttagttg gtcacttaat tctttctttt tcagaaagat    2880
agtatgttca ctggtatatt tggtcactct tagaaccttc cttcacattg tttttatgg     2940 gacccatgaa tggttagcct ttcttttcta ttgtagaagg aaataaatag gagtaaaaag    3000
accattgtag taaataagtt caaggggaac ttgggaccag aaaccactgt tatgtacaaa    3060
aaaatggcaa attcaataaa ctcaaattta aaataatttt taaattaaca gttatgataa    3120
attttatatt ttatacaaat agattgctta gaatggttct caagaattat aagagaaatg    3180
aactcacagt acaaaaattt tataattact atacttgtgt tttgtttggg ggctgggaaa    3240 tgtatttta cattgtagcc aatcatttta tatttgtcaa tttaaatctt atgggtcttt     3300 ttttttatc tctcttgatg tcagatttta tagtcttttt aaataaatcc atttaattaa     3360
aacgttaaaa aaaaaaaaaa aaaa                                           3384
```

<210> SEQ ID NO 5
<211> LENGTH: 290
<212> TYPE: PRT
<213> ORGANISM: Homo sapiens

<400> SEQUENCE: 5

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270
```

Gly Ile Gln Asp Thr Asn Ser Lys Lys Gln Ser Asp Thr His Leu Glu
            275                 280                 285
Glu Thr
    290

<210> SEQ ID NO 6
<211> LENGTH: 873
<212> TYPE: DNA
<213> ORGANISM: Homo sapiens

<400> SEQUENCE: 6

| | |
|---|---|
| atgaggatat ttgctgtctt tatattcatg acctactggc atttgctgaa cgcatttact | 60 |
| gtcacggttc ccaaggacct atatgtggta gagtatggta gcaatatgac aattgaatgc | 120 |
| aaattcccag tagaaaaaca attagacctg gctgcactaa ttgtctattg ggaaatggag | 180 |
| gataagaaca ttattcaatt tgtgcatgga gaggaagacc tgaaggttca gcatagtagc | 240 |
| tacagacaga gggcccggct gttgaaggac cagctctccc tgggaaatgc tgcacttcag | 300 |
| atcacagatg tgaaattgca ggatgcaggg gtgtaccgct gcatgatcag ctatggtggt | 360 |
| gccgactaca gcgaattac tgtgaaagtc aatgccccat acaacaaaat caaccaaaga | 420 |
| attttggttg tggatccagt cacctctgaa catgaactga catgtcaggc tgagggctac | 480 |
| cccaaggccg aagtcatctg gacaagcagt gaccatcaag tcctgagtgg taagaccacc | 540 |
| accaccaatt ccaagagaga ggagaagctt ttcaatgtga ccagcacact gagaatcaac | 600 |
| acaacaacta atgagatttt ctactgcact tttaggagat tagatcctga ggaaaaccat | 660 |
| acagctgaat tggtcatccc agaactacct ctggcacatc ctccaaatga aggactcac | 720 |
| ttggtaattc tgggagccat cttattatgc cttggtgtag cactgacatt catcttccgt | 780 |
| ttaagaaaag ggagaatgat ggatgtgaaa aaatgtggca tccaagatac aaactcaaag | 840 |
| aagcaaagtg atacacattt ggaggagacg taa | 873 |

<210> SEQ ID NO 7
<211> LENGTH: 4
<212> TYPE: PRT
<213> ORGANISM: Homo sapiens

<400> SEQUENCE: 7

Asp His His Cys
1

<210> SEQ ID NO 8
<211> LENGTH: 4
<212> TYPE: PRT
<213> ORGANISM: Homo sapiens

<400> SEQUENCE: 8

Ala Ala His Cys
1

<210> SEQ ID NO 9
<211> LENGTH: 4
<212> TYPE: PRT
<213> ORGANISM: Homo sapiens

<400> SEQUENCE: 9

Asp His His Ser
1